US012275944B2

(12) United States Patent
Flasinski et al.

(10) Patent No.: US 12,275,944 B2
(45) **Date of Patent: *Apr. 15, 2025**

(54) COMPOSITIONS AND METHODS FOR GENOME EDITING IN PLANTA

(71) Applicant: Monsanto Technology LLC, St. Louis, MO (US)

(72) Inventors: Stanislaw Flasinski, Ballwin, MO (US); Elysia Krieger, Kirkwood, MO (US); Ervin Nagy, Lake Saint Louis, MO (US); Krishnakumar Sridharan, Cary, NC (US); Xudong Ye, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/501,949

(22) Filed: Nov. 3, 2023

(65) Prior Publication Data

US 2024/0200086 A1 Jun. 20, 2024

Related U.S. Application Data

(63) Continuation of application No. 17/817,196, filed on Aug. 3, 2022, now Pat. No. 11,859,191, which is a continuation of application No. 16/563,581, filed on Sep. 6, 2019, now Pat. No. 11,414,669.

(60) Provisional application No. 62/727,784, filed on Sep. 6, 2018.

(51) Int. Cl.
*C12N 15/82* (2006.01)

(52) U.S. Cl.
CPC ..... *C12N 15/8213* (2013.01); *C12N 15/8205* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 7,022,896 | B1 | 4/2006 | Weeks et al. |
| 9,938,535 | B2 | 4/2018 | Chittoor et al. |
| 2009/0029861 | A1 | 1/2009 | Feng et al. |
| 2014/0283200 | A1 | 9/2014 | Chittoor et al. |
| 2017/0166912 | A1 | 6/2017 | Brower-Toland et al. |
| 2018/0105823 | A1 | 4/2018 | Flasinski |

FOREIGN PATENT DOCUMENTS

| | | | | |
|---|---|---|---|---|
| WO | 9741228 | A2 | 11/1997 | |
| WO | 2015131101 | A1 | 9/2015 | |
| WO | WO-2018138385 | A1 * | 8/2018 | ............. A61P 35/00 |
| WO | 2019084148 | A1 | 5/2019 | |

OTHER PUBLICATIONS

Gao, Linyi, et al. "Engineered Cpf1 variants with altered PAM specificities." Nature biotechnology 35.8 (2017): 789-792. (Year: 2017).*

Begemann, M. B. et al. (e-pub Sep. 14, 2017). "Precise Insertion and Guided Editing of Higher Plant Genomes Using Cpf1 CRISPR Nucleases," Scientific Reports 7:11606, 6 pages.

Chandrashekhar, P. J. et al. (1997). "Context Sequences of Translation Initiation Codon in Plants," Plant Molecular Biology 35:993-1001.

Christensen, A. J. et al. (1996). "Ubiquitin Promoter-Based Vectors for High-Level Expression of Selectable and/or Screenable Marker Genes in Monocotyledonous Plants," Transgenic Research 5:213-218.

Endo, A. et al. (Dec. 1, 2016). "Efficient Targeted Mutagenesis of Rice and Tobacco Genomes Using Cpf1 from Francisella Novicida," Scientific Reports 6:38169, 9 pages.

Gao, L. et al. (Aug. 2017). "Engineered Cpf1 Variants with Altered PAM Specificities," Nature biotechnology 35(8) 789-792.

Kim, G. B. et al. (2013). "Isolation and Characterization of Medicago Truncatula U6 Promoters for the Construction of Small Hairpin RNA-Mediated Gene Silencing Vectors," Plant Molecular Biology 31:581-593.

Misawa, N. et al. (Nov. 1993). "Functional Expression of the Erwinia Uredovora Carotenoid Biosynthesis Gene Crtl In Transgenic Plants Showing an Increase of Beta-carotene Biosynthesis Activity and Resistance to the Bleaching Heroicide Norflurazon," The Plant Journal 4(5):833-840.

Sahoo, D. K. et al. (2015). "Analysis of Dahlia Mosaic Virus Full-length Transcript Promoter-Driven Gene Expression in Transgenic Plants," Plant Molecular Biology 33:178-199.

Scharf, K. D. et al. (Apr. 1998). "The Tomato Hsf System: HsfA2 Needs Interaction with HsfA1 for Efficient Nuclear Import and May Be Localized in Cytoplasmic Heat Stress Granules, "Molecular and Cellular Biology 18(4):2240-2251.

Takebe, Y. et al. (Jan. 1988). "SR Alpha Promoter: An Efficient and Versatile Mammalian CDNA Expression System Composed of the Simian Virus 40 Early Promoter and the R-U5 Segment of human T-cell Leukemia virus type I Long Terminal Repeat," Molecular and Cellular Biology 8(1):466-472.

Tang, X. et al. (Feb. 17, 2017). "A CRISPR-Cpf1 System for Efficient Genome Editing and Transcriptional Repression in Plants," Nature Plants 3:17018, 22 pages.

(Continued)

*Primary Examiner* — Weihua Fan
*Assistant Examiner* — Brian James Sullivan
(74) *Attorney, Agent, or Firm* — Morrison & Foerster LLP

(57) ABSTRACT

This disclosure is related to plant-optimized recombinant nucleic acids encoding Cpf1 and their use in planta. Also disclosed are compositions, expression cassettes, and plant cells comprising the recombinant nucleic acids as well as methods and kits for modifying a target sequence in a plant genome using the recombinant nucleic acids.

18 Claims, 2 Drawing Sheets

Specification includes a Sequence Listing.

(56) References Cited

OTHER PUBLICATIONS

Thompson, J.D. (Nov. 11, 1994). "CLUSTAL W: Improving the Sensitivity of Progressive Multiple Sequence Alignment Through Sequence Weighting, Position-Specific Gap Penalties and Weight Matrix Choice," Nucleic Acids Res. 22(22):4673-4680.
Xu, R. et al. (2017). "Generation of Targeted Mutant Rice Using a CRISPR-Cpf1 System," Plant Biotechnology Journal 15:713-717.
Yang, L. et al. (2009). "The 3'-untranslated Region of Rice Glutelin GluB-1 Affects Accumulation of Heterologous Protein in Transgenic Rice," Biotechnology Letters 31:1625-1631.
Zetsche, B. et al. (Oct. 22, 2015). "Cpf1 Is a Single RNA-Guided Endonuclease of a Class 2 CRISPR-Cas System," Cell 163:759-771.

* cited by examiner

SEQUENCE LISTING

```
Sequence total quantity: 76
SEQ ID NO: 1            moltype = DNA  length = 3684
FEATURE                 Location/Qualifiers
misc_feature            1..3684
                        note = Synthetic polynucleotide. Codon optimized LbCpf1-CO1
source                  1..3684
                        mol_type = other DNA
                        organism = synthetic construct
SEQUENCE: 1
atgtccaagc ttgagaagtt tactaattgc tatagcctgt ctaagaccct tcgctttaag  60
gcgattcctg tgggcaagac gcaggaaaac atcgacaaca agcgactgct ggtggaagac  120
gagaagcgcg ctgaggacta taagggcgta aagaagctgc tcgatcggta ctacctgagt  180
tttatcaacg atgtgttgca ttccataaag ttgaagaatc ttaataacta catctccttg  240
tttcggaaaa agaccaggac cgagaaggag aataaagagt tggaaaatct ggagatcaac  300
ttgcgtaagg agatcgcgaa ggcgttcaag ggtaatgagg gttataagag tctctttaaa  360
aaagatataa ttgaaacgat tctacccgaa tttctggatg ataaggatga gattgccctc  420
gtcaattcgt tcaatggctt tacaacagcg tttacaggtt tcttcgataa cagggaaaat  480
atgtttagcg aggaggcaaa gtcgacctct atcgcttttc gctgtataaa cgaaaattta  540
actcgatata tctccaatat ggatattttc gagaaagtcg atgcgatctt tgataagcat  600
gaagtccagg agattaagga aaagattctt aattcagatt atgatgtgga agattttttc  660
gaaggtgagt tctttaactt cgtgcttacg caagaaggaa tcgacgttta caatgcaata  720
attggtgggt ttgttactga atctggtgaa aagatcaaag gcctcaatga gtacattaac  780
ttgtacaatc agaagacgaa gcagaagtta ccaaaattca agccgctgta caagcaagtg  840
ttatctgaca gggaatcttt gtccttttac ggtgaaggat acacttctga tgaagaggtg  900
cttgaggtct tcaggaatac actgaacaag aattctgaga tcttctcctc aattaagaaa  960
ctcgaaaaac ttttcaagaa ctttgatgaa tacagctctg ctggaatttt cgtaaagaat  1020
ggtcccgcca taagcactat ctcaaaggac attttcggtg agtggaatgt tataagagat  1080
aaatggaatg cagagtacga cgatatccat ttgaagaaaa aggcggtagt taccgaaaag  1140
tacgaggatg acagaaggaa atcgttcaag aagattggct cattctccct ggagcagctt  1200
caggagtacg cggacgcgga cctttctgtt gttgaaaagc tcaaggagat catcatacaa  1260
aaggtagacg agatttataa ggtctatggg agctcagaga aattgttcga cgccgatttc  1320
gttttggaga agtcactgaa aaagaacgac gctgtcgtcg ctattatgaa agaccttttg  1380
gattctgtca agtcttttga gaactatatt aaggcttttt tcggtgaggg taaggagacg  1440
aaccgcgacg agtcattcta cggagacttt gtactcgcat atgacatact gctcaaagtt  1500
gatcatattt atgacgcgat ccgcaattac gttacacaaa aaccatactc taaagataaa  1560
ttcaagctgt atttccaaaa cccgcaattc atgggggggct gggataagga taaggaaacc  1620
gattataggg cgaccatatt gcgctacggg agcaagtatt acttagcgat catggataaa  1680
aaatacgcaa agtgtttgca aaagatagac aaggacgatg tcaatggcaa ttatgagaag  1740
attaactata agttgctgcc aggacccaat aagatgttgc ccaaagtttt tttctccaaa  1800
aaatggatgg cttattataa ccctagcgag gacatccaga aaatatacaa aaacggcaca  1860
tttaagaagg gggatatgtt caatcttaat gattgtcaca agctgataga ctttttcaag  1920
gactcaatct ctcggtatcc caagtggtcg aatgcgtacg attttaattt ttctgagacc  1980
gaaaagtaca aggatattgc aggcttttat cgcgaagtgg aggaacaagg atacaaggtt  2040
tcattcgaat ccgcctcaaa aaaggaggtc gacaaactcg tcgaagaggg taaactgtac  2100
atgttccaaa tttacaataa agacttttca gacaaatcac acggaactcc taaccttcac  2160
acaatgtact ttaaattgct gttcgatgaa aataatcacg gtcaaattag gctgtcaggc  2220
ggagctgagc ttttcatgag gagggctagt ctgaagaaag aggagctggt ggtccatcct  2280
gcaaatagtc ccatagctaa taagaatcct gataacccta agaaaaccac cactctctcc  2340
tacgacgttt ataaggataa acggttcagt gaagatcagt atgagttgca tattcccatt  2400
gccataaata agtgccctaa gaacatcttc aaaattaaca cagaagtgag agttctcttg  2460
aaacacgatg ataatccata tgtgattggg atagataggg gagagcgtaa cctcctttat  2520
attgtcgtgg ttgacggaaa gggtaacata gtggagcaat acagcctcaa tgaaattatt  2580
aacaacttta atggtattag aataaagact gactatcata gtctcttgga taaaaaagag  2640
aaggagaggt tcgaagctag gcagaattgg acgtctattg aaaatattaa agaactcaaa  2700
```

-continued

```
gcagggtaca ttagccaagt cgttcacaag atatgcgagt tggttgagaa atatgatgct  2760
gtcattgcac tggaggatct caatagcggt ttcaaaaaca gtcgtgttaa ggtggagaag  2820
caggtttacc agaaattcga gaagatgctg attgataagc ttaactatat ggtggacaaa  2880
aagtctaatc catgcgcgac cggtggcgca cttaagggct atcagatcac aaacaagttc  2940
gagtcgttta agtccatgtc aacacagaac ggtttcatct tctatatccc ggcatggctg  3000
acctcaaaaa ttgatcctag cacggggttc gtaaacttac ttaaaactaa atacacctca  3060
attgctgatt caaaaaagtt tatatcctca tttgaccgaa ttatgtatgt gcccgaggag  3120
gacctgttcg aattcgctct ggactataag aacttttcaa gaacagatgc ggattatatc  3180
aagaagtgga aactttacag ttatggtaac cgcattagga tattccggaa ccccaaaaaa  3240
aataatgtct ttgattggga ggaggtatgt ctgacgtctg cttataagga gctatttaat  3300
aagtacggca tcaattatca gcagggggac atccgcgcgc ttctctgcga gcaatccgat  3360
aaggctttct acagctcctt catggcattg atgagcctca tgctgcagat gagaaacagt  3420
atcacaggta gaacggacgt agacttccta atttctccag tgaagaattc agatggcatc  3480
ttctatgata gccgcaacta tgaggcacag gagaacgcca tcctgcccaa aaatgctgat  3540
gccaacggtg cgtataacat tgctaggaag gtcctctggg ccataggtca attcaagaaa  3600
gctgaagacg agaagctcga caaggtaaaa attgccatat ccaacaagga gtggctcgaa  3660
tatgcacaga cctctgtgaa gcat                                        3684

SEQ ID NO: 2           moltype = AA  length = 1228
FEATURE                Location/Qualifiers
source                 1..1228
                       mol_type = protein
                       note = Lachnospiraceae bacterium ND2006
                       organism = unidentified
SEQUENCE: 2
MSKLEKFTNC YSLSKTLRFK AIPVGKTQEN IDNKRLLVED EKRAEDYKGV KKLLDRYYLS  60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNPQF MGGWDKDKET  540
DYRATILRYG SKYYLAIMDK KYAKCLQKID KDDVNGNYEK INYKLLPGPN KMLPKVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI AINKCPKNIF KINTEVRVLL KHDDNPYVIG IDRGERNLLY  840
IVVVDGKGNI VEQYSLNEII NNFNGIRIKT DYHSLLDKKE KERFEARQNW TSIENIKELK  900
AGYISQVVHK ICELVEKYDA VIALEDLNSG FKNSRVKVEK QVYQKFEKML IDKLNYMVDK  960
KSNPCATGGA LKGYQITNKF ESFKSMSTQN GFIFYIPAWL TSKIDPSTGF VNLLKTKYTS  1020
IADSKKFISS FDRIMYVPEE DLFEFALDYK NFSRTDADYI KKWKLYSYGN RIRIFRNPKK  1080
NNVFDWEEVC LTSAYKELFN KYGINYQQGD IRALLCEQSD KAFYSSFMAL MSLMLQMRNS  1140
ITGRTDVDFL ISPVKNSDGI FYDSRNYEAQ ENAILPKNAD ANGAYNIARK VLWAIGQFKK  1200
AEDEKLDKVK IAISNKEWLE YAQTSVKH                                    1228

SEQ ID NO: 3           moltype = DNA  length = 30
FEATURE                Location/Qualifiers
source                 1..30
                       mol_type = unassigned DNA
                       organism = Lycopersicon esculentum
SEQUENCE: 3
ggatctaaga agagaagaat taaacaagat                                  30

SEQ ID NO: 4           moltype = DNA  length = 3750
FEATURE                Location/Qualifiers
misc_feature           1..3750
                       note = Synthetic polynucleotide.NLS-LbCpf1-CO1-NLS
source                 1..3750
                       mol_type = other DNA
                       organism = synthetic construct
SEQUENCE: 4
atgggatcta agaagagaag aattaaacaa gatatgtcca agcttgagaa gtttactaat  60
tgctatagcc tgtctaagac ccttcgcttt aaggcgattc ctgtgggcaa gacgcaggaa  120
aacatcgaca acaagcgact gctggtggaa gacgagaagc gcgctgagga ctataagggc  180
gtaaagaagc tgctcgatcg gtactacctg agttttatca acgatgtgtt gcattccata  240
aagttgaaga atcttaataa ctacatctcc ttgtttcgga aaaagaccag gaccgagaag  300
gagaataaag agttggaaaa tctggagatc aacttgcgta aggagatcgc gaaggcgttc  360
aagggtaatg agggttataa gagtctcttt aaaaaagata taattgaaac gattctaccc  420
gaatttctgg atgataagga tgagattgcc ctcgtcaatt cgttcaatgg ctttacaaca  480
gcgtttacag gtttcttcga taacagggaa aatatgttta gcgaggaggc aaagtcgacc  540
tctatcgctt ttcgctgtat aaacgaaaat ttaactcgat atatctccaa tatggatatt  600
ttcgagaaag tcgatgcgat ctttgataag catgaagtcc aggagattaa ggaaaagatt  660
cttaattcag attatgatgt ggaagatttt ttcgaaggtg agttctttaa cttcgtgctt  720
acgcaagaag gaatcgacgt ttacaatgca ataattggtg ggtttgttac tgaatctggt  780
gaaaagatca aaggcctcaa tgagtacatt aacttgtaca atcagaagac gaagcagaag  840
ttaccaaaat tcaagccgct gtacaagcaa gtgttatctg acagggaatc tttgtccttt  900
tacggtgaag gatacacttc tgatgaagag gtgcttgagg tcttcaggaa tacactgaac  960
```

```
aagaattctg agatcttctc ctcaattaag aaactcgaaa aactttcaa gaactttgat  1020
gaatacagct ctgctggaat tttcgtaaag aatggtcccg ccataagcac tatctcaaag  1080
gacattttcg gtgagtggaa tgttataaga gataaatgga atgcagagta cgacgatatc  1140
catttgaaga aaaaggcggt agttaccgaa aagtacgagg atgacagaag gaaatcgttc  1200
aagaagattg gctcattctc cctggagcag cttcaggagt acgcggacgc ggacctttct  1260
gttgttgaaa agctcaagga gatcatcata caaaaggtag acgagattta taaggtctat  1320
gggagctcag agaaattgtt cgacgccgat ttcgttttgg agaagtcact gaaaaagaac  1380
gacgctgtcg tcgctattat gaaagacctt ttggattctg tcaagtcttt tgagaactat  1440
attaaggctt ttttcggtga gggtaaggag acgaaccgcg acgagtcatt ctacggagac  1500
tttgtactcg catatgacat actgctcaaa gttgatcata tttatgacgc gatccgcaat  1560
tacgttacac aaaaaccata ctctaaagat aaattcaagc tgtatttcca aaacccgcaa  1620
ttcatggggg gctgggataa ggataaggaa accgattata gggcgaccat attgcgctac  1680
gggagcaagt attacttagc gatcatggat aaaaaatacg caaagtgttt gcaaaagata  1740
gacaaggacg atgtcaatgg caattatgag aagattaact ataagttgct gccaggaccc  1800
aataagatgt tgcccaaagt ttttttctcc aaaaaatgga tggcttatta taaccctagc  1860
gaggacatcc agaaaatata caaaaacggc acatttaaga agggggatat gttcaatctt  1920
aatgattgtc acaagctgat agacttttttc aaggactcaa tctctcggta tcccaagtgg  1980
tcgaatgcgt acgattttaa tttttctgag accgaaaagt acaaggatat tgcaggcttt  2040
tatcgcgaag tggaggaaca aggatacaag gtttcattcg aatccgcctc aaaaaaggag  2100
gtcgacaaac tcgtcgaaga gggtaaactg tacatgttcc aaatttacaa taaagacttt  2160
tcagacaaat cacacggaac tcctaacctt cacacaatgt actttaaatt gctgttcgat  2220
gaaaataatc acggtcaaat taggctgtca ggcggagctg agcttttcat gaggagggct  2280
agtctgaaga aagaggagct ggtggtccat cctgcaaata gtcccatagc taataagaat  2340
cctgataacc ctaagaaaac caccactctc tcctacgacg tttataagga taaacggttc  2400
agtgaagatc agtatgagtt gcatattccc attgccataa ataagtgccc taagaacatc  2460
ttcaaaatta acacagaagt gagagttctc ttgaaacacg atgataatcc atatgtgatt  2520
gggatagata ggggagagcg taacctcctt tatattgtcg tggttgacgg aaagggtaac  2580
atagtggagc aatacagcct caatgaaatt attaacaact ttaatggtat tagaataaag  2640
actgactatc atagtctctt ggataaaaaa gagaaggaga ggttcgaagc taggcagaat  2700
tggacgtcta ttgaaaatat taaagaactc aaagcagggt acattagcca agtcgttcac  2760
aagatatgcg agttggttga gaaatatgat gctgtcattg cactggagga tctcaatagc  2820
ggtttcaaaa acagtcgtgt taaggtggag aagcaggttt accagaaatt cgagaagatg  2880
ctgattgata agcttaacta tatggtggac aaaaagtcta atccatgcgc gaccggtggc  2940
gcacttaagg gctatcagat cacaaacaag ttcgagtcgt ttaagtccat gtcaacacag  3000
aacggtttca tcttctatat cccggcatgg ctgacctcaa aaattgatcc tagcacgggg  3060
ttcgtaaact tacttaaaac taaatacacc tcaattgctg attcaaaaaa gtttatatcc  3120
tcatttgacc gaattatgta tgtgcccgag gaggacctgt tcgaattcgc tctggactat  3180
aagaactttt caagaacaga tgcggattat atcaagaagt ggaaacttta cagttatggt  3240
aaccgcatta ggatattccg gaaccccaaa aaaaataatg tctttgattg ggaggaggta  3300
tgtctgacgt ctgcttataa ggagctattt aataagtacg gcatcaatta tcagcagggg  3360
gacatccgcg cgcttctctg cgagcaatcc gataaggctt tctacagctc cttcatggca  3420
ttgatgagcc tcatgctgca gatgagaaac agtatcacag gtagaacgga cgtagacttc  3480
ctaatttctc cagtgaagaa ttcagatggc atcttctatg atagccgcaa ctatgaggca  3540
caggagaacg ccatcctgcc caaaaatgct gatgccaacg gtgcgtataa cattgctagg  3600
aaggtcctct gggccatagg tcaattcaag aaagctgaag acgagaagct cgacaaggta  3660
aaaattgcca tatccaacaa ggagtggctc gaatatgcac agacctctgt gaagcatgga  3720
tctaagaaga gaagaattaa acaagattga                                  3750
```

```
SEQ ID NO: 5            moltype = DNA  length = 189
FEATURE                 Location/Qualifiers
source                  1..189
                        mol_type = unassigned DNA
                        organism = Solanum tuberosum
SEQUENCE: 5
gtaagtttct gcttctacct ttgatatata tataataatt atcattaatt agtagtaata  60
taatatttca aatatttttt tcaaaataaa agaatgtagt atatagcaat tgcttttctg  120
tagtttataa gtgtgtatat tttaatttat aacttttcta atatatgacc aaaatttgtt  180
gatgtgcag                                                          189
```

```
SEQ ID NO: 6            moltype = DNA  length = 3939
FEATURE                 Location/Qualifiers
misc_feature            1..3939
                        note = Synthetic polynucleotide.NLS-
                         LbCpf15'-Intron-LbCpf13'-NLS
source                  1..3939
                        mol_type = other DNA
                        organism = synthetic construct
SEQUENCE: 6
atgggatcta agaagagaag aattaaacaa gatatgtcca agcttgagaa gtttactaat  60
tgctatagcc tgtctaagac ccttcgcttt aaggcgattc ctgtgggcaa gacgcaggaa  120
aacatcgaca acaagcgact gctggtggaa gacgagaagc gcgctgagga ctataagggc  180
gtaaagaagc tgctcgatcg gtactacctg agttttatca acgatgtgtt gcattccata  240
aagttgaaga atcttaataa ctacatctcc ttgtttcgga aaaagaccag gaccgagaag  300
gagaataaag agttggaaaa tctggagatc aacttgcgta aggagatcgc gaaggcgttc  360
aagggtaatg agggttataa gagtctcttt aaaaaagata taattgaaac gattctaccc  420
gaatttctgg atgataagga tgagattgcc ctcgtcaatt cgttcaatgg ctttacaaca  480
gcgtttacag gtaagtttct gcttctacct ttgatatata tataataatt atcattaatt  540
agtagtaata taatatttca aatatttttt tcaaaataaa agaatgtagt atatagcaat  600
tgcttttctg tagtttataa gtgtgtatat tttaatttat aacttttcta atatatgacc  660
```

-continued

```
aaaatttgtt gatgtgcagg tttcttcgat aacagggaaa atatgtttag cgaggaggca  720
aagtcgacct ctatcgcttt tcgctgtata aacgaaaatt taactcgata tatctccaat  780
atggatattt tcgagaaagt cgatgcgatc tttgataagc atgaagtcca ggagattaag  840
gaaaagattc ttaattcaga ttatgatgtg gaagattttt tcgaaggtga gttctttaac  900
ttcgtgctta cgcaagaagg aatcgacgtt tacaatgcaa taattggtgg gtttgttact  960
gaatctggtg aaaagatcaa aggcctcaat gagtacatta acttgtacaa tcagaagacg  1020
aagcagaagt taccaaaatt caagccgctg tacaagcaag tgttatctga cagggaatct  1080
ttgtcctttt acggtgaagg atacacttct gatgaagagg tgcttgaggt cttcaggaat  1140
acactgaaca agaattctga gatcttctcc tcaattaaga aactcgaaaa acttttcaag  1200
aactttgatg aatacagctc tgctggaatt ttcgtaaaga atggtcccgc cataagcact  1260
atctcaaagg acattttcgg tgagtggaat gttataagag ataaatggaa tgcagagtac  1320
gacgatatcc atttgaagaa aaaggcggta gttaccgaaa agtacgagga tgacagaagg  1380
aaatcgttca agaagattgg ctcattctcc ctggagcagc ttcaggagta cgcggacgcg  1440
gacctttctg ttgttgaaaa gctcaaggag atcatcatac aaaaggtaga cgagatttat  1500
aaggtctatg ggagctcaga gaaattgttc gacgccgatt tcgttttgga gaagtcactg  1560
aaaaagaacg acgctgtcgt cgctattatg aaagaccttt tggattctgt caagtctttt  1620
gagaactata ttaaggcttt tttcggtgag ggtaaggaga cgaaccgcga cgagtcattc  1680
tacggagact ttgtactcgc atatgacata ctgctcaaag ttgatcatat ttatgacgcg  1740
atccgcaatt acgttacaca aaaaccatac tctaaagata aattcaagct gtatttccaa  1800
aacccgcaat tcatgggggg ctgggataag gataaggaaa ccgattatag ggcgaccata  1860
ttgcgctacg ggagcaagta ttacttagcg atcatggata aaaaatacgc aaagtgtttg  1920
caaaagatag acaaggacga tgtcaatggc aattatgaga agattaacta taagttgctg  1980
ccaggaccca ataagatgtt gcccaaagtt tttttctcca aaaaatggat ggcttattat  2040
aaccctagcg aggacatcca gaaaatatac aaaaacggca catttaagaa gggggatatg  2100
ttcaatctta atgattgtca caagctgata gactttttca aggactcaat ctctcggtat  2160
cccaagtggt cgaatgcgta cgattttaat ttttctgaga ccgaaaagta caaggatatt  2220
gcaggctttt atcgcgaagt ggaggaacaa ggatacaagg tttcattcga atccgcctca  2280
aaaaaggagg tcgacaaact cgtcgaagag ggtaaactgt acatgttcca aatttacaat  2340
aaagactttt cagacaaatc acacggaact cctaaccttc acacaatgta ctttaaattg  2400
ctgttcgatg aaaataatca cggtcaaatt aggctgtcag gcggagctga gcttttcatg  2460
aggagggcta gtctgaagaa agaggagctg gtggtccatc ctgcaaatag tcccatagct  2520
aataagaatc ctgataaccc taagaaaacc accactctct cctacgacgt ttataaggat  2580
aaacggttca gtgaagatca gtatgagttg catattccca ttgccataaa taagtgccct  2640
aagaacatct tcaaaattaa cacagaagtg agagttctct tgaaacacga tgataatcca  2700
tatgtgattg ggatagatag gggagagcgt aacctccttt atattgtcgt ggttgacgga  2760
aagggtaaca tagtggagca atacagcctc aatgaaatta ttaacaactt taatggtatt  2820
agaataaaga ctgactatca tagtctcttg gataaaaaag agaaggagag gttcgaagct  2880
aggcagaatt ggacgtctat tgaaaatatt aaagaactca aagcaggtta cattagccaa  2940
gtcgttcaca agatatgcga gttggttgag aaatatgatg ctgtcattgc actggaggat  3000
ctcaatagcg gtttcaaaaa cagtcgtgtt aaggtggaga agcaggttta ccagaaattc  3060
gagaagatgc tgattgataa gcttaactat atggtggaca aaaagtctaa tccatgcgcg  3120
accggtggcg cacttaaggg ctatcagatc acaaacaagt tcgagtcgtt taagtccatg  3180
tcaacacaga acggtttcat cttctatatc ccggcatggc tgacctcaaa aattgatcct  3240
agcacggggt tcgtaaactt acttaaaact aaatacacct caattgctga ttcaaaaaag  3300
tttatatcct catttgaccg aattatgtat gtgcccgagg aggacctgtt cgaattcgct  3360
ctggactata agaacttttc aagaacagat gcggattata tcaagaagtg gaaactttac  3420
agttatggta accgcattag gatattccgg aaccccaaaa aaaataatgt ctttgattgg  3480
gaggaggtat gtctgacgtc tgcttataag gagctattta ataagtacgg catcaattat  3540
cagcaggggg acatccgcgc gcttctctgc gagcaatccg ataaggcttt ctacagctcc  3600
ttcatggcat tgatgagcct catgctgcag atgagaaaca gtatcacagg tagaacggac  3660
gtagacttcc taatttctcc agtgaagaat tcagatggca tcttctatga tagccgcaac  3720
tatgaggcac aggagaacgc catcctgccc aaaaatgctg atgccaacgg tgcgtataac  3780
attgctagga aggtcctctg ggccataggt caattcaaga aagctgaaga cgagaagctc  3840
gacaaggtaa aaattgccat atccaacaag gagtggctcg aatatgcaca gacctctgtg  3900
aagcatggat ctaagaagag aagaattaaa caagattga                         3939

SEQ ID NO: 7           moltype = DNA  length = 2008
FEATURE                Location/Qualifiers
source                 1..2008
                       mol_type = unassigned DNA
                       organism = Zea mays
SEQUENCE: 7
gtcgtgcccc tctctagaga taaagagcat tgcatgtcta aagtataaaa aattaccaca  60
tattttttg tcacacttat ttgaagtgta gtttatctat ctctatacat atatttaaac  120
ttcactctac aaataatata gtctataata ctaaaataat attagtgttt tagaggatca  180
tataaataaa ctgctagaca tggtctaaag gataattgaa tattttgaca atctacagtt  240
ttatcttttt agtgtgcatg tgatctctct gtttttttg caaatagctt gacctatata  300
atacttcatc cattttatta gtacatccat ttaggattta gggttgatgg tttctataga  360
ctaattttta gtacatccat tttattcttt ttagtctcta aattttttaa aactaaaact  420
ctattttagt tttttattta ataatttaga tataaaatga aataaaataa attgactaca  480
aataaaacaa ataccctta agaaataaaa aaactaagca aacatttttc ttgtttcgag  540
tagataatga caggctgttc aacgccgtcg acgagtctaa cggacaccaa ccagcgaacc  600
agcagcgtcg cgtcgggcca agcgaagcag acggcacggc atctctgtag ctgcctctgg  660
acccctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acgggggatt cctttcccac cgctccttcg ctttcccttc ctcgcccgcc  840
gtaataaata gacacccct ccacaccctc tttccccaac ctcgtgttcg ttcggagcgc  900
acacacacgc aaccagatct cccccaaatc cagccgtcgg cacctccgct tcaaggtacg  960
ccgctcatcc tcccccccc cctctctcta ccttctctag atcggcgatc cggtccatgg  1020
```

-continued

```
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc ttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgtttg gtgatacttc tgcaggtc                                      2008

SEQ ID NO: 8            moltype = DNA  length = 298
FEATURE                 Location/Qualifiers
source                  1..298
                        mol_type = unassigned DNA
                        organism = Oryza sativa
SEQUENCE: 8
taatcgatcc tccgatccct taattaccat accattacac catgcatcaa tatccatata  60
tatataaacc ctttcgcacg tacttatact atgttttgtc atacatatat atgtgtcgaa  120
cgatcgatct atcactgata tgatatgatt gatccatcag cctgatctct gtatcttgtt  180
atttgtatac cgtcaaataa aagtttcttc cacttgtgtt aataattagc tactctcatc  240
tcatgaaccc tatatataac tagtttaatt tgctgtcaat tgaacatgat gatcgatg    298

SEQ ID NO: 9            moltype = DNA  length = 200
FEATURE                 Location/Qualifiers
source                  1..200
                        mol_type = unassigned DNA
                        organism = Zea mays
SEQUENCE: 9
cggcgtatgt gccaaaaact tcgtcacaga gagggccata agaaacatgg cccacggccc  60
aatacgaagc accgcgacga agcccaaaca gcagtccgta ggtggagcaa agcgctgggt  120
aatacgcaaa cgttttgtcc caccttgact aatcacaaga gtggagcgta ccttataaac  180
cgagccgcaa gcaccgaatt                                               200

SEQ ID NO: 10           moltype = DNA  length = 3681
FEATURE                 Location/Qualifiers
misc_feature            1..3681
                        note = Synthetic polynucleotide.Codon optimized LbCpf1-CO2
source                  1..3681
                        mol_type = other DNA
                        organism = synthetic construct
SEQUENCE: 10
tcgaagctcg agaagttcac caactgctac tcgctgagca agacgctgcg gttcaaggcg  60
atccccgtcg ggaagaccca ggagaacatc gacaacaagc ggctcctggt cgaggacgag  120
aagcgcgccg aggactacaa gggcgtcaag aagctgctgg accggtacta cctctccttc  180
atcaacgacg tcctgcactc gatcaagctc aagaacctga acaactacat ctcgctgttc  240
cgcaagaaga cacggaccga gaaggagaac aaggagctcg agaacctcga gatcaacctg  300
cgcaaggaga tcgcgaaggc gttcaagggc aacgaggggt acaagagcct gttcaagaaa  360
gacatcatcg agaccatcct gccggagttc ctggacgaca aggacgagat cgcgctggtg  420
aactcgttca acgggttcac cacggccttc accgggtttt tcgacaaccg ggagaacatg  480
ttcagcgagg aggccaagtc gaccagcatc gccttccggt gcatcaacga gaacctcacc  540
cgctacatca gcaacatgga catcttcgag aaggtggacg ccatcttcga caagcacgag  600
gtccaggaga tcaaggaaaa gatcctgaac tcggactacg acgtggaaga cttctttgag  660
ggcgagttct tcaacttcgt cctcacccag gagggcatcg acgtctacaa cgccatcatc  720
ggcggcttcg tgacggagag cggcgagaag atcaagggcc tcaacgagta catcaacctc  780
tacaaccaga agactaagca gaagctcccg aagttcaagc cgctgtacaa gcaagtcctg  840
agcgaccggg agtccctctc gttctacggc gagggctaca cgagcgacga ggaggtgctg  900
gaggtgttcc gcaacacgct gaacaagaac agcgagatct tcagctcgat caagaaactc  960
gagaagctgt tcaagaactt cgacgagtac agcagcgccg gcatcttcgt caagaacggg  1020
cccgcgatca gcaccatcag caaggacatc ttcggggagt ggaacgtgat ccgcgacaag  1080
tggaacgccg agtacgacga catccacctc aagaaaaagg cggtggtcac ggagaagtac  1140
gaggacgacc gccggaagtc cttcaagaaa atcgggagct tcagcctcga gcagctccag  1200
gagtacgcgg acgccgacct gagcgtggtg gagaagctca aggagatcat catccagaag  1260
gtcgacgaga tctacaaggt ctacggctcg agcgagaagc tgttcgacgc ggacttcgtg  1320
ctggagaagt ccctcaagaa gaacgacgcc gtggtggcca tcatgaagga tctgctcgac  1380
agcgtgaagt cgttcgagaa ctacatcaag gcattctttg gggagggcaa ggagacgaac  1440
cgggacgagt ccttctacgg ggacttcgtg ctcgcgtacg acatcctcct gaaggtcgac  1500
cacatctacg acgcgatccg gaactacgtc acgcagaagc cctacagcaa ggacaagttc  1560
aagctctact tccagaaccc gcagttcatg ggcgggtggg acaaggacaa ggagaccgac  1620
taccgggcca cgatcctgcg gtacgggtcc aagtactacc tcgccatcat ggacaagaag  1680
tacgccaagt gcctccagaa gattgacaag gacgacgtga acgggaacta cgagaagatc  1740
aactacaagc tcctcccggg gcccaacaag atgctgccga aggtgttctt cagcaagaag  1800
```

-continued

```
tggatggcct actacaaccc ctcggaggac atccagaaga tatacaagaa cggcacgttc  1860
aaaaaggggg acatgttcaa cctgaacgac tgccacaagc tgatcgactt tttcaaggac  1920
agcatcagcc gctacccgaa gtggtcgaac gcctacgact tcaacttctc ggagacggag  1980
aagtacaagg acattgcggg cttctaccgg gaggtggagg agcagggcta caaggtctcc  2040
ttcgagagcg cctccaagaa agaggtggac aagctcgtgg aggagggcaa gctgtacatg  2100
ttccagatct acaacaagga cttctcggac aagtcgcacg gcaccccgaa cctccacacg  2160
atgtacttca agctgctgtt cgacgagaac aaccacgggc agatccgcct cagcggcggg  2220
gcggagctgt tcatgcgccg cgcgtccctc aagaaggagg agctggtcgt gcacccgcc  2280
aactccccga tcgcgaacaa gaaccccgac aaccccaaga agacaaccac cctctcgtac  2340
gacgtctaca aggacaagcg gttctcggag gaccagtacg agctgcacat cccgatcgcc  2400
atcaacaagt gccccaagaa catcttcaag atcaacaccg aggtgcgggt gctgctcaag  2460
cacgacgaca acccctacgt catcgggatc gaccgcggcg agcggaacct gctctacatc  2520
gtggtcgtgg acgggaaggg gaacatcgtg gagcagtaca gcctgaacga gatcatcaac  2580
aacttcaacg gcatccgcat caagacggac taccacagcc tcctggacaa gaaggagaag  2640
gagcggttcg aggcgcggca gaactggacc tccatcgaga acatcaagga gctgaaggcc  2700
ggctacatca gccaggtcgt gcacaagatc tgcgagctcg tggagaagta cgacgcggtg  2760
atcgcgctgg aggacttgaa cagcgggttc aagaactccc gggtcaaggt cgagaagcag  2820
gtctaccaga agttcgagaa gatgctgatc gacaagctca actacatggt ggacaagaag  2880
tccaacccct gcgccaccgg cggcgccctc aagggctacc agatcaccaa caagttcgag  2940
tccttcaagt cgatgtctac gcagaacggg ttcatttttct acatcccggc gtggctcacc  3000
agcaagatcg acccgagcac gggcttcgtc aacctcctga agaccaagta caccagcatc  3060
gcggacagca agaagttcat ctcctcgttc gaccgcatca tgtacgtccc cgaggaagac  3120
ctgttcgagt tcgccctcga ctacaagaac ttctcccgga cggacgccga ctacatcaaa  3180
aagtggaagc tctacagcta cggcaaccgg atccgcatct tccgcaaccc caagaagaac  3240
aatgtgttcg actgggagga ggtgtgcctg acgagcgcct acaaggagct cttcaacaag  3300
tacggcatca actaccagca aggggacatc cgcgcgctgc tctgcgagca gtccgacaag  3360
gcgttctact cgtcgttcat ggccctgatg agcctcatgc tccagatgcg caacagcatc  3420
accggccgga cggacgtgga cttcctgatc agcccggtca agaacagcga cggcattttc  3480
tacgacagcc ggaactacga ggcccaggag aacgccatcc tccccaagaa cgccgacgcg  3540
aacggcgcct acaacatcgc gcggaaggtg ctgtgggcca tcggccagtt taaaaaggcg  3600
gaggacgaga agctggacaa ggtcaagatc gccatcagca acaaggagtg gctcgagtac  3660
gcgcagacga gcgtgaagca c                                            3681
```

```
SEQ ID NO: 11          moltype = DNA  length = 3681
FEATURE                Location/Qualifiers
misc_feature           1..3681
                       note = Synthetic polynucleotide.Codon optimized LbCpf1-Os
source                 1..3681
                       mol_type = other DNA
                       organism = synthetic construct
SEQUENCE: 11
tccaagctgg agaagtttac aaactgttac agcctctcca aaaccctcag gtttaaagcg  60
atcccggtgg gcaagaccca ggagaacatc gacaacaaga ggctcctggt ggaagacgag  120
aagcgcgccg aagactacaa gggcgtgaag aagctgctcg ataggtacta cctcagcttt  180
attaacgacg tgctgcacag catcaaactc aagaatctca acaactacat ctccctcttc  240
cgcaaaaaga cccgcaccga gaaggagaac aaggagctgg agaacctgga gatcaacctc  300
cgcaaggaaa tcgccaaagc gttcaagggc aatgaagggt acaagagcct cttcaagaaa  360
gacatcatcg aaactatcct cccagagttt ctcgatgaca aggacgagat cgcgctggtg  420
aactccttta acgggttcac aaccgcgttt accggcttct ttgataacag ggaaaatatg  480
ttctccgagg aggccaagtc caccagcatc gccttcaggt gtatcaacga gaacctcacc  540
cgctacattt ccaatatgga cattttcgag aaggtggatg cgatcttcga taagcacgag  600
gtgcaggaga tcaaagagaa gattctcaat tccgattatg acgtcgagga tttcttcgaa  660
ggggagttct ttaattttgt gctcacacaa gagggcattg acgtgtacaa cgcgattatc  720
gggggcttcg tcacagagtc cggggagaag attaaggggc tgaatgagta catcaatctg  780
tacaatcaga agaccaagca gaaactgccg aaattcaagc cgctctacaa gcaagtcctg  840
tccgataggg aaagcctctc cttctacggc gagggctata ccagcgacga ggaggtgctg  900
gaagtcttcc gcaacacact gaataagaat agcgagattt tctcctccat caagaagctc  960
gagaagctct ttaagaactt tgacgagtac agctccgccg ggattttcgt gaagaacggg  1020
ccggcgatca gcaccatctc caaggacatc tttggcgagt ggaacgtcat cagggacaag  1080
tggaacgccg agtacgacga catccacctg aagaagaagg cggtggtgac cgagaagtat  1140
gaggacgatc gcaggaagtc cttcaaaaaa atcggctcct tcagcctcga acagctccag  1200
gagtatgccg atgcggatct gtccgtcgtc gagaagctga aggaaatcat cattcagaag  1260
gtcgacgaga tctataaagt gtacgggtcc agcgagaagc tgttcgacgc cgactttgtg  1320
ctcgagaagt ccctcaaaaa gaatgacgcc gtggtggcca ttatgaaaga cctgctcgac  1380
tccgtgaagt ccttcgaaaa ttacattaaa gcgttctttg gggaggggaa ggaaactaac  1440
agggatgagt ccttctatgg cgactttgtc ctcgcgtacg acatcctgct gaaggtcgac  1500
cacatttacg acgcgatccg caactacgtg acacagaagc cgtactccaa agacaagttc  1560
aagctgtact tccagaaccc gcaatttatg gggggctggg acaaggataa agagacagac  1620
taccgcgcga caattctccg ctatggctcc aaatactatc tggccatcat ggacaagaag  1680
tacgcgaagt gcctgcagaa gatcgacaaa gacgacgtca atggcaacta tgaaaagatc  1740
aactacaagc tgctgccggg cccgaacaag atgctcccga aggtgttctt cagcaagaag  1800
tggatggcct actacaatcc aagcgaggat attcagaaaa tctataaaaa cgggaccttc  1860
aagaaggggg acatgtttaa cctcaacgac tgccacaagc tcattgattt cttcaaggat  1920
agcatttccc gctacccgaa atggtccaat gcgtacgatt ttaacttctc cgagacagaa  1980
aagtacaaag acatcgcggg cttttacagg gaggtggagg agcaagggta taaagtttct  2040
tttgaatccg cgagcaagaa ggaagtcgac aagctcgtcg aggagggcaa gctctacatg  2100
ttccaaattt ataacaagga cttttccgac aagagccatg ggaccccaaa cctccacacc  2160
atgtacttca aactgctctt tgacgagaac aaccacgggc aaatcaggct gagcggcggc  2220
gccgaattat tcatgcgcag ggcctccctc aagaaggaag agctggtcgt ccatccagcc  2280
```

```
aattccccga tcgcgaacaa gaacccggac aatccgaaaa agaccaccac cctgtcctac  2340
gacgtctaca aggacaaacg cttcagcgaa gaccagtacg aattacacat cccaattgcg  2400
attaataagt gcccaaagaa tatcttcaaa attaatacag aggtcagggt gctgctcaaa  2460
cacgacgaca atccgtatgt catcggcatt gacaggggcg agcgcaatct gctctatatc  2520
gtggtcgtgg atgggaaggg caatattgtg gagcagtact ccctgaacga gattatcaac  2580
aacttcaatg ggattaggat taagaccgac tatcacagcc tgctcgacaa gaaagaaaaa  2640
gagaggtttg aggcccgcca aaactggacc tccattgaga atatcaaaga attaaaggcc  2700
ggctatattt cccaagtcgt ccacaagatc tgcgagctgg tggagaaata tgacgccgtg  2760
attgcgctcg aagacttaaa ttctgggttc aagaactccc gcgtgaaggt ggaaaaacag  2820
gtgtatcaga aattcgagaa aatgctgatc gacaaactca attatatggt ggataagaag  2880
tccaacccgt gtgccacagg gggcgcgctg aagggctatc agatcaccaa caagttcgag  2940
agcttcaaga gcatgagcac ccagaacggg tttatttttct acatcccggc gtggctcacc  3000
tccaagattg acccgagcac cggcttcgtg aacctcctga agacaaagta tacctccatt  3060
gccgacagca agaagtttat ctcctccttc gaccgcatta tgtatgtgcc ggaggaggac  3120
ctcttcgagt tcgccctcga ctacaaaaac ttcagccgca cagatgcgga ttacatcaag  3180
aagtggaagc tgtactccta cgggaacagg atccgcatct tcaggaatcc aaaaaaaaat  3240
aacgtctttg actgggagga agtgtgcctg acatccgcct acaaggaact gttcaataaa  3300
tacggcatca attaccagca gggcgacatt cgcgccctcc tctgtgagca gtccgacaaa  3360
gcgttttact ccagcttcat ggccctcatg tccctgatgc tccaaatgag gaatagcatc  3420
acagggcgca ccgacgtcga cttcctcatc agcccggtga agaactccga cgggatcttt  3480
tacgactccc gcaactatga ggcgcaagag aatgcgatcc tcccgaagaa cgccgatgcg  3540
aacggggcct ataatatcgc caggaaagtg ctctgggcca tcgggcagtt caaaaaggcg  3600
gaggatgaga agctcgacaa ggtgaaaatt gccatttcca acaaggagtg gctggagtac  3660
gcgcagacct ccgtgaagca c                                            3681
```

```
SEQ ID NO: 12           moltype = DNA  length = 3744
FEATURE                 Location/Qualifiers
misc_feature            1..3744
                        note = Synthetic polynucleotide.NLS-LbCpf1-CO2-NLS
source                  1..3744
                        mol_type = other DNA
                        organism = synthetic construct
SEQUENCE: 12
ggatctaaga agagaagaat taaacaagat tcgaagctcg agaagttcac caactgctac  60
tcgctgagca agacgctgcg gttcaaggcg atccccgtcg ggaagaccca ggagaacatc  120
gacaacaagc ggctcctggt cgaggacgag aagcgcgccg aggactacaa gggcgtcaag  180
aagctgctgg accggtacta cctctccttc atcaacgacg tcctgcactc gatcaagctc  240
aagaacctga acaactacat ctcgctgttc cgcaagaaga cacggaccga gaaggagaac  300
aaggagctcg agaacctcga gatcaacctg cgcaaggaga tcgcgaaggc gttcaagggc  360
aacgaggggt acaagagcct gttcaagaaa gacatcatcg agaccatcct gccggagttc  420
ctggacgaca aggacgagat cgcgctggtg aactcgttca acgggttcac cacggccttc  480
accgggtttt tcgacaaccg ggagaacatg ttcagcgagg aggccaagtc gaccagcatc  540
gccttccggt gcatcaacga gaacctcacc cgctacatca gcaacatgga catcttcgag  600
aaggtggacg ccatcttcga caagcacgag gtccaggaga tcaaggaaaa gatcctgaac  660
tcggactacg acgtggaaga cttctttgag ggcgagttct tcaacttcgt cctcacccag  720
gagggcatcg acgtctacaa cgccatcatc ggcggcttcg tgacggagag cggcgagaag  780
atcaagggcc tcaacgagta catcaacctc tacaaccaga agactaagca gaagctcccg  840
aagttcaagc cgctgtacaa gcaagtcctg agcgaccggg agtccctctc gttctacggc  900
gagggctaca cgagcgacga ggaggtgctg gaggtgttcc gcaacacgct gaacaagaac  960
agcgagatct tcagctcgat caagaaactc gagaagctgt tcaagaactt cgacgagtac  1020
agcagcgccg gcatcttcgt caagaacggg cccgcgatca gcaccatcag caaggacatc  1080
ttcggggagt ggaacgtgat ccgcgacaag tggaacgccg agtacgacga catccacctc  1140
aagaaaaagg cggtggtcac ggagaagtac gaggacgacc gccggaagtc cttcaagaaa  1200
atcgggagct tcagcctcga gcagctccag gagtacgcgg acgccgacct gagcgtggtg  1260
gagaagctca aggagatcat catccagaag gtcgacgaga tctacaaggt ctacggctcg  1320
agcgagaagc tgttcgacgc ggacttcgtg ctggagaagt ccctcaagaa gaacgacgcc  1380
gtggtggcca tcatgaagga tctgctcgac agcgtgaagt cgttcgagaa ctacatcaag  1440
gcattctttg gggagggcaa ggagacgaac cgggacgagt ccttctacgg ggacttcgtg  1500
ctcgcgtacg acatcctcct gaaggtcgac cacatctacg acgcgatccg gaactacgtc  1560
acgcagaagc cctacagcaa ggacaagttc aagctctact tccagaaccc gcagttcatg  1620
ggcgggtggg acaaggacaa ggagaccgac taccgggcca cgatcctgcg gtacgggtcc  1680
aagtactacc tcgccatcat ggacaagaag tacgccaagt gcctccagaa gattgacaag  1740
gacgacgtga acgggaacta cgagaagatc aactacaagc tcctcccggg gcccaacaag  1800
atgctgccga aggtgttctt cagcaagaag tggatggcct actacaaccc ctcggaggac  1860
atccagaaga tatacaagaa cggcacgttc aaaaaggggg acatgttcaa cctgaacgac  1920
tgccacaagc tgatcgactt tttcaaggac agcatcagcc gctacccgaa gtggtcgaac  1980
gcctacgact tcaacttctc ggagacggag aagtacaagg acattgcggg cttctaccgg  2040
gaggtggagg agcagggcta caaggtctcc ttcgagagcg cctccaagaa agaggtggac  2100
aagctcgtgg aggagggcaa gctgtacatg ttccagatct acaacaagga cttctcggac  2160
aagtcgcacg gcaccccgaa cctccacacg atgtacttca agctgctgtt cgacgagaac  2220
aaccacgggc agatccgcct cagcggcggg gcggagctgt tcatgcgccg cgcgtccctc  2280
aagaaggagg agctggtcgt gcaccccgcc aactccccga tcgcgaacaa gaaccccgac  2340
aaccccaaga agacaaccac cctctcgtac gacgtctaca aggacaagcg gttctcggag  2400
gaccagtacg agctgcacat cccgatcgcc atcaacaagt gccccaagaa catcttcaag  2460
atcaacaccg aggtgcgggt gctgctcaag cacgacgaca acccctacgt catcgggatc  2520
gaccgcggcg agcggaacct gctctacatc gtggtcgtgg acgggaaggg gaacatcgtg  2580
gagcagtaca gcctgaacga gatcatcaac aacttcaacg gcatccgcat caagacggac  2640
taccacagcc tcctggacaa gaaggagaag gagcggttcg aggcgcggca gaactggacc  2700
tccatcgaga acatcaagga gctgaaggcc ggctacatca gccaggtcgt gcacaagatc  2760
```

```
tgcgagctcg tggagaagta cgacgcggtg atcgcgctgg aggacttgaa cagcgggttc  2820
aagaactccc gggtcaaggt cgagaagcag gtctaccaga agttcgagaa gatgctgatc  2880
gacaagctca actacatggt ggacaagaag tccaacccct gcgccaccgg cggcgccctc  2940
aagggctacc agatcaccaa caagttcgag tccttcaagt cgatgtctac gcagaacggg  3000
ttcatttct acatcccggc gtggctcacc agcaagatcg acccgagcac gggcttcgtc  3060
aacctcctga agaccaagta caccagcatc gcggacagca agaagttcat ctcctcgttc  3120
gaccgcatca tgtacgtccc cgaggaagac ctgttcgagt tcgccctcga ctacaagaac  3180
ttctcccgga cggacgccga ctacatcaaa aagtggaagc tctacagcta cggcaaccgg  3240
atccgcatct tccgcaaccc caagaagaac aatgtgttcg actgggagga ggtgtgcctg  3300
acgagcgcct acaaggagct cttcaacaag tacggcatca actaccagca aggggacatc  3360
cgcgcgctgc tctgcgagca gtccgacaag gcgttctact cgtcgttcat ggccctgatg  3420
agcctcatgc tccagatgcg caacagcatc accggccgga cggacgtgga cttcctgatc  3480
agcccggtca agaacagcga cggcattttc tacgacagcc ggaactacga ggcccaggag  3540
aacgccatcc tccccaagaa cgccgacgcg aacggcgcct acaacatcgc gcggaaggtg  3600
ctgtgggcca tcggccagtt taaaaaggcg gaggacgaga agctggacaa ggtcaagatc  3660
gccatcagca acaaggagtg gctcgagtac gcgcagacga gcgtgaagca cggatctaag  3720
aagagaagaa ttaaacaaga ttga                                        3744

SEQ ID NO: 13          moltype = DNA  length = 12
FEATURE                Location/Qualifiers
misc_feature           1..12
                       note = Synthetic polynucleotide.kozak sequence
source                 1..12
                       mol_type = other DNA
                       organism = synthetic construct
SEQUENCE: 13
gccgccatgg cg                                                        12

SEQ ID NO: 14          moltype = DNA  length = 3756
FEATURE                Location/Qualifiers
misc_feature           1..3756
                       note = Synthetic polynucleotide.kozak-NLS-LbCpf1-CO2-NLS
source                 1..3756
                       mol_type = other DNA
                       organism = synthetic construct
SEQUENCE: 14
gccgccatgg cgggatctaa gaagagaaga attaaacaag attcgaagct cgagaagttc  60
accaactgct actcgctgag caagacgctg cggttcaagg cgatccccgt cgggaagacc  120
caggagaaca tcgacaacaa gcggctcctg gtcgaggacg agaagcgcgc cgaggactac  180
aagggcgtca agaagctgct ggaccggtac tacctctcct tcatcaacga cgtcctgcac  240
tcgatcaagc tcaagaacct gaacaactac atctcgctgt tccgcaagaa gacacggacc  300
gagaaggaga acaaggagct cgagaacctc gagatcaacc tgcgcaagga gatcgcgaag  360
gcgttcaagg gcaacgaggg gtacaagagc ctgttcaaga aagacatcat cgagaccatc  420
ctgccggagt tcctggacga caaggacgag atcgcgctgg tgaactcgtt caacgggttc  480
accacggcct tcaccgggtt tttcgacaac cgggagaaca tgttcagcga ggaggccaag  540
tcgaccagca tcgccttccg gtgcatcaac gagaacctca cccgctacat cagcaacatg  600
gacatcttcg agaaggtgga cgccatcttc gacaagcacg aggtccagga gatcaaggaa  660
aagatcctga actcggacta cgacgtggaa gacttctttg agggcgagtt cttcaacttc  720
gtcctcaccc aggagggcat cgacgtctac aacgccatca tcggcggctt cgtgacggag  780
agcggcgaga agatcaaggg cctcaacgag tacatcaacc tctacaacca gaagactaag  840
cagaagctcc cgaagttcaa gccgctgtac aagcaagtcc tgagcgaccg ggagtccctc  900
tcgttctacg gcgagggcta cacgagcgac gaggaggtgc tggaggtgtt ccgcaacacg  960
ctgaacaaga acagcgagat cttcagctcg atcaagaaac tcgagaagct gttcaagaac  1020
ttcgacgagt acagcagcgc cggcatcttc gtcaagaacg ggcccgcgat cagcaccatc  1080
agcaaggaca tcttcgggga gtggaacgtg atccgcgaca agtggaacgc cgagtacgac  1140
gacatccacc tcaagaaaaa ggcggtggtc acggagaagt acgaggacga ccgccggaag  1200
tccttcaaga aaatcgggag cttcagcctc gagcagctcc aggagtacgc ggacgccgac  1260
ctgagcgtgg tggagaagct caaggagatc atcatccaga aggtcgacga gatctacaag  1320
gtctacggct cgagcgagaa gctgttcgac gcggacttcg tgctggagaa gtccctcaag  1380
aagaacgacg ccgtggtggc catcatgaag gatctgctcg acagcgtgaa gtcgttcgag  1440
aactacatca aggcattctt tggggagggc aaggagacga accgggacga gtccttctac  1500
ggggacttcg tgctcgcgta cgacatcctc ctgaaggtcg accacatcta cgacgcgatc  1560
cggaactacg tcacgcagaa gccctacagc aaggacaagt tcaagctcta cttccagaac  1620
ccgcagttca tgggcgggtg ggacaaggac aaggagaccg actaccgggc cacgatcctg  1680
cggtacgggt ccaagtacta cctcgccatc atggacaaga agtacgccaa gtgcctccag  1740
aagattgaca aggacgacgt gaacgggaac tacgagaaga tcaactacaa gctcctcccg  1800
gggcccaaca agatgctgcc gaaggtgttc ttcagcaaga agtggatggc ctactacaac  1860
ccctcggagg acatccagaa gatatacaag aacggcacgt tcaaaaaggg ggacatgttc  1920
aacctgaacg actgccacaa gctgatcgac tttttcaagg acagcatcag ccgctacccg  1980
aagtggtcga acgcctacga cttcaacttc tcggagacgg agaagtacaa ggacattgcg  2040
ggcttctacc gggaggtgga ggagcagggc tacaaggtct ccttcgagag cgcctccaag  2100
aaagaggtgg acaagctcgt ggaggagggc aagctgtaca tgttccagat ctacaacaag  2160
gacttctcgg acaagtcgca cggcaccccg aacctccaca cgatgtactt caagctgctg  2220
ttcgacgaga acaaccacgg gcagatccgc ctcagcggcg gggcggagct gttcatgcgc  2280
cgcgcgtccc tcaagaagga ggagctggtc gtgcaccccg ccaactcccc gatcgcgaac  2340
aagaaccccg acaaccccaa gaagacaacc accctctcgt acgacgtcta caaggacaag  2400
cggttctcgg aggaccagta cgagctgcac atcccgatcg ccatcaacaa gtgccccaag  2460
aacatcttca agatcaacac cgaggtgcgg gtgctgctca agcacgacga caacccctac  2520
gtcatcggga tcgaccgcgg cgagcggaac ctgctctaca tcgtggtcgt ggacgggaag  2580
```

```
gggaacatcg tggagcagta cagcctgaac gagatcatca acaacttcaa cggcatccgc  2640
atcaagacgg actaccacag cctcctggac aagaaggaga aggagcggtt cgaggcgcgg  2700
cagaactgga cctccatcga gaacatcaag gagctgaagg ccggctacat cagccaggtc  2760
gtgcacaaga tctgcgagct cgtggagaag tacgacgcgg tgatcgcgct ggaggacttg  2820
aacagcgggt tcaagaactc ccgggtcaag gtcgagaagc aggtctacca gaagttcgag  2880
aagatgctga tcgacaagct caactacatg gtggacaaga agtccaaccc ctgcgccacc  2940
ggcggcgccc tcaagggcta ccagatcacc aacaagttcg agtccttcaa gtcgatgtct  3000
acgcagaacg ggttcatttt ctacatcccg gcgtggctca ccagcaagat cgacccgagc  3060
acgggcttcg tcaacctcct gaagaccaag tacaccagca tcgcggacag caagaagttc  3120
atctcctcgt tcgaccgcat catgtacgtc cccgaggaag acctgttcga gttcgccctc  3180
gactacaaga acttctcccg gacggacgcc gactacatca aaaagtggaa gctctacagc  3240
tacggcaacc ggatccgcat cttccgcaac cccaagaaga acaatgtgtt cgactgggag  3300
gaggtgtgcc tgacgagcgc ctacaaggag ctcttcaaca agtacggcat caactaccag  3360
caaggggaca tccgcgcgct gctctgcgag cagtccgaca aggcgttcta ctcgtcgttc  3420
atggccctga tgagcctcat gctccagatg cgcaacagca tcaccggccg gacggacgtg  3480
gacttcctga tcagcccggt caagaacagc gacggcattt tctacgacag ccggaactac  3540
gaggcccagg agaacgccat cctccccaag aacgccgacg cgaacggcgc ctacaacatc  3600
gcgcggaagg tgctgtgggc catcggccag tttaaaaagg cggaggacga gaagctggac  3660
aaggtcaaga tcgccatcag caacaaggag tggctcgagt acgcgcagac gagcgtgaag  3720
cacggatcta agaagagaag aattaaacaa gattga                            3756

SEQ ID NO: 15           moltype = DNA  length = 6062
FEATURE                 Location/Qualifiers
misc_feature            1..6062
                        note = Synthetic polynucleotide.Expression Cassette
                         comprising the ZmUbiqitin promoter cassette,
                         koz-NLS-LbCpf1-CO2-NLS cassette andthe Oryza sativa LTP
                         termination sequence
source                  1..6062
                        mol_type = other DNA
                        organism = synthetic construct
SEQUENCE: 15
gtcgtgcccc tctctagaga taaagagcat tgcatgtcta aagtataaaa aattaccaca  60
tatttttttg tcacacttat ttgaagtgta gtttatctat ctctatacat atatttaaac  120
ttcactctac aaataatata gtctataata ctaaaataat attagtgttt tagaggatca  180
tataaataaa ctgctagaca tggtctaaag gataattgaa tattttgaca atctacagtt  240
ttatcttttt agtgtgcatg tgatctctct gttttttttg caaatagctt gacctatata  300
atacttcatc cattttatta gtacatccat ttaggattta gggttgatgg tttctataga  360
ctaattttta gtacatccat tttattcttt ttagtctcta aatttttaa aactaaaact  420
ctattttagt tttttattta ataatttaga tataaaatga aataaaataa attgactaca  480
aataaaacaa atacccttta agaaataaaa aaactaagca aacatttttc ttgtttcgag  540
tagataatga caggctgttc aacgccgtcg acgagtctaa cggacaccaa ccagcgaacc  600
agcagcgtcg cgtcgggcca agcgaagcag acggcacggc atctctgtag ctgcctctgg  660
acccctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acgggggatt cctttcccac cgctccttcg ctttcccttc ctcgcccgcc  840
gtaataaata gacacccccct ccacaccctc tttccccaac ctcgtgttcg ttcggagcgc  900
acacacacgc aaccagatct cccccaaatc cagccgtcgg cacctccgct tcaaggtacg  960
ccgctcatcc tccccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc ttttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgtttg gtgatacttc tgcaggtcgc cgccatggcg ggatctaaga agagaagaat  2040
taaacaagat tcgaagctcg agaagttcac caactgctac tcgctgagca agacgctgcg  2100
gttcaaggcg atccccgtcg ggaagaccca ggagaacatc gacaacaagc ggctcctggt  2160
cgaggacgag aagcgcgccg aggactacaa gggcgtcaag aagctgctgg accggtacta  2220
cctctccttc atcaacgacg tcctgcactc gatcaagctc aagaacctga acaactacat  2280
ctcgctgttc cgcaagaaga cacggaccga gaaggagaac aaggagctcg agaacctcga  2340
gatcaacctg cgcaaggaga tcgcgaaggc gttcaagggc aacgaggggt acaagagcct  2400
gttcaagaaa gacatcatcg agaccatcct gccggagttc ctggacgaca aggacgagat  2460
cgcgctggtg aactcgttca acgggttcac cacggccttc accgggtttt tcgacaaccg  2520
ggagaacatg ttcagcgagg aggccaagtc gaccagcatc gccttccggt gcatcaacga  2580
gaacctcacc cgctacatca gcaacatgga catcttcgag aaggtggacg ccatcttcga  2640
caagcacgag gtccaggaga tcaaggaaaa gatcctgaac tcggactacg acgtggaaga  2700
cttctttgag ggcgagttct tcaacttcgt cctcacccag gagggcatcg acgtctacaa  2760
cgccatcatc ggcggcttcg tgacggagag cggcgagaag atcaagggcc tcaacgagta  2820
```

```
catcaacctc tacaaccaga agactaagca gaagctcccg aagttcaagc cgctgtacaa  2880
gcaagtcctg agcgaccggg agtccctctc gttctacggc gagggctaca cgagcgacga  2940
ggaggtgctg gaggtgttcc gcaacacgct gaacaagaac agcgagatct tcagctcgat  3000
caagaaactc gagaagctgt tcaagaactt cgacgagtac agcagcgccg gcatcttcgt  3060
caagaacggg cccgcgatca gcaccatcag caaggacatc ttcggggagt ggaacgtgat  3120
ccgcgacaag tggaacgccg agtacgacga catccacctc aagaaaaagg cggtggtcac  3180
ggagaagtac gaggacgacc gccggaagtc cttcaagaaa atcgggagct tcagcctcga  3240
gcagctccag gagtacgcgg acgccgacct gagcgtggtg gagaagctca aggagatcat  3300
catccagaag gtcgacgaga tctacaaggt ctacggctcg agcgagaagc tgttcgacgc  3360
ggacttcgtg ctggagaagt ccctcaagaa gaacgacgcc gtggtggcca tcatgaagga  3420
tctgctcgac agcgtgaagt cgttcgagaa ctacatcaag gcattctttg ggagggcaa  3480
ggagacgaac cgggacgagt ccttctacgg ggacttcgtg ctcgcgtacg acatcctcct  3540
gaaggtcgac cacatctacg acgcgatccg gaactacgtc acgcagaagc cctacagcaa  3600
ggacaagttc aagctctact tccagaaccc gcagttcatg ggcgggtggg acaaggacaa  3660
ggagaccgac taccgggcca cgatcctgcg gtacgggtcc aagtactacc tcgccatcat  3720
ggacaagaag tacgccaagt gcctccagaa gattgacaag gacgacgtga acgggaacta  3780
cgagaagatc aactacaagc tcctcccggg gcccaacaag atgctgccga aggtgttctt  3840
cagcaagaag tggatggcct actacaaccc ctcggaggac atccagaaga tatacaagaa  3900
cggcacgttc aaaaaggggg acatgttcaa cctgaacgac tgccacaagc tgatcgactt  3960
tttcaaggac agcatcagcc gctacccgaa gtggtcgaac gcctacgact tcaacttctc  4020
ggagacggag aagtacaagg acattgcggg cttctaccgg gaggtggagg agcagggcta  4080
caaggtctcc ttcgagagcg cctccaagaa agaggtggac aagctcgtgg aggagggcaa  4140
gctgtacatg ttccagatct acaacaagga cttctcggac aagtcgcacg gcaccccgaa  4200
cctccacacg atgtacttca agctgctgtt cgacgagaac aaccacgggc agatccgcct  4260
cagcggcggg gcggagctgt tcatgcgccg cgcgtccctc aagaaggagg agctggtcgt  4320
gcaccccgcc aactccccga tcgcgaacaa gaaccccgac aaccccaaga agacaaccac  4380
cctctcgtac gacgtctaca aggacaagcg gttctcggag gaccagtacg agctgcacat  4440
cccgatcgcc atcaacaagt gccccaagaa catcttcaag atcaacaccg aggtgcgggt  4500
gctgctcaag cacgacgaca acccctacgt catcgggatc gaccgcggcg agcggaacct  4560
gctctacatc gtggtcgtgg acgggaaggg gaacatcgtg gagcagtaca gcctgaacga  4620
gatcatcaac aacttcaacg gcatccgcat caagacggac taccacagcc tcctggacaa  4680
gaaggagaag gagcggttcg aggcgcggca gaactggacc tccatcgaga acatcaagga  4740
gctgaaggcc ggctacatca gccaggtcgt gcacaagatc tgcgagctcg tggagaagta  4800
cgacgcggtg atcgcgctgg aggacttgaa cagcgggttc aagaactccc gggtcaaggt  4860
cgagaagcag gtctaccaga agttcgagaa gatgctgatc gacaagctca actacatggt  4920
ggacaagaag tccaacccct gcgccaccgg cggcgccctc aagggctacc agatcaccaa  4980
caagttcgag tccttcaagt cgatgtctac gcagaacggg ttcattttct acatcccggc  5040
gtggctcacc agcaagatcg acccgagcac gggcttcgtc aacctcctga agaccaagta  5100
caccagcatc gcggacagca agaagttcat ctcctcgttc gaccgcatca tgtacgtccc  5160
cgaggaagac ctgttcgagt tcgccctcga ctacaagaac ttctcccgga cggacgccga  5220
ctacatcaaa aagtggaagc tctacagcta cggcaaccgg atccgcatct tccgcaaccc  5280
caagaagaac aatgtgttcg actgggagga ggtgtgcctg acgagcgcct acaaggagct  5340
cttcaacaag tacggcatca actaccagca aggggacatc cgcgcgctgc tctgcgagca  5400
gtccgacaag gcgttctact cgtcgttcat ggccctgatg agcctcatgc tccagatgcg  5460
caacagcatc accggccgga cggacgtgga cttcctgatc agcccggtca agaacagcga  5520
cggcattttc tacgacagcc ggaactacga ggcccaggag aacgccatcc tccccaagaa  5580
cgccgacgcg aacggcgcct acaacatcgc gcggaaggtg ctgtgggcca tcggccagtt  5640
taaaaaggcg gaggacgaga agctggacaa ggtcaagatc gccatcagca acaaggagtg  5700
gctcgagtac gcgcagacga gcgtgaagca cggatctaag aagagaagaa ttaaacaaga  5760
ttgataatcg atcctccgat cccttaatta ccataccatt acaccatgca tcaatatcca  5820
tatatatata aaccctttcg cacgtactta tactatgttt tgtcatacat atatatgtgt  5880
cgaacgatcg atctatcact gatatgatat gattgatcca tcagcctgat ctctgtatct  5940
tgttatttgt ataccgtcaa ataaaagttt cttccacttg tgttaataat tagctactct  6000
catctcatga accctatata taactagttt aatttgctgt caattgaaca tgatgatcga  6060
tg                                                                 6062
```

```
SEQ ID NO: 16          moltype = DNA  length = 3744
FEATURE                Location/Qualifiers
misc_feature           1..3744
                       note = Synthetic polynucleotide.NLS-LbCpf1-Os-NLS
source                 1..3744
                       mol_type = other DNA
                       organism = synthetic construct
SEQUENCE: 16
ggatctaaga agagaagaat taaacaagat tccaagctgg agaagtttac aaactgttac  60
agcctctcca aaaccctcag gtttaaagcg atcccggtgg gcaagaccca ggagaacatc  120
gacaacaaga ggctcctggt ggaagacgag aagcgcgccg aagactacaa gggcgtgaag  180
aagctgctcg ataggtacta cctcagcttt attaacgacg tgctgcacag catcaaactc  240
aagaatctca acaactacat ctccctcttc cgcaaaaaga cccgcaccga gaaggagaac  300
aaggagctgg agaacctgga gatcaacctc cgcaaggaaa tcgccaaagc gttcaagggc  360
aatgaagggt acaagagcct cttcaagaaa gacatcatcg aaactatcct cccagagttt  420
ctcgatgaca aggacgagat cgcgctggtg aactccttta acgggttcac aaccgcgttt  480
accggcttct ttgataacag ggaaaatatg ttctccgagg aggccaagtc caccagcatc  540
gccttcaggt gtatcaacga gaacctcacc cgctacattt ccaatatgga cattttcgag  600
aaggtggatg cgatcttcga taagcacgag gtgcaggaga tcaaagagaa gattctcaat  660
tccgattatg acgtcgagga tttcttcgaa ggggagttct ttaattttgt gctcacacaa  720
gagggcattg acgtgtacaa cgcgattatc gggggcttcg tcacagagtc cggggagaag  780
attaagggc tgaatgagta catcaatctg tacaatcaga agaccaagca gaaactgccg  840
aaattcaagc cgctctacaa gcaagtcctg tccgataggg aaagcctctc cttctacggc  900
```

```
gagggctata ccagcgacga ggaggtgctg gaagtcttcc gcaacacact gaataagaat  960
agcgagattt tctcctccat caagaagctc gagaagctct ttaagaactt tgacgagtac  1020
agctccgccg ggattttcgt gaagaacggg ccggcgatca gcaccatctc caaggacatc  1080
tttggcgagt ggaacgtcat cagggacaag tggaacgccg agtacgacga catccacctg  1140
aagaagaagg cggtggtgac cgagaagtat gaggacgatc gcaggaagtc cttcaaaaaa  1200
atcggctcct tcagcctcga acagctccag gagtatgccg atgcggatct gtccgtcgtc  1260
gagaagctga aggaaatcat cattcagaag gtcgacgaga tctataaagt gtacgggtcc  1320
agcgagaagc tgttcgacgc cgactttgtg ctcgagaagt ccctcaaaaa gaatgacgcc  1380
gtggtggcca ttatgaaaga cctgctcgac tccgtgaagt ccttcgaaaa ttacattaaa  1440
gcgttctttg gggaggggaa ggaaactaac agggatgagt ccttctatgg cgactttgtc  1500
ctcgcgtacg acatcctgct gaaggtcgac cacatttacg acgcgatccg caactacgtg  1560
acacagaagc cgtactccaa agacaagttc aagctgtact tccagaaccc gcaatttatg  1620
gggggctggg acaaggataa agagacagac taccgcgcga caattctccg ctatggctcc  1680
aaatactatc tggccatcat ggacaagaag tacgcgaagt gcctgcagaa gatcgacaaa  1740
gacgacgtca atggcaacta tgaaaagatc aactacaagc tgctgccggg cccgaacaag  1800
atgctcccga aggtgttctt cagcaagaag tggatggcct actacaatcc aagcgaggat  1860
attcagaaaa tctataaaaa cgggaccttc aagaaggggg acatgtttaa cctcaacgac  1920
tgccacaagc tcattgattt cttcaaggat agcatttccc gctacccgaa atggtccaat  1980
gcgtacgatt ttaacttctc cgagacagaa aagtacaaag acatcgcggg cttttacagg  2040
gaggtggagg agcaagggta taaagtttct tttgaatccg cgagcaagaa ggaagtcgac  2100
aagctcgtcg aggagggcaa gctctacatg ttccaaattt ataacaagga cttttccgac  2160
aagagccatg ggaccccaaa cctccacacc atgtacttca aactgctctt tgacgagaac  2220
aaccacgggc aaatcaggct gagcggcggc gccgaattat tcatgcgcag ggcctccctc  2280
aagaaggaag agctggtcgt ccatccagcc aattccccga tcgcgaacaa gaacccggac  2340
aatccgaaaa agaccaccac cctgtcctac gacgtctaca aggacaaacg cttcagcgaa  2400
gaccagtacg aattacacat cccaattgcg attaataagt gcccaaagaa tatcttcaaa  2460
attaatacag aggtcagggt gctgctcaaa cacgacgaca atccgtatgt catcggcatt  2520
gacaggggcg agcgcaatct gctctatatc gtggtcgtgg atgggaaggg caatattgtg  2580
gagcagtact ccctgaacga gattatcaac aacttcaatg ggattaggat taagaccgac  2640
tatcacagcc tgctcgacaa gaaagaaaaa gagaggtttg aggcccgcca aaactggacc  2700
tccattgaga atatcaaaga attaaaggcc ggctatattt cccaagtcgt ccacaagatc  2760
tgcgagctgg tggagaaata tgacgccgtg attgcgctcg aagacttaaa ttctgggttc  2820
aagaactccc gcgtgaaggt ggaaaaacag gtgtatcaga aattcgagaa aatgctgatc  2880
gacaaactca attatatggt ggataagaag tccaaccccgt gtgccacagg gggcgcgctg  2940
aagggctatc agatcaccaa caagttcgag agcttcaaga gcatgagcac ccagaacggg  3000
tttatttttct acatcccggc gtggctcacc tccaagattg acccgagcac cggcttcgtg  3060
aacctcctga agacaaagta tacctccatt gccgacagca agaagtttat ctcctccttc  3120
gaccgcatta tgtatgtgcc ggaggaggac ctcttcgagt tcgccctcga ctacaaaaac  3180
ttcagccgca cagatgcgga ttacatcaag aagtggaagc tgtactccta cgggaacagg  3240
atccgcatct tcaggaatcc aaaaaaaaat aacgtctttg actgggagga agtgtgcctg  3300
acatccgcct acaaggaact gttcaataaa tacggcatca attaccagca gggcgacatt  3360
cgcgccctcc tctgtgagca gtccgacaaa gcgttttact ccagcttcat ggccctcatg  3420
tccctgatgc tccaaatgag gaatagcatc acagggcgca ccgacgtcga cttcctcatc  3480
agcccggtga agaactccga cgggatcttt tacgactccc gcaactatga ggcgcaagag  3540
aatgcgatcc tcccgaagaa cgccgatgcg aacggggcct ataatatcgc caggaaagtg  3600
ctctgggcca tcgggcagtt caaaaaggcg gaggatgaga agctcgacaa ggtgaaaatt  3660
gccatttcca acaaggagtg gctggagtac gcgcagacct ccgtgaagca cggatctaag  3720
aagagaagaa ttaaacaaga ttga                                         3744
```

```
SEQ ID NO: 17          moltype = DNA  length = 3756
FEATURE                Location/Qualifiers
misc_feature           1..3756
                       note = Synthetic polynucleotide.kozak-NLS-LbCpf1-Os-NLS
source                 1..3756
                       mol_type = other DNA
                       organism = synthetic construct
SEQUENCE: 17
gccgccatgg cgggatctaa gaagagaaga attaaacaag attccaagct ggagaagttt  60
acaaactgtt acagcctctc caaaaccctc aggtttaaag cgatcccggt gggcaagacc  120
caggagaaca tcgacaacaa gaggctcctg gtggaagacg agaagcgcgc cgaagactac  180
aagggcgtga agaagctgct cgataggtac tacctcagct ttattaacga cgtgctgcac  240
agcatcaaac tcaagaatct caacaactac atctccctct tccgcaaaaa gacccgcacc  300
gagaaggaga acaaggagct ggagaacctg gagatcaacc tccgcaagga aatcgccaaa  360
gcgttcaagg gcaatgaagg gtacaagagc ctcttcaaga aagacatcat cgaaactatc  420
ctcccagagt ttctcgatga caaggacgag atcgcgctgg tgaactcctt taacgggttc  480
acaaccgcgt ttaccggctt ctttgataac agggaaaata tgttctccga ggaggccaag  540
tccaccagca tcgccttcag gtgtatcaac gagaacctca cccgctacat ttccaatatg  600
gacattttcg agaaggtgga tgcgatcttc gataagcacg aggtgcagga gatcaaagag  660
aagattctca attccgatta tgacgtcgag gatttcttcg aaggggagtt ctttaatttt  720
gtgctcacac aagagggcat tgacgtgtac aacgcgatta tcgggggctt cgtcacagag  780
tccggggaga agattaaggg gctgaatgag tacatcaatc tgtacaatca gaagaccaag  840
cagaaactgc cgaaattcaa gccgctctac aagcaagtcc tgtccgatag ggaaagcctc  900
tccttctacg gcgagggcta taccagcgac gaggaggtgc tggaagtctt ccgcaacaca  960
ctgaataaga atagcgagat ttctcctcc atcaagaagc tcgagaagct ctttaagaac  1020
tttgacgagt acagctccgc cgggattttc gtgaagaacg ggccggcgat cagcaccatc  1080
tccaaggaca tctttggcga gtggaacgtc atcagggaca agtggaacgc cgagtacgac  1140
gacatccacc tgaagaagaa ggcggtggtg accgagaagt atgaggacga tcgcaggaag  1200
tccttcaaaa aaatcggctc cttcagcctc gaacagctcc aggagtatgc cgatgcggat  1260
ctgtccgtcg tcgagaagct gaaggaaatc atcattcaga aggtcgacga gatctataaa  1320
```

-continued

```
gtgtacgggt ccagcgagaa gctgttcgac gccgactttg tgctcgagaa gtccctcaaa  1380
aagaatgacg ccgtggtggc cattatgaaa gacctgctcg actccgtgaa gtccttcgaa  1440
aattacatta aagcgttctt tggggagggg aaggaaacta acagggatga gtccttctat  1500
ggcgactttg tcctcgcgta cgacatcctg ctgaaggtcg accacattta cgacgcgatc  1560
cgcaactacg tgacacagaa gccgtactcc aaagacaagt tcaagctgta cttccagaac  1620
ccgcaattta tgggggctg ggacaaggat aaagagacag actaccgcgc gacaattctc  1680
cgctatggct ccaaatacta tctggccatc atggacaaga agtacgcgaa gtgcctgcag  1740
aagatcgaca aagacgacgt caatggcaac tatgaaaaga tcaactacaa gctgctgccg  1800
ggcccgaaca agatgctccc gaaggtgttc ttcagcaaga agtggatggc ctactacaat  1860
ccaagcgagg atattcagaa aatctataaa aacgggacct tcaagaaggg ggacatgttt  1920
aacctcaacg actgccacaa gctcattgat ttcttcaagg atagcatttc ccgctacccg  1980
aaatggtcca atgcgtacga ttttaacttc tccgagacag aaaagtacaa agacatcgcg  2040
ggcttttaca gggaggtgga ggagcaaggg tataaagttt cttttgaatc cgcgagcaag  2100
aaggaagtcg acaagctcgt cgaggagggc aagctctaca tgttccaaat ttataacaag  2160
gacttttccg acaagagcca tggacccca aacctccaca ccatgtactt caaactgctc  2220
tttgacgaga acaaccacgg gcaaatcagg ctgagcggcg gcgccgaatt attcatgcgc  2280
agggcctccc tcaagaagga agagctggtc gtccatccag ccaattcccc gatcgcgaac  2340
aagaacccgg acaatccgaa aaagaccacc accctgtcct acgacgtcta caaggacaaa  2400
cgcttcagcg aagaccagta cgaattacac atcccaattg cgattaataa gtgcccaaag  2460
aatatcttca aaattaatac agaggtcagg gtgctgctca aacacgacga caatccgtat  2520
gtcatcggca ttgacagggg cgagcgcaat ctgctctata tcgtggtcgt ggatgggaag  2580
ggcaatattg tggagcagta ctccctgaac gagattatca acaacttcaa tgggattagg  2640
attaagaccg actatcacag cctgctcgac aagaaagaaa aagagaggtt tgaggcccgc  2700
caaaactgga cctccattga gaatatcaaa gaattaaagg ccggctatat ttcccaagtc  2760
gtccacaaga tctgcgagct ggtggagaaa tatgacgccg tgattgcgct cgaagactta  2820
aattctgggt tcaagaactc ccgcgtgaag gtggaaaaac aggtgtatca gaaattcgag  2880
aaaatgctga tcgacaaact caattatatg gtggataaga agtccaaccc gtgtgccaca  2940
gggggcgcgc tgaagggcta tcagatcacc aacaagttcg agagcttcaa gagcatgagc  3000
acccagaacg ggtttatttt ctacatcccg gcgtggctca cctccaagat tgacccgagc  3060
accggcttcg tgaacctcct gaagacaaag tatacctcca ttgccgacag caagaagttt  3120
atctcctcct tcgaccgcat tatgtatgtg ccggaggagg acctcttcga gttcgccctc  3180
gactacaaaa acttcagccg cacagatgcg gattacatca agaagtggaa gctgtactcc  3240
tacgggaaca ggatccgcat cttcaggaat ccaaaaaaaa ataacgtctt tgactgggag  3300
gaagtgtgcc tgacatccgc ctacaaggaa ctgttcaata aatacggcat caattaccag  3360
cagggcgaca ttcgcgccct cctctgtgag cagtccgaca aagcgtttta ctccagcttc  3420
atggccctca tgtccctgat gctccaaatg aggaatagca tcacagggcg caccgacgtc  3480
gacttcctca tcagcccggt gaagaactcc gacgggatct tttacgactc ccgcaactat  3540
gaggcgcaag agaatgcgat cctcccgaag aacgccgatg cgaacggggc ctataatatc  3600
gccaggaaag tgctctgggc catcgggcag ttcaaaaagg cggaggatga gaagctcgac  3660
aaggtgaaaa ttgccatttc caacaaggag tggctggagt acgcgcagac ctccgtgaag  3720
cacggatcta agaagagaag aattaaacaa gattga                            3756
```

```
SEQ ID NO: 18          moltype = DNA  length = 6062
FEATURE                Location/Qualifiers
misc_feature           1..6062
                       note = Synthetic polynucleotide.Expression Cassette
                        comprising the ZmUbiqitin promoter cassette,
                        koz-NLS-LbCpf1-Os-NLS cassette andthe Oryza sativa LTP
                        termination sequence
source                 1..6062
                       mol_type = other DNA
                       organism = synthetic construct
SEQUENCE: 18
gtcgtgcccc tctctagaga taaagagcat tgcatgtcta aagtataaaa aattaccaca  60
tattttttg tcacacttat ttgaagtgta gtttatctat ctctatacat atatttaaac  120
ttcactctac aaataatata gtctataata ctaaaataat attagtgttt tagaggatca  180
tataaataaa ctgctagaca tggtctaaag gataattgaa tattttgaca atctacagtt  240
ttatcttttt agtgtgcatg tgatctctct gtttttttg caaatagctt gacctatata  300
atacttcatc cattttatta gtacatccat ttaggattta gggttgatgg tttctataga  360
ctaattttta gtacatccat tttattcttt ttagtctcta aatttttaa aactaaaact  420
ctattttagt tttttattta ataatttaga tataaaatga aataaaataa attgactaca  480
aataaaacaa ataccttta agaaataaaa aaactaagca aacatttttc ttgtttcgag  540
tagataatga caggctgttc aacgccgtcg acgagtctaa cggacaccaa ccagcgaacc  600
agcagcgtcg cgtcgggcca agcgaagcag acggcacggc atctctgtag ctgcctctgg  660
acccctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acgggggatt cctttcccac cgctccttcg ctttcccttc ctcgcccgcc  840
gtaataaata gacacccct ccacaccctc tttccccaac ctcgtgttcg ttcggagcgc  900
acacacacgc aaccagatct cccccaaatc cagccgtcgg cacctccgct tcaaggtacg  960
ccgctcatcc tcccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
```

-continued

```
acagagatgc ttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgtttg gtgatacttc tgcaggtcgc cgccatggcg ggatctaaga agagaagaat  2040
taaacaagat tccaagctgg agaagtttac aaactgttac agcctctcca aaaccctcag  2100
gtttaaagcg atcccggtgg gcaagaccca ggagaacatc gacaacaaga ggctcctggt  2160
ggaagacgag aagcgcgccg aagactacaa gggcgtgaag aagctgctcg ataggtacta  2220
cctcagcttt attaacgacg tgctgcacag catcaaactc aagaatctca acaactacat  2280
ctccctcttc cgcaaaaaga cccgcaccga gaaggagaac aaggagctgg agaacctgga  2340
gatcaacctc cgcaaggaaa tcgccaaagc gttcaagggc aatgaagggt acaagagcct  2400
cttcaagaaa gacatcatcg aaactatcct cccagagttt ctcgatgaca aggacgagat  2460
cgcgctggtg aactccttta acgggttcac aaccgcgttt accggcttct ttgataacag  2520
ggaaaatatg ttctccgagg aggccaagtc caccagcatc gccttcaggt gtatcaacga  2580
gaacctcacc cgctacattt ccaatatgga cattttcgag aaggtggatg cgatcttcga  2640
taagcacgag gtgcaggaga tcaaagagaa gattctcaat tccgattatg acgtcgagga  2700
tttcttcgaa ggggagttct ttaattttgt gctcacacaa gagggcattg acgtgtacaa  2760
cgcgattatc gggggcttcg tcacagagtc cggggagaag attaaggggc tgaatgagta  2820
catcaatctg tacaatcaga agaccaagca gaaactgccg aaattcaagc cgctctacaa  2880
gcaagtcctg tccgataggg aaagcctctc cttctacggc gagggctata ccagcgacga  2940
ggaggtgctg gaagtcttcc gcaacacact gaataagaat agcgagattt tctcctccat  3000
caagaagctc gagaagctct ttaagaactt tgacgagtac agctccgccg ggattttcgt  3060
gaagaacggg ccggcgatca gcaccatctc caaggacatc tttggcgagt ggaacgtcat  3120
cagggacaag tggaacgccg agtacgacga catccacctg aagaagaagg cggtggtgac  3180
cgagaagtat gaggacgatc gcaggaagtc cttcaaaaaa atcggctcct tcagcctcga  3240
acagctccag gagtatgccg atgcggatct gtccgtcgtc gagaagctga aggaaatcat  3300
cattcagaag gtcgacgaga tctataaagt gtacgggtcc agcgagaagc tgttcgacgc  3360
cgactttgtg ctcgagaagt ccctcaaaaa gaatgacgcc gtggtggcca ttatgaaaga  3420
cctgctcgac tccgtgaagt ccttcgaaaa ttacattaaa gcgttctttg gggaggggaa  3480
ggaaactaac agggatgagt ccttctatgg cgactttgtc ctcgcgtacg acatcctgct  3540
gaaggtcgac cacatttacg acgcgatccg caactacgtg acacagaagc cgtactccaa  3600
agacaagttc aagctgtact tccagaaccc gcaatttatg gggggctggg acaaggataa  3660
agagacagac taccgcgcga caattctccg ctatggctcc aaatactatc tggccatcat  3720
ggacaagaag tacgcgaagt gcctgcagaa gatcgacaaa gacgacgtca atggcaacta  3780
tgaaaagatc aactacaagc tgctgccggg cccgaacaag atgctcccga aggtgttctt  3840
cagcaagaag tggatggcct actacaatcc aagcgaggat attcagaaaa tctataaaaa  3900
cgggaccttc aagaaggggg acatgtttaa cctcaacgac tgccacaagc tcattgattt  3960
cttcaaggat agcatttccc gctacccgaa atggtccaat gcgtacgatt ttaacttctc  4020
cgagacagaa aagtacaaag acatcgcggg cttttacagg gaggtggagg agcaagggta  4080
taaagtttct tttgaatccg cgagcaagaa ggaagtcgac aagctcgtcg aggagggcaa  4140
gctctacatg ttccaaattt ataacaagga cttttccgac aagagccatg ggaccccaaa  4200
cctccacacc atgtacttca aactgctctt tgacgagaac aaccacgggc aaatcaggct  4260
gagcggcggc gccgaattat tcatgcgcag ggcctccctc aagaaggaag agctggtcgt  4320
ccatccagcc aattccccga tcgcgaacaa gaacccggac aatccgaaaa agaccaccac  4380
cctgtcctac gacgtctaca aggacaaacg cttcagcgaa gaccagtacg aattacacat  4440
cccaattgcg attaataagt gcccaaagaa tatcttcaaa attaatacag aggtcagggt  4500
gctgctcaaa cacgacgaca atccgtatgt catcggcatt gacaggggcg agcgcaatct  4560
gctctatatc gtggtcgtgg atgggaaggg caatattgtg gagcagtact ccctgaacga  4620
gattatcaac aacttcaatg ggattaggat taagaccgac tatcacagcc tgctcgacaa  4680
gaaagaaaaa gagaggtttg aggcccgcca aaactggacc tccattgaga atatcaaaga  4740
attaaaggcc ggctatattt cccaagtcgt ccacaagatc tgcgagctgg tggagaaata  4800
tgacgccgtg attgcgctcg aagacttaaa ttctgggttc aagaactccc gcgtgaaggt  4860
ggaaaaacag gtgtatcaga aattcgagaa aatgctgatc gacaaactca attatatggt  4920
ggataagaag tccaacccgt gtgccacagg gggcgcgctg aagggctatc agatcaccaa  4980
caagttcgag agcttcaaga gcatgagcac ccagaacggg tttattttct acatcccggc  5040
gtggctcacc tccaagattg acccgagcac cggcttcgtg aacctcctga agacaaagta  5100
tacctccatt gccgacagca agaagtttat ctcctccttc gaccgcatta tgtatgtgcc  5160
ggaggaggac ctcttcgagt tcgccctcga ctacaaaaac ttcagccgca cagatgcgga  5220
ttacatcaag aagtggaagc tgtactccta cgggaacagg atccgcatct tcaggaatcc  5280
aaaaaaaaat aacgtctttg actgggagga agtgtgcctg acatccgcct acaaggaact  5340
gttcaataaa tacggcatca attaccagca gggcgacatt cgcgccctcc tctgtgagca  5400
gtccgacaaa gcgttttact ccagcttcat ggccctcatg tccctgatgc tccaaatgag  5460
gaatagcatc acagggcgca ccgacgtcga cttcctcatc agcccggtga agaactccga  5520
cgggatcttt tacgactccc gcaactatga ggcgcaagag aatgcgatcc tcccgaagaa  5580
cgccgatgcg aacggggcct ataatatcgc caggaaagtg ctctgggcca tcgggcagtt  5640
caaaaaggcg gaggatgaga agctcgacaa ggtgaaaatt gccatttcca acaaggagtg  5700
gctggagtac gcgcagacct ccgtgaagca cggatctaag aagagaagaa ttaaacaaga  5760
ttgataatcg atcctccgat cccttaatta ccataccatt acaccatgca tcaatatcca  5820
tatatatata aacccttcg cacgtactta tactatgttt tgtcatacat atatatgtgt  5880
cgaacgatcg atctatcact gatatgatat gattgatcca tcagcctgat ctctgtatct  5940
tgttatttgt ataccgtcaa ataaaagttt cttccacttg tgttaataat tagctactct  6000
catctcatga accctatata taactagttt aatttgctgt caattgaaca tgatgatcga  6060
tg                                                                6062
```

SEQ ID NO: 19 moltype = DNA length = 6072
FEATURE Location/Qualifiers

-continued

```
misc_feature            1..6072
                        note = Synthetic polynucleotide.Expression Cassette
                         comprising the ZmUbiqitin promoter cassette,
                         NLS-LbCpf1-Os-NLS cassette and theOryza sativa LTP
                         termination sequence
source                  1..6072
                        mol_type = other DNA
                        organism = synthetic construct
SEQUENCE: 19
gtcgtgcccc tctctagaga taaagagcat tgcatgtcta aagtataaaa aattaccaca  60
tattttttg tcacacttat ttgaagtgta gtttatctat ctctatacat atatttaaac  120
ttcactctac aaataatata gtctataata ctaaaataat attagtgttt tagaggatca  180
tataaataaa ctgctagaca tggtctaaag gataattgaa tattttgaca atctacagtt  240
ttatcttttt agtgtgcatg tgatctctct gtttttttg caaatagctt gacctatata  300
atacttcatc cattttatta gtacatccat ttaggattta gggttgatgg tttctataga  360
ctaattttta gtacatccat tttattcttt ttagtctcta aatttttaa aactaaaact  420
ctattttagt tttttattta ataatttaga tataaaatga aataaaataa attgactaca  480
aataaaacaa ataccettta agaaataaaa aaactaagca aacatttttc ttgtttcgag  540
tagataatga caggctgttc aacgccgtcg acgagtctaa cggacaccaa ccagcgaacc  600
agcagcgtcg cgtcgggcca agcgaagcag acggcacggc atctctgtag ctgcctctgg  660
acccctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acgggggatt cctttcccac cgctccttcg ctttcccttc ctcgcccgcc  840
gtaataaata gacacccct ccacaccctc tttccccaac ctcgtgttcg ttcggagcgc  900
acacacacgc aaccagatct cccccaaatc cagccgtcgg cacctccgct tcaaggtacg  960
ccgctcatcc tcccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc ttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgtttg gtgatacttc tgcaggtccg gtaccatggg atctaagaag agaagaatta  2040
aacaagatat gtccaagctg gagaagttta caaactgtta cagcctctcc aaaaccctca  2100
ggtttaaagc gatcccggtg ggcaagaccc aggagaacat cgacaacaag aggctcctgg  2160
tggaagacga gaagcgcgcc gaagactaca agggcgtgaa gaagctgctc gataggtact  2220
acctcagctt tattaacgac gtgctgcaca gcatcaaact caagaatctc aacaactaca  2280
tctccctctt ccgcaaaaag acccgcaccg agaaggagaa caaggagctg gagaacctgg  2340
agatcaacct ccgcaaggaa atcgccaaag cgttcaaggg caatgaaggg tacaagagcc  2400
tcttcaagaa agacatcatc gaaactatcc tcccagagtt tctcgatgac aaggacgaga  2460
tcgcgctggt gaactccttt aacgggttca caaccgcgtt taccggcttc tttgataaca  2520
gggaaaatat gttctccgag gaggccaagt ccaccagcat cgccttcagg tgtatcaacg  2580
agaacctcac ccgctacatt tccaatatgg acattttcga gaaggtggat gcgatcttcg  2640
ataagcacga ggtgcaggag atcaaagaga agattctcaa ttccgattat gacgtcgagg  2700
atttcttcga aggggagttc tttaattttg tgctcacaca agagggcatt gacgtgtaca  2760
acgcgattat cgggggcttc gtcacagagt ccggggagaa gattaagggg ctgaatgagt  2820
acatcaatct gtacaatcag aagaccaagc agaaactgcc gaaattcaag ccgctctaca  2880
agcaagtcct gtccgatagg gaaagcctct ccttctacgg cgagggctat accagcgacg  2940
aggaggtgct ggaagtcttc cgcaacacac tgaataagaa tagcgagatt ttctcctcca  3000
tcaagaagct cgagaagctc tttaagaact ttgacgagta cagctccgcc gggattttcg  3060
tgaagaacgg gccggcgatc agcaccatct ccaaggacat ctttggcgag tggaacgtca  3120
tcagggacaa gtggaacgcc gagtacgacg acatccacct gaagaagaag gcggtggtga  3180
ccgagaagta tgaggacgat cgcaggaagt ccttcaaaaa aatcggctcc ttcagcctcg  3240
aacagctcca ggagtatgcc gatgcggatc tgtccgtcgt cgagaagctg aaggaaatca  3300
tcattcagaa ggtcgacgag atctataaag tgtacgggtc cagcgagaag ctgttcgacg  3360
ccgactttgt gctcgagaag tccctcaaaa agaatgacgc cgtggtggcc attatgaaag  3420
acctgctcga ctccgtgaag tccttcgaaa attacattaa agcgttcttt ggggagggga  3480
aggaaactaa cagggatgag tccttctatg gcgactttgt cctcgcgtac gacatcctgc  3540
tgaaggtcga ccacatttac gacgcgatcc gcaactacgt gacacagaag ccgtactcca  3600
aagacaagtt caagctgtac ttccagaacc cgcaatttat ggggggctgg gacaaggata  3660
aagagacaga ctaccgcgcg acaattctcc gctatggctc caaatactat ctggccatca  3720
tggacaagaa gtacgcgaag tgcctgcaga agatcgacaa agacgacgtc aatggcaact  3780
atgaaaagat caactacaag ctgctgccgg gcccgaacaa gatgctcccg aaggtgttct  3840
tcagcaagaa gtggatggcc tactacaatc caagcgagga tattcagaaa atctataaaa  3900
acgggacctt caagaagggg gacatgttta acctcaacga ctgccacaag ctcattgatt  3960
tcttcaagga tagcatttcc cgctacccga aatggtccaa tgcgtacgat tttaacttct  4020
ccgagacaga aaagtacaaa gacatcgcgg gcttttacag ggaggtggag gagcaagggt  4080
ataaagtttc ttttgaatcc gcgagcaaga aggaagtcga caagctcgtc gaggagggca  4140
agctctacat gttccaaatt tataacaagg acttttccga caagagccat gggaccccaa  4200
```

-continued

```
acctccacac catgtacttc aaactgctct ttgacgagaa caaccacggg caaatcaggc  4260
tgagcggcgg cgccgaatta ttcatgcgca gggcctccct caagaaggaa gagctggtcg  4320
tccatccagc caattccccg atcgcgaaca agaacccgga caatccgaaa aagaccacca  4380
ccctgtccta cgacgtctac aaggacaaac gcttcagcga agaccagtac gaattacaca  4440
tcccaattgc gattaataag tgcccaaaga atatcttcaa aattaataca gaggtcaggg  4500
tgctgctcaa acacgacgac aatccgtatg tcatcggcat tgacaggggc gagcgcaatc  4560
tgctctatat cgtggtcgtg gatgggaagg gcaatattgt ggagcagtac tccctgaacg  4620
agattatcaa caacttcaat gggattagga ttaagaccga ctatcacagc ctgctcgaca  4680
agaaagaaaa agagaggttt gaggcccgcc aaaactggac ctccattgag aatatcaaag  4740
aattaaaggc cggctatatt tcccaagtcg tccacaagat ctgcgagctg gtggagaaat  4800
atgacgccgt gattgcgctc gaagacttaa attctgggtt caagaactcc cgcgtgaagg  4860
tggaaaaaca ggtgtatcag aaattcgaga aaatgctgat cgacaaactc aattatatgg  4920
tggataagaa gtccaacccg tgtgccacag gggcgcgct gaagggctat cagatcacca  4980
acaagttcga gagcttcaag agcatgagca cccagaacgg gtttattttc tacatcccgg  5040
cgtggctcac ctccaagatt gacccgagca ccggcttcgt gaacctcctg aagacaaagt  5100
atacctccat tgccgacagc aagaagttta tctcctcctt cgaccgcatt atgtatgtgc  5160
cggaggagga cctcttcgag ttcgccctcg actacaaaaa cttcagccgc acagatgcgg  5220
attacatcaa gaagtggaag ctgtactcct acgggaacag gatccgcatc ttcaggaatc  5280
caaaaaaaaa taacgtcttt gactgggagg aagtgtgcct gacatccgcc tacaaggaac  5340
tgttcaataa atacggcatc aattaccagc agggcgacat tcgcgccctc ctctgtgagc  5400
agtccgacaa agcgttttac tccagcttca tggccctcat gtccctgatg ctccaaatga  5460
ggaatagcat cacagggcgc accgacgtcg acttcctcat cagcccggtg aagaactccg  5520
acgggatctt ttacgactcc cgcaactatg aggcgcaaga gaatgcgatc ctcccgaaga  5580
acgccgatgc gaacggggcc tataatatcg ccaggaaagt gctctgggcc atcgggcagt  5640
tcaaaaaggc ggaggatgag aagctcgaca aggtgaaaat tgccatttcc aacaaggagt  5700
ggctggagta cgcgcagacc tccgtgaagc acggatctaa gaagagaaga attaaacaag  5760
attgattaat taatcgatcc tccgatccct taattaccat gccattacac catgcatcaa  5820
tatccatata tatataaacc ctttcgcacg tacttatact atgttttgtc atacatatat  5880
atgtgtcgaa cgatcgatct atcactgata tgatatgatt gatccatcag cctgatctct  5940
gtatcttgtt atttgtatac cgtcaaataa aagtttcttc cacttgtgtt aataattagc  6000
tactctcatc tcatgaaccc tatatataac tagtttaatt tgctgtcaat tgaacatgat  6060
gatcgatgcc tg                                                     6072

SEQ ID NO: 20          moltype = DNA  length = 5091
FEATURE                Location/Qualifiers
misc_feature           1..5091
                       note = Synthetic polynucleotide.Expression Cassette
                        comprising the DaMVpromoter cassette, NLS-LbCpf1-CO2-NLS
                        cassette and a Medicagotruncatula termination sequence
source                 1..5091
                       mol_type = other DNA
                       organism = synthetic construct
SEQUENCE: 20
agacatcctg gaccaatatg ctgaagatta tgctacctac accaggatag gacttgaagc  60
acttaacctt gaagattggt tcgaagaacc agaacccgat ccacctaacc ctgtggaccg  120
ccagaggata gaggacatcc tggacctact gaacgtcagc aatgacgact gaaagattcc  180
caggacaccg gcggaagtgg tggacccagt ctaggtgcga tgcttagtcg cgcacgatga  240
ctatgtcgga aggcatcttt gctttcggca aactttagta atactttaag gaaagtattg  300
tacaagttag gtgcagagac aataatgcac ccagctttag ctttgtttat ggaattattg  360
tgtcggttgc attattggat gcctgcgtgc accctaagca atcaacggag aaacaaagat  420
aaaaatcaat tactcacatg aaagagtatt gatcacgagt cactatggag cgacaatctc  480
cagacaggat gtcagcatct tatcttcctt tgaagaaagc atcatcaata acgatgtaat  540
ggtggggaca tccactaagt tattgctctg caaacagctc aaaaagctac tggccgacaa  600
tcataattgc tcggcatgtg caggtggggc ctccactagc aataatacaa gctttacagc  660
ttgcagtgac tcatcctcca ataatggaga aaaagacgtc agcagtgacg aacaagggtc  720
gaaagacttg cctatataag ggcattctcc cctcagttga agatcatcga aagttggagc  780
aataaactct ctcttcaaca aatctatctt ttatctttta tcggtaccaa aaaatggcgg  840
gatctaagaa gagaagaatt aaacaagatt cgaagctcga gaagttcacc aactgctact  900
cgctgagcaa gacgctgcgg ttcaaggcga tccccgtcgg gaagacccag gagaacatcg  960
acaacaagcg gctcctggtc gaggacgaga agcgcgccga ggactacaag ggcgtcaaga  1020
agctgctgga ccggtactac ctctccttca tcaacgacgt cctgcactcg atcaagctca  1080
agaacctgaa caactacatc tcgctgttcc gcaagaagac acggaccgag aaggagaaca  1140
aggagctcga gaacctcgag atcaacctgc gcaaggagat cgcgaaggcg ttcaagggca  1200
acgaggggta caagagcctg ttcaagaaag acatcatcga gaccatcctg ccggagttcc  1260
tggacgacaa ggacgagatc gcgctggtga actcgttcaa cgggttcacc acggccttca  1320
ccgggttttt cgacaaccgg gagaacatgt tcagcgagga ggccaagtcg accagcatcg  1380
ccttccggtg catcaacgag aacctcaccc gctacatcag caacatggac atcttcgaga  1440
aggtggacgc catcttcgac aagcacgagg tccaggagat caaggaaaag atcctgaact  1500
cggactacga cgtggaagac ttctttgagg gcgagttctt caacttcgtc ctcacccagg  1560
agggcatcga cgtctacaac gccatcatcg gcggcttcgt gacggagagc ggcgagaaga  1620
tcaagggcct caacgagtac atcaacctct acaaccagaa gactaagcag aagctcccga  1680
agttcaagcc gctgtacaag caagtcctga gcgaccggga gtccctctcg ttctacggcg  1740
agggctacac gagcgacgag gaggtgctgg aggtgttccg caacacgctg aacaagaaca  1800
gcgagatctt cagctcgatc aagaaactcg agaagctgtt caagaacttc gacgagtaca  1860
gcagcgccgg catcttcgtc aagaacgggc ccgcgatcag caccatcagc aaggacatct  1920
tcggggagtg gaacgtgatc cgcgacaagt ggaacgccga gtacgacgac atccacctca  1980
agaaaaaggc ggtggtcacg gagaagtacg aggacgaccg ccggaagtcc ttcaagaaaa  2040
tcgggagctt cagcctcgag cagctccagg agtacgcgga cgccgacctg agcgtggtgg  2100
agaagctcaa ggagatcatc atccagaagg tcgacgagat ctacaaggtc tacggctcga  2160
```

-continued

```
gcgagaagct gttcgacgcg gacttcgtgc tggagaagtc cctcaagaag aacgacgccg  2220
tggtggccat catgaaggat ctgctcgaca gcgtgaagtc gttcgagaac tacatcaagg  2280
cattctttgg ggagggcaag gagacgaacc gggacgagtc cttctacggg gacttcgtgc  2340
tcgcgtacga catcctcctg aaggtcgacc acatctacga cgcgatccgg aactacgtca  2400
cgcagaagcc ctacagcaag gacaagttca agctctactt ccagaacccg cagttcatgg  2460
gcgggtggga caaggacaag gagaccgact accgggccac gatcctgcgg tacgggtcca  2520
agtactacct cgccatcatg gacaagaagt acgccaagtg cctccagaag attgacaagg  2580
acgacgtgaa cgggaactac gagaagatca actacaagct cctcccgggg cccaacaaga  2640
tgctgccgaa ggtgttcttc agcaagaagt ggatggccta ctacaacccc tcggaggaca  2700
tccagaagat atacaagaac ggcacgttca aaaaggggga catgttcaac ctgaacgact  2760
gccacaagct gatcgacttt ttcaaggaca gcatcagccg ctacccgaag tggtcgaacg  2820
cctacgactt caacttctcg gagacggaga agtacaagga cattgcgggc ttctaccggg  2880
aggtggagga gcagggctac aaggtctcct tcgagagcgc ctccaagaaa gaggtggaca  2940
agctcgtgga ggagggcaag ctgtacatgt tccagatcta caacaaggac ttctcggaca  3000
agtcgcacgg caccccgaac ctccacacga tgtacttcaa gctgctgttc gacgagaaca  3060
accacgggca gatccgcctc agcggcgggg cggagctgtt catgcgccgc gcgtccctca  3120
agaaggagga gctggtcgtg caccccgcca actccccgat cgcgaacaag aaccccgaca  3180
accccaagaa gacaaccacc ctctcgtacg acgtctacaa ggacaagcgg ttctcggagg  3240
accagtacga gctgcacatc ccgatcgcca tcaacaagtg ccccaagaac atcttcaaga  3300
tcaacaccga ggtgcgggtg ctgctcaagc acgacgacaa cccctacgtc atcgggatcg  3360
accgcggcga gcggaacctg ctctacatcg tggtcgtgga cgggaagggg aacatcgtgg  3420
agcagtacag cctgaacgag atcatcaaca acttcaacgg catccgcatc aagacggact  3480
accacagcct cctggacaag aaggagaagg agcggttcga ggcgcggcag aactggacct  3540
ccatcgagaa catcaaggag ctgaaggccg gctacatcag ccaggtcgtg cacaagatct  3600
gcgagctcgt ggagaagtac gacgcggtga tcgcgctgga ggacttgaac agcgggttca  3660
agaactcccg ggtcaaggtc gagaagcagg tctaccagaa gttcgagaag atgctgatcg  3720
acaagctcaa ctacatggtg gacaagaagt ccaacccctg cgccaccggc ggcgccctca  3780
agggctacca gatcaccaac aagttcgagt ccttcaagtc gatgtctacg cagaacgggt  3840
tcatttttcta catcccggcg tggctcacca gcaagatcga cccgagcacg ggcttcgtca  3900
acctcctgaa gaccaagtac accagcatcg cggacagcaa gaagttcatc tcctcgttcg  3960
accgcatcat gtacgtcccc gaggaagacc tgttcgagtt cgccctcgac tacaagaact  4020
tctcccggac ggacgccgac tacatcaaaa agtggaagct ctacagctac ggcaaccgga  4080
tccgcatctt ccgcaacccc aagaagaaca atgtgttcga ctgggaggag gtgtgcctga  4140
cgagcgccta caaggagctc ttcaacaagt acggcatcaa ctaccagcaa ggggacatcc  4200
gcgcgctgct ctgcgagcag tccgacaagg cgttctactc gtcgttcatg gccctgatga  4260
gcctcatgct ccagatgcgc aacagcatca ccggccggac ggacgtggac ttcctgatca  4320
gcccggtcaa gaacagcgac ggcattttct acgacagccg gaactacgag gcccaggaga  4380
acgccatcct ccccaagaac gccgacgcga acggcgccta caacatcgcg cggaaggtgc  4440
tgtgggccat cggccagttt aaaaaggcgg aggacgagaa gctggacaag gtcaagatcg  4500
ccatcagcaa caaggagtgg ctcgagtacg cgcagacgag cgtgaagcac ggatctaaga  4560
agagaagaat taaacaagat tgacttaatt aaagggctct ctgtcatgat ttcatacttt  4620
cattattgag ctctgtaatt acaattatga ccatgagaac atctcttatt gtgtggcctt  4680
ttaattgctg atgttagtac tgaaccaaag cttatcgtga tgatgtaaaa gcaataagta  4740
cttgtttgta gcttctttgt gtctcccttt gggcttaata catctgttta gtgttgtggc  4800
tttggcatag acttctcttg gtaataatgc cttgcaatgc aaaatttcaa ttatcaaatt  4860
ctattatgtt ctcaccttat ggtaacagct taccctgtgg aagatgagat tcttgagttg  4920
agtcattgcc aatttttggc attagctttt gaattagtga atttgacaa aaattaccgt  4980
gacactgatt ttgttgaagc tcttaagtgt agtttttaca aaatttcagt ggctcgttgt  5040
gattatgtca aactcacggc gaatgtagtt cttacagaat ttcagtggct c           5091
```

```
SEQ ID NO: 21          moltype = DNA  length = 5091
FEATURE                Location/Qualifiers
misc_feature           1..5091
                       note = Synthetic polynucleotide.Expression Cassette
                        comprising the DaMVpromoter cassette, NLS-LbCpf1-Os-NLS
                        cassette and a Medicagotruncatula termination sequence
source                 1..5091
                       mol_type = other DNA
                       organism = synthetic construct
SEQUENCE: 21
agacatcctg gaccaatatg ctgaagatta tgctacctac accaggatag gacttgaagc  60
acttaacctt gaagattggt tcgaagaacc agaacccgat ccacctaacc ctgtggaccg  120
ccagaggata gaggacatcc tggacctact gaacgtcagc aatgacgact gaaagattcc  180
caggacaccg gcggaagtgg tggacccagt ctaggtgcga tgcttagtcg cgcacgatga  240
ctatgtcgga aggcatcttt gctttcggca aactttagta atactttaag gaaagtattg  300
tacaagttag gtgcagagac aataatgcac ccagctttag ctttgtttat ggaattattg  360
tgtcggttgc attattggat gcctgcgtgc accctaagca atcaacggag aaacaaagat  420
aaaaatcaat tactcacatg aaagagtatt gatcacgagt cactatggag cgacaatctc  480
cagacaggat gtcagcatct tatcttcctt tgaagaaagc atcatcaata acgatgtaat  540
ggtggggaca tccactaagt tattgctctg caaacagctc aaaaagctac tggccgacaa  600
tcataattgc tcggcatgtg caggtggggc ctccactagc aataatacaa gctttacagc  660
ttgcagtgac tcatcctcca ataatggaga aaaagacgtc agcagtgacg aacaagggtc  720
gaaagacttg cctatataag ggcattctcc cctcagttga agatcatcga aagttggagc  780
aataaactct ctcttcaaca aatctatctt ttatctttta tcggtaccaa aaaatggcgg  840
gatctaagaa gagaagaatt aaacaagatt ccaagctgga gaagtttaca aactgttaca  900
gcctctccaa aaccctcagg tttaaagcga tcccggtggg caagacccag gagaacatcg  960
acaacaagag gctcctggtg gaagacgaga agcgcgccga agactacaag ggcgtgaaga  1020
agctgctcga taggtactac ctcagcttta ttaacgacgt gctgcacagc atcaaactca  1080
agaatctcaa caactacatc tccctcttcc gcaaaaagac ccgcaccgag aaggagaaca  1140
```

-continued

```
aggagctgga gaacctggag atcaacctcc gcaaggaaat cgccaaagcg ttcaagggca  1200
atgaagggta caagagcctc ttcaagaaag acatcatcga aactatcctc ccagagtttc  1260
tcgatgacaa ggacgagatc gcgctggtga actcctttaa cgggttcaca accgcgttta  1320
ccggcttctt tgataacagg gaaaatatgt tctccgagga ggccaagtcc accagcatcg  1380
ccttcaggtg tatcaacgag aacctcaccc gctacatttc caatatggac attttcgaga  1440
aggtggatgc gatcttcgat aagcacgagg tgcaggagat caaagagaag attctcaatt  1500
ccgattatga cgtcgaggat ttcttcgaag gggagttctt taattttgtg ctcacacaag  1560
agggcattga cgtgtacaac gcgattatcg ggggcttcgt cacagagtcc ggggagaaga  1620
ttaaggggct gaatgagtac atcaatctgt acaatcagaa gaccaagcag aaactgccga  1680
aattcaagcc gctctacaag caagtcctgt ccgataggga aagcctctcc ttctacggcg  1740
agggctatac cagcgacgag gaggtgctgg aagtcttccg caacacactg aataagaata  1800
gcgagatttt ctcctccatc aagaagctcg agaagctctt taagaacttt gacgagtaca  1860
gctccgccgg gattttcgtg aagaacgggc cggcgatcag caccatctcc aaggacatct  1920
ttggcgagtg gaacgtcatc agggacaagt ggaacgccga gtacgacgac atccacctga  1980
agaagaaggc ggtggtgacc gagaagtatg aggacgatcg caggaagtcc ttcaaaaaaa  2040
tcggctcctt cagcctcgaa cagctccagg agtatgccga tgcggatctg tccgtcgtcg  2100
agaagctgaa ggaaatcatc attcagaagg tcgacgagat ctataaagtg tacgggtcca  2160
gcgagaagct gttcgacgcc gactttgtgc tcgagaagtc cctcaaaaag aatgacgccg  2220
tggtggccat tatgaaagac ctgctcgact ccgtgaagtc cttcgaaaat tacattaaag  2280
cgttctttgg ggaggggaag gaaactaaca gggatgagtc cttctatggc gactttgtcc  2340
tcgcgtacga catcctgctg aaggtcgacc acatttacga cgcgatccgc aactacgtga  2400
cacagaagcc gtactccaaa gacaagttca agctgtactt ccagaacccg caatttatgg  2460
ggggctggga caaggataaa gagacagact accgcgcgac aattctccgc tatggctcca  2520
aatactatct ggccatcatg gacaagaagt acgcgaagtg cctgcagaag atcgacaaag  2580
acgacgtcaa tggcaactat gaaaagatca actacaagct gctgccgggc ccgaacaaga  2640
tgctcccgaa ggtgttcttc agcaagaagt ggatggccta ctacaatcca agcgaggata  2700
ttcagaaaat ctataaaaac gggaccttca agaaggggga catgtttaac ctcaacgact  2760
gccacaagct cattgatttc ttcaaggata gcatttcccg ctacccgaaa tggtccaatg  2820
cgtacgattt taacttctcc gagacagaaa agtacaaaga catcgcgggc ttttacaggg  2880
aggtggagga gcaagggtat aaagtttctt ttgaatccgc gagcaagaag gaagtcgaca  2940
agctcgtcga ggagggcaag ctctacatgt tccaaattta taacaaggac ttttccgaca  3000
agagccatgg gaccccaaac ctccacacca tgtacttcaa actgctcttt gacgagaaca  3060
accacgggca aatcaggctg agcggcggcg ccgaattatt catgcgcagg gcctccctca  3120
agaaggaaga gctggtcgtc catccagcca attccccgat cgcgaacaag aacccggaca  3180
atccgaaaaa gaccaccacc ctgtcctacg acgtctacaa ggacaaacgc ttcagcgaag  3240
accagtacga attacacatc ccaattgcga ttaataagtg cccaaagaat atcttcaaaa  3300
ttaatacaga ggtcagggtg ctgctcaaac acgacgacaa tccgtatgtc atcggcattg  3360
acaggggcga gcgcaatctg ctctatatcg tggtcgtgga tgggaagggc aatattgtgg  3420
agcagtactc cctgaacgag attatcaaca acttcaatgg gattaggatt aagaccgact  3480
atcacagcct gctcgacaag aaagaaaaag agaggtttga ggcccgccaa aactggacct  3540
ccattgagaa tatcaaagaa ttaaaggccg gctatatttc ccaagtcgtc cacaagatct  3600
gcgagctggt ggagaaatat gacgccgtga ttgcgctcga agacttaaat tctgggttca  3660
agaactcccg cgtgaaggtg gaaaaacagg tgtatcagaa attcgagaaa atgctgatcg  3720
acaaactcaa ttatatggtg gataagaagt ccaacccgtg tgccacaggg ggcgcgctga  3780
agggctatca gatcaccaac aagttcgaga gcttcaagag catgagcacc cagaacgggt  3840
ttattttcta catcccggcg tggctcacct ccaagattga cccgagcacc ggcttcgtga  3900
acctcctgaa gacaaagtat acctccattg ccgacagcaa gaagtttatc tcctccttcg  3960
accgcattat gtatgtgccg gaggaggacc tcttcgagtt cgccctcgac tacaaaaact  4020
tcagccgcac agatgcggat tacatcaaga agtggaagct gtactcctac gggaacagga  4080
tccgcatctt caggaatcca aaaaaaaata acgtctttga ctgggaggaa gtgtgcctga  4140
catccgccta caaggaactg ttcaataaat acggcatcaa ttaccagcag ggcgacattc  4200
gcgccctcct ctgtgagcag tccgacaaag cgttttactc cagcttcatg gccctcatgt  4260
ccctgatgct ccaaatgagg aatagcatca cagggcgcac cgacgtcgac ttcctcatca  4320
gcccggtgaa gaactccgac gggatctttt acgactcccg caactatgag gcgcaagaga  4380
atgcgatcct cccgaagaac gccgatgcga acggggccta taatatcgcc aggaaagtgc  4440
tctgggccat cggcagttc aaaaaggcgg aggatgagaa gctcgacaag gtgaaaattg  4500
ccatttccaa caaggagtgg ctggagtacg cgcagacctc cgtgaagcac ggatctaaga  4560
agagaagaat taaacaagat tgacttaatt aaagggctct ctgtcatgat ttcatacttt  4620
cattattgag ctctgtaatt acaattatga ccatgagaac atctcttatt gtgtggcctt  4680
ttaattgctg atgttagtac tgaaccaaag cttatcgtga tgatgtaaaa gcaataagta  4740
cttgtttgta gcttctttgt gtctcccttt gggcttaata catctgttta gtgttgtggc  4800
tttggcatag acttctcttg gtaataatgc cttgcaatgc aaaatttcaa ttatcaaatt  4860
ctattatgtt ctcaccttat ggtaacagct taccctgtgg aagatgagat tcttgagttg  4920
agtcattgcc aatttttggc attagctttt gaattagtga attttgacaa aaattaccgt  4980
gacactgatt ttgttgaagc tcttaagtgt agtttttaca aaatttcagt ggctcgttgt  5040
gattatgtca aactcacggc gaatgtagtt cttacagaat ttcagtggct c            5091
```

```
SEQ ID NO: 22          moltype = DNA  length = 1000
FEATURE                Location/Qualifiers
source                 1..1000
                       mol_type = unassigned DNA
                       organism = Medicago truncatula
SEQUENCE: 22
actgttaata atttttaaac gtcagcgcac taaaaaaacg aaaagacgga cacgtgaaaa  60
taaaaaacac acactagttt atgacgcaat actattttac ttatgatttg ggtacattag  120
acaaaaccgt gaaagagatg tatcagctat gaaacctgta tacttcaata cagagacgta  180
ctcatatcgg atacgtacgc acgaagtatc atattaatta ttttaatttt taataaatat  240
tttatcggat acttatgtga tactctacat atacacaagg atatttctaa gatactttat  300
agatacgtat cctagaaaaa catgaagagt aaaaaagtga gacaatgttg taaaaattca  360
```

-continued

```
ttataaatgt atatgattca attttagata tgcatcagta taattgattc tcgatgaaac  420
acttaaaatt atatttcttg tggaagaacg tagcgagaga ggtgattcag ttagacaaca  480
ttaaataaaa ttaatgttaa gttcttttaa tgatgtttct ctcaatatca catcatatga  540
aaatgtaata tgatttataa gaaaattttt aaaaaattta ttttaataat cacatgtact  600
atttttttaaa aattgtatct tttataataa tacaataata aagagtaatc agtgttaatt  660
tttcttcaaa tataagtttt attataaatc attgttaacg tatcataagt cattaccgta  720
tcgtatctta attttttttt aaaaaccgct aattcacgta cccgtattgt attgtacccg  780
cacctgtatc acaatcgatc ttagttagaa gaattgtctc gaggcggtgc aagacagcat  840
ataatagacg tggactctct tataccaaac gttgtcgtat cacaaagggt taggtaacaa  900
gtcacagttt gtccacgtgt cacgttttaa ttggaagagc tgccgttggc gtaatataac  960
agccaatcga tttttgctat aaaagcaaat caggtaaact                        1000

SEQ ID NO: 23          moltype = DNA  length = 92
FEATURE                Location/Qualifiers
source                 1..92
                       mol_type = unassigned DNA
                       organism = Medicago truncatula
SEQUENCE: 23
aaacttcttc attcttttct tccccatcgc tacaaaaccg gttcctttgg aaaagagatt  60
cattcaaacc tagcacccaa ttccgtttca ag                                92

SEQ ID NO: 24          moltype = DNA  length = 499
FEATURE                Location/Qualifiers
source                 1..499
                       mol_type = unassigned DNA
                       organism = Medicago truncatula
SEQUENCE: 24
gtataatcta ctttctattc ttcgattatt ttattattat tagctactat cgtttaatcg  60
atcttttctt ttgatccgtc aaatttaaat tcaattaggg ttttgttctt ttctttcatc  120
tgattgaaat ccttctgaat tgaaccgttt acttgatttt actgtttatt gtatgattta  180
atcctttgtt tttcaaagac agtctttaga ttgtgattag gggttcatat aaatttttag  240
atttggattt ttgtattgta tgattcaaaa aatacgtcct ttaattagat tagtacatgg  300
atattttttta cccgatttat tgattgtcag ggagaatttg atgagcaagt tttttttgatg  360
tctgttgtaa attgaattga ttataattgc tgatctgctg cttccagttt tcataaccca  420
tattcttttta accttgttgt acacacaatg aaaaattggt gattgattca tttgtttttc  480
tttgttttgg attatacag                                               499

SEQ ID NO: 25          moltype = DNA  length = 500
FEATURE                Location/Qualifiers
source                 1..500
                       mol_type = unassigned DNA
                       organism = Medicago truncatula
SEQUENCE: 25
ttaatcatct gaaactgttc accatgcatg caatcttgtg aaatatatgg ttttaattag  60
acttcaatct tatgttggct attgtactaa taaaagcatg tcatgttatt ttcatttgat  120
tttatctgta ctttggtttg tttgaagaat aaagatgagc ttgctatgca tgcatgcatg  180
ccatcgatta tcagggtttc ctttttttctt ttctggcttc ccatcaattt ggtgtgaatt  240
agtgtgtgtg atatattata ttatgctatt tatgaaataa attgttggtt atatttgatc  300
tacaatctac atacatgtga tttttatcaa caaaatatct cgggaaacaa taccttttttg  360
gtagcaaaat tcaaataata ctattttaaa taaatcaaag ttaaccaata ccttattcaa  420
gttggagggg tctcaaacaa gcaaaagaat tcaagttgtt aatgaacttc ggttaatgat  480
aaaagaattc gcatttaaaa                                              500

SEQ ID NO: 26          moltype = DNA  length = 5856
FEATURE                Location/Qualifiers
misc_feature           1..5856
                       note = Synthetic polynucleotide.Expression cassette
                        comprising Medicagotruncatula promoter cassette,
                        NLS-LbCpf1-CO2-NLS and Medicagotruncatula termination
                        sequence
source                 1..5856
                       mol_type = other DNA
                       organism = synthetic construct
SEQUENCE: 26
actgttaata atttttaaac gtcagcgcac taaaaaaacg aaaagacgga cacgtgaaaa  60
taaaaaacac acactagttt atgacgcaat actattttac ttatgatttg ggtacattag  120
acaaaaccgt gaaagagatg tatcagctat gaaacctgta tacttcaata cagagacgta  180
ctcatatcgg atacgtacgc acgaagtatc atattaatta ttttaatttt taataaatat  240
tttatcggat acttatgtga tactctacat atacacaagg atatttctaa gatactttat  300
agatacgtat cctagaaaaa catgaagagt aaaaaagtga gacaatgttg taaaaattca  360
ttataaatgt atatgattca attttagata tgcatcagta taattgattc tcgatgaaac  420
acttaaaatt atatttcttg tggaagaacg tagcgagaga ggtgattcag ttagacaaca  480
ttaaataaaa ttaatgttaa gttcttttaa tgatgtttct ctcaatatca catcatatga  540
aaatgtaata tgatttataa gaaaattttt aaaaaattta ttttaataat cacatgtact  600
atttttttaaa aattgtatct tttataataa tacaataata aagagtaatc agtgttaatt  660
tttcttcaaa tataagtttt attataaatc attgttaacg tatcataagt cattaccgta  720
tcgtatctta attttttttt aaaaaccgct aattcacgta cccgtattgt attgtacccg  780
cacctgtatc acaatcgatc ttagttagaa gaattgtctc gaggcggtgc aagacagcat  840
ataatagacg tggactctct tataccaaac gttgtcgtat cacaaagggt taggtaacaa  900
```

-continued gtcacagttt gtccacgtgt cacgttttaa ttggaagagc tgccgttggc gtaatataac 960
agccaatcga tttttgctat aaaagcaaat caggtaaact aaacttcttc attcttttct 1020
tccccatcgc tacaaaaccg gttcctttgg aaaagagatt cattcaaacc tagcacccaa 1080
ttccgtttca aggtataatc tactttctat tcttcgatta ttttattatt attagctact 1140
atcgtttaat cgatcttttc ttttgatccg tcaaatttaa attcaattag ggttttgttc 1200
ttttctttca tctgattgaa atccttctga attgaaccgt ttacttgatt ttactgttta 1260
ttgtatgatt taatcctttg tttttcaaag acagtcttta gattgtgatt aggggttcat 1320
ataaattttt agatttggat ttttgtattg tatgattcaa aaaatacgtc ctttaattag 1380
attagtacat ggatattttt tacccgattt attgattgtc agggagaatt tgatgagcaa 1440
gtttttttga tgtctgttgt aaattgaatt gattataatt gctgatctgc tgcttccagt 1500
tttcataacc catattcttt taaccttgtt gtacacacaa tgaaaaattg gtgattgatt 1560
catttgtttt tctttgtttt ggattataca gggtaccaaa aaatggcggg atctaagaag 1620
agaagaatta aacaagattc gaagctcgag aagttcacca actgctactc gctgagcaag 1680
acgctgcggt tcaaggcgat ccccgtcggg aagacccagg agaacatcga caacaagcgg 1740
ctcctggtcg aggacgagaa gcgcgccgag gactacaagg gcgtcaagaa gctgctggac 1800
cggtactacc tctccttcat caacgacgtc ctgcactcga tcaagctcaa gaacctgaac 1860
aactacatct cgctgttccg caagaagaca cggaccgaga aggagaacaa ggagctcgag 1920
aacctcgaga tcaacctgcg caaggagatc gcgaaggcgt tcaagggcaa cgaggggtac 1980
aagagcctgt tcaagaaaga catcatcgag accatcctgc cggagttcct ggacgacaag 2040
gacgagatcg cgctggtgaa ctcgttcaac gggttcacca cggccttcac cgggtttttc 2100
gacaaccggg agaacatgtt cagcgaggag gccaagtcga ccagcatcgc cttccggtgc 2160
atcaacgaga acctcacccg ctacatcagc aacatggaca tcttcgagaa ggtggacgcc 2220
atcttcgaca agcacgaggt ccaggagatc aaggaaaaga tcctgaactc ggactacgac 2280
gtggaagact tctttgaggg cgagttcttc aacttcgtcc tcacccagga gggcatcgac 2340
gtctacaacg ccatcatcgg cggcttcgtg acggagagcg gcgagaagat caagggcctc 2400
aacgagtaca tcaacctcta caaccagaag actaagcaga agctcccgaa gttcaagccg 2460
ctgtacaagc aagtcctgag cgaccgggag tccctctcgt tctacggcga gggctacacg 2520
agcgacgagg aggtgctgga ggtgttccgc aacacgctga acaagaacag cgagatcttc 2580
agctcgatca agaaactcga gaagctgttc aagaacttcg acgagtacag cagcgccggc 2640
atcttcgtca agaacgggcc cgcgatcagc accatcagca aggacatctt cggggagtgg 2700
aacgtgatcc gcgacaagtg gaacgccgag tacgacgaca tccacctcaa gaaaaaggcg 2760
gtggtcacgg agaagtacga ggacgaccgc cggaagtcct tcaagaaaat cgggagcttc 2820
agcctcgagc agctccagga gtacgcggac gccgacctga gcgtggtgga gaagctcaag 2880
gagatcatca tccagaaggt cgacgagatc tacaaggtct acggctcgag cgagaagctg 2940
ttcgacgcgg acttcgtgct ggagaagtcc ctcaagaaga acgacgccgt ggtggccatc 3000
atgaaggatc tgctcgacag cgtgaagtcg ttcgagaact acatcaaggc attctttggg 3060
gagggcaagg agacgaaccg ggacgagtcc ttctacgggg acttcgtgct cgcgtacgac 3120
atcctcctga aggtcgacca catctacgac gcgatccgga actacgtcac gcagaagccc 3180
tacagcaagg acaagttcaa gctctacttc cagaacccgc agttcatggg cgggtgggac 3240
aaggacaagg agaccgacta ccgggccacg atcctgcggt acgggtccaa gtactacctc 3300
gccatcatgg acaagaagta cgccaagtgc ctccagaaga ttgacaagga cgacgtgaac 3360
gggaactacg agaagatcaa ctacaagctc ctcccggggc ccaacaagat gctgccgaag 3420
gtgttcttca gcaagaagtg gatggcctac tacaacccct cggaggacat ccagaagata 3480
tacaagaacg gcacgttcaa aaagggggac atgttcaacc tgaacgactg ccacaagctg 3540
atcgactttt tcaaggacag catcagccgc tacccgaagt ggtcgaacgc ctacgacttc 3600
aacttctcgg agacggagaa gtacaaggac attgcgggct tctaccggga ggtggaggag 3660
cagggctaca aggtctcctt cgagagcgcc tccaagaaag aggtggacaa gctcgtggag 3720
gagggcaagc tgtacatgtt ccagatctac aacaaggact tctcggacaa gtcgcacggc 3780
accccgaacc tccacacgat gtacttcaag ctgctgttcg acgagaacaa ccacgggcag 3840
atccgcctca gcggcggggc ggagctgttc atgcgccgcg cgtccctcaa gaaggaggag 3900
ctggtcgtgc accccgccaa ctccccgatc gcgaacaaga accccgacaa ccccaagaag 3960
acaaccaccc tctcgtacga cgtctacaag gacaagcggt tctcggagga ccagtacgag 4020
ctgcacatcc cgatcgccat caacaagtgc cccaagaaca tcttcaagat caacaccgag 4080
gtgcgggtgc tgctcaagca cgacgacaac ccctacgtca tcgggatcga ccgcggcgag 4140
cggaacctgc tctacatcgt ggtcgtggac gggaagggga acatcgtgga gcagtacagc 4200
ctgaacgaga tcatcaacaa cttcaacggc atccgcatca agacggacta ccacagcctc 4260
ctggacaaga aggagaagga gcggttcgag gcgcggcaga actggacctc catcgagaac 4320
atcaaggagc tgaaggccgg ctacatcagc caggtcgtgc acaagatctg cgagctcgtg 4380
gagaagtacg acgcggtgat cgcgctggag gacttgaaca gcgggttcaa gaactcccgg 4440
gtcaaggtcg agaagcaggt ctaccagaag ttcgagaaga tgctgatcga caagctcaac 4500
tacatggtgg acaagaagtc caacccctgc gccaccggcg gcgccctcaa gggctaccag 4560
atcaccaaca agttcgagtc cttcaagtcg atgtctacgc agaacgggtt cattttctac 4620
atcccggcgt ggctcaccag caagatcgac ccgagcacgg gcttcgtcaa cctcctgaag 4680
accaagtaca ccagcatcgc ggacagcaag aagttcatct cctcgttcga ccgcatcatg 4740
tacgtccccg aggaagacct gttcgagttc gccctcgact acaagaactt ctcccggacg 4800
gacgccgact acatcaaaaa gtggaagctc tacagctacg gcaaccggat ccgcatcttc 4860
cgcaacccca agaagaacaa tgtgttcgac tgggaggagg tgtgcctgac gagcgcctac 4920
aaggagctct tcaacaagta cggcatcaac taccagcaag ggacatccg cgcgctgctc 4980
tgcgagcagt ccgacaaggc gttctactcg tcgttcatgg ccctgatgag cctcatgctc 5040
cagatgcgca acagcatcac cggccggacg gacgtggact tcctgatcag cccggtcaag 5100
aacagcgacg gcattttcta cgacagccgg aactacgagg cccaggagaa cgccatcctc 5160
cccaagaacg ccgacgcgaa cggcgcctac aacatcgcgc ggaaggtgct gtgggccatc 5220
ggccagttta aaaaggcgga ggacgagaag ctggacaagg tcaagatcgc catcagcaac 5280
aaggagtggc tcgagtacgc gcagacgagc gtgaagcacg gatctaagaa gagaagaatt 5340
aaacaagatt gattaattaa tcatctgaaa ctgttcacca tgcatgcaat cttgtgaaat 5400
atatggtttt aattagactt caatcttatg ttggctattg tactaataaa agcatgtcat 5460
gttattttca tttgatttta tctgtacttt ggtttgtttg aagaataaag atgagcttgc 5520
tatgcatgca tgcatgccat cgattatcag ggtttccttt tttcttttct ggcttcccat 5580
caatttggtg tgaattagtg tgtgtgatat attatattat gctatttatg aaataaattg 5640

```
ttggttatat ttgatctaca atctacatac atgtgatttt tatcaacaaa atatctcggg  5700
aaacaatacc tttttggtag caaaattcaa ataatactat tttaaataaa tcaaagttaa  5760
ccaatacctt attcaagttg gaggggtctc aaacaagcaa aagaattcaa gttgttaatg  5820
aacttcggtt aatgataaaa gaattcgcat ttaaaa                            5856

SEQ ID NO: 27          moltype = DNA  length = 617
FEATURE                Location/Qualifiers
source                 1..617
                       mol_type = unassigned DNA
                       organism = Cucumis melo
SEQUENCE: 27
aaattttaat aattaaaatg aacaattttt caagagtaat agagtttgag agatgtcaga  60
gaagtttgag gaagaagata acaagtggga gaagagaata agtttgttgt gtgaaagaga  120
aggggaaatt tcattcaagg gtatattgaa ctttttactc aaattttgta agtctatttt  180
ttccgatcaa tcctaaaatc acacacaccc ttaaaaaatg gattatattt ggcaattttc  240
catgataaac tcatttttaa tttagagtta ttttttcaac gagatattaa cagttttagt  300
tcatatacta attgtaagaa tagtttcttt taagttgaat agaatttttg aaacttttaa  360
tagttcaaaa ggtatttttg aaacaaaata agaatgtttt tgaacttttt ataaaaagaa  420
ttgagatttt tttgaaattt ttgataaaga gaaaagaaaa gaagaaagaa aaaagaaaaa  480
caagtttgta gaactccgtg ggaaaatcgt cgagggccct gtgaaggaat tttgaaatta  540
taatgagggt attttcgtca acaagggaat ttagacatcg tatataagca tcctcaaacc  600
ctataattaa gcccttc                                                 617

SEQ ID NO: 28          moltype = DNA  length = 54
FEATURE                Location/Qualifiers
source                 1..54
                       mol_type = unassigned DNA
                       organism = Cucumis melo
SEQUENCE: 28
aatccaattg ccattctcca tctctcgccg caagggttta agagcagctt ctct       54

SEQ ID NO: 29          moltype = DNA  length = 545
FEATURE                Location/Qualifiers
source                 1..545
                       mol_type = unassigned DNA
                       organism = Cucumis melo
SEQUENCE: 29
cctcaggttg gggtttcccc ctatcttctt cattcttcct cttctcgatt tctttcttct  60
atttgctcga tagtctctta tttcttgagc ttttgctgtt tttctcctgt acatcctaac  120
atgaattata acttggtttt gattttgtct tttacttctg tattaaacaa cttttcttac  180
ccttttattc ttctcttctt cttcgtgtcc ctgccctttt gtttttatgc taattttatg  240
tttctgttta tcaatctatc gaggcgtgac ctgtcgttct tccaatagcg tagatctgca  300
cttaatctat tctagctgat tggattggtc gtttttcgtt tttttaattt attttctctg  360
ttctagttcc gataaatttt tttatatata attaacaagt tctccagcca aaagggttaa  420
tattgcgttg gatattttaa tttttacgtt atttagatgt gtgaatctaa taaaattagg  480
gttattcata aatttcagta atgatatttt ggttatctgt tcttgctgtt cctgtttcgc  540
agttc                                                              545

SEQ ID NO: 30          moltype = DNA  length = 19
FEATURE                Location/Qualifiers
source                 1..19
                       mol_type = unassigned DNA
                       organism = Cucumis melo
SEQUENCE: 30
ttttacctaa tattcaagc                                               19

SEQ ID NO: 31          moltype = DNA  length = 5500
FEATURE                Location/Qualifiers
misc_feature           1..5500
                       note = Synthetic polynucleotide.Expression cassette
                        comprising Cucumismelo EF1a promoter cassette,
                        NLS-LbCpf1-CO2-NLS and Medicagotruncatula termination
                        sequence
source                 1..5500
                       mol_type = other DNA
                       organism = synthetic construct
SEQUENCE: 31
aaattttaat aattaaaatg aacaattttt caagagtaat agagtttgag agatgtcaga  60
gaagtttgag gaagaagata acaagtggga gaagagaata agtttgttgt gtgaaagaga  120
aggggaaatt tcattcaagg gtatattgaa ctttttactc aaattttgta agtctatttt  180
ttccgatcaa tcctaaaatc acacacaccc ttaaaaaatg gattatattt ggcaattttc  240
catgataaac tcatttttaa tttagagtta ttttttcaac gagatattaa cagttttagt  300
tcatatacta attgtaagaa tagtttcttt taagttgaat agaatttttg aaacttttaa  360
tagttcaaaa ggtatttttg aaacaaaata agaatgtttt tgaacttttt ataaaaagaa  420
ttgagatttt tttgaaattt ttgataaaga gaaaagaaaa gaagaaagaa aaaagaaaaa  480
caagtttgta gaactccgtg ggaaaatcgt cgagggccct gtgaaggaat tttgaaatta  540
taatgagggt attttcgtca acaagggaat ttagacatcg tatataagca tcctcaaacc  600
ctataattaa gcccttcaat ccaattgcca ttctccatct ctcgccgcaa gggtttaaga  660
gcagcttctc tcctcaggtt ggggtttccc cctatcttct tcattcttcc tcttctcgat  720
```

-continued ttctttcttc tatttgctcg atagtctctt atttcttgag cttttgctgt ttttctcctg 780
tacatcctaa catgaattat aacttggttt tgattttgtc ttttacttct gtattaaaca 840
acttttctta cccttttatt cttctcttct tcttcgtgtc cctgcccttt tgtttttatg 900
ctaattttat gtttctgttt atcaatctat cgaggcgtga cctgtcgttc ttccaatagc 960
gtagatctgc acttaatcta ttctagctga ttggattggt cgtttttcgt ttttttaatt 1020
tattttctct gttctagttc cgataaattt ttttatatat aattaacaag ttctccagcc 1080
aaaagggtta atattgcgtt ggatatttta atttttacgt tatttagatg tgtgaatcta 1140
ataaaattag ggttattcat aaatttcagt aatgatattt tggttatctg ttcttgctgt 1200
tcctgtttcg cagttctttt acctaatatt caagcggtac caaaaaatgg cgggatctaa 1260
gaagagaaga attaaacaag attcgaagct cgagaagttc accaactgct actcgctgag 1320
caagacgctg cggttcaagg cgatccccgt cgggaagacc caggagaaca tcgacaacaa 1380
gcggctcctg gtcgaggacg agaagcgcgc cgaggactac aagggcgtca agaagctgct 1440
ggaccggtac tacctctcct tcatcaacga cgtcctgcac tcgatcaagc tcaagaacct 1500
gaacaactac atctcgctgt tccgcaagaa gacacggacc gagaaggaga acaaggagct 1560
cgagaacctc gagatcaacc tgcgcaagga gatcgcgaag gcgttcaagg gcaacgaggg 1620
gtacaagagc ctgttcaaga aagacatcat cgagaccatc ctgccggagt tcctggacga 1680
caaggacgag atcgcgctgg tgaactcgtt caacgggttc accacggcct tcaccgggtt 1740
tttcgacaac cgggagaaca tgttcagcga ggaggccaag tcgaccagca tcgccttccg 1800
gtgcatcaac gagaacctca cccgctacat cagcaacatg gacatcttcg agaaggtgga 1860
cgccatcttc gacaagcacg aggtccagga gatcaaggaa aagatcctga actcggacta 1920
cgacgtggaa gacttctttg agggcgagtt cttcaacttc gtcctcaccc aggagggcat 1980
cgacgtctac aacgccatca tcggcggctt cgtgacggag agcggcgaga agatcaaggg 2040
cctcaacgag tacatcaacc tctacaacca gaagactaag cagaagctcc cgaagttcaa 2100
gccgctgtac aagcaagtcc tgagcgaccg ggagtccctc tcgttctacg gcgagggcta 2160
cacgagcgac gaggaggtgc tggaggtgtt ccgcaacacg ctgaacaaga acagcgagat 2220
cttcagctcg atcaagaaac tcgagaagct gttcaagaac ttcgacgagt acagcagcgc 2280
cggcatcttc gtcaagaacg ggcccgcgat cagcaccatc agcaaggaca tcttcgggga 2340
gtggaacgtg atccgcgaca agtggaacgc cgagtacgac gacatccacc tcaagaaaaa 2400
ggcggtggtc acggagaagt acgaggacga ccgccggaag tccttcaaga aaatcgggag 2460
cttcagcctc gagcagctcc aggagtacgc ggacgccgac ctgagcgtgg tggagaagct 2520
caaggagatc atcatccaga aggtcgacga gatctacaag gtctacggct cgagcgagaa 2580
gctgttcgac gcggacttcg tgctggagaa gtccctcaag aagaacgacg ccgtggtggc 2640
catcatgaag gatctgctcg acagcgtgaa gtcgttcgag aactacatca aggcattctt 2700
tggggagggc aaggagacga accgggacga gtccttctac ggggacttcg tgctcgcgta 2760
cgacatcctc ctgaaggtcg accacatcta cgacgcgatc cggaactacg tcacgcagaa 2820
gccctacagc aaggacaagt tcaagctcta cttccagaac ccgcagttca tgggcgggtg 2880
ggacaaggac aaggagaccg actaccgggc cacgatcctg cggtacgggt ccaagtacta 2940
cctcgccatc atggacaaga agtacgccaa gtgcctccag aagattgaca aggacgacgt 3000
gaacgggaac tacgagaaga tcaactacaa gctcctcccg gggcccaaca agatgctgcc 3060
gaaggtgttc ttcagcaaga agtggatggc ctactacaac cccctcggagg acatccagaa 3120
gatatacaag aacggcacgt tcaaaaaggg ggacatgttc aacctgaacg actgccacaa 3180
gctgatcgac tttttcaagg acagcatcag ccgctacccg aagtggtcga acgcctacga 3240
cttcaacttc tcggagacgg agaagtacaa ggacattgcg ggcttctacc gggaggtgga 3300
ggagcagggc tacaaggtct ccttcgagag cgcctccaag aaagaggtgg acaagctcgt 3360
ggaggagggc aagctgtaca tgttccagat ctacaacaag gacttctcgg acaagtcgca 3420
cggcaccccg aacctccaca cgatgtactt caagctgctg ttcgacgaga acaaccacgg 3480
gcagatccgc ctcagcggcg gggcggagct gttcatgcgc cgcgcgtccc tcaagaagga 3540
ggagctggtc gtgcaccccg ccaactcccc gatcgcgaac aagaaccccg acaaccccaa 3600
gaagacaacc accctctcgt acgacgtcta caaggacaag cggttctcgg aggaccagta 3660
cgagctgcac atcccgatcg ccatcaacaa gtgccccaag aacatcttca agatcaacac 3720
cgaggtgcgg gtgctgctca agcacgacga caacccctac gtcatcggga tcgaccgcgg 3780
cgagcggaac ctgctctaca tcgtggtcgt ggacgggaag gggaacatcg tggagcagta 3840
cagcctgaac gagatcatca acaacttcaa cggcatccgc atcaagacgg actaccacag 3900
cctcctggac aagaaggaga aggagcggtt cgaggcgcgg cagaactgga cctccatcga 3960
gaacatcaag gagctgaagg ccggctacat cagccaggtc gtgcacaaga tctgcgagct 4020
cgtggagaag tacgacgcgg tgatcgcgct ggaggacttg aacagcgggt tcaagaactc 4080
ccgggtcaag gtcgagaagc aggtctacca gaagttcgag aagatgctga tcgacaagct 4140
caactacatg gtggacaaga agtccaaccc ctgcgccacc ggcggcgccc tcaagggcta 4200
ccagatcacc aacaagttcg agtccttcaa gtcgatgtct acgcagaacg ggttcatttt 4260
ctacatcccg gcgtggctca ccagcaagat cgacccgagc acgggcttcg tcaacctcct 4320
gaagaccaag tacaccagca tcgcggacag caagaagttc atctcctcgt tcgaccgcat 4380
catgtacgtc cccgaggaag acctgttcga gttcgccctc gactacaaga acttctcccg 4440
gacggacgcc gactacatca aaaagtggaa gctctacagc tacggcaacc ggatccgcat 4500
cttccgcaac cccaagaaga acaatgtgtt cgactgggag gaggtgtgcc tgacgagcgc 4560
ctacaaggag ctcttcaaca agtacggcat caactaccag caaggggaca tccgcgcgct 4620
gctctgcgag cagtccgaca aggcgttcta ctcgtcgttc atggccctga tgagcctcat 4680
gctccagatg cgcaacagca tcaccggccg gacggacgtg gacttcctga tcagcccggt 4740
caagaacagc gacggcattt tctacgacag ccggaactac gaggcccagg agaacgccat 4800
cctccccaag aacgccgacg cgaacggcgc ctacaacatc gcgcggaagg tgctgtgggc 4860
catcggccag tttaaaaagg cggaggacga gaagctggac aaggtcaaga tcgccatcag 4920
caacaaggag tggctcgagt acgcgcagac gagcgtgaag cacggatcta agaagagaag 4980
aattaaacaa gattgattaa ttaatcatct gaaactgttc accatgcatg caatcttgtg 5040
aaatatatgg ttttaattag acttcaatct tatgttggct attgtactaa taaaagcatg 5100
tcatgttatt ttcatttgat tttatctgta ctttggtttg tttgaagaat aaagatgagc 5160
ttgctatgca tgcatgcatg ccatcgatta tcagggtttc ctttttttctt ttctggcttc 5220
ccatcaattt ggtgtgaatt agtgtgtgtg atatattata ttatgctatt tatgaaataa 5280
attgttggtt atatttgatc tacaatctac atacatgtga tttttatcaa caaaatatct 5340
cgggaaacaa tacctttttg gtagcaaaat tcaaataata ctattttaaa taaatcaaag 5400
ttaaccaata ccttattcaa gttggagggg tctcaaacaa gcaaaagaat tcaagttgtt 5460

```
aatgaacttc ggttaatgat aaaagaattc gcatttaaaa                      5500

SEQ ID NO: 32           moltype = DNA  length = 829
FEATURE                 Location/Qualifiers
source                  1..829
                        mol_type = unassigned DNA
                        organism = Arabidopsis thaliana
SEQUENCE: 32
gttttgtgta tcattcttgt tacattgtta ttaatgaaaa aatattattg gtcattggac  60
tgaacacgag tgttaaatat ggaccaggcc ccaaataaga tccattgata tatgaattaa  120
ataacaagaa taaatcgagt caccaaacca cttgcctttt ttaacgagac ttgttcacca  180
acttgataca aaagtcatta tcctatgcaa atcaataatc atacaaaaat atccaataac  240
actaaaaaat taaaagaaat ggataatttc acaatatgtt atacgataaa gaagttactt  300
ttccaagaaa ttcactgatt ttataagccc acttgcatta gataaatggc aaaaaaaaac  360
aaaaaggaaa agaaataaag cacgaagaat tctagaaaat acgaaatacg cttcaatgca  420
gtgggaccca cggttcaatt attgccaatt ttcagctcca ccgtatattt aaaaaataaa  480
acgataatgc taaaaaaata taaatcgtaa cgatcgttaa atctcaacgg ctggatctta  540
tgacgaccgt tagaaattgt ggttgtcgac gagtcagtaa taaacggcgt caaagtggtt  600
gcagccggca cacacgagtc gtgtttatca actcaaagca caaatacttt tcctcaacct  660
aaaaataagg caattagcca aaaacaactt tgcgtgtaaa caacgctcaa tacacgtgtc  720
attttattat tagctattgc ttcaccgcct tagctttctc gtgacctagt cgtcctcgtc  780
ttttcttctt cttcttctat aaaacaatac ccaaagagct cttcttctt             829

SEQ ID NO: 33           moltype = DNA  length = 67
FEATURE                 Location/Qualifiers
source                  1..67
                        mol_type = unassigned DNA
                        organism = Arabidopsis thaliana
SEQUENCE: 33
cacaattcag atttcaattt ctcaaaatct taaaaacttt ctctcaattc tctctaccgt  60
gatcaag                                                           67

SEQ ID NO: 34           moltype = DNA  length = 306
FEATURE                 Location/Qualifiers
source                  1..306
                        mol_type = unassigned DNA
                        organism = Arabidopsis thaliana
SEQUENCE: 34
gtaaatttct gtgttcctta ttctctcaaa atcttcgatt ttgttttcgt tcgatcccaa  60
tttcgtatat gttctttggt ttagattctg ttaatcttag atcgaagacg attttctggg  120
tttgatcgtt agatatcatc ttaattctcg attagggttt catagatatc atccgatttg  180
ttcaaataat ttgagttttg tcgaataatt actcttcgat ttgtgatttc tatctagatc  240
tggtgttagt ttctagtttg tgcgatcgaa tttgtcgatt aatctgagtt tttctgatta  300
acaggt                                                            306

SEQ ID NO: 35           moltype = DNA  length = 315
FEATURE                 Location/Qualifiers
source                  1..315
                        mol_type = unassigned DNA
                        organism = Gossypium barbadense
SEQUENCE: 35
accatatgac actggtgcat gtgccatcat catgcagtaa tttcatggta tatcttaatt  60
atatggttaa taaaaaaaag atggtgagtg aataatgtgc gtgcattcct ccatgcacca  120
atggtgaatc tctttgcata catagagatt ctgaatgatt atagtttatg ttgtagtgaa  180
attaattttg aatgttgttt ttaaatttta atgtcacttg gcttgattta tgttttaacg  240
aagcttatgt tatgtatttt actttaatga tattgcatgt attgttaatt taacattgct  300
tgatcagtat actct                                                  315

SEQ ID NO: 36           moltype = DNA  length = 5292
FEATURE                 Location/Qualifiers
misc_feature            1..5292
                        note = Synthetic polynucleotide.Expression cassette
                         comprisingArabidopsis thaliana Ubiquitin promoter
                         cassette,NLS-LbCpf1-CO2-NLS and Gossypium barbadense
                         termination sequence.
source                  1..5292
                        mol_type = other DNA
                        organism = synthetic construct
SEQUENCE: 36
gttttgtgta tcattcttgt tacattgtta ttaatgaaaa aatattattg gtcattggac  60
tgaacacgag tgttaaatat ggaccaggcc ccaaataaga tccattgata tatgaattaa  120
ataacaagaa taaatcgagt caccaaacca cttgcctttt ttaacgagac ttgttcacca  180
acttgataca aaagtcatta tcctatgcaa atcaataatc atacaaaaat atccaataac  240
actaaaaaat taaaagaaat ggataatttc acaatatgtt atacgataaa gaagttactt  300
ttccaagaaa ttcactgatt ttataagccc acttgcatta gataaatggc aaaaaaaaac  360
aaaaaggaaa agaaataaag cacgaagaat tctagaaaat acgaaatacg cttcaatgca  420
gtgggaccca cggttcaatt attgccaatt ttcagctcca ccgtatattt aaaaaataaa  480
acgataatgc taaaaaaata taaatcgtaa cgatcgttaa atctcaacgg ctggatctta  540
tgacgaccgt tagaaattgt ggttgtcgac gagtcagtaa taaacggcgt caaagtggtt  600
```

-continued

```
gcagccggca cacacgagtc gtgtttatca actcaaagca caaatacttt tcctcaacct  660
aaaaataagg caattagcca aaaacaactt tgcgtgtaaa caacgctcaa tacacgtgtc  720
attttattat tagctattgc ttcaccgcct tagctttctc gtgacctagt cgtcctcgtc  780
ttttcttctt cttcttctat aaaacaatac ccaaagagct cttcttcttc acaattcaga  840
tttcaatttc tcaaaatctt aaaaactttc tctcaattct ctctaccgtg atcaaggtaa  900
atttctgtgt tccttattct ctcaaaatct tcgattttgt tttcgttcga tcccaatttc  960
gtatatgttc tttggtttag attctgttaa tcttagatcg aagacgattt tctgggtttg  1020
atcgttagat atcatcttaa ttctcgatta gggtttcata gatatcatcc gatttgttca  1080
aataatttga gttttgtcga ataattactc ttcgatttgt gatttctatc tagatctggt  1140
gttagtttct agtttgtgcg atcgaatttg tcgattaatc tgagtttttc tgattaacag  1200
gtggtaccaa aaaatggcgg gatctaagaa gagaagaatt aaacaagatt cgaagctcga  1260
gaagttcacc aactgctact cgctgagcaa gacgctgcgg ttcaaggcga tccccgtcgg  1320
gaagacccag gagaacatcg acaacaagcg gctcctggtc gaggacgaga agcgcgccga  1380
ggactacaag ggcgtcaaga agctgctgga ccggtactac ctctccttca tcaacgacgt  1440
cctgcactcg atcaagctca agaacctgaa caactacatc tcgctgttcc gcaagaagac  1500
acggaccgag aaggagaaca aggagctcga gaacctcgag atcaacctgc gcaaggagat  1560
cgcgaaggcg ttcaagggca acgaggggta caagagcctg ttcaagaaag acatcatcga  1620
gaccatcctg ccggagttcc tggacgacaa ggacgagatc gcgctggtga actcgttcaa  1680
cgggttcacc acggccttca ccgggttttt cgacaaccgg gagaacatgt tcagcgagga  1740
ggccaagtcg accagcatcg ccttccggtg catcaacgag aacctcaccc gctacatcag  1800
caacatggac atcttcgaga aggtggacgc catcttcgac aagcacgagg tccaggagat  1860
caaggaaaag atcctgaact cggactacga cgtggaagac ttctttgagg gcgagttctt  1920
caacttcgtc ctcacccagg agggcatcga cgtctacaac gccatcatcg gcggcttcgt  1980
gacggagagc ggcgagaaga tcaagggcct caacgagtac atcaacctct acaaccagaa  2040
gactaagcag aagctcccga agttcaagcc gctgtacaag caagtcctga gcgaccggga  2100
gtccctctcg ttctacggcg agggctacac gagcgacgag gaggtgctgg aggtgttccg  2160
caacacgctg aacaagaaca gcgagatctt cagctcgatc aagaaactcg agaagctgtt  2220
caagaacttc gacgagtaca gcagcgccgg catcttcgtc aagaacgggc ccgcgatcag  2280
caccatcagc aaggacatct tcggggagtg gaacgtgatc cgcgacaagt ggaacgccga  2340
gtacgacgac atccacctca agaaaaaggc ggtggtcacg gagaagtacg aggacgaccg  2400
ccggaagtcc ttcaagaaaa tcgggagctt cagcctcgag cagctccagg agtacgcgga  2460
cgccgacctg agcgtggtgg agaagctcaa ggagatcatc atccagaagg tcgacgagat  2520
ctacaaggtc tacggctcga gcgagaagct gttcgacgcg gacttcgtgc tggagaagtc  2580
cctcaagaag aacgacgccg tggtggccat catgaaggat ctgctcgaca gcgtgaagtc  2640
gttcgagaac tacatcaagg cattctttgg ggagggcaag gagacgaacc gggacgagtc  2700
cttctacggg gacttcgtgc tcgcgtacga catcctcctg aaggtcgacc acatctacga  2760
cgcgatccgg aactacgtca cgcagaagcc ctacagcaag gacaagttca agctctactt  2820
ccagaacccg cagttcatgg gcgggtggga caaggacaag gagaccgact accgggccac  2880
gatcctgcgg tacgggtcca agtactacct cgccatcatg gacaagaagt acgccaagtg  2940
cctccagaag attgacaagg acgacgtgaa cgggaactac gagaagatca actacaagct  3000
cctcccgggg cccaacaaga tgctgccgaa ggtgttcttc agcaagaagt ggatggccta  3060
ctacaacccc tcggaggaca tccagaagat atacaagaac ggcacgttca aaaaggggga  3120
catgttcaac ctgaacgact gccacaagct gatcgacttt ttcaaggaca gcatcagccg  3180
ctacccgaag tggtcgaacg cctacgactt caacttctcg gagacggaga agtacaagga  3240
cattgcgggc ttctaccggg aggtggagga gcagggctac aaggtctcct tcgagagcgc  3300
ctccaagaaa gaggtggaca agctcgtgga ggagggcaag ctgtacatgt tccagatcta  3360
caacaaggac ttctcggaca agtcgcacgg caccccgaac ctccacacga tgtacttcaa  3420
gctgctgttc gacgagaaca accacgggca gatccgcctc agcggcgggg cggagctgtt  3480
catgcgccgc gcgtccctca agaaggagga gctggtcgtg caccccgcca actccccgat  3540
cgcgaacaag aaccccgaca accccaagaa gacaaccacc ctctcgtacg acgtctacaa  3600
ggacaagcgg ttctcggagg accagtacga gctgcacatc ccgatcgcca tcaacaagtg  3660
ccccaagaac atcttcaaga tcaacaccga ggtgcgggtg ctgctcaagc acgacgacaa  3720
cccctacgtc atcgggatcg accgcggcga gcggaacctg ctctacatcg tggtcgtgga  3780
cgggaagggg aacatcgtgg agcagtacag cctgaacgag atcatcaaca acttcaacgg  3840
catccgcatc aagacggact accacagcct cctggacaag aaggagaagg agcggttcga  3900
ggcgcggcag aactggacct ccatcgagaa catcaaggag ctgaaggccg gctacatcag  3960
ccaggtcgtg cacaagatct gcgagctcgt ggagaagtac gacgcggtga tcgcgctgga  4020
ggacttgaac agcgggttca agaactcccg ggtcaaggtc gagaagcagg tctaccagaa  4080
gttcgagaag atgctgatcg acaagctcaa ctacatggtg gacaagaagt ccaacccctg  4140
cgccaccggc ggcgccctca agggctacca gatcaccaac aagttcgagt ccttcaagtc  4200
gatgtctacg cagaacgggt tcattttcta catcccggcg tggctcacca gcaagatcga  4260
cccgagcacg ggcttcgtca acctcctgaa gaccaagtac accagcatcg cggacagcaa  4320
gaagttcatc tcctcgttcg accgcatcat gtacgtcccc gaggaagacc tgttcgagtt  4380
cgccctcgac tacaagaact tctcccggac ggacgccgac tacatcaaaa agtggaagct  4440
ctacagctac ggcaaccgga tccgcatctt ccgcaacccc aagaagaaca atgtgttcga  4500
ctgggaggag gtgtgcctga cgagcgccta caaggagctc ttcaacaagt acggcatcaa  4560
ctaccagcaa ggggacatcc gcgcgctgct ctgcgagcag tccgacaagg cgttctactc  4620
gtcgttcatg gccctgatga gcctcatgct ccagatgcgc aacagcatca ccggccggac  4680
ggacgtggac ttcctgatca gcccggtcaa gaacagcgac ggcattttct acgacagccg  4740
gaactacgag gcccaggaga acgccatcct ccccaagaac gccgacgcga acggcgccta  4800
caacatcgcg cggaaggtgc tgtgggccat cggccagttt aaaaaggcgg aggacgagaa  4860
gctggacaag gtcaagatcg ccatcagcaa caaggagtgg ctcgagtacg cgcagacgag  4920
cgtgaagcac ggatctaaga agagaagaat taaacaagat tgattaatta agggcccacc  4980
atatgacact ggtgcatgtg ccatcatcat gcagtaattt catggtatat cttaattata  5040
tggttaataa aaaaaagatg gtgagtgaat aatgtgcgtg cattcctcca tgcaccaatg  5100
gtgaatctct ttgcatacat agagattctg aatgattata gtttatgttg tagtgaaatt  5160
aattttgaat gttgttttta aattttaatg tcacttggct tgatttatgt tttaacgaag  5220
cttatgttat gtattttact ttaatgatat tgcatgtatt gttaatttaa cattgcttga  5280
tcagtatact ct                                                     5292
```

```
SEQ ID NO: 37           moltype = DNA  length = 822
FEATURE                 Location/Qualifiers
misc_feature            1..822
                        note = Synthetic polynucleotide.Chimeric promoter cassette
                         comprisingthe enhancer sequence from the Banana Streak
                         Virus strainAcuminata Vietnam fused to apromoter sequence
                         fromDahliaMosaic Virus (DaMV).
source                  1..822
                        mol_type = other DNA
                        organism = synthetic construct
SEQUENCE: 37
agacatcctg gaccaatatg ctgaagatta tgctacctac accaggatag gacttgaagc  60
acttaacctt gaagattggt tcgaagaacc agaacccgat ccacctaacc ctgtggaccg  120
ccagaggata gaggacatcc tggacctact gaacgtcagc aatgacgact gaaagattcc  180
caggacaccg gcggaagtgg tggacccagt ctaggtgcga tgcttagtcg cgcacgatga  240
ctatgtcgga aggcatcttt gctttcggca aactttagta atactttaag gaaagtattg  300
tacaagttag gtgcagagac aataatgcac ccagctttag ctttgtttat ggaattattg  360
tgtcggttgc attattggat gcctgcgtgc accctaagca atcaacggag aaacaaagat  420
aaaaatcaat tactcacatg aaagagtatt gatcacgagt cactatggag cgacaatctc  480
cagacaggat gtcagcatct tatcttcctt tgaagaaagc atcatcaata acgatgtaat  540
ggtggggaca tccactaagt tattgctctg caaacagctc aaaaagctac tggccgacaa  600
tcataattgc tcggcatgtg caggtggggc ctccactagc aataatacaa gctttacagc  660
ttgcagtgac tcatcctcca ataatggaga aaaagacgtc agcagtgacg aacaagggtc  720
gaaagacttg cctatataag ggcattctcc cctcagttga agatcatcga aagttggagc  780
aataaactct ctcttcaaca aatctatctt ttatctttta tc                    822

SEQ ID NO: 38           moltype = DNA  length = 3681
FEATURE                 Location/Qualifiers
misc_feature            1..3681
                        note = Synthetic polynucleotide.Codon optimized LbCpf1(TYC)
                        -CO2
source                  1..3681
                        mol_type = other DNA
                        organism = synthetic construct
SEQUENCE: 38
tcgaagctcg agaagttcac caactgctac tcgctgagca agacgctgcg gttcaaggcg  60
atccccgtcg ggaagaccca ggagaacatc gacaacaagc ggctcctggt cgaggacgag  120
aagcgcgccg aggactacaa gggcgtcaag aagctgctgg accggtacta cctctccttc  180
atcaacgacg tcctgcactc gatcaagctc aagaacctga acaactacat ctcgctgttc  240
cgcaagaaga cacggaccga gaaggagaac aaggagctcg agaacctcga gatcaacctg  300
cgcaaggaga tcgcgaaggc gttcaagggc aacgaggggt acaagagcct gttcaagaaa  360
gacatcatcg agaccatcct gccggagttc ctggacgaca aggacgagat cgcgctggtg  420
aactcgttca acgggttcac cacggccttc accgggtttt tcgacaaccg ggagaacatg  480
ttcagcgagg aggccaagtc gaccagcatc gccttccggt gcatcaacga gaacctcacc  540
cgctacatca gcaacatgga catcttcgag aaggtggacg ccatcttcga caagcacgag  600
gtccaggaga tcaaggaaaa gatcctgaac tcggactacg acgtggaaga cttctttgag  660
ggcgagttct tcaacttcgt cctcacccag gagggcatcg acgtctacaa cgccatcatc  720
ggcggcttcg tgacggagag cggcgagaag atcaagggcc tcaacgagta catcaacctc  780
tacaaccaga agactaagca gaagctcccg aagttcaagc cgctgtacaa gcaagtcctg  840
agcgaccggg agtccctctc gttctacggc gagggctaca cgagcgacga ggaggtgctg  900
gaggtgttcc gcaacacgct gaacaagaac agcgagatct tcagctcgat caagaaactc  960
gagaagctgt tcaagaactt cgacgagtac agcagcgccg gcatcttcgt caagaacggg  1020
cccgcgatca gcaccatcag caaggacatc ttcggggagt ggaacgtgat ccgcgacaag  1080
tggaacgccg agtacgacga catccacctc aagaaaaagg cggtggtcac ggagaagtac  1140
gaggacgacc gccggaagtc cttcaagaaa atcgggagct tcagcctcga gcagctccag  1200
gagtacgcgg acgccgacct gagcgtggtg gagaagctca aggagatcat catccagaag  1260
gtcgacgaga tctacaaggt ctacggctcg agcgagaagc tgttcgacgc ggacttcgtg  1320
ctggagaagt ccctcaagaa gaacgacgcc gtggtggcca tcatgaagga tctgctcgac  1380
agcgtgaagt cgttcgagaa ctacatcaag gcattctttg gggagggcaa ggagacgaac  1440
cgggacgagt ccttctacgg ggacttcgtg ctcgcgtacg acatcctcct gaaggtcgac  1500
cacatctacg acgcgatccg gaactacgtc acgcagaagc cctacagcaa ggacaagttc  1560
aagctctact tccagaaccc gcagttcatg cgcgggtggg acaaggacaa ggagaccgac  1620
taccgggcca cgatcctgcg gtacgggtcc aagtactacc tcgccatcat ggacaagaag  1680
tacgccaagt gcctccagaa gattgacaag gacgacgtga acgggaacta cgagaagatc  1740
aactacaagc tcctcccggg gcccaacaag atgctgccga gggtgttctt cagcaagaag  1800
tggatggcct actacaaccc ctcggaggac atccagaaga tatacaagaa cggcacgttc  1860
aaaaaggggg acatgttcaa cctgaacgac tgccacaagc tgatcgactt tttcaaggac  1920
agcatcagcc gctacccgaa gtggtcgaac gcctacgact tcaacttctc ggagacggag  1980
aagtacaagg acattgcggg cttctaccgg gaggtggagg agcagggcta caaggtctcc  2040
ttcgagagcg cctccaagaa agaggtggac aagctcgtgg aggagggcaa gctgtacatg  2100
ttccagatct acaacaagga cttctcggac aagtcgcacg gcaccccgaa cctccacacg  2160
atgtacttca agctgctgtt cgacgagaac aaccacgggc agatccgcct cagcggcggg  2220
gcggagctgt tcatgcgccg cgcgtccctc aagaaggagg agctggtcgt gcaccccgcc  2280
aactccccga tcgcgaacaa gaaccccgac aaccccaaga agacaaccac cctctcgtac  2340
gacgtctaca aggacaagcg gttctcggag gaccagtacg agctgcacat cccgatcgcc  2400
atcaacaagt gccccaagaa catcttcaag atcaacaccg aggtgcgggt gctgctcaag  2460
cacgacgaca accccctacgt catcgggatc gaccgcggcg agcggaacct gctctacatc  2520
gtggtcgtgg acgggaaggg gaacatcgtg gagcagtaca gcctgaacga gatcatcaac  2580
```

-continued

```
aacttcaacg gcatccgcat caagacggac taccacagcc tcctggacaa gaaggagaag  2640
gagcggttcg aggcgcggca gaactggacc tccatcgaga acatcaagga gctgaaggcc  2700
ggctacatca gccaggtcgt gcacaagatc tgcgagctcg tggagaagta cgacgcggtg  2760
atcgcgctgg aggacttgaa cagcgggttc aagaactccc gggtcaaggt cgagaagcag  2820
gtctaccaga agttcgagaa gatgctgatc gacaagctca actacatggt ggacaagaag  2880
tccaacccct gcgccaccgg cggcgccctc aagggctacc agatcaccaa caagttcgag  2940
tccttcaagt cgatgtctac gcagaacggg ttcatttct acatcccggc gtggctcacc  3000
agcaagatcg acccgagcac gggcttcgtc aacctcctga agaccaagta caccagcatc  3060
gcggacagca agaagttcat ctcctcgttc gaccgcatca tgtacgtccc cgaggaagac  3120
ctgttcgagt tcgccctcga ctacaagaac ttctcccgga cggacgccga ctacatcaaa  3180
aagtggaagc tctacagcta cggcaaccgg atccgcatct tccgcaaccc caagaagaac  3240
aatgtgttcg actgggagga ggtgtgcctg acgagcgcct acaaggagct cttcaacaag  3300
tacggcatca actaccagca aggggacatc cgcgcgctgc tctgcgagca gtccgacaag  3360
gcgttctact cgtcgttcat ggccctgatg agcctcatgc tccagatgcg caacagcatc  3420
accggccgga cggacgtgga cttcctgatc agcccggtca agaacagcga cggcattttc  3480
tacgacagcc ggaactacga ggcccaggag aacgccatcc tccccaagaa cgccgacgcg  3540
aacggcgcct acaacatcgc gcggaaggtg ctgtgggcca tcggccagtt taaaaaggcg  3600
gaggacgaga agctggacaa ggtcaagatc gccatcagca acaaggagtg gctcgagtac  3660
gcgcagacga gcgtgaagca t                                           3681

SEQ ID NO: 39          moltype = AA  length = 1227
FEATURE                Location/Qualifiers
REGION                 1..1227
                       note = Synthetic polypeptide.LbCpf1(TYC) variant
                        comprisingG532R andK595R substitutions
source                 1..1227
                       mol_type = protein
                       organism = synthetic construct
SEQUENCE: 39
SKLEKFTNCY SLSKTLRFKA IPVGKTQENI DNKRLLVEDE KRAEDYKGVK KLLDRYYLSF  60
INDVLHSIKL KNLNNYISLF RKKTRTEKEN KELENLEINL RKEIAKAFKG NEGYKSLFKK  120
DIIETILPEF LDDKDEIALV NSFNGFTTAF TGFFDNRENM FSEEAKSTSI AFRCINENLT  180
RYISNMDIFE KVDAIFDKHE VQEIKEKILN SDYDVEDFFE GEFFNFVLTQ EGIDVYNAII  240
GGFVTESGEK IKGLNEYINL YNQKTKQKLP KFKPLYKQVL SDRESLSFYG EGYTSDEEVL  300
EVFRNTLNKN SEIFSSIKKL EKLFKNFDEY SSAGIFVKNG PAISTISKDI FGEWNVIRDK  360
WNAEYDDIHL KKKAVVTEKY EDDRRKSFKK IGSFSLEQLQ EYADADLSVV EKLKEIIIQK  420
VDEIYKVYGS SEKLFDADFV LEKSLKKNDA VVAIMKDLLD SVKSFENYIK AFFGEGKETN  480
RDESFYGDFV LAYDILLKVD HIYDAIRNYV TQKPYSKDKF KLYFQNPQFM RGWDKDKETD  540
YRATILRYGS KYYLAIMDKK YAKCLQKIDK DDVNGNYEKI NYKLLPGPNK MLPRVFFSKK  600
WMAYYNPSED IQKIYKNGTF KKGDMFNLND CHKLIDFFKD SISRYPKWSN AYDFNFSETE  660
KYKDIAGFYR EVEEQGYKVS FESASKKEVD KLVEEGKLYM FQIYNKDFSD KSHGTPNLHT  720
MYFKLLFDEN NHGQIRLSGG AELFMRRASL KKEELVVHPA NSPIANKNPD NPKKTTTLSY  780
DVYKDKRFSE DQYELHIPIA INKCPKNIFK INTEVRVLLK HDDNPYVIGI DRGERNLLYI  840
VVVDGKGNIV EQYSLNEIIN NFNGIRIKTD YHSLLDKKEK ERFEARQNWT SIENIKELKA  900
GYISQVVHKI CELVEKYDAV IALEDLNSGF KNSRVKVEKQ VYQKFEKMLI DKLNYMVDKK  960
SNPCATGGAL KGYQITNKFE SFKSMSTQNG FIFYIPAWLT SKIDPSTGFV NLLKTKYTSI  1020
ADSKKFISSF DRIMYVPEED LFEFALDYKN FSRTDADYIK KWKLYSYGNR IRIFRNPKKN  1080
NVFDWEEVCL TSAYKELFNK YGINYQQGDI RALLCEQSDK AFYSSFMALM SLMLQMRNSI  1140
TGRTDVDFLI SPVKNSDGIF YDSRNYEAQE NAILPKNADA NGAYNIARKV LWAIGQFKKA  1200
EDEKLDKVKI AISNKEWLEY AQTSVKH                                     1227

SEQ ID NO: 40          moltype = DNA  length = 6080
FEATURE                Location/Qualifiers
misc_feature           1..6080
                       note = Synthetic polynucleotide.Expression cassette
                        comprising Zea maysUbiquitin promoter cassette,
                        NLS-LbCpf1(TYC)-CO2-NLS and an Oryzasativa transcription
                        termination sequence
source                 1..6080
                       mol_type = other DNA
                       organism = synthetic construct
SEQUENCE: 40
gtcgtgcccc tctctagaga taaagagcat tgcatgtcta aagtataaaa aattaccaca  60
tattttttg tcacacttat ttgaagtgta gtttatctat ctctatacat atatttaaac  120
ttcactctac aaataatata gtctataata ctaaaataat attagtgttt tagaggatca  180
tataaataaa ctgctagaca tggtctaaag gataattgaa tattttgaca atctacagtt  240
ttatcttttt agtgtgcatg tgatctctct gtttttttg caaatagctt gacctatata  300
atacttcatc cattttatta gtacatccat ttaggattta gggttgatgg tttctataga  360
ctaattttta gtacatccat tttattcttt ttagtctcta atttttttaa aactaaaact  420
ctattttagt tttttattta ataatttaga tataaaatga aataaaataa attgactaca  480
aataaaacaa ataccottta agaaataaaa aaactaagca aacatttttc ttgtttcgag  540
tagataatga caggctgttc aacgccgtcg acgagtctaa cggacaccaa ccagcgaacc  600
agcagcgtcg cgtcgggcca agcgaagcag acggcacggc atctctgtag ctgcctctgg  660
acccctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acgggggatt cctttcccac cgctccttcg ctttcccttc ctcgcccgcc  840
gtaataaata gacacccct ccacaccctc tttccccaac ctcgtgttcg ttcggagcgc  900
acacacacgc aaccagatct cccccaaatc cagccgtcgg cacctccgct tcaaggtacg  960
ccgctcatcc tcccccccc cctctctcta ccttctctag atcggcgatc cggtccatgg  1020
```

-continued

```
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctggtatgt gtgtgccata catcttcata  1200
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc ttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgtttg gtgatacttc tgcaggtccg gtacctcagc atgggtagca aaaagaggcg  2040
tatcaagcag gacgcgtcga agctcgagaa gttcaccaac tgctactcgc tgagcaagac  2100
gctgcggttc aaggcgatcc ccgtcgggaa gacccaggag aacatcgaca acaagcggct  2160
cctggtcgag gacgagaagc gcgccgagga ctacaagggc gtcaagaagc tgctggaccg  2220
gtactacctc tccttcatca acgacgtcct gcactcgatc aagctcaaga acctgaacaa  2280
ctacatctcg ctgttccgca agaagacacg gaccgagaag gagaacaagg agctcgagaa  2340
cctcgagatc aacctgcgca aggagatcgc gaaggcgttc aagggcaacg aggggtacaa  2400
gagcctgttc aagaaagaca tcatcgagac catcctgccg gagttcctgg acgacaagga  2460
cgagatcgcg ctggtgaact cgttcaacgg gttcaccacg gccttcaccg ggtttttcga  2520
caaccgggag aacatgttca gcgaggaggc caagtcgacc agcatcgcct tccggtgcat  2580
caacgagaac ctcacccgct acatcagcaa catggacatc ttcgagaagg tggacgccat  2640
cttcgacaag cacgaggtcc aggagatcaa ggaaaagatc ctgaactcgg actacgacgt  2700
ggaagacttc tttgagggcg agttcttcaa cttcgtcctc acccaggagg gcatcgacgt  2760
ctacaacgcc atcatcggcg gcttcgtgac ggagagcggc gagaagatca agggcctcaa  2820
cgagtacatc aacctctaca accagaagac taagcagaag ctcccgaagt tcaagccgct  2880
gtacaagcaa gtcctgagcg accgggagtc cctctcgttc tacggcgagg gctacacgag  2940
cgacgaggag gtgctggagg tgttccgcaa cacgctgaac aagaacagcg agatcttcag  3000
ctcgatcaag aaactcgaga agctgttcaa gaacttcgac gagtacagca gcgccggcat  3060
cttcgtcaag aacgggcccg cgatcagcac catcagcaag gacatcttcg gggagtggaa  3120
cgtgatccgc gacaagtgga acgccgagta cgacgacatc cacctcaaga aaaaggcggt  3180
ggtcacggag aagtacgagg acgaccgccg gaagtccttc aagaaaatcg ggagcttcag  3240
cctcgagcag ctccaggagt acgcggacgc cgacctgagc gtggtggaga agctcaagga  3300
gatcatcatc cagaaggtcg acgagatcta caaggtctac ggctcgagcg agaagctgtt  3360
cgacgcggac ttcgtgctgg agaagtccct caagaagaac gacgccgtgg tggccatcat  3420
gaaggatctg ctcgacagcg tgaagtcgtt cgagaactac atcaaggcat tctttgggga  3480
gggcaaggag acgaaccggg acgagtcctt ctacggggac ttcgtgctcg cgtacgacat  3540
cctcctgaag gtcgaccaca tctacgacgc gatccggaac tacgtcacgc agaagcccta  3600
cagcaaggac aagttcaagc tctacttcca gaacccgcag ttcatgcgcg ggtgggacaa  3660
ggacaaggag accgactacc gggccacgat cctgcggtac gggtccaagt actacctcgc  3720
catcatggac aagaagtacg ccaagtgcct ccagaagatt gacaaggacg acgtgaacgg  3780
gaactacgag aagatcaact acaagctcct cccggggccc aacaagatgc tgccgagggt  3840
gttcttcagc aagaagtgga tggcctacta caacccctcg gaggacatcc agaagatata  3900
caagaacggc acgttcaaaa aggggggacat gttcaacctg aacgactgcc acaagctgat  3960
cgactttttc aaggacagca tcagccgcta cccgaagtgg tcgaacgcct acgacttcaa  4020
cttctcggag acggagaagt acaaggacat tgcgggcttc taccgggagg tggaggagca  4080
gggctacaag gtctccttcg agagcgcctc caagaaagag gtggacaagc tcgtggagga  4140
gggcaagctg tacatgttcc agatctacaa caaggacttc tcggacaagt cgcacggcac  4200
cccgaacctc cacacgatgt acttcaagct gctgttcgac gagaacaacc acgggcagat  4260
ccgcctcagc ggcggggcgg agctgttcat gcgccgcgcg tccctcaaga aggaggagct  4320
ggtcgtgcac cccgccaact ccccgatcgc gaacaagaac cccgacaacc ccaagaagac  4380
aaccaccctc tcgtacgacg tctacaagga caagcggttc tcggaggacc agtacgagct  4440
gcacatcccg atcgccatca acaagtgccc caagaacatc ttcaagatca acaccgaggt  4500
gcgggtgctg ctcaagcacg acgacaaccc ctacgtcatc gggatcgacc gcggcgagcg  4560
gaacctgctc tacatcgtgg tcgtggacgg gaaggggaac atcgtggagc agtacagcct  4620
gaacgagatc atcaacaact tcaacggcat ccgcatcaag acggactacc acagcctcct  4680
ggacaagaag gagaaggagc ggttcgaggc gcggcagaac tggacctcca tcgagaacat  4740
caaggagctg aaggccggct acatcagcca ggtcgtgcac aagatctgcg agctcgtgga  4800
gaagtacgac gcggtgatcg cgctggagga cttgaacagc gggttcaaga actcccgggt  4860
caaggtcgag aagcaggtct accagaagtt cgagaagatg ctgatcgaca agctcaacta  4920
catggtggac aagaagtcca accccctgcgc caccggcggc gccctcaagg gctaccagat  4980
caccaacaag ttcgagtcct tcaagtcgat gtctacgcag aacgggttca ttttctacat  5040
cccggcgtgg ctcaccagca agatcgaccc gagcacgggc ttcgtcaacc tcctgaagac  5100
caagtacacc agcatcgcgg acagcaagaa gttcatctcc tcgttcgacc gcatcatgta  5160
cgtccccgag gaagacctgt tcgagttcgc cctcgactac aagaacttct cccggacgga  5220
cgccgactac atcaaaaagt ggaagctcta cagctacggc aaccggatcc gcatcttccg  5280
caaccccaag aagaacaatg tgttcgactg ggaggaggtg tgcctgacga gcgcctacaa  5340
ggagctcttc aacaagtacg gcatcaacta ccagcaaggg gacatccgcg cgctgctctg  5400
cgagcagtcc gacaaggcgt tctactcgtc gttcatggcc ctgatgagcc tcatgctcca  5460
gatgcgcaac agcatcaccg gccggacgga cgtggacttc ctgatcagcc cggtcaagaa  5520
cagcgacggc attttctacg acagccggaa ctacgaggcc caggagaacg ccatcctccc  5580
caagaacgcc gacgcgaacg gcgcctacaa catcgcgcgg aaggtgctgt gggccatcgg  5640
ccagtttaaa aaggcggagg acgagaagct ggacaaggtc aagatcgcca tcagcaacaa  5700
ggagtggctc gagtacgcgc agacgagcgt gaagcatgca ggatctaaga agcgtaggat  5760
```

-continued

```
caagcaagat taagaggtta attaatcgat cctccgatcc cttaattacc ataccattac  5820
accatgcatc aatatccata tatatataaa ccctttcgca cgtacttata ctatgttttg  5880
tcatacatat atatgtgtcg aacgatcgat ctatcactga tatgatatga ttgatccatc  5940
agcctgatct ctgtatcttg ttatttgtat accgtcaaat aaaagtttct tccacttgtg  6000
ttaataatta gctactctca tctcatgaac cctatatata actagtttaa tttgctgtca  6060
attgaacatg atgatcgatg                                              6080

SEQ ID NO: 41          moltype = DNA  length = 3753
FEATURE                Location/Qualifiers
misc_feature           1..3753
                       note = Synthetic polynucleotide.NLS-LbCpf1(TYC)-CO2-NLS
source                 1..3753
                       mol_type = other DNA
                       organism = synthetic construct
SEQUENCE: 41
atgggtagca aaaagaggcg tatcaagcag gacgcgtcga agctcgagaa gttcaccaac  60
tgctactcgc tgagcaagac gctgcggttc aaggcgatcc ccgtcgggaa gacccaggag  120
aacatcgaca acaagcggct cctggtcgag gacgagaagc gcgccgagga ctacaagggc  180
gtcaagaagc tgctggaccg gtactacctc tccttcatca acgacgtcct gcactcgatc  240
aagctcaaga acctgaacaa ctacatctcg ctgttccgca agaagacacg gaccgagaag  300
gagaacaagg agctcgagaa cctcgagatc aacctgcgca aggagatcgc gaaggcgttc  360
aagggcaacg aggggtacaa gagcctgttc aagaaagaca tcatcgagac catcctgccg  420
gagttcctgg acgacaagga cgagatcgcg ctggtgaact cgttcaacgg gttcaccacg  480
gccttcaccg ggtttttcga caaccgggag aacatgttca gcgaggaggc caagtcgacc  540
agcatcgcct tccggtgcat caacgagaac ctcacccgct acatcagcaa catggacatc  600
ttcgagaagg tggacgccat cttcgacaag cacgaggtcc aggagatcaa ggaaaagatc  660
ctgaactcgg actacgacgt ggaagacttc tttgagggcg agttcttcaa cttcgtcctc  720
acccaggagg gcatcgacgt ctacaacgcc atcatcggcg gcttcgtgac ggagagcggc  780
gagaagatca agggcctcaa cgagtacatc aacctctaca accagaagac taagcagaag  840
ctcccgaagt tcaagccgct gtacaagcaa gtcctgagcg accgggagtc cctctcgttc  900
tacggcgagg gctacacgag cgacgaggag gtgctggagg tgttccgcaa cacgctgaac  960
aagaacagcg agatcttcag ctcgatcaag aaactcgaga agctgttcaa gaacttcgac  1020
gagtacagca gcgccggcat cttcgtcaag aacgggcccg cgatcagcac catcagcaag  1080
gacatcttcg gggagtggaa cgtgatccgc gacaagtgga acgccgagta cgacgacatc  1140
cacctcaaga aaaaggcggt ggtcacggag aagtacgagg acgaccgccg gaagtccttc  1200
aagaaaatcg ggagcttcag cctcgagcag ctccaggagt acgcggacgc cgacctgagc  1260
gtggtggaga agctcaagga gatcatcatc cagaaggtcg acgagatcta caaggtctac  1320
ggctcgagcg agaagctgtt cgacgcggac ttcgtgctgg agaagtccct caagaagaac  1380
gacgccgtgg tggccatcat gaaggatctg ctcgacagcg tgaagtcgtt cgagaactac  1440
atcaaggcat tctttgggga gggcaaggag acgaaccggg acgagtcctt ctacggggac  1500
ttcgtgctcg cgtacgacat cctcctgaag gtcgaccaca tctacgacgc gatccggaac  1560
tacgtcacgc agaagcccta cagcaaggac aagttcaagc tctacttcca gaacccgcag  1620
ttcatgcgcg ggtgggacaa ggacaaggag accgactacc gggccacgat cctgcggtac  1680
gggtccaagt actacctcgc catcatggac aagaagtacg ccaagtgcct ccagaagatt  1740
gacaaggacg acgtgaacgg gaactacgag aagatcaact acaagctcct cccggggccc  1800
aacaagatgc tgccgagggt gttcttcagc aagaagtgga tggcctacta caacccctcg  1860
gaggacatcc agaagatata caagaacggc acgttcaaaa aggggggacat gttcaacctg  1920
aacgactgcc acaagctgat cgactttttc aaggacagca tcagccgcta cccgaagtgg  1980
tcgaacgcct acgacttcaa cttctcggag acggagaagt acaaggacat tgcgggcttc  2040
taccgggagg tggaggagca gggctacaag gtctccttcg agagcgcctc caagaaagag  2100
gtggacaagc tcgtggagga gggcaagctg tacatgttcc agatctacaa caaggacttc  2160
tcggacaagt cgcacggcac cccgaacctc cacacgatgt acttcaagct gctgttcgac  2220
gagaacaacc acgggcagat ccgcctcagc ggcggggcgg agctgttcat gcgccgcgcg  2280
tccctcaaga aggaggagct ggtcgtgcac cccgccaact ccccgatcgc gaacaagaac  2340
cccgacaacc ccaagaagac aaccaccctc tcgtacgacg tctacaagga caagcggttc  2400
tcggaggacc agtacgagct gcacatcccg atcgccatca acaagtgccc caagaacatc  2460
ttcaagatca acaccgaggt gcgggtgctg ctcaagcacg acgacaaccc ctacgtcatc  2520
gggatcgacc gcggcgagcg gaacctgctc tacatcgtgg tcgtggacgg gaaggggaac  2580
atcgtggagc agtacagcct gaacgagatc atcaacaact tcaacggcat ccgcatcaag  2640
acggactacc acagcctcct ggacaagaag gagaaggagc ggttcgaggc gcggcagaac  2700
tggacctcca tcgagaacat caaggagctg aaggccggct acatcagcca ggtcgtgcac  2760
aagatctgcg agctcgtgga gaagtacgac gcggtgatcg cgctggagga cttgaacagc  2820
gggttcaaga actcccgggt caaggtcgag aagcaggtct accagaagtt cgagaagatg  2880
ctgatcgaca agctcaacta catggtggac aagaagtcca acccctgcgc caccggcggc  2940
gccctcaagg gctaccagat caccaacaag ttcgagtcct tcaagtcgat gtctacgcag  3000
aacgggttca ttttctacat cccggcgtgg ctcaccagca agatcgaccc gagcacgggc  3060
ttcgtcaacc tcctgaagac caagtacacc agcatcgcgg acagcaagaa gttcatctcc  3120
tcgttcgacc gcatcatgta cgtccccgag gaagacctgt tcgagttcgc cctcgactac  3180
aagaacttct cccggacgga cgccgactac atcaaaaagt ggaagctcta cagctacggc  3240
aaccggatcc gcatcttccg caaccccaag aagaacaatg tgttcgactg ggaggaggtg  3300
tgcctgacga gcgcctacaa ggagctcttc aacaagtacg gcatcaacta ccagcaaggg  3360
gacatccgcg cgctgctctg cgagcagtcc gacaaggcgt tctactcgtc gttcatggcc  3420
ctgatgagcc tcatgctcca gatgcgcaac agcatcaccg gccggacgga cgtggacttc  3480
ctgatcagcc cggtcaagaa cagcgacggc attttctacg acagccggaa ctacgaggcc  3540
caggagaacg ccatcctccc caagaacgcc gacgcgaacg gcgcctacaa catcgcgcgg  3600
aaggtgctgt gggccatcgg ccagtttaaa aaggcggagg acgagaagct ggacaaggtc  3660
aagatcgcca tcagcaacaa ggagtggctc gagtacgcgc agacgagcgt gaagcatgca  3720
ggatctaaga agcgtaggat caagcaagat taa                               3753
```

```
SEQ ID NO: 42          moltype = DNA  length = 33
FEATURE                Location/Qualifiers
source                 1..33
                       mol_type = unassigned DNA
                       organism = Solanum tuberosum
SEQUENCE: 42
atgggtagca aaaagaggcg tatcaagcag gac                                33

SEQ ID NO: 43          moltype = AA  length = 1300
FEATURE                Location/Qualifiers
source                 1..1300
                       mol_type = protein
                       note = subsp. novicida U112
                       organism = Francisella tularensis
SEQUENCE: 43
MSIYQEFVNK YSLSKTLRFE LIPQGKTLEN IKARGLILDD EKRAKDYKKA KQIIDKYHQF  60
FIEEILSSVC ISEDLLQNYS DVYFKLKKSD DDNLQKDFKS AKDTIKKQIS EYIKDSEKFK  120
NLFNQNLIDA KKGQESDLIL WLKQSKDNGI ELFKANSDIT DIDEALEIIK SFKGWTTYFK  180
GFHENRKNVY SSNDIPTSII YRIVDDNLPK FLENKAKYES LKDKAPEAIN YEQIKKDLAE  240
ELTFDIDYKT SEVNQRVFSL DEVFEIANFN NYLNQSGITK FNTIIGGKFV NGENTKRKGI  300
NEYINLYSQQ INDKTLKKYK MSVLFKQILS DTESKSFVID KLEDDSDVVT TMQSFYEQIA  360
AFKTVEEKSI KETLSLLFDD LKAQKLDLSK IYFKNDKSLT DLSQQVFDDY SVIGTAVLEY  420
ITQQIAPKNL DNPSKKEQEL IAKKTEKAKY LSLETIKLAL EEFNKHRDID KQCRFEEILA  480
NFAAIPMIFD EIAQNKDNLA QISIKYQNQG KKDLLQASAE DDVKAIKDLL DQTNNLLHKL  540
KIFHISQSED KANILDKDEH FYLVFEECYF ELANIVPLYN KIRNYITQKP YSDEKFKLNF  600
ENSTLANGWD KNKEPDNTAI LFIKDDKYYL GVMNKKNNKI FDDKAIKENK GEGYKKIVYK  660
LLPGANKMLP KVFFSAKSIK FYNPSEDILR IRNHSTHTKN GSPQKGYEKF EFNIEDCRKF  720
IDFYKQSISK HPEWKDFGFR FSDTQRYNSI DEFYREVENQ GYKLTFENIS ESYIDSVVNQ  780
GKLYLFQIYN KDFSAYSKGR PNLHTLYWKA LFDERNLQDV VYKLNGEAEL FYRKQSIPKK  840
ITHPAKEAIA NKNKDNPKKE SVFEYDLIKD KRFTEDKFFF HCPITINFKS SGANKFNDEI  900
NLLLKEKAND VHILSIDRGE RHLAYYTLVD GKGNIIKQDT FNIIGNDRMK TNYHDKLAAI  960
EKDRDSARKD WKKINNIKEM KEGYLSQVVH EIAKLVIEYN AIVVFEDLNF GFKRGRFKVE  1020
KQVYQKLEKM LIEKLNYLVF KDNEFDKTGG VLRAYQLTAP FETFKKMGKQ TGIIYYVPAG  1080
FTSKICPVTG FVNQLYPKYE SVSKSQEFFS KFDKICYNLD KGYFEFSFDY KNFGDKAAKG  1140
KWTIASFGSR LINFRNSDKN HNWDTREVYP TKELEKLLKD YSIEYGHGEC IKAAICGESD  1200
KKFFAKLTSV LNTILQMRNS KTGTELDYLI SPVADVNGNF FDSRQAPKNM PQDADANGAY  1260
HIGLKGLMLL GRIKNNQEGK KLNLVIKNEE YFEFVQNRNN                         1300

SEQ ID NO: 44          moltype = DNA  length = 3897
FEATURE                Location/Qualifiers
misc_feature           1..3897
                       note = Synthetic polynucleotide.Codon optimized FnCpf1-Hs
source                 1..3897
                       mol_type = other DNA
                       organism = synthetic construct
SEQUENCE: 44
agcatctacc aggagttcgt caacaagtat tcactgagta agacactgcg gttcgagctg  60
atcccacagg gcaagacact ggagaacatc aaggcccgag gcctgattct ggacgatgag  120
aagcgggcaa aagactataa gaaagccaag cagatcattg ataaatacca ccagttcttt  180
atcgaggaaa ttctgagctc cgtgtgcatc agtgaggatc tgctgcagaa ttactcagac  240
gtgtacttca agctgaagaa gagcgacgat gacaacctgc agaaggactt caagtccgcc  300
aaggacacca tcaagaaaca gattagcgag tacatcaagg actccgaaaa gtttaaaaat  360
ctgttcaacc agaatctgat cgatgctaag aaaggccagg agtccgacct gatcctgtgg  420
ctgaaacagt ctaaggacaa tgggattgaa ctgttcaagg ctaactccga tatcactgat  480
attgacgagg cactggaaat catcaagagc ttcaagggat ggaccacata ctttaaaggc  540
ttccacgaga accgcaagaa cgtgtactcc agcaacgaca ttcctacctc catcatctac  600
cgaatcgtcg atgacaatct gccaaagttc ctggagaaca aggccaaata tgaatctctg  660
aaggacaaag ctcccgaggc aattaattac gaacagatca agaaagatct ggctgaggaa  720
ctgacattcg atatcgacta taagactagc gaggtgaacc agagggtctt ttccctggac  780
gaggtgtttg aaatcgccaa tttcaacaat tacctgaacc agtccggcat tactaaattc  840
aataccatca ttggcgggaa gtttgtgaac ggggagaata ccaagcgcaa gggaattaac  900
gaatacatca atctgtatag ccagcagatc aacgacaaaa ctctgaagaa atacaagatg  960
tctgtgctgt tcaaacagat cctgagtgat accgagtcca agtcttttgt cattgataaa  1020
ctggaagatg actcagacgt ggtcactacc atgcagagct tttatgagca gatcgccgct  1080
ttcaagacag tggaggaaaa atctattaag gaaactctga gtctgctgtt cgatgacctg  1140
aaagcccaga agctggacct gagtaagatc tacttcaaaa acgataagag tctgacagac  1200
ctgtcacagc aggtgtttga tgactattcc gtgattggga ccgccgtcct ggagtacatt  1260
acacagcaga tcgctccaaa gaacctggat aatccctcta agaaagagca ggaactgatc  1320
gctaagaaaa ccgagaaggc aaaatatctg agtctggaaa caattaagct ggcactggag  1380
gagttcaaca agcacaggga tattgacaaa cagtgccgct ttgaggaaat cctggccaac  1440
ttcgcagcca tccccatgat ttttgatgag atcgcccaga acaaagacaa tctggctcag  1500
atcagtatta agtaccagaa ccagggcaag aaagacctgc tgcaggcttc agcagaagat  1560
gacgtgaaag ccatcaagga tctgctggac cagaccaaca atctgctgca caagctgaaa  1620
atcttccata ttagtcagtc agaggataag gctaatatcc tggataaaga cgaacacttc  1680
tacctggtgt tcgaggaatg ttacttcgag ctggcaaaca ttgtccccct gtataacaag  1740
attaggaact acatcacaca gaagccttac tctgacgaga agtttaaact gaacttcgaa  1800
aatagtaccc tggccaacgg gtgggataag aacaaggagc ctgacaacac agctatcctg  1860
ttcatcaagg atgacaagta ctatctggga gtgatgaata agaaaaacaa taagatcttc  1920
gatgacaaag ccattaagga gaacaaaggg gaaggataca agaaaatcgt gtataagctg  1980
```

-continued

```
ctgcccggcg caaataagat gctgcctaag gtgttcttca gcgccaagag tatcaaattc  2040
tacaacccat ccgaggacat cctgcggatt agaaatcact caacacatac taagaacggg  2100
agcccccaga agggatatga gaaatttgag ttcaacatcg aggattgcag gaagtttatt  2160
gacttctaca agcagagcat ctccaaacac cctgaatgga aggattttgg cttccggttt  2220
tccgacacac agagatataa ctctatcgac gagttctacc gcgaggtgga aaatcagggg  2280
tataagctga cttttgagaa catttctgaa agttacatcg acagcgtggt caatcaggga  2340
aagctgtacc tgttccagat ctataacaaa gatttttcag catacagcaa gggcagacca  2400
aacctgcata cactgtactg gaaggccctg ttcgatgaga ggaatctgca ggacgtggtc  2460
tataaactga acggagaggc cgaactgttt taccggaagc agtctattcc taagaaaatc  2520
actcacccag ctaaggaggc catcgctaac aagaacaagg acaatcctaa gaaagagagc  2580
gtgttcgaat acgatctgat taaggacaag cggttcaccg aagataagtt ctttttccat  2640
tgtccaatca ccattaactt caagtcaagc ggcgctaaca agttcaacga cgagatcaat  2700
ctgctgctga aggaaaaagc aaacgatgtg cacatcctga gcattgaccg aggagagcgg  2760
catctggcct actataccct ggtggatggc aaagggaata tcattaagca ggatacattc  2820
aacatcattg gcaatgaccg gatgaaaacc aactaccacg ataaactggc tgcaatcgag  2880
aaggatagag actcagctag gaaggactgg aagaaaatca acaacattaa ggagatgaag  2940
gaaggctatc tgagccaggt ggtccatgag attgcaaagc tggtcatcga atacaatgcc  3000
attgtggtgt tcgaggatct gaacttcggc tttaagaggg ggcgctttaa ggtggaaaaa  3060
caggtctatc agaagctgga gaaaatgctg atcgaaaagc tgaattacct ggtgtttaaa  3120
gataacgagt tcgacaagac cggaggcgtc ctgagagcct accagctgac agctcccttt  3180
gaaactttca agaaaatggg aaaacagaca ggcatcatct actatgtgcc agccggattc  3240
acttccaaga tctgccccgt gaccggcttt gtcaaccagc tgtaccctaa atatgagtca  3300
gtgagcaagt cccaggaatt tttcagcaag ttcgataaga tctgttataa tctggacaag  3360
gggtacttcg agttttcctt cgattacaag aacttcggcg acaaggccgc taaggggaaa  3420
tggaccattg cctccttcgg atctcgcctg atcaactttc gaaattccga taaaaaccac  3480
aattgggaca ctagggaggt gtacccaacc aaggagctgg aaaagctgct gaaagactac  3540
tctatcgagt atggacatgg cgaatgcatc aaggcagcca tctgtggcga gagtgataag  3600
aaatttttcg ccaagctgac ctcagtgctg aatacaatcc tgcagatgcg gaactcaaag  3660
accgggacag aactggacta tctgattagc cccgtggctg atgtcaacgg aaacttcttc  3720
gacagcagac aggcacccaa aaatatgcct caggatgcag acgccaacgg ggcctaccac  3780
atcgggctga agggactgat gctgctgggc cggatcaaga acaatcagga ggggaagaag  3840
ctgaacctgg tcattaagaa cgaggaatac ttcgagtttg tccagaatag aaataac     3897
```

```
SEQ ID NO: 45          moltype = DNA  length = 3900
FEATURE                Location/Qualifiers
misc_feature           1..3900
                       note = Synthetic polynucleotide.Codon optimized FnCpf1-CO1
source                 1..3900
                       mol_type = other DNA
                       organism = synthetic construct
SEQUENCE: 45
atgtctatct atcaagagtt tgtcaacaag tacagcttaa gtaagacact tcgcttcgag  60
ttgatccctc aggggaagac actggaaaac atcaaggcga ggggccttat cctggacgac  120
gagaagcggg ctaaagacta caaaaaagct aaacagataa ttgacaagta tcaccaattt  180
tttattgagg agatcctctc ctctgtgtgc ataagtgagg atctgctcca gaactattcg  240
gatgtttact ttaaactcaa gaagtccgat gatgacaacc ttcagaagga cttcaagtcc  300
gccaaagaca cgattaagaa acaaatcagt gagtacatca aggatagcga gaaattcaag  360
aacctgttca accagaactt aattgatgcc aaaaagggcc aagaatccga cctcatcctg  420
tggttaaagc aatctaaaga caacggtatt gagctgttca aggcaaacag cgacattaca  480
gacattgacg aggccctaga gatcatcaag tcattcaaag gctggacgac ttactttaaa  540
ggttttcacg agaaccgtaa gaatgtttac tcaagtaacg atataccaac gagcattatc  600
taccgaatag tggatgataa cctaccgaag ttccttgaga acaaagcgaa gtacgagtct  660
ctcaaagaca aggcccctga ggccatcaac tacgagcaga ttaagaagga tctcgccgag  720
gagctaacct tcgacattga ctacaaaaca tcggaagtga atcagagggt gttctcgctt  780
gatgaagtat tcgagattgc taacttcaac aattacctga accagagtgg tattactaag  840
ttcaacacaa tcattggagg caaattcgtg aacggcgaaa acacaaagcg aaaagggata  900
aacgagtaca ttaacttgta cagccagcag atcaacgata agacactcaa gaagtataag  960
atgtctgtgc tgttcaaaca aatcttaagc gacacggaaa gcaagtcgtt cgtaattgac  1020
aagctggaag acgattctga cgtggttaca accatgcagt ccttttacga gcagattgcc  1080
gcattcaaga ccgtggagga aaagtcgatc aaggaaacac tttcgttgct tttcgacgac  1140
cttaaagctc agaagctcga cttaagcaag atatacttta agaacgataa gagcttgaca  1200
gacttgagcc agcaagtctt tgacgactac agcgttatcg gaactgccgt tctggagtac  1260
ataacacagc agatcgcacc caagaacctt gacaaccctt ccaagaaaga acaagagttg  1320
atcgccaaga agactgaaaa ggctaagtac ctctctctgg agactatcaa gctcgctctt  1380
gaggagttta acaagcacag ggacattgac aagcaatgcc gattcgagga aatactggca  1440
aacttcgcag ccatacccat gatattcgat gagatagccc agaacaagga taacttggcc  1500
caaatctcga ttaagtatca gaaccagggc aaaaaggacc ttctacaggc tagtgcagag  1560
gacgatgtga aggctattaa ggacttatta gatcagacaa acaaccttct gcataagctc  1620
aagatattcc atatctccca gtcagaggac aaggccaaca ttctggataa ggacgagcac  1680
ttctatctcg tattcgagga atgttacttt gagctggcca atatcgttcc cttgtacaac  1740
aaaatccgga actacatcac acagaagccc tacagtgatg agaagttcaa attgaacttt  1800
gaaaactcaa cacttgctaa tggttgggac aagaataagg aacctgacaa cactgccatc  1860
ctctttatta aagatgataa gtactacctc ggggtgatga ataagaagaa caacaaaatc  1920
ttcgatgaca aagctattaa ggagaacaaa ggtgaagggt acaagaagat tgtctacaaa  1980
ctgctgcctg gtgccaacaa aatgctacca aaggtatttt tcagcgccaa atctattaag  2040
ttctacaatc caagcgagga tattctccgg atacggaatc actctacaca taccaagaat  2100
ggaagtccac aaaagggtta cgagaaattc gagttcaaca ttgaagactg ccggaaattc  2160
attgacttct acaagcaatc catctctaaa catcctgaat ggaaagactt cggtttccgc  2220
ttcagtgata ctcaacggta caattcaatt gacgaattct accgtgaggt tgagaaccag  2280
```

```
gggtacaaac tgaccttcga gaacatatca gagagctaca tcgactcagt ggttaatcag  2340
gggaagctat atctgtttca aatctacaac aaagacttta gtgcctactc taaagggcgg  2400
ccaaacttac acacacttta ctggaaggca ctattcgacg aacgcaatct acaagatgta  2460
gtttacaaat tgaacggtga ggctgagttg ttctaccgta aacaatctat acccaagaag  2520
ataacacacc ctgctaaaga ggcaattgca aacaaaaaca aggataatcc caaaaaggag  2580
tctgtctttg agtatgacct cattaaggat aagcggttca cggaggacaa gttcttcttc  2640
cattgtccaa taaccatcaa cttcaaatca tccggcgcaa acaaattcaa tgacgagatc  2700
aacctgttac taaaggagaa ggctaacgat gttcacatct tatctattga tcgaggtgag  2760
agacacctag cctactacac tttagtggat gggaaggga acatcatcaa gcaagacacc  2820
ttcaacatca ttgggaacga caggatgaag actaactacc atgataagct cgccgctatt  2880
gaaaaggaca gggactctgc caggaaggac tggaaaaaaa ttaacaatat taaagagatg  2940
aaggagggct acctgagcca agtagtccat gagatagcaa aactggtgat tgagtacaac  3000
gcaatagtcg tattcgagga cttaaacttc ggcttcaaac gtgggcggtt taaggtggag  3060
aaacaagtct atcagaaatt ggagaagatg ctaatcgaga agctcaacta cctcgtgttt  3120
aaagacaacg agtttgacaa aactggagga gtcctgcggg cataccaact gaccgcaccc  3180
ttcgagacat tcaagaagat gggaaagcag actggcatca tctattacgt gccagcgggt  3240
tttacttcca aaatctgtcc agttacaggc ttcgtgaacc agttgtaccc gaagtacgag  3300
tctgtttcca agtcacagga attcttctca aagtttgaca agatatgtta caatctcgat  3360
aagggatact ttgagtttag tttcgactac aagaactttg gcgataaggc cgcaaaaggg  3420
aaatggacaa ttgcatcctt cgggtcacgc cttattaact ttcgtaactc agacaagaac  3480
cacaattggg acaccaggga ggtgtaccct actaaggagc tggagaagct acttaaagac  3540
tactcgattg agtacggaca tggagagtgc atcaaggcag caatatgtgg ggaatctgac  3600
aaaaagttct ttgccaagct gacctctgta ctgaacacta ttctccaaat gagaaatagt  3660
aagactggca cagagttgga ctacctgatc tctccagtgg ctgacgttaa tgggaatttt  3720
ttcgactcaa gacaagctcc caagaatatg ccacaggacg cagatgcaaa cggggcatat  3780
cacatcgggc ttaaaggact catgctacta gggcggatca agaataatca ggagggcaaa  3840
aagctgaacc tagtcatcaa gaacgaggag tacttcgaat ttgtccagaa tcgtaacaac  3900

SEQ ID NO: 46          moltype = DNA  length = 3900
FEATURE                Location/Qualifiers
misc_feature           1..3900
                       note = Synthetic polynucleotide.Codon optimized FnCpf1-CO2
source                 1..3900
                       mol_type = other DNA
                       organism = synthetic construct
SEQUENCE: 46
atgtccatat accaggagtt cgtcaacaag tactcgctca gcaagacgct ccgcttcgag  60
ctgatccccc agggtaagac cctggagaac atcaaggcgc gcggactcat cctcgacgac  120
gagaagcggg ctaaggacta caaaaaggcc aagcagatca tcgacaagta ccaccagttc  180
ttcatcgagg agatcctctc ctccgtctgc atctccgagg acctcctcca gaactacagc  240
gacgtctact tcaagctcaa aaagtcggac gacgacaacc tccagaagga cttcaagtcg  300
gcgaaggaca ccatcaagaa gcagatcagc gagtacatca aggactccga gaagttcaag  360
aacctgttca accagaacct gatcgacgcc aagaagggcc aggagtcgga cctgatcctg  420
tggctcaagc agagcaagga caacggcatc gagctcttca aggccaacag cgacatcacg  480
gacatcgacg aggccctgga gatcatcaag tcgttcaagg gctggacgac ctacttcaag  540
ggcttccacg agaaccgcaa gaacgtctat agctccaacg acatccccac ctcgatcatc  600
taccggatcg tggacgacaa cctccccaag ttcctggaga acaaggcgaa gtacgagtcg  660
ttgaaggaca aggcgccgga ggcgatcaac tacgagcaga tcaagaagga cctggccgag  720
gagctgacct tcgacatcga ctacaagacg tcggaggtga accagcgggt gttcagtctg  780
gacgaggtct tcgagatcgc gaacttcaac aactacctga accagtcggg gatcaccaag  840
ttcaacacga tcataggcgg caagttcgtg aacggcgaga acaccaagcg caaggggata  900
aacgagtaca tcaacctgta cagccagcag atcaacgaca agacgctcaa gaagtacaag  960
atgagcgtgc tcttcaagca gatcctcagt gacaccgagt ccaagagctt cgtgatcgac  1020
aagctggagg acgacagcga cgtcgtgaca accatgcaga gcttctacga gcagatcgcc  1080
gcgttcaaga ccgtcgagga gaagtcaatc aaggagacgc tctccttgct gttcgacgac  1140
ctgaaggcac aaaagctgga cctcagcaag atctacttca agaacgacaa gtccctgacc  1200
gacctgagcc agcaggtttt cgacgactac tccgtcatcg ggactgccgt cctggagtac  1260
atcacccagc agatcgctcc gaagaacctc gacaacccgt ccaagaagga gcaggagctg  1320
attgcgaaga agacagagaa ggccaagtac ctctccctcg agaccatcaa gctcgccctg  1380
gaggagttca acaagcacag ggacattgac aagcagtgcc gtttcgagga gatcctggcc  1440
aacttcgcgg ccatccccat gatcttcgac gagatcgccc agaacaagga caacctggcg  1500
cagatctcta tcaagtacca gaaccagggg aagaaggact tgctccaggc ctcagcggag  1560
gacgacgtga aggccatcaa ggacctgctc gaccagacga acaacttgct ccacaagctc  1620
aagatctttc acatcagcca gagcgaggac aaggccaaca tcctcgacaa ggacgagcac  1680
ttctacctcg tgttcgagga gtgctacttc gagctggcca acatcgtgcc actttacaac  1740
aagatccgca actacatcac gcagaagccg tactccgacg agaagttcaa gctgaacttc  1800
gagaactcca ccctcgccaa cggctgggac aagaacaagg agccggacaa caccgcgatc  1860
ctgttcataa aggacgacaa gtactacttg ggggtcatga acaagaagaa caacaagata  1920
ttcgacgaca aggccatcaa ggagaacaag gggggagggct acaagaagat cgtctacaag  1980
ctcctccccg gcgcgaacaa gatgctgcct aaggtcttct tttccgccaa gagtatcaag  2040
ttctacaacc cctccgagga catcctccgc atccggaacc acagcacgca cacaaagaac  2100
ggctcgcctc agaagggcta cgagaagttc gagttcaaca tcgaggactg ccggaagttc  2160
atcgacttct acaagcagag catctccaag cacccggagt ggaaggactt tggcttcagg  2220
ttctcagaca cccagcggta caactccatc gacgagttct accgcgaggt ggagaaccag  2280
ggctacaagc tgaccttcga gaatatatca gagtcgtaca tcgacagcgt ggtgaaccag  2340
ggcaagttgt acctgttcca gatctacaac aaggacttct ccgcctactc aaaggggcgt  2400
ccaaacctgc acacgctgta ctggaaggcg ctcttcgacg agcgcaacct acaagatgtt  2460
gtatacaagc tcaacggcga ggcggaactg ttctatagga agcagtcgat ccccaagaag  2520
attacgcacc cggctaagga ggccatcgcc aacaagaaca aggacaaccc caagaaggag  2580
```

-continued

```
tccgtgttcg agtacgacct catcaaggac aagaggttca cggaggacaa gtttttcttc  2640
cactgcccaa tcactatcaa tttcaagtcg agcggagcca acaagttcaa cgacgagata  2700
aacctgctcc tcaaggagaa ggccaatgac gtgcacatcc tctccatcga ccggggcgag  2760
cggcacctgg cgtactacac gctggtggac ggcaagggca acatcatcaa gcaggacacc  2820
ttcaacatca tcgggaacga ccgcatgaag accaactacc acgacaagct cgccgccatc  2880
gagaaggaca gggactccgc gcgcaaggac tggaagaaga ttaacaacat caaggagatg  2940
aaggagggct acctcagcca ggtggtccac gagatcgcca agctcgtcat tgagtacaac  3000
gccatcgtcg tcttcgagga cctgaatttc ggcttcaagc gcggccggtt caaggtggag  3060
aagcaggtct accagaagct tgagaagatg ctgatcgaga agctgaacta cctggtgttc  3120
aaggacaacg agttcgacaa gaccggcgga gtgctgcgcg cctaccagct cacggcgcct  3180
ttcgagacgt tcaagaagat gggcaagcag acgggcatca tctactacgt gcccgccggc  3240
ttcacctcta agatctgccc agtgaccggc ttcgttaacc agctgtaccc gaagtacgag  3300
agcgtgtcca agtcccagga gttcttctcc aagttcgaca agatttgtta caacctcgac  3360
aagggctact tcgagttttc gttcgactac aagaactttg gcgacaaggc ggccaagggg  3420
aagtggacca tcgcctcttt cggcagcagg ctcatcaatt tccggaactc cgacaagaac  3480
cacaactggg acacgcgcga ggtgtacccg acgaaggagc tggagaagct gctcaaggac  3540
tactccatcg agtacggcca cggcgagtgc atcaaggcgg cgatctgcgg ggagagcgac  3600
aagaagttct ttgccaagct gaccagcgtg ctgaacacca tcctccagat gcggaactcc  3660
aagaccggca ccgagctgga ctacctgatc tccccggtcg cggacgtcaa cgggaacttc  3720
ttcgactccc gacaggctcc caagaacatg ccccaggacg ccgacgcgaa cggcgcgtac  3780
cacatcggcc tcaagggcct gatgctgctg gggcgcatca agaacaacca ggagggcaag  3840
aagctgaacc tcgtgatcaa gaacgaggaa tacttcgagt tcgtgcagaa ccgcaacaac  3900

SEQ ID NO: 47          moltype = DNA  length = 3900
FEATURE                Location/Qualifiers
misc_feature           1..3900
                       note = Synthetic polynucleotide.Codon optimized FnCpf1-CO3
source                 1..3900
                       mol_type = other DNA
                       organism = synthetic construct
SEQUENCE: 47
atgagcatct accaggagtt cgtgaacaag tacagcctgt cgaagaccct ccggttcgag  60
ctgatccctc aggggaagac gctggagaac atcaaggcgc gcggcctcat cctcgacgac  120
gagaagcggg cgaaggacta caaaaaggca aagcagatca tcgacaagta ccaccaattc  180
tttattgagg agatcctcag ctccgtctgc atcagcgagg acttgctcca gaactactcc  240
gacgtctatt tcaagctcaa gaagtcagac gacgacaacc tccagaagga cttcaagtcc  300
gcgaaggaca cgatcaaaaa gcagatcagc gagtacatca aggactccga gaagttcaag  360
aacctcttca accagaacct gatcgacgcc aagaagggcc gggaatcgga cctcatcctg  420
tggctcaagc agtcgaagga caacggcatc gagctgttca aggccaactc cgacatcacc  480
gacatcgacg aggcgctgga gatcatcaag tcgttcaagg ggtggaccac ctacttcaag  540
ggcttccacg agaaccgcaa gaacgtttac tccagcaacg acatccccac ctcgatcatc  600
taccggatcg tggacgacaa cctgcccaag ttcctggaga acaaggccaa gtacgagtcc  660
ctcaaggaca aggccccgga ggcgatcaac tacgagcaga ttaaaaagga ccttgctgag  720
gagctgacct tcgacatcga ctacaagacc tccgaggtga accagcgggt gttcagcctc  780
gacgaggtgt tcgagatcgc caacttcaac aactacctga accagtccgg gatcaccaag  840
ttcaacacga tcatcggcgg gaagttcgtc aacggcgaga acacgaagcg gaagggcatc  900
aacgagtaca tcaacctcta cagccagcag atcaacgaca agaccctcaa aaaatacaaa  960
atgtcggtcc tgttcaagca gatcctgtcc gacaccgagt ccaagagctt cgtcatcgac  1020
aagctggagg acgactccga cgtcgtgacc accatgcagt ccttctacga gcagatcgcc  1080
gccttcaaga ccgtggagga gaagtccatc aaggagaccc tcagcctcct cttcgacgac  1140
ctcaaggcgc agaagctgga cctctccaag atatacttca agaacgacaa gagcctcacc  1200
gacctgtccc agcaagtatt cgacgactac agcgtgatcg ggacggcggt gctggagtac  1260
atcacccagc agatagcgcc caagaacctg gacaacccct ccaagaaaga acaggagctg  1320
attgctaaaa agaccgaaaa ggctaagtac ctgtccctgg agaccatcaa gctcgcgctg  1380
gaggagttca acaagcaccg ggacatcgac aagcagtgcc ggttcgagga gatcctagca  1440
aacttcgccg cgatccccat gatcttcgac gagatcgccc agaacaagga caacctggcc  1500
cagatcagca tcaagtacca gaaccagggc aagaaggacc ttcttcaagc tagtgccgag  1560
gacgacgtga aggcgattaa ggatctgctc gaccagacca acaacctgct ccacaagctc  1620
aagatattcc acatctccca gtccgaggac aaggccaaca tcctcgacaa ggacgagcac  1680
ttctacctgg tgttcgagga gtgctacttc gagctggcca acatcgtgcc gctgtacaac  1740
aagatccgga actacatcac ccagaagccc tactccgacg agaagttcaa gctgaacttc  1800
gagaactcca ccctggcgaa cgggtgggac aagaacaagg agcccgacaa cacggccatc  1860
ctcttcatca aggacgacaa atattatctg ggcgtcatga acaaaaagaa caacaagata  1920
ttcgatgaca aggcgatcaa ggagaacaag ggcgagggct acaagaaaat agtatataaa  1980
ctactgcccg gcgcgaacaa gatgctcccg aaggtgtttt ttagtgcaaa gtctattaag  2040
ttctacaacc ccagcgagga catcctccgc atccggaacc acagcacgca caccaagaac  2100
ggcagcccac agaagggcta cgagaagttc gagttcaaca tcgaggactg ccgcaagttc  2160
atcgacttct acaagcagtc catctccaag caccccgagt ggaaggactt cgggttccgg  2220
ttcagcgaca cccagcgcta caacagcatc gacgagttct accgggaggt cgagaaccag  2280
gggtacaagc tgacgttcga gaacatctcc gagagctaca tcgacagcgt ggtgaaccag  2340
gggaagctgt acctgtttca gatatacaac aaggacttct cagcctacag caaggggcgg  2400
ccgaacctgc acaccctgta ctggaaggcc ctgttcgacg agcggaacct ccaggacgtc  2460
gtgtacaagc tcaacggcga ggcggagctg ttctaccgga agcagtccat ccccaaaaag  2520
attactcacc ccgcgaagga ggccatcgcc aacaagaaca aggacaaccc caaaaaggaa  2580
tcagtgttcg agtacgacct catcaaggac aagcgcttca ccgaggacaa attcttcttt  2640
cactgcccga tcacgatcaa cttcaagtcc tccggggcga acaagttcaa cgacgagatc  2700
aacctgctgc tcaaggagaa ggccaacgac gtgcacatcc tcagcatcga ccggggcgag  2760
cgccacctgg cctactacac cctggtggac gggaagggca acatcataaa gcaagatacc  2820
ttcaacatca tcgggaacga ccggatgaag acgaactacc acgacaagct ggcggccatc  2880
```

-continued

```
gagaaggacc gggacagcgc ccgcaaggac tggaaaaaga taaacaacat taaggagatg  2940
aaggagggct acctgtccca ggtggtccac gagatcgcca agctcgtcat cgagtacaac  3000
gccatcgtcg tgttcgagga cttgaacttc gggttcaagc ggggccggtt caaggtggag  3060
aaacaagtct atcaaaagct ggagaagatg ctcatcgaga agctcaacta cctcgtgttc  3120
aaggacaacg agttcgacaa gaccggcggc gtcctgcggg cctaccagct caccgcgccg  3180
ttcgagacgt tcaagaagat ggggaagcag acggggatca tctactacgt ccccgccggg  3240
ttcaccagca agatatgccc ggtcacgggg ttcgtcaacc agctctaccc caagtacgag  3300
tcggtgagca agagccagga gttcttcagc aagttcgaca agatctgcta caacctggac  3360
aagggctact tcgagttctc gttcgactac aagaacttcg ggacaaggc ggcgaagggc  3420
aagtggacca tcgccagctt cggctcccgc ctcatcaact tccggaactc ggacaagaac  3480
cacaactggg acacccgcga ggtgtacccc acgaaggagc tggagaagct gctcaaggac  3540
tacagcatcg agtacgggca cggcgagtgc atcaaggccg ccatctgcgg ggagtccgac  3600
aagaaattct ttgccaagct gacctccgtg ctgaacacca tcctccagat gcggaacagc  3660
aagaccggga ccgagctgga ctacctgatc tccccggtcg ccgacgtcaa cggcaacttc  3720
ttcgattctc gccaggctcc caagaacatg ccccaggacg ccgacgccaa cggggcctac  3780
cacatcgggc tcaagggcct catgctgctc gggcggatca agaacaacca ggagggcaag  3840
aaactcaacc tggtcatcaa gaacgaggag tactttgagt tcgtccagaa ccggaacaac  3900

SEQ ID NO: 48          moltype = DNA  length = 3900
FEATURE                Location/Qualifiers
misc_feature           1..3900
                       note = Synthetic polynucleotide.Codon optimized FnCpf1-CO4
source                 1..3900
                       mol_type = other DNA
                       organism = synthetic construct
SEQUENCE: 48
atgagcatct accaggagtt cgtgaacaag tacagcctga gcaagaccct gcgcttcgag  60
ctgattcctc aggggaagac cctggagaac atcaaggcgc gcggcctgat cctggacgac  120
gagaagcggg cgaaggacta caaaaaggcg aagcagatca tcgacaagta ccatcagttt  180
ttcatcgagg agattctcag ctccgtgtgc atcagcgaag acctgctcca gaactacagc  240
gacgtttact tcaagctcaa gaaatcggac gacgacaacc tccagaagga cttcaagagc  300
gcgaaggaca cgattaagaa acagatcagc gagtacatca aggactccga gaagttcaag  360
aacctgttca accagaacct catcgacgcc aagaaaggcc aagagtcgga cctcatcctc  420
tggctcaagc agagcaagga caacggcatc gagctgttca aggcgaacag cgacatcacc  480
gacatcgacg aggcgctgga gatcatcaag tcgttcaagg gctggacgac ctacttcaag  540
ggcttccacg agaaccgcaa gaatgtctac tcgagcaacg acatccccac gtcgatcatc  600
taccgcatcg tggacgacaa cctcccgaag ttcctggaga acaaggcgaa gtacgagagc  660
ctcaaggaca aggccccgga ggccatcaac tacgagcaga tcaaaaagga tttggctgag  720
gagctgacgt tcgacatcga ctacaagacc tccgaggtga accagcgcgt cttcagcctc  780
gacgaggtgt tcgagatcgc caacttcaac aactacctca accagtcggg catcaccaag  840
ttcaacacca tcatcggcgg gaagttcgtc aacggcgaga acacgaagcg caaggggatc  900
aacgagtaca tcaacctgta cagccagcag atcaacgaca agaccctcaa gaagtataaa  960
atgtcggtgc tgttcaagca gatcctctcg gacaccgaga gcaagtcgtt cgtcatcgac  1020
aagctggagg acgacagcga cgtggtgacc accatgcaga gcttctacga gcagatcgcg  1080
gccttcaaga ccgtcgagga gaagtcgatc aaggagacgc tcagcctgct gttcgacgac  1140
ctcaaggccc agaagctcga cctgtccaag atatacttta agaacgacaa gagcctcacg  1200
gacctgtccc agcaggtatt cgacgactac agcgtgatcg ggacggccgt gctggagtac  1260
atcacccaac agatcgcgcc caagaacctg gacaacccgt ccaagaagga acaagagcta  1320
atcgccaaaa agactgagaa ggcgaagtac ctgtcgctgg agacgatcaa gctcgcgctt  1380
gaggagttta acaagcaccg cgacatcgac aagcagtgcc ggttcgagga gatcctggcc  1440
aacttcgcgg cgatcccgat gatcttcgac gagatcgccc agaacaagga caacctggcg  1500
cagatcagca tcaagtacca gaaccagggc aaaaaagact tgctccaagc tagtgcggag  1560
gacgacgtga aggcgattaa ggatctgctg gaccagacta acaatctgct gcacaagctc  1620
aagatctttc acatctctca gtcggaggac aaggcgaaca tcctggacaa ggacgagcac  1680
ttctacctag tgttcgagga gtgctacttc gagctggcga acatcgtgcc cctgtacaac  1740
aagatccgga actacatcac ccagaagccc tacagcgacg agaagttcaa gctgaacttc  1800
gagaacagca cgctggcgaa cgggtgggac aagaacaagg agcccgacaa caccgccatc  1860
ctgttcatca aggacgacaa atattacctc ggcgtcatga acaaaaagaa taacaagata  1920
ttcgatgaca aggcgatcaa ggagaacaag ggcgagggct acaagaagat cgtatataaa  1980
ctcctgccgg gagcgaacaa gatgctcccg aaggttttct ttagtgccaa gtccatcaag  2040
ttctacaacc ccagcgagga catcctccgc atccggaacc actccaccca caccaagaac  2100
ggctcgccgc agaagggcta cgagaagttc gagttcaaca tcgaggactg ccgcaagttc  2160
atcgacttct acaagcagtc catctccaag cacccggagt ggaaggactt cgggttccgg  2220
ttctccgaca cgcagcgcta caactccatc gacgagttct accgggaggt ggagaaccag  2280
ggctacaagc tgacgttcga gaacatctcg gagtcctaca tcgactccgt ggtcaaccag  2340
ggcaagctgt acctcttcca gatatacaat aaggacttct ccgcctacag caaggggcgg  2400
cccaacctcc acaccctgta ctggaaggcg ctcttcgacg agcggaacct ccaggacgtc  2460
gtgtacaagc tgaacggcga ggcggagctg ttctaccgca agcagagcat ccccaagaag  2520
atcacgcacc ccgcgaagga ggccatcgcc aacaagaaca aggacaaccc caagaaggaa  2580
tcggtcttcg agtacgacct catcaaggac aagcggttca cggaggacaa attctttttc  2640
cactgcccga tcactattaa cttcaagtcc agcggcgcga acaagttcaa cgacgagatc  2700
aacctgctcc tcaaggagaa ggcgaacgac gtgcacatcc tcagcatcga ccggggcgag  2760
cgccacctcg cctactacac gctggtggac gggaagggca acatcatcaa gcaagacacc  2820
ttcaacatca tcggcaacga ccggatgaag accaactacc acgacaagct ggccgccatc  2880
gagaaggacc gcgactcggc ccgcaaggac tggaaaaaga tcaacaatat caaggagatg  2940
aaggagggct acctgagcca agttgtccac gagatcgcca agctggtgat cgagtacaac  3000
gccatcgtcg tgttcgaaga cctgaacttc ggcttcaagc gcggccggtt caaggtcgag  3060
aaacaagtct atcagaaact tgagaagatg ctgatcgaga agctgaacta cctcgtcttc  3120
aaggacaacg agttcgacaa gaccggcggc gtcctccgcg cgtaccagct caccgcgccg  3180
```

```
ttcgagacgt tcaagaaaat gggcaagcag accggcatca tctactacgt gcccgccggg  3240
ttcacgagca aaatatgtcc cgtgaccggc ttcgtcaacc agctctaccc caagtacgag  3300
tccgtgtcga agtcccagga attcttcagc aagttcgaca agatatgcta caacctggac  3360
aagggctact tcgagttctc cttcgactac aagaacttcg ggacaaggc ggcgaagggg  3420
aagtggacca tcgcctcgtt cggtcgcgc ctcatcaact tccggaacag cgacaagaac  3480
cacaactggg acacccgcga ggtgtacccg acgaaggagc tggagaagct cctcaaggac  3540
tacagcatcg agtacggcca cgggagtgc atcaaggcgg ccatctgcgg cgagtcggac  3600
aaaaagttct ttgccaaact cacctcggtc ctcaacacca tcctccagat gcggaacagc  3660
aagacgggca cggagctgga ctacctcatc agcccggtgg ccgacgtgaa cggcaatttc  3720
tttgactcac gccaggcccc taagaacatg ccccaggacg ccgacgccaa cggcgcgtac  3780
cacatcggcc tcaagggcct gatgctgctc ggccggatca agaacaacca ggagggcaag  3840
aagctcaacc tggtcatcaa gaacgaggag tatttcgagt tcgtccagaa ccgcaacaac  3900
```

```
SEQ ID NO: 49          moltype = DNA  length = 3900
FEATURE                Location/Qualifiers
misc_feature           1..3900
                       note = Synthetic polynucleotide.Codon optimized FnCpf1-CO5
source                 1..3900
                       mol_type = other DNA
                       organism = synthetic construct
SEQUENCE: 49
atgtccatat accaggagtt tgttaataaa tatagcttgt ccaaaaccct gcggtttgaa  60
ctcatacctc aggggaagac tttggagaat atcaaagcgc ggggactgat actggacgac  120
gaaaagcgcg caaaagatta caagaaagcg aaacagatca tcgataaata ccatcaattt  180
ttcatagagg agattctcag ttctgtctgt atcagtgagg acctcctcca aaattattca  240
gacgtctatt ttaaactcaa gaagtcggac gacgacaacc ttcagaaaga ttttaagtca  300
gcaaaagaca caatcaaaaa acaaatatcg gaatacataa aggactcaga aaagttcaag  360
aatcttttta accaaaatct gatagacgcg aagaaagggc aggaatctga tcttatactc  420
tggcttaagc agtctaaaga caacggcata gaactcttta aggcaaacag cgatataacc  480
gacatagatg aagccctcga gataattaag tccttcaaag gctggactac atattttaaa  540
gggttccatg agaataggaa gaacgtgtat tcctcgaatg atattcccac ctcgataatc  600
taccggattg tggatgataa tctgcctaaa tttttggaaa ataaagcgaa gtacgaaagt  660
ttgaaagata aagcaccaga agcaattaat tatgaacaaa ttaagaaaga tctggctgag  720
gaacttacgt tcgatatcga ttataaaaca tcagaagtta atcagcgggt ttttagcctg  780
gatgaagttt ttgagatcgc caacttcaac aattatctta atcagagcgg gattaccaaa  840
ttcaacacta ttatcggtgg taaattcgtt aatggtgaga acacaaagag aaaaggtata  900
aacgaataca taaatttgta cagtcaacag attaacgata aaactttgaa aaagtacaag  960
atgtcagtgc ttttcaaaca aatcctttcc gacacagaat ccaaaagttt tgtgatagac  1020
aaattggaag atgatagcga cgtcgtcacg accatgcaat cattttatga gcaaattgca  1080
gccttcaaga cggttgagga aaaaagtata aaagaaacgt tgtcgctctt gttcgacgac  1140
ctgaaagcac agaaattgga tttgtctaag atatacttta aaaacgacaa atccctcacg  1200
gacttgtcgc agcaagtctt tgatgattat tcggtgattg ggacagccgt gctcgaatac  1260
atcacccagc aaatcgctcc gaaaaatctg gacaatccgt ctaaaaaaga gcaagagctg  1320
atcgcaaaga aaaccgaaaa agcgaaatac ctgtctctgg agacaatcaa attggccttg  1380
gaagagttca ataagcacag agacattgat aaacaatgtc ggtttgagga aattcttgct  1440
aactttgccg ctatcccgat gatcttcgat gagattgcgc aaaataagga taatctggcc  1500
caaatctcga tcaagtatca aaatcagggt aagaaggacc tgcttcaagc atcggcggag  1560
gatgatgtga aagcgattaa ggacttgttg gatcagacca acaatttgtt gcacaagctg  1620
aagatattcc acatctccca gagtgaggat aaggccaaca tcctggacaa ggatgaacat  1680
ttctatttgg tcttcgaaga gtgttatttt gaattggcca acatagttcc tctttataac  1740
aagatccgca attatattac acaaaagcct tattccgatg aaaaatttaa acttaacttc  1800
gaaaatagca cattggcgaa tggttgggat aaaaataagg agcctgacaa tactgctata  1860
cttttcatta aggacgataa gtactacctc ggcgttatga acaagaagaa taataagatc  1920
tttgacgaca aagcaatcaa agagaacaaa ggcgaaggtt acaaaaaaat cgtgtacaaa  1980
ctcctgcctg gcgcgaataa aatgcttccg aaggtttttt tcagtgcgaa gtccattaag  2040
ttttataacc cttccgagga tattttgaga attagaaatc actccaccca taccaagaat  2100
ggcagccccc agaaggggta tgaaaagttc gaatttaata tcgaagactg ccgcaagttt  2160
atagactttt ataaacagtc catatctaaa catcccgaat ggaaagattt tggtttccgg  2220
ttttctgaca ctcagaggta caacagcata gatgagttct accgcgaagt tgaaaaccaa  2280
ggctacaagc ttacatttga gaacatcagc gagtcatata ttgactcagt cgttaatcag  2340
ggcaaacttt atttgttcca aatttacaac aaagactttt cagcgtacag caagggaagg  2400
ccaaatctcc atacactgta ttggaaggcg ctgtttgacg agcggaatct tcaagatgtt  2460
gtgtataaac tcaacgggga ggccgaattg ttctacagga agcaaagcat tcctaagaaa  2520
attacccacc ccgctaagga agcgatagca aataaaaata aagacaatcc gaaaaaagag  2580
agcgtttttg agtacgacct tataaaggat aagagattca ccgaggataa gtttttcttc  2640
cactgtccaa taactattaa ctttaaatcc tccggagcca acaagtttaa cgacgaaatt  2700
aatttgctgc tgaaagagaa ggcgaacgac gttcacattc tgtcaataga cagaggggag  2760
agacacttgg catactacac gctcgttgat ggaaaaggta acattattaa gcaagatact  2820
ttcaacatca ttgggaatga cagaatgaaa acaaactatc acgataaact cgcggcaatt  2880
gagaaggacc gggattcggc gaggaaagac tggaagaaaa tcaacaatat aaaggagatg  2940
aaggaaggat acctgtctca agtcgtccac gaaatagcca agcttgttat agagtataat  3000
gcgattgtgg tctttgaaga ccttaacttt ggatttaaac gcggccggtt taaagtcgag  3060
aaacaagtgt atcaaaaact ggaaaaaatg ttgatcgaga aactgaatta tctcgtcttc  3120
aaggacaacg agttcgataa aaccgggggc gtcttgcgcg cttatcaact gacggcaccg  3180
tttgaaactt tcaagaagat gggcaaacag actgggatta tctactacgt tcctgccgga  3240
ttcacctcca aaatatgccc agttactgga tttgttaacc agttgtaccc taagtacgaa  3300
tcagtcagca agtcccaaga gtttttctca aaatttgata agatctgcta taacctggac  3360
aaggggtact tcgagttttc cttcgactat aaaaatttcg gcgacaaggc agctaaaggt  3420
aaatggacga ttgcaagttt cggctccagg cttattaatt tcagaaacag cgacaaaaac  3480
```

```
cataactggg acacgcgcga ggtctaccct acgaaggaac tggaaaaact tctcaaggat  3540
tacagtatag aatacggaca cggggagtgt atcaaagctg cgatatgcgg agagtcggat  3600
aaaaagtttt tcgcaaagtt gacatcagtt ttgaacacta tcttgcagat gagaaattcc  3660
aagactggca cggagttgga ctaccttatt agcccagtgg cggatgtcaa cgggaacttt  3720
tttgattcga ggcaagcccc taagaatatg cctcaagacg ctgatgcaaa cggggcatat  3780
cacataggac tcaaagggtt gatgctgctg ggcagaatta agaacaacca ggaaggaaag  3840
aagctcaatc ttgttatcaa aaatgaagag tactttgaat tcgttcaaaa ccggaataac  3900

SEQ ID NO: 50          moltype = DNA  length = 3900
FEATURE                Location/Qualifiers
misc_feature           1..3900
                       note = Synthetic polynucleotide.Codon optimized FnCpf1-CO6
source                 1..3900
                       mol_type = other DNA
                       organism = synthetic construct
SEQUENCE: 50
atgagtattt atcaagagtt cgttaataag tacagtcttt ctaagacgct caggtttgag  60
ctcattccac aaggtaagac ccttgagaat attaaagccc gcggactgat cctggacgac  120
gagaagcgcg ccaaagacta taagaaggcg aaacagatca tagataagta tcaccaattc  180
ttcatagaag agatacttag ctctgtttgt atctcagagg atctgctcca gaactactcg  240
gatgtgtact ttaaactcaa gaagtctgac gatgacaatc tccagaagga ctttaagtcc  300
gccaaagaca caatcaagaa gcagatttcg gaatacataa aggacagtga gaagttcaag  360
aacttgttca accagaatct catagacgcc aagaagggtc aggagagcga tcttattctg  420
tggttgaaac aatcaaagga caacggtatt gagttgttta aagcaaactc tgacatcacc  480
gacattgacg aggctctgga gatcattaag agttttaaag ggtggacaac ctactttaag  540
ggatttcatg agaatcgcaa gaacgtgtac tcgagcaatg acatacctac aagcataatc  600
tatcggatag tcgacgataa cctcccgaag ttcctcgaga ataaagcgaa gtacgaatcg  660
cttaaggata aggcgccgga ggcgataaac tatgaacaga ttaagaagga tctggctgaa  720
gaattgacct ttgatattga ctataagacc agcgaagtca accaacgcgt tttcagcctg  780
gatgaagtgt ttgagatcgc caacttcaat aattacttga atcaatcggg gataacaaag  840
tttaatacga ttatcggcgg gaagtttgtc aacggggaga acacaaagag gaagggcata  900
aatgagtaca ttaatctcta tagtcaacag ataaatgaca agacgttgaa gaaatacaag  960
atgtcagtcc ttttcaagca gatcctgtct gacacagaat cgaagagctt cgtgatagat  1020
aagctggaag atgattccga cgttgtcaca accatgcaat cgttttacga gcagatcgcg  1080
gccttcaaga ccgttgagga gaagtctatt aaagagactc tttctcttct gtttgatgac  1140
ttgaaggccc agaagcttga cttgtccaag atctacttca agaacgataa atctctgaca  1200
gatctcagcc agcaagtgtt tgacgactat tctgttatcg gaacggccgt gctggagtac  1260
atcacacagc agatcgcgcc taagaacctt gataatccga gcaagaaaga acaggagttg  1320
attgcaaaga agacagagaa ggccaaatac ctttctctgg agacaattaa acttgcactg  1380
gaagaattca ataagcacag agatatcgac aagcagtgtc gctttgagga gatcctggca  1440
aattttgctg ccatcccaat gatttttgat gagattgccc agaacaagga caatctcgcg  1500
cagatatcaa tcaagtatca gaaccaaggc aagaaggacc tcctgcaagc ctcagccgaa  1560
gatgacgtta aggccataaa ggatctcctt gatcagacca ataacttgct gcacaagctg  1620
aagatctttc atatcagcca gtcggaagac aaagcaaata tccttgacaa ggacgagcat  1680
ttctatctgg tgttcgaaga atgctatttc gagctggcca atatcgtgcc tctgtacaat  1740
aagatccgca attatatcac gcagaagccg tatagcgacg agaagttcaa gctgaatttc  1800
gagaactcca ccttggccaa tggttgggat aagaacaaag aaccggacaa tacggccatc  1860
ttgtttatca aagatgacaa gtactatctg ggagtgatga ataagaagaa caataagatc  1920
ttcgatgaca aagccattaa ggagaataaa ggggaaggtt acaagaagat tgtctataaa  1980
ctgctccccg gggccaacaa gatgctgccc aaagtttttt tcagtgccaa gagcatcaag  2040
ttttataatc cctcagaaga catactgaga atcagaaacc actcgaccca taccaagaac  2100
ggctctccgc agaaggggta cgagaaattc gaattcaaca tcgaagactg tagaaagttc  2160
atcgattttt acaagcaatc gatatcaaag caccctgaat ggaaggattt tggttttcgc  2220
tttagtgaca ctcagcggta taatagcatt gatgagttct accgcgaagt tgagaatcag  2280
ggatacaaat tgacattcga gaatatcagc gaatcgtaca ttgatagcgt cgtcaaccag  2340
gggaaacttt acctcttcca gatttataat aaagacttct cggcgtactc caagggaaga  2400
ccaaatcttc atactctgta ttggaaggca ctcttcgatg agagaaatct tcaggatgtc  2460
gtttataaac ttaatgggga agcggagctg ttctaccgca agcagagcat ccctaagaag  2520
atcacgcacc ccgcgaagga ggcgatagcc aataagaaca aggataaccc gaagaaggag  2580
tccgtcttcg aatatgacct gatcaaggat aagagattca ctgaggacaa attcttcttc  2640
cattgcccta ttacgattaa ttttaaatcg agcggcgcga ataaattcaa cgacgagatc  2700
aacctgctcc tcaaagagaa ggccaatgat gtccacattc tctcaatcga cagaggggag  2760
aggcaccttg cctactatac gctcgttgat ggtaaaggta acatcattaa gcaggacacg  2820
ttcaacatca tcgggaacga ccgcatgaag acaaactatc acgataaatt ggcggcaatc  2880
gagaaggatc gggatagtgc caggaaggac tggaagaaga ttaataacat caaggagatg  2940
aaggagggat atctttctca agtcgtccac gagatcgcga agctggttat cgagtacaac  3000
gccatagtgg tcttcgaaga tctgaacttc ggattcaaga gagggagatt taaggtggag  3060
aagcaagttt atcagaaact ggagaagatg ctgatagaga agctcaacta cctcgtgttt  3120
aaagacaacg agtttgacaa gacaggtggg gtgttgaggg cctatcagct cacggccccc  3180
ttcgagacct tcaagaagat gggaaagcag acggggataa tctactacgt ccctgctggc  3240
ttcacttcga agatctgccc agttacagga ttcgttaacc agttgtatcc caaatacgag  3300
tccgtctcaa agtcacaaga attcttttct aaattcgata agatctgcta caacctggat  3360
aagggctact tcgagtttag ctttgactat aagaatttcg gggacaaagc ggcaaagggg  3420
aagtggacaa tcgcaagttt tggctcccgg ctgattaact ttcggaattc tgacaagaat  3480
cacaactggg atactagaga ggtctatcca actaaagagt tggagaagtt gctcaaggac  3540
tactccattg aatatggtca cggggaatgc attaaagcgg ccatctgcgg agagtccgat  3600
aagaagttct ttgccaaact tacatcggtc ttgaacacca tactgcagat gcggaacagc  3660
aagacgggaa cggaactcga ctaccttatc tcacctgtgg cggatgttaa tggaaacttt  3720
ttcgattcga ggcaggcgcc caagaacatg ccgcaagatg cagatgccaa tggagcatat  3780
```

```
cacatcggtc ttaaagggct catgctgctt ggccgcatca agaacaacca agaggggaag  3840
aagttgaacc tggttattaa gaacgaagaa tacttcgaat ttgtccagaa ccgcaacaac  3900

SEQ ID NO: 51          moltype = DNA  length = 3900
FEATURE                Location/Qualifiers
misc_feature           1..3900
                       note = Synthetic polynucleotide.Codon optimized FnCpf1-CO7
source                 1..3900
                       mol_type = other DNA
                       organism = synthetic construct
SEQUENCE: 51
atgtccatct atcaggaatt tgttaacaag tactctctta gcaaaactct taggttcgaa  60
ttgatacctc agggaaagac acttgagaat attaaggcgc gcgggctgat acttgatgat  120
gaaaagcggg caaaggacta taagaaagct aagcaaataa ttgataagta ccaccagttt  180
tttattgaag agatcctgtc ctccgtttgt atatccgaag acttgcttca gaattactca  240
gatgtttatt ttaaattgaa gaaatctgac gatgataatc ttcaaaagga tttcaaatcg  300
gcaaaagaca caatcaaaaa acagattagc gagtacatca aggactccga aaagtttaag  360
aatctcttta atcagaatct tatagacgca aagaaaggac aggaatcgga cttgattttg  420
tggttgaagc agtccaagga taacgggata gaactcttta aagccaactc cgatataacg  480
gacatcgacg aagccctcga aatcattaag tcgtttaaag gttggaccac gtacttcaaa  540
ggattccacg agaacagaaa gaacgtttac tcgagcaacg acattcctac tagcatcata  600
tatagaatag tggatgataa tttgcccaaa ttccttgaga acaaggcaaa atatgaatcc  660
ctgaaagaca aggcgcccga agctatcaac tacgagcaga taaagaaaga tctggctgag  720
gagctgacgt ttgacattga ttacaaaaca agcgaggtca accagagggt tttttcgctg  780
gacgaggttt ttgaaatagc gaattttaat aactacctga accaatccgg catcactaaa  840
tttaacacaa tcataggggg gaagttcgtg aacggagaga acacaaagcg caaagggatt  900
aatgagtaca tcaatttgta cagccagcag atcaatgaca aaacgttgaa gaaatataag  960
atgagcgtct tgtttaagca gattctctcg gatacggaat ccaaatcatt cgtcattgac  1020
aagctggagg atgacagcga tgtggtgaca actatgcagt ccttctatga acaaattgca  1080
gcttttaaaa cggtcgaaga gaagtcgatt aaagaaacgc tttcgctcct gttcgatgac  1140
ctgaaagcgc agaagctgga cctttcgaag atatatttca aaaacgataa gtcactcacg  1200
gaccttagcc aacaggtttt cgatgactat tctgtcatag ggactgctgt gcttgagtat  1260
attactcagc aaatagcccc caaaaacctg gacaacccgt ctaagaagga acaagagctg  1320
atagcgaaga aaacagagaa agctaaatat ctttcacttg aaactataaa gcttgcactg  1380
gaggaattca acaaacatcg cgacatcgac aagcagtgca gatttgagga gatcttggcc  1440
aacttcgcag ctattccaat gatttttgac gagatagcac agaataagga caacctggca  1500
cagattagca taaaatacca gaatcagggg aagaaggatc ttcttcaggc ttcggctgag  1560
gacgatgtca aagccatcaa agatctgctc gaccagacca acaatttgtt gcataaactc  1620
aagatcttcc acatatcgca gtccgaagat aaagcgaaca tacttgacaa agacgaacat  1680
ttttatcttg ttttcgagga gtgttatttt gagttggcaa acatcgttcc cctctacaac  1740
aaaattcgca actatataac tcagaagccc tattctgacg agaaattcaa acttaatttc  1800
gaaaacagca ctctcgcaaa cggctgggat aaaaacaagg aacccgacaa caccgccata  1860
ctttttatta aggatgataa atattatttg ggcgtgatga ataaaaagaa caataaaata  1920
ttcgatgata aagcaattaa ggaaaataaa ggggaagggt ataaaaaaat cgtgtataag  1980
ctgcttccag gagctaataa aatgctgcca aaagtcttct tctctgccaa gtcgatcaag  2040
ttttacaatc cttctgaaga tattttgcgg atcagaaatc actctactca cactaaaaac  2100
ggttcacccc agaaaggata cgagaagttt gagttcaaca tcgaagactg tcggaagttt  2160
atcgactttt acaagcagtc tatatcaaaa caccccgaat ggaaagattt tggttttcgg  2220
ttcagcgaca cgcagagata taattcaatt gatgagttct acagggaggt ggagaaccaa  2280
gggtataaac ttacttttga gaacatttcc gaatcctata ttgattcggt ggtcaatcag  2340
gggaaactgt acctgtttca gatatataac aaagacttct ccgcgtattc taaaggacgg  2400
cccaatctcc atactcttta ttggaaggcg ctgtttgacg agcggaacct tcaggatgtt  2460
gtctataagt tgaacgggga agctgagctg ttctatcgga agcagtctat tccaaaaaag  2520
ataacgcacc ccgcgaagga ggcaattgca aacaagaaca aagacaatcc aaagaaggag  2580
tcggtgtttg agtacgatct gataaaagac aaaaggttta ccgaggacaa gttttttttc  2640
cactgtccga tcaccatcaa ttttaagtct tccggcgcca acaaattcaa tgacgaaata  2700
aatctgctgc tcaaggaaaa ggcaaatgat gttcatattc tgtcgataga ccgcggggaa  2760
agacacctcg cgtattatac attggtcgat gggaaaggca atattatcaa acaagacacc  2820
ttcaatatca ttggtaacga taggatgaaa acgaactatc atgataaact tgcagctatt  2880
gaaaaggaca gagactcggc tcggaaagat tggaaaaaga tcaataacat caaggaaatg  2940
aaggaagggt atctctccca ggtcgttcat gaaatcgcca aactggttat tgagtacaat  3000
gctatagtgg tttttgaaga tcttaatttt gggtttaaga gagggagatt taaagtcgag  3060
aaacaggttt atcaaaaact tgaaaaaatg ttgatagaaa aattgaacta tcttgtgttt  3120
aaggacaatg agttcgataa aaccgggggg gttttgagag cttatcaact gacggctccc  3180
ttcgagacat tcaaaaaaat ggggaagcag accggcatca tttattatgt gcccgcgggc  3240
ttcacttcta aaatttgtcc tgtgacaggg ttcgtgaacc aattgtaccc caagtacgaa  3300
agcgtctcca agtcccaaga attctttagc aagtttgaca aaatttgcta taacctggac  3360
aaagggtact ttgagttttc ctttgattat aagaatttcg gggataaagc tgcgaaaggt  3420
aagtggacga tagcctcttt cgggtcgcgc cttattaact tcaggaattc cgacaaaaac  3480
cataattggg acacccgcga ggtctaccct acaaaggaac tcgaaaagtt gcttaaggat  3540
tattcaatag agtatggtca tggcgagtgt attaaggctg ctatctgtgg tgagtcagat  3600
aagaaattct tcgcgaaatt gacatctgtt ttgaacacca tcctccaaat gaggaactct  3660
aaaacgggga cggagcttga ttatctcatc tcacccgttg ctgatgtgaa cggtaatttc  3720
tttgattcac gccaagcccc gaagaacatg ccccaagacg ccgatgctaa cggcgcttat  3780
catataggc tgaaggggct catgcttctg ggcgcatca aaaataacca agaagggaag  3840
aaactcaatc tggttatcaa aaatgaggaa tatttcgaat tcgtgcaaaa ccgcaacaat  3900

SEQ ID NO: 52          moltype = DNA  length = 705
FEATURE                Location/Qualifiers
```

```
source                  1..705
                        mol_type = unassigned DNA
                        organism = Entacmaea quadricolor
SEQUENCE: 52
gtgagcaagg gcgaggagaa taacatggcc atcatcaagg agttcatgcg cttcaaggtg  60
cgcatggagg gctccgtgaa cggccacgag ttcgagatcg agggcgaggg cgagggccgc  120
ccctacgagg gctttcagac cgctaagctg aaggtgacca agggtggccc cctgcccttc  180
gcctgggaca tcctgtcccc tcatttcacc tacggctcca aggcctacgt gaagcacccc  240
gccgacatcc ccgactactt caagctgtcc ttccccgagg gcttcaagtg ggagcgcgtg  300
atgaactacg aggacggcgg cgtggtgacc gtgacccagg actcctccct gcaggacggc  360
gagttcatct acaaggtgaa gctgcgcggc accaacttcc cctccgacgg ccccgtgatg  420
cagaagaaga ccatgggctg ggaggcctcc tccgagcgga tgtaccccga ggacggtgcc  480
ctgaagggca agatcaagat gaggctgaag ctgaaggacg gcggccacta cacctccgag  540
gtcaagacca cctacaaggc caagaagccc gtgcagctgc ccggcgccta catcgtcgac  600
atcaagttgg acatcacctc ccacaacgag gactacacca tcgtggaaca gtacgaacgc  660
gccgagggcc gccactccac cggcggcatg gacgagctgt acaag                 705

SEQ ID NO: 53           moltype = DNA  length = 4674
FEATURE                 Location/Qualifiers
misc_feature            1..4674
                        note = Synthetic polynucleotide.NLS-FnCpf1-CO1-mOR-NLS
source                  1..4674
                        mol_type = other DNA
                        organism = synthetic construct
SEQUENCE: 53
ggtagcaaaa agaggcgtat caagcaggac atgtctatct atcaagagtt tgtcaacaag  60
tacagcttaa gtaagacact tcgcttcgag ttgatccctc aggggaagac actggaaaac  120
atcaaggcga ggggccttat cctggacgac gagaagcggg ctaaagacta caaaaaagct  180
aaacagataa ttgacaagta tcaccaattt tttattgagg agatcctctc ctctgtgtgc  240
ataagtgagg atctgctcca gaactattcg gatgtttact ttaaactcaa gaagtccgat  300
gatgacaacc ttcagaagga cttcaagtcc gccaaagaca cgattaagaa acaaatcagt  360
gagtacatca aggatagcga gaaattcaag aacctgttca accagaactt aattgatgcc  420
aaaaagggcc aagaatccga cctcatcctg tggttaaagc aatctaaaga caacggtatt  480
gagctgttca aggcaaacag cgacattaca gacattgacg aggccctaga gatcatcaag  540
tcattcaaag gctggacgac ttactttaaa ggttttcacg agaaccgtaa gaatgtttac  600
tcaagtaacg atataccaac gagcattatc taccgaatag tggatgataa cctaccgaag  660
ttccttgaga acaaagcgaa gtacgagtct ctcaaagaca aggcccctga ggccatcaac  720
tacgagcaga ttaagaagga tctcgccgag gagctaacct tcgacattga ctacaaaaca  780
tcggaagtga atcagagggt gttctcgctt gatgaagtat tcgagattgc taacttcaac  840
aattacctga accagagtgg tattactaag ttcaacacaa tcattggagg caaattcgtg  900
aacggcgaaa acacaaagcg aaaagggata aacgagtaca ttaacttgta cagccagcag  960
atcaacgata agacactcaa gaagtataag atgtctgtgc tgttcaaaca aatcttaagc  1020
gacacggaaa gcaagtcgtt cgtaattgac aagctggaag acgattctga cgtggttaca  1080
accatgcagt ccttttacga gcagattgcc gcattcaaga ccgtggagga aaagtcgatc  1140
aaggaaacac tttcgttgct tttcgacgac cttaaagctc agaagctcga cttaagcaag  1200
atatacttta agaacgataa gagcttgaca gacttgagcc agcaagtctt tgacgactac  1260
agcgttatcg gaactgccgt tctggagtac ataacacagc agatcgcacc caagaacctt  1320
gacaaccctt ccaagaaaga acaagagttg atcgccaaga agactgaaaa ggctaagtac  1380
ctctctctgg agactatcaa gctcgctctt gaggagttta acaagcacag ggacattgac  1440
aagcaatgcc gattcgagga aatactggca aacttcgcag ccatacccat gatattcgat  1500
gagatagccc agaacaagga taacttggcc caaatctcga ttaagtatca gaaccagggc  1560
aaaaaggacc ttctacaggc tagtgcagag gacgatgtga aggctattaa ggacttatta  1620
gatcagacaa acaaccttct gcataagctc aagatattcc atatctccca gtcagaggac  1680
aaggccaaca ttctggataa ggacgagcac ttctatctcg tattcgagga atgttacttt  1740
gagctggcca atatcgttcc cttgtacaac aaaatccgga actacatcac acagaagccc  1800
tacagtgatg agaagttcaa attgaacttt gaaaactcaa cacttgctaa tggttgggac  1860
aagaataagg aacctgacaa cactgccatc ctctttatta aagatgataa gtactacctc  1920
ggggtgatga ataagaagaa caacaaaatc ttcgatgaca aagctattaa ggagaacaaa  1980
ggtgaagggt acaagaagat tgtctacaaa ctgctgcctg gtgccaacaa aatgctacca  2040
aaggtatttt tcagcgccaa atctattaag ttctacaatc caagcgagga tattctccgg  2100
atacggaatc actctacaca taccaagaat ggaagtccac aaaagggtta cgagaaattc  2160
gagttcaaca ttgaagactg ccggaaattc attgacttct acaagcaatc catctctaaa  2220
catcctgaat ggaaagactt cggtttccgc ttcagtgata ctcaacggta caattcaatt  2280
gacgaattct accgtgaggt tgagaaccag ggtacaaac tgaccttcga gaacatatca  2340
gagagctaca tcgactcagt ggttaatcag gggaagctat atctgtttca aatctacaac  2400
aaagacttta gtgcctactc taaagggcgg ccaaacttac acacacttta ctggaaggca  2460
ctattcgacg aacgcaatct acaagatgta gtttacaaat tgaacggtga ggctgagttg  2520
ttctaccgta aacaatctat acccaagaag ataacacacc ctgctaaaga ggcaattgca  2580
aacaaaaaca aggataatcc caaaaaggag tctgtctttg agtatgacct cattaaggat  2640
aagcggttca cggaggacaa gttcttcttc cattgtccaa taaccatcaa cttcaaatca  2700
tccggcgcaa acaaattcaa tgacgagatc aacctgttac taaaggagaa ggctaacgat  2760
gttcacatct tatctattga tcgaggtgag agacacctag cctactacac tttagtggat  2820
gggaagggga acatcatcaa gcaagacacc ttcaacatca ttgggaacga caggatgaag  2880
actaactacc atgataagct cgccgctatt gaaaaggaca gggactctgc caggaaggac  2940
tggaaaaaaa ttaacaatat taaagagatg aaggagggct acctgagcca agtagtccat  3000
gagatagcaa aactggtgat tgagtacaac gcaatagtcg tattcgagga cttaaacttc  3060
ggcttcaaac gtgggcggtt taaggtggag aaacaagtct atcagaaatt ggagaagatg  3120
ctaatcgaga agctcaacta cctcgtgttt aaagacaacg agtttgacaa aactggagga  3180
gtcctgcggg cataccaact gaccgcaccc ttcgagacat tcaagaagat gggaaagcag  3240
```

-continued

```
actggcatca tctattacgt gccagcgggt tttacttcca aaatctgtcc agttacaggc  3300
ttcgtgaacc agttgtaccc gaagtacgag tctgtttcca agtcacagga attcttctca  3360
aagtttgaca agatatgtta caatctcgat aagggatact ttgagtttag tttcgactac  3420
aagaactttg gcgataaggc cgcaaaaggg aaatggacaa ttgcatcctt cgggtcacgc  3480
cttattaact ttcgtaactc agacaagaac cacaattggg acaccaggga ggtgtaccct  3540
actaaggagc tggagaagct acttaaagac tactcgattg agtacggaca tggagagtgc  3600
atcaaggcag caatatgtgg ggaatctgac aaaaagttct ttgccaagct gacctctgta  3660
ctgaacacta ttctccaaat gagaaatagt aagactggca cagagttgga ctacctgatc  3720
tctccagtgg ctgacgttaa tgggaatttt ttcgactcaa gacaagctcc caagaatatg  3780
ccacaggacg cagatgcaaa cggggcatat cacatcgggc ttaaaggact catgctacta  3840
gggcggatca agaataatca ggagggcaaa aagctgaacc tagtcatcaa gaacgaggag  3900
tacttcgaat ttgtccagaa tcgtaacaac ggatctggag tgagcaaggg cgaggagaat  3960
aacatggcca tcatcaagga gttcatgcgc ttcaaggtgc gcatggaggg ctccgtgaac  4020
ggccacgagt tcgagatcga gggcgagggc gagggccgcc cctacgaggg ctttcagacc  4080
gctaagctga aggtgaccaa gggtggcccc ctgcccttcg cctgggacat cctgtcccct  4140
catttcacct acggctccaa ggcctacgtg aagcaccccg ccgacatccc cgactacttc  4200
aagctgtcct tccccgaggg cttcaagtgg gagcgcgtga tgaactacga ggacggcggc  4260
gtggtgaccg tgacccagga ctcctccctg caggacggcg agttcatcta caaggtgaag  4320
ctgcgcggca ccaacttccc ctccgacggc cccgtgatgc agaagaagac catgggctgg  4380
gaggcctcct ccgagcggat gtaccccgag gacggtgccc tgaagggcaa gatcaagatg  4440
aggctgaagc tgaaggacgg cggccactac acctccgagg tcaagaccac ctacaaggcc  4500
aagaagcccg tgcagctgcc cggcgcctac atcgtcgaca tcaagttgga catcacctcc  4560
cacaacgagg actacaccat cgtggaacag tacgaacgcg ccgagggccg ccactccacc  4620
ggcggcatgg acgagctgta caagggatct aagaagcgta ggatcaagca agat        4674

SEQ ID NO: 54          moltype = DNA  length = 33
FEATURE                Location/Qualifiers
misc_feature           1..33
                       note = Synthetic polynucleotide.MGSS7H His tag comprising
                        sevenHistidine residues
source                 1..33
                       mol_type = other DNA
                       organism = synthetic construct
SEQUENCE: 54
atgggcagca gccatcatca ccaccatcac cat                               33

SEQ ID NO: 55          moltype = DNA  length = 4710
FEATURE                Location/Qualifiers
misc_feature           1..4710
                       note = Synthetic
                        polynucleotide.MGSS7H-NLS-FnCpf1-CO1-mOR-NLS
source                 1..4710
                       mol_type = other DNA
                       organism = synthetic construct
SEQUENCE: 55
atgggcagca gccatcatca ccaccatcac catatgggta gcaaaaagag gcgtatcaag  60
caggacatgt ctatctatca agagtttgtc aacaagtaca gcttaagtaa gacacttcgc  120
ttcgagttga tccctcaggg gaagacactg gaaaacatca aggcgagggg ccttatcctg  180
gacgacgaga agcgggctaa agactacaaa aaagctaaac agataattga caagtatcac  240
caattttta ttgaggagat cctctcctct gtgtgcataa gtgaggatct gctccagaac  300
tattcggatg tttactttaa actcaagaag tccgatgatg acaaccttca gaaggacttc  360
aagtccgcca aagacacgat taagaaacaa atcagtgagt acatcaagga tagcgagaaa  420
ttcaagaacc tgttcaacca gaacttaatt gatgccaaaa agggccaaga atccgacctc  480
atcctgtggt taaagcaatc taaagacaac ggtattgagc tgttcaaggc aaacagcgac  540
attacagaca ttgacgaggc cctagagatc atcaagtcat tcaaaggctg gacgacttac  600
tttaaaggtt ttcacgagaa ccgtaagaat gtttactcaa gtaacgatat accaacgagc  660
attatctacc gaatagtgga tgataaccta ccgaagttcc ttgagaacaa agcgaagtac  720
gagtctctca aagacaaggc cctgaggcc atcaactacg agcagattaa gaaggatctc  780
gccgaggagc taaccttcga cattgactac aaaacatcgg aagtgaatca gagggtgttc  840
tcgcttgatg aagtattcga gattgctaac ttcaacaatt acctgaacca gagtggtatt  900
actaagttca acacaatcat tggaggcaaa ttcgtgaacg gcgaaaacac aaagcgaaaa  960
gggataaacg agtacattaa cttgtacagc cagcagatca acgataagac actcaagaag  1020
tataagatgt ctgtgctgtt caaacaaatc ttaagcgaca cggaaagcaa gtcgttcgta  1080
attgacaagc tggaagacga ttctgacgtg gttacaacca tgcagtcctt ttacgagcag  1140
attgccgcat tcaagaccgt ggaggaaaag tcgatcaagg aaacactttc gttgcttttc  1200
gacgacctta aagctcagaa gctcgactta agcaagatat actttaagaa cgataagagc  1260
ttgacagact tgagccagca agtctttgac gactacagcg ttatcggaac tgccgttctg  1320
gagtacataa cacagcagat cgcacccaag aaccttgaca acccttccaa gaaagaacaa  1380
gagttgatcg ccaagaagac tgaaaaggct aagtacctct ctctggagac tatcaagctc  1440
gctcttgagg agtttaacaa gcacagggac attgacaagc aatgccgatt cgaggaaata  1500
ctggcaaact tcgcagccat acccatgata ttcgatgaga tagcccagaa caaggataac  1560
ttggcccaaa tctcgattaa gtatcagaac cagggcaaaa aggaccttct acaggctagt  1620
gcagaggacg atgtgaaggc tattaaggac ttattagatc agacaaacaa ccttctgcat  1680
aagctcaaga tattccatat ctcccagtca gaggacaagg ccaacattct ggataaggac  1740
gagcacttct atctcgtatt cgaggaatgt tactttgagc tggccaatat cgttccccttg  1800
tacaacaaaa tccggaacta catcacacag aagccctaca gtgatgagaa gttcaaattg  1860
aactttgaaa actcaacact tgctaatggt tgggacaaga ataaggaacc tgacaacact  1920
gccatcctct ttattaaaga tgataagtac tacctcgggg tgatgaataa gaagaacaac  1980
aaaatcttcg atgacaaagc tattaaggag aacaaaggtg aagggtacaa gaagattgtc  2040
```

-continued

```
tacaaactgc tgcctggtgc caacaaaatg ctaccaaagg tatttttcag cgccaaatct  2100
attaagttct acaatccaag cgaggatatt ctccggatac ggaatcactc tacacatacc  2160
aagaatggaa gtccacaaaa gggttacgag aaattcgagt tcaacattga agactgccgg  2220
aaattcattg acttctacaa gcaatccatc tctaaacatc ctgaatggaa agacttcggt  2280
ttccgcttca gtgatactca acggtacaat tcaattgacg aattctaccg tgaggttgag  2340
aaccaggggt acaaactgac cttcgagaac atatcagaga gctacatcga ctcagtggtt  2400
aatcagggga agctatatct gtttcaaatc tacaacaaag actttagtgc ctactctaaa  2460
gggcggccaa acttacacac actttactgg aaggcactat tcgacgaacg caatctacaa  2520
gatgtagttt acaaattgaa cggtgaggct gagttgttct accgtaaaca atctataccc  2580
aagaagataa cacaccctgc taaagaggca attgcaaaca aaaacaagga taatcccaaa  2640
aaggagtctg tctttgagta tgacctcatt aaggataagc ggttcacgga ggacaagttc  2700
ttcttccatt gtccaataac catcaacttc aaatcatccg gcgcaaacaa attcaatgac  2760
gagatcaacc tgttactaaa ggagaaggct aacgatgttc acatcttatc tattgatcga  2820
ggtgagagac acctagccta ctacacttta gtggatggga aggggaacat catcaagcaa  2880
gacaccttca acatcattgg gaacgacagg atgaagacta actaccatga taagctcgcc  2940
gctattgaaa aggacaggga ctctgccagg aaggactgga aaaaaattaa caatattaaa  3000
gagatgaagg agggctacct gagccaagta gtccatgaga tagcaaaact ggtgattgag  3060
tacaacgcaa tagtcgtatt cgaggactta aacttcggct tcaaacgtgg gcggtttaag  3120
gtggagaaac aagtctatca gaaattggag aagatgctaa tcgagaagct caactacctc  3180
gtgtttaaag acaacgagtt tgacaaaact ggaggagtcc tgcgggcata ccaactgacc  3240
gcacccttcg agacattcaa gaagatggga aagcagactg gcatcatcta ttacgtgcca  3300
gcgggtttta cttccaaaat ctgtccagtt acaggcttcg tgaaccagtt gtacccgaag  3360
tacgagtctg tttccaagtc acaggaattc ttctcaaagt ttgacaagat atgttacaat  3420
ctcgataagg gatactttga gtttagtttc gactacaaga actttggcga taaggccgca  3480
aaagggaaat ggacaattgc atccttcggg tcacgcctta ttaactttcg taactcagac  3540
aagaaccaca attgggacac cagggaggtg taccctacta aggagctgga gaagctactt  3600
aaagactact cgattgagta cggacatgga gagtgcatca aggcagcaat atgtggggaa  3660
tctgacaaaa agttctttgc caagctgacc tctgtactga acactattct ccaaatgaga  3720
aatagtaaga ctggcacaga gttggactac ctgatctctc cagtggctga cgttaatggg  3780
aattttttcg actcaagaca agctcccaag aatatgccac aggacgcaga tgcaaacggg  3840
gcatatcaca tcgggcttaa aggactcatg ctactagggc ggatcaagaa taatcaggag  3900
ggcaaaaagc tgaacctagt catcaagaac gaggagtact tcgaatttgt ccagaatcgt  3960
aacaacggat ctggagtgag caagggcgag gagaataaca tggccatcat caaggagttc  4020
atgcgcttca aggtgcgcat ggagggctcc gtgaacggcc acgagttcga gatcgagggc  4080
gagggcgagg gccgccccta cgagggcttt cagaccgcta agctgaaggt gaccaagggt  4140
ggccccctgc ccttcgcctg ggacatcctg tcccctcatt tcacctacgg ctccaaggcc  4200
tacgtgaagc accccgccga catccccgac tacttcaagc tgtccttccc cgagggcttc  4260
aagtgggagc gcgtgatgaa ctacgaggac ggcggcgtgg tgaccgtgac ccaggactcc  4320
tccctgcagg acggcgagtt catctacaag gtgaagctgc gcggcaccaa cttccccctcc 4380
gacggccccg tgatgcagaa gaagaccatg ggctgggagg cctcctccga gcggatgtac  4440
cccgaggacg gtgccctgaa gggcaagatc aagatgaggc tgaagctgaa ggacggcggc  4500
cactacacct ccgaggtcaa gaccacctac aaggccaaga agcccgtgca gctgcccggc  4560
gcctacatcg tcgacatcaa gttggacatc acctcccaca acgaggacta caccatcgtg  4620
gaacagtacg aacgcgccga gggccgccac tccaccggcg gcatggacga gctgtacaag  4680
ggatctaaga agcgtaggat caagcaagat                                    4710
```

```
SEQ ID NO: 56          moltype = DNA  length = 6465
FEATURE                Location/Qualifiers
misc_feature           1..6465
                       note = Synthetic polynucleotide.Expression cassette
                        comprising 35Spromoter cassette,
                        MGSS7H-NLS-FnCpf1-CO1-mOr-NLS and NOStranscription
                        termination sequence
source                 1..6465
                       mol_type = other DNA
                       organism = synthetic construct
SEQUENCE: 56
ggtccgattg agacttttca acaaagggta atatccggaa acctcctcgg attccattgc  60
ccagctatct gtcactttat tgtgaagata gtggaaaagg aaggtggctc ctacaaatgc  120
catcattgcg ataaaggaaa ggccatcgtt gaagatgcct ctgccgacag tggtcccaaa  180
gatggacccc cacccacgag gagcatcgtg gaaaaagaag acgttccaac cacgtcttca  240
aagcaagtgg attgatgtga tggtccgatt gagacttttc aacaaagggt aatatccgga  300
aacctcctcg gattccattg cccagctatc tgtcacttta ttgtgaagat agtggaaaag  360
gaaggtggct cctacaaatg ccatcattgc gataaaggaa aggccatcgt tgaagatgcc  420
tctgccgaca gtggtcccaa agatggaccc ccacccacga ggagcatcgt ggaaaaagaa  480
gacgttccaa ccacgtcttc aaagcaagtg gattgatgtg atatctccac tgacgtaagg  540
gatgacgcac aatcccacta tccttcgcaa gacccttcct ctatataagg aagttcattt  600
catttggaga ggacacgctg acaagctgac tctagcagat ctaccgtctt cggtacgcgc  660
tcactccgcc ctctgccttt gttactgcca cgtttctctg aatgctctct tgtgtggtga  720
ttgctgagag tggtttagct ggatctagaa ttacactctg aaatcgtgtt ctgcctgtgc  780
tgattacttg ccgtcctttg tagcagcaaa atatagggac atggtagtac gaaacgaaga  840
tagaacctac acagcaatac gagaaatgtg taatttggtg cttagcggta tttatttaag  900
cacatgttgg tgttataggg cacttggatt cagaagtttg ctgttaattt aggcacaggc  960
ttcatactac atgggtcaat agtataggga ttcatattat aggcgatact ataataattt  1020
gttcgtctgc agagcttatt atttgccaaa attagatatt cctattctgt ttttgtttgt  1080
gtgctgttaa attgttaacg cctgaaggaa taaatataaa tgacgaaatt ttgatgttta  1140
tctctgctcc tttattgtga ccataagtca agatcagatg cacttgtttt aaatattgtt  1200
gtctgaagaa ataagtactg acagtatttt gatgcattga tctgcttgtt tgttgtaaca  1260
aaatttaaaa ataaagagtt tcctttttgt tgctctcctt acctcctgat ggtatctagt  1320
```

-continued

```
atctaccaac tgacactata ttgcttctct ttacatacgt atcttgctcg atgccttctc  1380
cctagtgttg accagtgtta ctcacatagt ctttgctcat ttcattgtaa tgcagatacc  1440
aagcggcctc tagaggatcc aggagcaacc atgggcagca gccatcatca ccaccatcac  1500
catatgggta gcaaaaagag gcgtatcaag caggacatgt ctatctatca agagtttgtc  1560
aacaagtaca gcttaagtaa gacacttcgc ttcgagttga tccctcaggg gaagacactg  1620
gaaaacatca aggcgagggg ccttatcctg gacgacgaga agcgggctaa agactacaaa  1680
aaagctaaac agataattga caagtatcac caatttttta ttgaggagat cctctcctct  1740
gtgtgcataa gtgaggatct gctccagaac tattcggatg tttactttaa actcaagaag  1800
tccgatgatg acaaccttca gaaggacttc aagtccgcca aagacacgat taagaaacaa  1860
atcagtgagt acatcaagga tagcgagaaa ttcaagaacc tgttcaacca gaacttaatt  1920
gatgccaaaa agggccaaga atccgacctc atcctgtggt taaagcaatc taaagacaac  1980
ggtattgagc tgttcaaggc aaacagcgac attacagaca ttgacgaggc cctagagatc  2040
atcaagtcat tcaaaggctg gacgacttac tttaaaggtt ttcacgagaa ccgtaagaat  2100
gtttactcaa gtaacgatat accaacgagc attatctacc gaatagtgga tgataaccta  2160
ccgaagttcc ttgagaacaa agcgaagtac gagtctctca aagacaaggc ccctgaggcc  2220
atcaactacg agcagattaa gaaggatctc gccgaggagc taaccttcga cattgactac  2280
aaaacatcgg aagtgaatca gagggtgttc tcgcttgatg aagtattcga gattgctaac  2340
ttcaacaatt acctgaacca gagtggtatt actaagttca acacaatcat tggaggcaaa  2400
ttcgtgaacg gcgaaaacac aaagcgaaaa gggataaacg agtacattaa cttgtacagc  2460
cagcagatca acgataagac actcaagaag tataagatgt ctgtgctgtt caaacaaatc  2520
ttaagcgaca cggaaagcaa gtcgttcgta attgacaagc tggaagacga ttctgacgtg  2580
gttacaacca tgcagtcctt ttacgagcag attgccgcat tcaagaccgt ggaggaaaag  2640
tcgatcaagg aaacactttc gttgcttttc gacgacctta aagctcagaa gctcgactta  2700
agcaagatat actttaagaa cgataagagc ttgacagact tgagccagca agtctttgac  2760
gactacagcg ttatcggaac tgccgttctg gagtacataa cacagcagat cgcacccaag  2820
aaccttgaca acccttccaa gaaagaacaa gagttgatcg ccaagaagac tgaaaaggct  2880
aagtacctct ctctggagac tatcaagctc gctcttgagg agtttaacaa gcacagggac  2940
attgacaagc aatgccgatt cgaggaaata ctggcaaact tcgcagccat acccatgata  3000
ttcgatgaga tagcccagaa caaggataac ttggcccaaa tctcgattaa gtatcagaac  3060
cagggcaaaa aggaccttct acaggctagt gcagaggacg atgtgaaggc tattaaggac  3120
ttattagatc agacaaacaa ccttctgcat aagctcaaga tattccatat ctcccagtca  3180
gaggacaagg ccaacattct ggataaggac gagcacttct atctcgtatt cgaggaatgt  3240
tactttgagc tggccaatat cgttcccttg tacaacaaaa tccggaacta catcacacag  3300
aagccctaca gtgatgagaa gttcaaattg aactttgaaa actcaacact tgctaatggt  3360
tgggacaaga ataaggaacc tgacaacact gccatcctct ttattaaaga tgataagtac  3420
tacctcgggg tgatgaataa gaagaacaac aaaatcttcg atgacaaagc tattaaggag  3480
aacaaaggtg aagggtacaa gaagattgtc tacaaactgc tgcctggtgc caacaaaatg  3540
ctaccaaagg tatttttcag cgccaaatct attaagttct acaatccaag cgaggatatt  3600
ctccggatac ggaatcactc tacacatacc aagaatggaa gtccacaaaa gggttacgag  3660
aaattcgagt tcaacattga agactgccgg aaattcattg acttctacaa gcaatccatc  3720
tctaaacatc ctgaatggaa agacttcggt ttccgcttca gtgatactca acggtacaat  3780
tcaattgacg aattctaccg tgaggttgag aaccaggggt acaaactgac cttcgagaac  3840
atatcagaga gctacatcga ctcagtggtt aatcagggga agctatatct gtttcaaatc  3900
tacaacaaag actttagtgc ctactctaaa gggcggccaa acttacacac actttactgg  3960
aaggcactat tcgacgaacg caatctacaa gatgtagttt acaaattgaa cggtgaggct  4020
gagttgttct accgtaaaca atctataccc aagaagataa cacaccctgc taaagaggca  4080
attgcaaaca aaaacaagga taatcccaaa aaggagtctg tctttgagta tgacctcatt  4140
aaggataagc ggttcacgga ggacaagttc ttcttccatt gtccaataac catcaacttc  4200
aaatcatccg gcgcaaacaa attcaatgac gagatcaacc tgttactaaa ggagaaggct  4260
aacgatgttc acatcttatc tattgatcga ggtgagagac acctagccta ctacacttta  4320
gtggatggga aggggaacat catcaagcaa gacaccttca acatcattgg gaacgacagg  4380
atgaagacta actaccatga taagctcgcc gctattgaaa aggacaggga ctctgccagg  4440
aaggactgga aaaaaattaa caatattaaa gagatgaagg agggctacct gagccaagta  4500
gtccatgaga tagcaaaact ggtgattgag tacaacgcaa tagtcgtatt cgaggactta  4560
aacttcggct tcaaacgtgg gcggtttaag gtggagaaac aagtctatca gaaattggag  4620
aagatgctaa tcgagaagct caactacctc gtgtttaaag acaacgagtt tgacaaaact  4680
ggaggagtcc tgcgggcata ccaactgacc gcacccttcg agacattcaa gaagatggga  4740
aagcagactg gcatcatcta ttacgtgcca gcgggtttta cttccaaaat ctgtccagtt  4800
acaggcttcg tgaaccagtt gtacccgaag tacgagtctg tttccaagtc acaggaattc  4860
ttctcaaagt ttgacaagat atgttacaat ctcgataagg gatactttga gtttagtttc  4920
gactacaaga actttggcga taaggccgca aaagggaaat ggacaattgc atccttcggg  4980
tcacgcctta ttaactttcg taactcagac aagaaccaca attgggacac cagggaggtg  5040
taccctacta aggagctgga gaagctactt aaagactact cgattgagta cggacatgga  5100
gagtgcatca aggcagcaat atgtggggaa tctgacaaaa agttctttgc caagctgacc  5160
tctgtactga acactattct ccaaatgaga aatagtaaga ctggcacaga gttggactac  5220
ctgatctctc cagtggctga cgttaatggg aatttttttcg actcaagaca agctcccaag  5280
aatatgccac aggacgcaga tgcaaacggg gcatatcaca tcgggcttaa aggactcatg  5340
ctactagggc ggatcaagaa taatcaggag ggcaaaaagc tgaacctagt catcaagaac  5400
gaggagtact tcgaatttgt ccagaatcgt aacaacggat ctggagtgag caagggcgag  5460
gagaataaca tggccatcat caaggagttc atgcgcttca aggtgcgcat ggagggctcc  5520
gtgaacggcc acgagttcga gatcgagggc gagggcgagg gccgccccta cgagggcttt  5580
cagaccgcta agctgaaggt gaccaagggt ggccccctgc ccttcgcctg ggacatcctg  5640
tcccctcatt tcacctacgg ctccaaggcc tacgtgaagc accccgccga catccccgac  5700
tacttcaagc tgtccttccc cgagggcttc aagtgggagc gcgtgatgaa ctacgaggac  5760
ggcggcgtgg tgaccgtgac ccaggactcc tccctgcagg acggcgagtt catctacaag  5820
gtgaagctgc gcggcaccaa cttcccctcc gacggccccg tgatgcagaa gaagaccatg  5880
ggctgggagg cctcctccga gcggatgtac cccgaggacg gtgccctgaa gggcaagatc  5940
aagatgaggc tgaagctgaa ggacggcggc cactacacct ccgaggtcaa gaccacctac  6000
aaggccaaga agcccgtgca gctgcccggc gcctacatcg tcgacatcaa gttggacatc  6060
```

```
acctcccaca acgaggacta caccatcgtg gaacagtacg aacgcgccga gggccgccac  6120
tccaccggcg gcatggacga gctgtacaag ggatctaaga agcgtaggat caagcaagat  6180
tagaacccag cggtactcgc tgaggaattc gcgatcgttc aaacatttgg caataaagtt  6240
tcttaagatt gaatcctgtt gccggtcttg cgatgattat catataattt ctgttgaatt  6300
acgttaagca tgtaataatt aacatgtaat gcatgacgtt atttatgaga tgggttttta  6360
tgattagagt cccgcaatta tacatttaat acgcgataga aaacaaaata tagcgcgcaa  6420
actaggataa attatcgcgc gcggtgtcat ctatgttact agatc                  6465

SEQ ID NO: 57           moltype = DNA  length = 4674
FEATURE                 Location/Qualifiers
misc_feature            1..4674
                        note = Synthetic polynucleotide.NLS-FnCpf1-CO2-mOR-NLS
source                  1..4674
                        mol_type = other DNA
                        organism = synthetic construct
SEQUENCE: 57
ggtagcaaaa agaggcgtat caagcaggac atgtccatat accaggagtt cgtcaacaag  60
tactcgctca gcaagacgct ccgcttcgag ctgatccccc agggtaagac cctggagaac  120
atcaaggcgc gcggactcat cctcgacgac gagaagcggg ctaaggacta caaaaaggcc  180
aagcagatca tcgacaagta ccaccagttc ttcatcgagg agatcctctc ctccgtctgc  240
atctccgagg acctcctcca gaactacagc gacgtctact tcaagctcaa aaagtcggac  300
gacgacaacc tccagaagga cttcaagtcg gcgaaggaca ccatcaagaa gcagatcagc  360
gagtacatca aggactccga gaagttcaag aacctgttca accagaacct gatcgacgcc  420
aagaagggcc aggagtcgga cctgatcctg tggctcaagc agagcaagga caacggcatc  480
gagctcttca aggccaacag cgacatcacg gacatcgacg aggccctgga gatcatcaag  540
tcgttcaagg gctggacgac ctacttcaag ggcttccacg agaaccgcaa gaacgtctat  600
agctccaacg acatccccac ctcgatcatc taccggatcg tggacgacaa cctccccaag  660
ttcctggaga acaaggcgaa gtacgagtcg ttgaaggaca aggcgccgga ggcgatcaac  720
tacgagcaga tcaagaagga cctggccgag gagctgacct tcgacatcga ctacaagacg  780
tcggaggtga accagcgggt gttcagtctg gacgaggtct tcgagatcgc gaacttcaac  840
aactacctga accagtcggg gatcaccaag ttcaacacga tcataggcgg caagttcgtg  900
aacggcgaga acaccaagcg caaggggata aacgagtaca tcaacctgta cagccagcag  960
atcaacgaca agacgctcaa gaagtacaag atgagcgtgc tcttcaagca gatcctcagt  1020
gacaccgagt ccaagagctt cgtgatcgac aagctggagg acgacagcga cgtcgtgaca  1080
accatgcaga gcttctacga gcagatcgcc gcgttcaaga ccgtcgagga gaagtcaatc  1140
aaggagacgc tctccttgct gttcgacgac ctgaaggcac aaaagctgga cctcagcaag  1200
atctacttca agaacgacaa gtccctgacc gacctgagcc agcaggtttt cgacgactac  1260
tccgtcatcg ggactgccgt cctggagtac atcacccagc agatcgctcc gaagaacctc  1320
gacaacccgt ccaagaagga gcaggagctg attgcgaaga agacagagaa ggccaagtac  1380
ctctccctcg agaccatcaa gctcgccctg gaggagttca acaagcacag ggacattgac  1440
aagcagtgcc gtttcgagga gatcctggcc aacttcgcgg ccatccccat gatcttcgac  1500
gagatcgccc agaacaagga caacctggcg cagatctcta tcaagtacca gaaccagggg  1560
aagaaggact tgctccaggc ctcagcggag gacgacgtga aggccatcaa ggacctgctc  1620
gaccagacga acaacttgct ccacaagctc aagatctttc acatcagcca gagcgaggac  1680
aaggccaaca tcctcgacaa ggacgagcac ttctacctcg tgttcgagga gtgctacttc  1740
gagctggcca acatcgtgcc actttacaac aagatccgca actacatcac gcagaagccg  1800
tactccgacg agaagttcaa gctgaacttc gagaactcca ccctcgccaa cggctgggac  1860
aagaacaagg agccggacaa caccgcgatc ctgttcataa aggacgacaa gtactacttg  1920
ggggtcatga acaagaagaa caacaagata ttcgacgaca aggccatcaa ggagaacaag  1980
ggggagggct acaagaagat cgtctacaag ctcctccccg gcgcgaacaa gatgctgcct  2040
aaggtcttct tttccgccaa gagtatcaag ttctacaacc cctccgagga catcctccgc  2100
atccggaacc acagcacgca cacaaagaac ggctcgcctc agaagggcta cgagaagttc  2160
gagttcaaca tcgaggactg ccggaagttc atcgacttct acaagcagag catctccaag  2220
caccccgagt ggaaggactt tggcttcagg ttctcagaca cccagcggta caactccatc  2280
gacgagttct accgcgaggt ggagaaccag ggctacaagc tgaccttcga gaatatatca  2340
gagtcgtaca tcgacagcgt ggtgaaccag ggcaagttgt acctgttcca gatctacaac  2400
aaggacttct ccgcctactc aaagggggcgt ccaaacctgc acacgctgta ctggaaggcg  2460
ctcttcgacg agcgcaacct acaagatgtt gtatacaagc tcaacggcga ggcggaactg  2520
ttctatagga agcagtcgat ccccaagaag attacgcacc cggctaagga ggccatcgcc  2580
aacaagaaca aggacaaccc caagaaggag tccgtgttcg agtacgacct catcaaggac  2640
aagaggttca cggaggacaa gtttttcttc cactgcccaa tcactatcaa tttcaagtcg  2700
agcggagcca acaagttcaa cgacgagata aacctgctcc tcaaggagaa ggccaatgac  2760
gtgcacatcc tctccatcga ccggggcgag cggcacctgg cgtactacac gctggtggac  2820
ggcaagggca acatcatcaa gcaggacacc ttcaacatca tcgggaacga ccgcatgaag  2880
accaactacc acgacaagct cgccgccatc gagaaggaca gggactccgc gcgcaaggac  2940
tggaagaaga ttaacaacat caaggagatg aaggagggct acctcagcca ggtggtccac  3000
gagatcgcca agctcgtcat tgagtacaac gccatcgtcg tcttcgagga cctgaatttc  3060
ggcttcaagc gcggccggtt caaggtggag aagcaggtct accagaagct tgagaagatg  3120
ctgatcgaga agctgaacta cctggtgttc aaggacaacg agttcgacaa gaccggcgga  3180
gtgctgcgcg cctaccagct cacggcgcct ttcgagacgt tcaagaagat gggcaagcag  3240
acgggcatca tctactacgt gcccgccggc ttcacctcta agatctgccc agtgaccggc  3300
ttcgttaacc agctgtaccc gaagtacgag agcgtgtcca agtcccagga gttcttctcc  3360
aagttcgaca agatttgtta caacctcgac aagggctact tcgagttttc gttcgactac  3420
aagaactttg gcgacaaggc ggccaagggg aagtggacca tcgcctcttt cggcagcagg  3480
ctcatcaatt tccggaactc cgacaagaac cacaactggg acacgcgcga ggtgtacccg  3540
acgaaggagc tggagaagct gctcaaggac tactccatcg agtacggcca cggcgagtgc  3600
atcaaggcgg cgatctgcgg ggagagcgac aagaagttct ttgccaagct gaccagcgtg  3660
ctgaacacca tcctccagat gcggaactcc aagaccggca ccgagctgga ctacctgatc  3720
tccccggtcg cggacgtcaa cgggaacttc ttcgactccc gacaggctcc caagaacatg  3780
```

```
ccccaggacg ccgacgcgaa cggcgcgtac cacatcggcc tcaagggcct gatgctgctg  3840
gggcgcatca agaacaacca ggagggcaag aagctgaacc tcgtgatcaa gaacgaggaa  3900
tacttcgagt tcgtgcagaa ccgcaacaac ggatctggag tgagcaaggg cgaggagaat  3960
aacatggcca tcatcaagga gttcatgcgc ttcaaggtgc gcatggaggg ctccgtgaac  4020
ggccacgagt tcgagatcga gggcgagggc gagggccgcc cctacgaggg ctttcagacc  4080
gctaagctga aggtgaccaa gggtggcccc ctgcccttcg cctgggacat cctgtcccct  4140
catttcacct acggctccaa ggcctacgtg aagcaccccg ccgacatccc cgactacttc  4200
aagctgtcct tccccgaggg cttcaagtgg gagcgcgtga tgaactacga ggacggcggc  4260
gtggtgaccg tgacccagga ctcctccctg caggacggcg agttcatcta caaggtgaag  4320
ctgcgcggca ccaacttccc ctccgacggc cccgtgatgc agaagaagac catgggctgg  4380
gaggcctcct ccgagcggat gtaccccgag gacggtgccc tgaagggcaa gatcaagatg  4440
aggctgaagc tgaaggacgg cggccactac acctccgagg tcaagaccac ctacaaggcc  4500
aagaagcccg tgcagctgcc cggcgcctac atcgtcgaca tcaagttgga catcacctcc  4560
cacaacgagg actacaccat cgtggaacag tacgaacgcg ccgagggccg ccactccacc  4620
ggcggcatgg acgagctgta caagggatct aagaagcgta ggatcaagca agat        4674

SEQ ID NO: 58           moltype = DNA  length = 4710
FEATURE                 Location/Qualifiers
misc_feature            1..4710
                        note = Synthetic polynucleotide.
                         MGSS7H-NLS-FnCpf1-CO2-mOR-NLS
source                  1..4710
                        mol_type = other DNA
                        organism = synthetic construct
SEQUENCE: 58
atgggcagca gccatcatca ccaccatcac catatgggta gcaaaaagag gcgtatcaag  60
caggacatgt ccatatacca ggagttcgtc aacaagtact cgctcagcaa gacgctccgc  120
ttcgagctga tcccccaggg taagaccctg gagaacatca aggcgcgcgg actcatcctc  180
gacgacgaga agcgggctaa ggactacaaa aaggccaagc agatcatcga caagtaccac  240
cagttcttca tcgaggagat cctctcctcc gtctgcatct ccgaggacct cctccagaac  300
tacagcgacg tctacttcaa gctcaaaaag tcggacgacg acaacctcca gaaggacttc  360
aagtcggcga aggacaccat caagaagcag atcagcgagt acatcaagga ctccgagaag  420
ttcaagaacc tgttcaacca gaacctgatc gacgccaaga agggccagga gtcggacctg  480
atcctgtggc tcaagcagag caaggacaac ggcatcgagc tcttcaaggc caacagcgac  540
atcacggaca tcgacgaggc cctggagatc atcaagtcgt tcaagggctg gacgacctac  600
ttcaagggct tccacgagaa ccgcaagaac gtctatagct ccaacgacat ccccacctcg  660
atcatctacc ggatcgtgga cgacaacctc cccaagttcc tggagaacaa ggcgaagtac  720
gagtcgttga aggacaaggc gccggaggcg atcaactacg agcagatcaa gaaggacctg  780
gccgaggagc tgaccttcga catcgactac aagacgtcgg aggtgaacca gcgggtgttc  840
agtctggacg aggtcttcga gatcgcgaac ttcaacaact acctgaacca gtcggggatc  900
accaagttca acacgatcat aggcggcaag ttcgtgaacg gcgagaacac caagcgcaag  960
gggataaacg agtacatcaa cctgtacagc cagcagatca acgacaagac gctcaagaag  1020
tacaagatga gcgtgctctt caagcagatc ctcagtgaca ccgagtccaa gagcttcgtg  1080
atcgacaagc tggaggacga cagcgacgtc gtgacaacca tgcagagctt ctacgagcag  1140
atcgccgcgt tcaagaccgt cgaggagaag tcaatcaagg agacgctctc cttgctgttc  1200
gacgacctga aggcacaaaa gctggacctc agcaagatct acttcaagaa cgacaagtcc  1260
ctgaccgacc tgagccagca ggttttcgac gactactccg tcatcgggac tgccgtcctg  1320
gagtacatca cccagcagat cgctccgaag aacctcgaca acccgtccaa gaaggagcag  1380
gagctgattg cgaagaagac agagaaggcc aagtacctct ccctcgagac catcaagctc  1440
gccctggagg agttcaacaa gcacagggac attgacaagc agtgccgttt cgaggagatc  1500
ctggccaact tcgcggccat ccccatgatc ttcgacgaga tcgcccagaa caaggacaac  1560
ctggcgcaga tctctatcaa gtaccagaac caggggaaga aggacttgct ccaggcctca  1620
gcggaggacg acgtgaaggc catcaaggac ctgctcgacc agacgaacaa cttgctccac  1680
aagctcaaga tctttcacat cagccagagc gaggacaagg ccaacatcct cgacaaggac  1740
gagcacttct acctcgtgtt cgaggagtgc tacttcgagc tggccaacat cgtgccactt  1800
tacaacaaga tccgcaacta catcacgcag aagccgtact ccgacgagaa gttcaagctg  1860
aacttcgaga actccaccct cgccaacggc tgggacaaga acaaggagcc ggacaacacc  1920
gcgatcctgt tcataaagga cgacaagtac tacttggggg tcatgaacaa gaagaacaac  1980
aagatattcg acgacaaggc catcaaggag aacaaggggg agggctacaa gaagatcgtc  2040
tacaagctcc tccccggcgc gaacaagatg ctgcctaagg tcttcttttc cgccaagagt  2100
atcaagttct acaacccctc cgaggacatc ctccgcatcc ggaaccacag cacgcacaca  2160
aagaacggct cgcctcagaa gggctacgag aagttcgagt tcaacatcga ggactgccgg  2220
aagttcatcg acttctacaa gcagagcatc tccaagcacc cggagtggaa ggactttggc  2280
ttcaggttct cagacaccca gcggtacaac tccatcgacg agttctaccg cgaggtggag  2340
aaccagggct acaagctgac cttcgagaat atatcagagt cgtacatcga cagcgtggtg  2400
aaccagggca agttgtacct gttccagatc tacaacaagg acttctccgc ctactcaaag  2460
gggcgtccaa acctgcacac gctgtactgg aaggcgctct tcgacgagcg caacctacaa  2520
gatgttgtat acaagctcaa cggcgaggcg gaactgttct ataggaagca gtcgatcccc  2580
aagaagatta cgcacccggc taaggaggcc atcgccaaca agaacaagga caaccccaag  2640
aaggagtccg tgttcgagta cgacctcatc aaggacaaga ggttcacgga ggacaagttt  2700
ttcttccact gcccaatcac tatcaatttc aagtcgagcg gagccaacaa gttcaacgac  2760
gagataaacc tgctcctcaa ggagaaggcc aatgacgtgc acatcctctc catcgaccgg  2820
ggcgagcggc acctggcgta ctacacgctg gtggacggca agggcaacat catcaagcag  2880
gacaccttca acatcatcgg gaacgaccgc atgaagacca actaccacga caagctcgcc  2940
gccatcgaga aggacaggga ctccgcgcgc aaggactgga agaagattaa caacatcaag  3000
gagatgaagg agggctacct cagccaggtg gtccacgaga tcgccaagct cgtcattgag  3060
tacaacgcca tcgtcgtctt cgaggacctg aatttcggct tcaagcgcgg ccggttcaag  3120
gtggagaagc aggtctacca gaagcttgag aagatgctga tcgagaagct gaactacctg  3180
gtgttcaagg acaacgagtt cgacaagacc ggcggagtgc tgcgcgccta ccagctcacg  3240
```

```
gcgcctttcg agacgttcaa gaagatgggc aagcagacgg gcatcatcta ctacgtgccc  3300
gccggcttca cctctaagat ctgcccagtg accggcttcg ttaaccagct gtacccgaag  3360
tacgagagcg tgtccaagtc ccaggagttc ttctccaagt tcgacaagat ttgttacaac  3420
ctcgacaagg gctacttcga gttttcgttc gactacaaga actttggcga caaggcggcc  3480
aaggggaagt ggaccatcgc ctctttcggc agcaggctca tcaatttccg gaactccgac  3540
aagaaccaca actgggacac gcgcgaggtg tacccgacga aggagctgga gaagctgctc  3600
aaggactact ccatcgagta cggccacggc gagtgcatca aggcggcgat ctgcggggag  3660
agcgacaaga agttctttgc caagctgacc agcgtgctga acaccatcct ccagatgcgg  3720
aactccaaga ccggcaccga gctggactac ctgatctccc cggtcgcgga cgtcaacggg  3780
aacttcttcg actcccgaca ggctcccaag aacatgcccc aggacgccga cgcgaacggc  3840
gcgtaccaca tcggcctcaa gggcctgatg ctgctggggc gcatcaagaa caaccaggag  3900
ggcaagaagc tgaacctcgt gatcaagaac gaggaatact tcgagttcgt gcagaaccgc  3960
aacaacggat ctggagtgag caagggcgag gagaataaca tggccatcat caaggagttc  4020
atgcgcttca aggtgcgcat ggagggctcc gtgaacggcc acgagttcga gatcgagggc  4080
gagggcgagg gccgccccta cgagggcttt cagaccgcta agctgaaggt gaccaagggt  4140
ggccccctgc ccttcgcctg ggacatcctg tcccctcatt tcacctacgg ctccaaggcc  4200
tacgtgaagc accccgccga catccccgac tacttcaagc tgtccttccc cgagggcttc  4260
aagtgggagc gcgtgatgaa ctacgaggac ggcggcgtgg tgaccgtgac ccaggactcc  4320
tccctgcagg acggcgagtt catctacaag gtgaagctgc gcggcaccaa cttcccctcc  4380
gacggccccg tgatgcagaa gaagaccatg ggctgggagg cctcctccga gcggatgtac  4440
cccgaggacg gtgccctgaa gggcaagatc aagatgaggc tgaagctgaa ggacggcggc  4500
cactacacct ccgaggtcaa gaccacctac aaggccaaga agcccgtgca gctgcccggc  4560
gcctacatcg tcgacatcaa gttggacatc acctcccaca acgaggacta caccatcgtg  4620
gaacagtacg aacgcgccga gggccgccac tccaccggcg gcatggacga gctgtacaag  4680
ggatctaaga agcgtaggat caagcaagat                                  4710

SEQ ID NO: 59           moltype = DNA  length = 6465
FEATURE                 Location/Qualifiers
misc_feature            1..6465
                        note = Synthetic polynucleotide.Expression cassette
                         comprising 35Spromoter cassette,
                         MGSS7H-NLS-FnCpf1-CO2-mOr-NLS and NOStranscription
                         termination sequence
source                  1..6465
                        mol_type = other DNA
                        organism = synthetic construct
SEQUENCE: 59
ggtccgattg agacttttca acaaagggta atatccggaa acctcctcgg attccattgc  60
ccagctatct gtcactttat tgtgaagata gtggaaaagg aaggtggctc ctacaaatgc  120
catcattgcg ataaaggaaa ggccatcgtt gaagatgcct ctgccgacag tggtcccaaa  180
gatggacccc cacccacgag gagcatcgtg gaaaaagaag acgttccaac cacgtcttca  240
aagcaagtgg attgatgtga tggtccgatt gagacttttc aacaaagggt aatatccgga  300
aacctcctcg gattccattg cccagctatc tgtcacttta ttgtgaagat agtggaaaag  360
gaaggtggct cctacaaatg ccatcattgc gataaaggaa aggccatcgt tgaagatgcc  420
tctgccgaca gtggtcccaa agatggaccc ccacccacga ggagcatcgt ggaaaaagaa  480
gacgttccaa ccacgtcttc aaagcaagtg gattgatgtg atatctccac tgacgtaagg  540
gatgacgcac aatcccacta tccttcgcaa gacccttcct ctatataagg aagttcattt  600
catttggaga ggacacgctg acaagctgac tctagcagat ctaccgtctt cggtacgcgc  660
tcactccgcc ctctgccttt gttactgcca cgtttctctg aatgctctct tgtgtggtga  720
ttgctgagag tggtttagct ggatctagaa ttacactctg aaatcgtgtt ctgcctgtgc  780
tgattacttg ccgtcctttg tagcagcaaa atatagggac atggtagtac gaaacgaaga  840
tagaacctac acagcaatac gagaaatgtg taatttggtg cttagcggta tttatttaag  900
cacatgttgg tgttataggg cacttggatt cagaagtttg ctgttaattt aggcacaggc  960
ttcatactac atgggtcaat agtataggga ttcatattat aggcgatact ataataattt  1020
gttcgtctgc agagcttatt atttgccaaa attagatatt cctattctgt ttttgtttgt  1080
gtgctgttaa attgttaacg cctgaaggaa taaatataaa tgacgaaatt ttgatgttta  1140
tctctgctcc tttattgtga ccataagtca agatcagatg cacttgtttt aaatattgtt  1200
gtctgaagaa ataagtactg acagtatttt gatgcattga tctgcttgtt tgttgtaaca  1260
aaatttaaaa ataaagagtt tcctttttgt tgctctcctt acctcctgat ggtatctagt  1320
atctaccaac tgacactata ttgcttctct ttacatacgt atcttgctcg atgccttctc  1380
cctagtgttg accagtgtta ctcacatagt ctttgctcat ttcattgtaa tgcagatacc  1440
aagcggcctc tagaggatcc aggagcaacc atgggcagca gccatcatca ccaccatcac  1500
catatgggta gcaaaaagag gcgtatcaag caggacatgt ccatatacca ggagttcgtc  1560
aacaagtact cgctcagcaa gacgctccgc ttcgagctga tcccccaggg taagaccctg  1620
gagaacatca aggcgcgcgg actcatcctc gacgacgaga agcgggctaa ggactacaaa  1680
aaggccaagc agatcatcga caagtaccac cagttcttca tcgaggagat cctctcctcc  1740
gtctgcatct ccgaggacct cctccagaac tacagcgacg tctacttcaa gctcaaaaag  1800
tcggacgacg acaacctcca gaaggacttc aagtcggcga aggacaccat caagaagcag  1860
atcagcgagt acatcaagga ctccgagaag ttcaagaacc tgttcaacca gaacctgatc  1920
gacgccaaga agggccagga gtcggacctg atcctgtggc tcaagcagag caaggacaac  1980
ggcatcgagc tcttcaaggc caacagcgac atcacggaca tcgacgaggc cctggagatc  2040
atcaagtcgt tcaagggctg gacgacctac ttcaagggct tccacgagaa ccgcaagaac  2100
gtctatagct ccaacgacat ccccacctcg atcatctacc ggatcgtgga cgacaacctc  2160
cccaagttcc tggagaacaa ggcgaagtac gagtcgttga aggacaaggc gccggaggcg  2220
atcaactacg agcagatcaa gaaggacctg gccgaggagc tgaccttcga catcgactac  2280
aagacgtcgg aggtgaacca gcgggtgttc agtctggacg aggtcttcga gatcgcgaac  2340
ttcaacaact acctgaacca gtcggggatc accaagttca acacgatcat aggcggcaag  2400
ttcgtgaacg gcgagaacac caagcgcaag ggataaacg  agtacatcaa cctgtacagc  2460
cagcagatca acgacaagac gctcaagaag tacaagatga gcgtgctctt caagcagatc  2520
```

```
ctcagtgaca ccgagtccaa gagcttcgtg atcgacaagc tggaggacga cagcgacgtc  2580
gtgacaacca tgcagagctt ctacgagcag atcgccgcgt tcaagaccgt cgaggagaag  2640
tcaatcaagg agacgctctc cttgctgttc gacgacctga aggcacaaaa gctggacctc  2700
agcaagatct acttcaagaa cgacaagtcc ctgaccgacc tgagccagca ggttttcgac  2760
gactactccg tcatcgggac tgccgtcctg gagtacatca cccagcagat cgctccgaag  2820
aacctcgaca acccgtccaa gaaggagcag gagctgattg cgaagaagac agagaaggcc  2880
aagtacctct ccctcgagac catcaagctc gccctggagg agttcaacaa gcacagggac  2940
attgacaagc agtgccgttt cgaggagatc ctggccaact tcgcggccat ccccatgatc  3000
ttcgacgaga tcgcccagaa caaggacaac ctggcgcaga tctctatcaa gtaccagaac  3060
caggggaaga aggacttgct ccaggcctca gcggaggacg acgtgaaggc catcaaggac  3120
ctgctcgacc agacgaacaa cttgctccac aagctcaaga tctttcacat cagccagagc  3180
gaggacaagg ccaacatcct cgacaaggac gagcacttct acctcgtgtt cgaggagtgc  3240
tacttcgagc tggccaacat cgtgccactt tacaacaaga tccgcaacta catcacgcag  3300
aagccgtact ccgacgagaa gttcaagctg aacttcgaga actccaccct cgccaacggc  3360
tgggacaaga acaaggagcc ggacaacacc gcgatcctgt tcataaagga cgacaagtac  3420
tacttggggg tcatgaacaa gaagaacaac aagatattcg acgacaaggc catcaaggag  3480
aacaaggggg agggctacaa gaagatcgtc tacaagctcc tccccggcgc gaacaagatg  3540
ctgcctaagg tcttctttc cgccaagagt atcaagttct acaacccctc cgaggacatc  3600
ctccgcatcc ggaaccacag cacgcacaca aagaacggct cgcctcagaa gggctacgag  3660
aagttcgagt tcaacatcga ggactgccgg aagttcatcg acttctacaa gcagagcatc  3720
tccaagcacc cggagtggaa ggactttggc ttcaggttct cagacaccca gcggtacaac  3780
tccatcgacg agttctaccg cgaggtggag aaccagggct acaagctgac cttcgagaat  3840
atatcagagt cgtacatcga cagcgtggtg aaccagggca agttgtacct gttccagatc  3900
tacaacaagg acttctccgc ctactcaaag gggcgtccaa acctgcacac gctgtactgg  3960
aaggcgctct tcgacgagcg caacctacaa gatgttgtat acaagctcaa cggcgaggcg  4020
gaactgttct ataggaagca gtcgatcccc aagaagatta cgcacccggc taaggaggcc  4080
atcgccaaca agaacaagga caaccccaag aaggagtccg tgttcgagta cgacctcatc  4140
aaggacaaga ggttcacgga ggacaagttt ttcttccact gcccaatcac tatcaatttc  4200
aagtcgagcg gagccaacaa gttcaacgac gagataaacc tgctcctcaa ggagaaggcc  4260
aatgacgtgc acatcctctc catcgaccgg ggcgagcggc acctggcgta ctacacgctg  4320
gtggacggca agggcaacat catcaagcag gacaccttca acatcatcgg gaacgaccgc  4380
atgaagacca actaccacga caagctcgcc gccatcgaga aggacaggga ctccgcgcgc  4440
aaggactgga agaagattaa caacatcaag gagatgaagg agggctacct cagccaggtg  4500
gtccacgaga tcgccaagct cgtcattgag tacaacgcca tcgtcgtctt cgaggacctg  4560
aatttcggct tcaagcgcgg ccggttcaag gtggagaagc aggtctacca gaagcttgag  4620
aagatgctga tcgagaagct gaactacctg gtgttcaagg acaacgagtt cgacaagacc  4680
ggcggagtgc tgcgcgccta ccagctcacg gcgcctttcg agacgttcaa gaagatgggc  4740
aagcagacgg gcatcatcta ctacgtgccc gccggcttca cctctaagat ctgcccagtg  4800
accggcttcg ttaaccagct gtacccgaag tacgagagcg tgtccaagtc ccaggagttc  4860
ttctccaagt tcgacaagat ttgttacaac ctcgacaagg gctacttcga gttttcgttc  4920
gactacaaga actttggcga caaggcggcc aaggggaagt ggaccatcgc ctctttcggc  4980
agcaggctca tcaatttccg gaactccgac aagaaccaca actgggacac gcgcgaggtg  5040
tacccgacga aggagctgga gaagctgctc aaggactact ccatcgagta cggccacggc  5100
gagtgcatca aggcggcgat ctgcggggag agcgacaaga agttctttgc caagctgacc  5160
agcgtgctga acaccatcct ccagatgcgg aactccaaga ccggcaccga gctggactac  5220
ctgatctccc cggtcgcgga cgtcaacggg aacttcttcg actcccgaca ggctcccaag  5280
aacatgcccc aggacgccga cgcgaacggc gcgtaccaca tcggcctcaa gggcctgatg  5340
ctgctggggc gcatcaagaa caaccaggag ggcaagaagc tgaacctcgt gatcaagaac  5400
gaggaatact tcgagttcgt gcagaaccgc aacaacggat ctggagtgag caagggcgag  5460
gagaataaca tggccatcat caaggagttc atgcgcttca aggtgcgcat ggagggctcc  5520
gtgaacggcc acgagttcga gatcgagggc gagggcgagg gccgccccta cgagggcttt  5580
cagaccgcta agctgaaggt gaccaagggt ggcccccctgc ccttcgcctg ggacatcctg  5640
tcccctcatt tcacctacgg ctccaaggcc tacgtgaagc accccgccga catccccgac  5700
tacttcaagc tgtccttccc cgagggcttc aagtgggagc gcgtgatgaa ctacgaggac  5760
ggcggcgtgg tgaccgtgac ccaggactcc tccctgcagg acggcgagtt catctacaag  5820
gtgaagctgc gcggcaccaa cttcccctcc gacggccccg tgatgcagaa gaagaccatg  5880
ggctgggagg cctcctccga gcggatgtac cccgaggacg gtgccctgaa gggcaagatc  5940
aagatgaggc tgaagctgaa ggacggcggc cactacacct ccgaggtcaa gaccacctac  6000
aaggccaaga agcccgtgca gctgcccggc gcctacatcg tcgacatcaa gttggacatc  6060
acctcccaca acgaggacta caccatcgtg gaacagtacg aacgcgccga gggccgccac  6120
tccaccggcg gcatggacga gctgtacaag ggatctaaga agcgtaggat caagcaagat  6180
tagaacccag cggtactcgc tgaggaattc gcgatcgttc aaacatttgg caataaagtt  6240
tcttaagatt gaatcctgtt gccggtcttg cgatgattat catataattt ctgttgaatt  6300
acgttaagca tgtaataatt aacatgtaat gcatgacgtt atttatgaga tgggttttta  6360
tgattagagt cccgcaatta tacatttaat acgcgataga aaacaaaata tagcgcgcaa  6420
actaggataa attatcgcgc gcggtgtcat ctatgttact agatc              6465
```

```
SEQ ID NO: 60          moltype = DNA  length = 4671
FEATURE                Location/Qualifiers
misc_feature           1..4671
                       note = Synthetic polynucleotide.NLS-FnCpf1-Hs-mOR-NLS
source                 1..4671
                       mol_type = other DNA
                       organism = synthetic construct
SEQUENCE: 60
ggtagcaaaa agaggcgtat caagcaggac agcatctacc aggagttcgt caacaagtat  60
tcactgagta agacactgcg gttcgagctg atcccacagg gcaagacact ggagaacatc  120
aaggcccgag gcctgattct ggacgatgag aagcgggcaa aagactataa gaaagccaag  180
cagatcattg ataaatacca ccagttcttt atcgaggaaa ttctgagctc cgtgtgcatc  240
```

-continued

```
agtgaggatc tgctgcagaa ttactcagac gtgtacttca agctgaagaa gagcgacgat  300
gacaacctgc agaaggactt caagtccgcc aaggacacca tcaagaaaca gattagcgag  360
tacatcaagg actccgaaaa gtttaaaaat ctgttcaacc agaatctgat cgatgctaag  420
aaaggccagg agtccgacct gatcctgtgg ctgaaacagt ctaaggacaa tgggattgaa  480
ctgttcaagg ctaactccga tatcactgat attgacgagg cactggaaat catcaagagc  540
ttcaagggat ggaccacata ctttaaaggc ttccacgaga accgcaagaa cgtgtactcc  600
agcaacgaca ttcctacctc catcatctac cgaatcgtcg atgacaatct gccaaagttc  660
ctggagaaca aggccaaata tgaatctctg aaggacaaag ctcccgaggc aattaattac  720
gaacagatca agaaagatct ggctgaggaa ctgacattcg atatcgacta taagactagc  780
gaggtgaacc agagggtctt ttccctggac gaggtgtttg aaatcgccaa tttcaacaat  840
tacctgaacc agtccggcat tactaaattc aataccatca ttggcgggaa gtttgtgaac  900
ggggagaata ccaagcgcaa gggaattaac gaatacatca atctgtatag ccagcagatc  960
aacgacaaaa ctctgaagaa atacaagatg tctgtgctgt tcaaacagat cctgagtgat  1020
accgagtcca agtcttttgt cattgataaa ctggaagatg actcagacgt ggtcactacc  1080
atgcagagct tttatgagca gatcgccgct ttcaagacag tggaggaaaa atctattaag  1140
gaaactctga gtctgctgtt cgatgacctg aaagcccaga agctggacct gagtaagatc  1200
tacttcaaaa acgataagag tctgacagac ctgtcacagc aggtgtttga tgactattcc  1260
gtgattggga ccgccgtcct ggagtacatt acacagcaga tcgctccaaa gaacctggat  1320
aatccctcta agaaagagca ggaactgatc gctaagaaaa ccgagaaggc aaaatatctg  1380
agtctggaaa caattaagct ggcactggag gagttcaaca agcacaggga tattgacaaa  1440
cagtgccgct ttgaggaaat cctggccaac ttcgcagcca tccccatgat ttttgatgag  1500
atcgcccaga acaaagacaa tctggctcag atcagtatta agtaccagaa ccagggcaag  1560
aaagacctgc tgcaggcttc agcagaagat gacgtgaaag ccatcaagga tctgctggac  1620
cagaccaaca atctgctgca caagctgaaa atcttccata ttagtcagtc agaggataag  1680
gctaatatcc tggataaaga cgaacacttc tacctggtgt tcgaggaatg ttacttcgag  1740
ctggcaaaca ttgtccccct gtataacaag attaggaact acatcacaca gaagccttac  1800
tctgacgaga agtttaaact gaacttcgaa aatagtaccc tggccaacgg gtgggataag  1860
aacaaggagc ctgacaacac agctatcctg ttcatcaagg atgacaagta ctatctggga  1920
gtgatgaata agaaaaacaa taagatcttc gatgacaaag ccattaagga gaacaaaggg  1980
gaaggataca agaaaatcgt gtataagctg ctgcccggcg caaataagat gctgcctaag  2040
gtgttcttca gcgccaagag tatcaaattc tacaacccat ccgaggacat cctgcggatt  2100
agaaatcact caacacatac taagaacggg agcccccaga agggatatga gaaatttgag  2160
ttcaacatcg aggattgcag gaagtttatt gacttctaca agcagagcat ctccaaacac  2220
cctgaatgga aggattttgg cttccggttt tccgacacac agagatataa ctctatcgac  2280
gagttctacc gcgaggtgga aaatcagggg tataagctga cttttgagaa catttctgaa  2340
agttacatcg acagcgtggt caatcaggga aagctgtacc tgttccagat ctataacaaa  2400
gatttttcag catacagcaa gggcagacca aacctgcata cactgtactg gaaggccctg  2460
ttcgatgaga ggaatctgca ggacgtggtc tataaactga acggagaggc cgaactgttt  2520
taccggaagc agtctattcc taagaaaatc actcacccag ctaaggaggc catcgctaac  2580
aagaacaagg acaatcctaa gaaagagagc gtgttcgaat acgatctgat taaggacaag  2640
cggttcaccg aagataagtt ctttttccat tgtccaatca ccattaactt caagtcaagc  2700
ggcgctaaca agttcaacga cgagatcaat ctgctgctga aggaaaaagc aaacgatgtg  2760
cacatcctga gcattgaccg aggagagcgg catctggcct actataccct ggtggatggc  2820
aaagggaata tcattaagca ggatacattc aacatcattg gcaatgaccg gatgaaaacc  2880
aactaccacg ataaactggc tgcaatcgag aaggatagag actcagctag gaaggactgg  2940
aagaaaatca acaacattaa ggagatgaag gaaggctatc tgagccaggt ggtccatgag  3000
attgcaaagc tggtcatcga atacaatgcc attgtggtgt tcgaggatct gaacttcggc  3060
tttaagaggg ggcgctttaa ggtggaaaaa caggtctatc agaagctgga gaaaatgctg  3120
atcgaaaagc tgaattacct ggtgtttaaa gataacgagt tcgacaagac cggaggcgtc  3180
ctgagagcct accagctgac agctcccttt gaaactttca agaaaatggg aaaacagaca  3240
ggcatcatct actatgtgcc agccggattc acttccaaga tctgccccgt gaccggcttt  3300
gtcaaccagc tgtaccctaa atatgagtca gtgagcaagt cccaggaatt tttcagcaag  3360
ttcgataaga tctgttataa tctggacaag ggtacttcg agttttcctt cgattacaag  3420
aacttcggcg acaaggccgc taaggggaaa tggaccattg cctccttcgg atctcgcctg  3480
atcaactttc gaaattccga taaaaaccac aattgggaca ctagggaggt gtacccaacc  3540
aaggagctgg aaaagctgct gaaagactac tctatcgagt atggacatgg cgaatgcatc  3600
aaggcagcca tctgtggcga gagtgataag aaatttttcg ccaagctgac ctcagtgctg  3660
aatacaatcc tgcagatgcg gaactcaaag accgggacag aactggacta tctgattagc  3720
cccgtggctg atgtcaacgg aaacttcttc gacagcagac aggcacccaa aaatatgcct  3780
caggatgcag acgccaacgg ggcctaccac atcgggctga agggactgat gctgctgggc  3840
cggatcaaga acaatcagga ggggaagaag ctgaacctgg tcattaagaa cgaggaatac  3900
ttcgagtttg tccagaatag aaataacgga tctggagtga gcaagggcga ggagaataac  3960
atggccatca tcaaggagtt catgcgcttc aaggtgcgca tggagggctc cgtgaacggc  4020
cacgagttcg agatcgaggg cgagggcgag ggccgcccct acgagggctt tcagaccgct  4080
aagctgaagg tgaccaaggg tggccccctg cccttcgcct gggacatcct gtcccctcat  4140
ttcacctacg gctccaaggc ctacgtgaag caccccgccg acatccccga ctacttcaag  4200
ctgtccttcc ccgagggctt caagtgggag cgcgtgatga actacgagga cggcggcgtg  4260
gtgaccgtga cccaggactc ctccctgcag gacggcgagt tcatctacaa ggtgaagctg  4320
cgcggcacca acttcccctc cgacggcccc gtgatgcaga agaagaccat gggctgggag  4380
gcctcctccg agcggatgta ccccgaggac ggtgccctga agggcaagat caagatgagg  4440
ctgaagctga aggacggcgg ccactacacc tccgaggtca agaccaccta caaggccaag  4500
aagcccgtgc agctgcccgg cgcctacatc gtcgacatca agttggacat cacctcccac  4560
aacgaggact acaccatcgt ggaacagtac gaacgcgccg agggccgcca ctccaccggc  4620
ggcatggacg agctgtacaa gggatctaag aagcgtagga tcaagcaaga t          4671
```

```
SEQ ID NO: 61          moltype = DNA  length = 4707
FEATURE                Location/Qualifiers
misc_feature           1..4707
                       note = Synthetic polynucleotide.MGSS7H-NLS-FnCpf1-Hs-mOR-NLS
```

```
source                  1..4707
                        mol_type = other DNA
                        organism = synthetic construct
SEQUENCE: 61
atgggcagca gccatcatca ccaccatcac catatgggta gcaaaaagag gcgtatcaag  60
caggacagca tctaccagga gttcgtcaac aagtattcac tgagtaagac actgcggttc  120
gagctgatcc cacagggcaa gacactggag aacatcaagg cccgaggcct gattctggac  180
gatgagaagc gggcaaaaga ctataagaaa gccaagcaga tcattgataa ataccaccag  240
ttctttatcg aggaaattct gagctccgtg tgcatcagtg aggatctgct gcagaattac  300
tcagacgtgt acttcaagct gaagaagagc gacgatgaca acctgcagaa ggacttcaag  360
tccgccaagg acaccatcaa gaaacagatt agcgagtaca tcaaggactc cgaaaagttt  420
aaaaatctgt tcaaccagaa tctgatcgat gctaagaaag gccaggagtc cgacctgatc  480
ctgtggctga aacagtctaa ggacaatggg attgaactgt tcaaggctaa ctccgatatc  540
actgatattg acgaggcact ggaaatcatc aagagcttca agggatggac cacatacttt  600
aaaggcttcc acgagaaccg caagaacgtg tactccagca acgacattcc tacctccatc  660
atctaccgaa tcgtcgatga caatctgcca aagttcctgg agaacaaggc caaatatgaa  720
tctctgaagg acaaagctcc cgaggcaatt aattacgaac agatcaagaa agatctggct  780
gaggaactga cattcgatat cgactataag actagcgagg tgaaccagag ggtcttttcc  840
ctggacgagg tgtttgaaat cgccaatttc aacaattacc tgaaccagtc cggcattact  900
aaattcaata ccatcattgg cgggaagttt gtgaacgggg agaataccaa gcgcaaggga  960
attaacgaat acatcaatct gtatagccag cagatcaacg acaaaactct gaagaaatac  1020
aagatgtctg tgctgttcaa acagatcctg agtgataccg agtccaagtc ttttgtcatt  1080
gataaactgg aagatgactc agacgtggtc actaccatgc agagctttta tgagcagatc  1140
gccgctttca agacagtgga ggaaaaatct attaaggaaa ctctgagtct gctgttcgat  1200
gacctgaaag cccagaagct ggacctgagt aagatctact tcaaaaacga taagagtctg  1260
acagacctgt cacagcaggt gtttgatgac tattccgtga ttgggaccgc cgtcctggag  1320
tacattacac agcagatcgc tccaaagaac ctggataatc cctctaagaa agagcaggaa  1380
ctgatcgcta agaaaaccga gaaggcaaaa tatctgagtc tggaaacaat taagctggca  1440
ctggaggagt tcaacaagca cagggatatt gacaaacagt gccgctttga ggaaatcctg  1500
gccaacttcg cagccatccc catgattttt gatgagatcg cccagaacaa agacaatctg  1560
gctcagatca gtattaagta ccagaaccag ggcaagaaag acctgctgca ggcttcagca  1620
gaagatgacg tgaaagccat caaggatctg ctggaccaga ccaacaatct gctgcacaag  1680
ctgaaaatct tccatattag tcagtcagag gataaggcta atatcctgga taaagacgaa  1740
cacttctacc tggtgttcga ggaatgttac ttcgagctgg caaacattgt cccccctgtat  1800
aacaagatta ggaactacat cacacagaag ccttactctg acgagaagtt taaactgaac  1860
ttcgaaaata gtaccctggc caacgggtgg gataagaaca aggagcctga caacacagct  1920
atcctgttca tcaaggatga caagtactat ctgggagtga tgaataagaa aaacaataag  1980
atcttcgatg acaaagccat taaggagaac aaaggggaag gatacaagaa aatcgtgtat  2040
aagctgctgc ccggcgcaaa taagatgctg cctaaggtgt tcttcagcgc caagagtatc  2100
aaattctaca acccatccga ggacatcctg cggattagaa atcactcaac acatactaag  2160
aacgggagcc cccagaaggg atatgagaaa tttgagttca acatcgagga ttgcaggaag  2220
tttattgact tctacaagca gagcatctcc aaacaccctg aatggaagga ttttggcttc  2280
cggttttccg acacacagag atataactct atcgacgagt tctaccgcga ggtggaaaat  2340
caggggtata agctgacttt tgagaacatt tctgaaagtt acatcgacag cgtggtcaat  2400
cagggaaagc tgtacctgtt ccagatctat aacaaagatt tttcagcata cagcaagggc  2460
agaccaaacc tgcatacact gtactggaag gccctgttcg atgagaggaa tctgcaggac  2520
gtggtctata aactgaacgg agaggccgaa ctgttttacc ggaagcagtc tattcctaag  2580
aaaatcactc acccagctaa ggaggccatc gctaacaaga acaaggacaa tcctaagaaa  2640
gagagcgtgt tcgaatacga tctgattaag gacaagcggt tcaccgaaga taagttcttt  2700
ttccattgtc caatcaccat taacttcaag tcaagcggcg ctaacaagtt caacgacgag  2760
atcaatctgc tgctgaagga aaaagcaaac gatgtgcaca tcctgagcat tgaccgagga  2820
gagcggcatc tggcctacta taccctggtg gatggcaaag ggaatatcat taagcaggat  2880
acattcaaca tcattggcaa tgaccggatg aaaaccaact accacgataa actggctgca  2940
atcgagaagg atagagactc agctaggaag gactggaaga aaatcaacaa cattaaggag  3000
atgaaggaag gctatctgag ccaggtggtc catgagattg caaagctggt catcgaatac  3060
aatgccattg tggtgttcga ggatctgaac ttcggcttta agaggggggcg ctttaaggtg  3120
gaaaaacagg tctatcagaa gctggagaaa atgctgatcg aaaagctgaa ttacctggtg  3180
tttaaagata acgagttcga caagaccgga ggcgtcctga gagcctacca gctgacagct  3240
ccctttgaaa ctttcaagaa aatgggaaaa cagacaggca tcatctacta tgtgccagcc  3300
ggattcactt ccaagatctg ccccgtgacc ggctttgtca accagctgta ccctaaatat  3360
gagtcagtga gcaagtccca ggaatttttc agcaagttcg ataagatctg ttataatctg  3420
gacaaggggt acttcgagtt ttccttcgat tacaagaact tcggcgacaa ggccgctaag  3480
gggaaatgga ccattgcctc cttcggatct cgcctgatca actttcgaaa ttccgataaa  3540
aaccacaatt gggacactag ggaggtgtac ccaaccaagg agctggaaaa gctgctgaaa  3600
gactactcta tcgagtatgg acatggcgaa tgcatcaagg cagccatctg tggcgagagt  3660
gataagaaat ttttcgccaa gctgacctca gtgctgaata caatcctgca gatgcggaac  3720
tcaaagaccg ggacagaact ggactatctg attagccccg tggctgatgt caacggaaac  3780
ttcttcgaca gcagacaggc acccaaaaat atgcctcagg atgcagacgc caacggggcc  3840
taccacatcg ggctgaaggg actgatgctg ctgggccgga tcaagaacaa tcaggagggg  3900
aagaagctga acctggtcat taagaacgag gaatacttcg agtttgtcca gaatagaaat  3960
aacggatctg gagtgagcaa gggcgaggag aataacatgg ccatcatcaa ggagttcatg  4020
cgcttcaagg tgcgcatgga gggctccgtg aacggccacg agttcgagat cgagggcgag  4080
ggcgagggcc gcccctacga gggctttcag accgctaagc tgaaggtgac caagggtggc  4140
cccctgccct tcgcctggga catcctgtcc cctcatttca cctacggctc caaggcctac  4200
gtgaagcacc ccgccgacat ccccgactac ttcaagctgt ccttccccga gggcttcaag  4260
tgggagcgcg tgatgaacta cgaggacggc ggcgtggtga ccgtgaccca ggactcctcc  4320
ctgcaggacg gcgagttcat ctacaaggtg aagctgcgcg gcaccaactt cccctccgac  4380
ggccccgtga tgcagaagaa gaccatgggc tgggaggcct cctccgagcg gatgtacccc  4440
gaggacggtg ccctgaaggg caagatcaag atgaggctga agctgaagga cggcggccac  4500
```

```
tacacctccg aggtcaagac cacctacaag gccaagaagc ccgtgcagct gcccggcgcc  4560
tacatcgtcg acatcaagtt ggacatcacc tcccacaacg aggactacac catcgtggaa  4620
cagtacgaac gcgccgaggg ccgccactcc accggcggca tggacgagct gtacaaggga  4680
tctaagaagc gtaggatcaa gcaagat                                      4707

SEQ ID NO: 62           moltype = DNA  length = 6462
FEATURE                 Location/Qualifiers
misc_feature            1..6462
                        note = Synthetic polynucleotide.Expression cassette
                         comprising 35Spromoter cassette,
                         MGSS7H-NLS-FnCpf1-Hs-mOr-NLS and NOStranscription
                         termination sequence
source                  1..6462
                        mol_type = other DNA
                        organism = synthetic construct
SEQUENCE: 62
ggtccgattg agacttttca acaaagggta atatccggaa acctcctcgg attccattgc  60
ccagctatct gtcactttat tgtgaagata gtggaaaagg aaggtggctc ctacaaatgc  120
catcattgcg ataaaggaaa ggccatcgtt gaagatgcct ctgccgacag tggtcccaaa  180
gatggacccc cacccacgag gagcatcgtg gaaaaagaag acgttccaac cacgtcttca  240
aagcaagtgg attgatgtga tggtccgatt gagacttttc aacaaagggt aatatccgga  300
aacctcctcg gattccattg cccagctatc tgtcacttta ttgtgaagat agtggaaaag  360
gaaggtggct cctacaaatg ccatcattgc gataaaggaa aggccatcgt tgaagatgcc  420
tctgccgaca gtggtcccaa agatggaccc ccacccacga ggagcatcgt ggaaaaagaa  480
gacgttccaa ccacgtcttc aaagcaagtg gattgatgtg atatctccac tgacgtaagg  540
gatgacgcac aatcccacta tccttcgcaa gacccttcct ctatataagg aagttcattt  600
catttggaga ggacacgctg acaagctgac tctagcagat ctaccgtctt cggtacgcgc  660
tcactccgcc ctctgccttt gttactgcca cgtttctctg aatgctctct tgtgtggtga  720
ttgctgagag tggtttagct ggatctagaa ttacactctg aaatcgtgtt ctgcctgtgc  780
tgattacttg ccgtcctttg tagcagcaaa atatagggac atggtagtac gaaacgaaga  840
tagaacctac acagcaatac gagaaatgtg taatttggtg cttagcggta tttatttaag  900
cacatgttgg tgttataggg cacttggatt cagaagtttg ctgttaattt aggcacaggc  960
ttcatactac atgggtcaat agtataggga ttcatattat aggcgatact ataataattt  1020
gttcgtctgc agagcttatt atttgccaaa attagatatt cctattctgt ttttgtttgt  1080
gtgctgttaa attgttaacg cctgaaggaa taaatataaa tgacgaaatt ttgatgttta  1140
tctctgctcc tttattgtga ccataagtca agatcagatg cacttgtttt aaatattgtt  1200
gtctgaagaa ataagtactg acagtatttt gatgcattga tctgcttgtt tgttgtaaca  1260
aaatttaaaa ataaagagtt tcctttttgt tgctctcctt acctcctgat ggtatctagt  1320
atctaccaac tgacactata ttgcttctct ttacatacgt atcttgctcg atgccttctc  1380
cctagtgttg accagtgtta ctcacatagt ctttgctcat ttcattgtaa tgcagatacc  1440
aagcggcctc tagaggatcc aggagcaacc atgggcagca gccatcatca ccaccatcac  1500
catatgggta gcaaaaagag gcgtatcaag caggacagca tctaccagga gttcgtcaac  1560
aagtattcac tgagtaagac actgcggttc gagctgatcc cacagggcaa gacactggag  1620
aacatcaagg cccgaggcct gattctggac gatgagaagc gggcaaaaga ctataagaaa  1680
gccaagcaga tcattgataa ataccaccag ttctttatcg aggaaattct gagctccgtg  1740
tgcatcagtg aggatctgct gcagaattac tcagacgtgt acttcaagct gaagaagagc  1800
gacgatgaca acctgcagaa ggacttcaag tccgccaagg acaccatcaa gaaacagatt  1860
agcgagtaca tcaaggactc cgaaaagttt aaaaatctgt tcaaccagaa tctgatcgat  1920
gctaagaaag gccaggagtc cgacctgatc ctgtggctga aacagtctaa ggacaatggg  1980
attgaactgt tcaaggctaa ctccgatatc actgatattg acgaggcact ggaaatcatc  2040
aagagcttca agggatggac cacatacttt aaaggcttcc acgagaaccg caagaacgtg  2100
tactccagca acgacattcc tacctccatc atctaccgaa tcgtcgatga caatctgcca  2160
aagttcctgg agaacaaggc caaatatgaa tctctgaagg acaaagctcc cgaggcaatt  2220
aattacgaac agatcaagaa agatctggct gaggaactga cattcgatat cgactataag  2280
actagcgagg tgaaccagag ggtcttttcc ctggacgagg tgtttgaaat cgccaatttc  2340
aacaattacc tgaaccagtc cggcattact aaattcaata ccatcattgg cgggaagttt  2400
gtgaacgggg agaataccaa gcgcaaggga attaacgaat acatcaatct gtatagccag  2460
cagatcaacg acaaaactct gaagaaatac aagatgtctg tgctgttcaa acagatcctg  2520
agtgataccg agtccaagtc ttttgtcatt gataaactgg aagatgactc agacgtggtc  2580
actaccatgc agagctttta tgagcagatc gccgctttca agacagtgga ggaaaaatct  2640
attaaggaaa ctctgagtct gctgttcgat gacctgaaag cccagaagct ggacctgagt  2700
aagatctact tcaaaaacga taagagtctg acagacctgt cacagcaggt gtttgatgac  2760
tattccgtga ttgggaccgc cgtcctggag tacattacac agcagatcgc tccaaagaac  2820
ctggataatc cctctaagaa agagcaggaa ctgatcgcta agaaaaccga gaaggcaaaa  2880
tatctgagtc tggaaacaat taagctggca ctggaggagt tcaacaagca cagggatatt  2940
gacaaacagt gccgctttga ggaaatcctg gccaacttcg cagccatccc catgattttt  3000
gatgagatcg cccagaacaa agacaatctg gctcagatca gtattaagta ccagaaccag  3060
ggcaagaaag acctgctgca ggcttcagca gaagatgacg tgaaagccat caaggatctg  3120
ctggaccaga ccaacaatct gctgcacaag ctgaaaatct tccatattag tcagtcagag  3180
gataaggcta atatcctgga taaagacgaa cacttctacc tggtgttcga ggaatgttac  3240
ttcgagctgg caaacattgt cccccctgtat aacaagatta ggaactacat cacacagaag  3300
ccttactctg acgagaagtt taaactgaac ttcgaaaata gtaccctggc caacgggtgg  3360
gataagaaca aggagcctga caacacagct atcctgttca tcaaggatga caagtactat  3420
ctgggagtga tgaataagaa aaacaataag atcttcgatg acaaagccat taaggagaac  3480
aaagggggaag gatacaagaa aatcgtgtat aagctgctgc ccggcgcaaa taagatgctg  3540
cctaaggtgt tcttcagcgc caagagtatc aaattctaca acccatccga ggacatcctg  3600
cggattagaa atcactcaac acatactaag aacgggagcc cccagaaggg atatgagaaa  3660
tttgagttca acatcgagga ttgcaggaag tttattgact tctacaagca gagcatctcc  3720
aaacaccctg aatggaagga ttttggcttc cggttttccg acacacagag atataactct  3780
```

-continued

```
atcgacgagt tctaccgcga ggtggaaaat caggggtata agctgacttt tgagaacatt  3840
tctgaaagtt acatcgacag cgtggtcaat cagggaaagc tgtacctgtt ccagatctat  3900
aacaaagatt tttcagcata cagcaagggc agaccaaacc tgcatacact gtactggaag  3960
gccctgttcg atgagaggaa tctgcaggac gtggtctata aactgaacgg agaggccgaa  4020
ctgttttacc ggaagcagtc tattcctaag aaaatcactc acccagctaa ggaggccatc  4080
gctaacaaga acaaggacaa tcctaagaaa gagagcgtgt tcgaatacga tctgattaag  4140
gacaagcggt tcaccgaaga taagttcttt ttccattgtc caatcaccat taacttcaag  4200
tcaagcggcg ctaacaagtt caacgacgag atcaatctgc tgctgaagga aaaagcaaac  4260
gatgtgcaca tcctgagcat tgaccgagga gagcggcatc tggcctacta taccctggtg  4320
gatggcaaag ggaatatcat taagcaggat acattcaaca tcattggcaa tgaccggatg  4380
aaaaccaact accacgataa actggctgca atcgagaagg atagagactc agctaggaag  4440
gactggaaga aaatcaacaa cattaaggag atgaaggaag gctatctgag ccaggtggtc  4500
catgagattg caaagctggt catcgaatac aatgccattg tggtgttcga ggatctgaac  4560
ttcggcttta agagggggcg ctttaaggtg gaaaaacagg tctatcagaa gctggagaaa  4620
atgctgatcg aaaagctgaa ttacctggtg tttaaagata acgagttcga caagaccgga  4680
ggcgtcctga gagcctacca gctgacagct ccctttgaaa ctttcaagaa aatgggaaaa  4740
cagacaggca tcatctacta tgtgccagcc ggattcactt ccaagatctg ccccgtgacc  4800
ggctttgtca accagctgta ccctaaatat gagtcagtga gcaagtccca ggaatttttc  4860
agcaagttcg ataagatctg ttataatctg gacaaggggt acttcgagtt ttccttcgat  4920
tacaagaact tcggcgacaa ggccgctaag ggaaatgga ccattgcctc cttcggatct  4980
cgcctgatca actttcgaaa ttccgataaa aaccacaatt gggacactag ggaggtgtac  5040
ccaaccaagg agctggaaaa gctgctgaaa gactactcta tcgagtatgg acatggcgaa  5100
tgcatcaagg cagccatctg tggcgagagt gataagaaat ttttcgccaa gctgacctca  5160
gtgctgaata caatcctgca gatgcggaac tcaaagaccg ggacagaact ggactatctg  5220
attagccccg tggctgatgt caacggaaac ttcttcgaca gcagacaggc acccaaaaat  5280
atgcctcagg atgcagacgc caacggggcc taccacatcg ggctgaaggg actgatgctg  5340
ctgggccgga tcaagaacaa tcaggagggg aagaagctga acctggtcat taagaacgag  5400
gaatacttcg agtttgtcca gaatagaaat aacggatctg gagtgagcaa gggcgaggag  5460
aataacatgg ccatcatcaa ggagttcatg cgcttcaagg tgcgcatgga gggctccgtg  5520
aacggccacg agttcgagat cgagggcgag ggcgagggcc gcccctacga gggctttcag  5580
accgctaagc tgaaggtgac caagggtggc cccctgccct tcgcctggga catcctgtcc  5640
cctcatttca cctacggctc caaggcctac gtgaagcacc ccgccgacat ccccgactac  5700
ttcaagctgt ccttccccga gggcttcaag tgggagcgcg tgatgaacta cgaggacggc  5760
ggcgtggtga ccgtgaccca ggactcctcc ctgcaggacg gcgagttcat ctacaaggtg  5820
aagctgcgcg gcaccaactt cccctccgac ggccccgtga tgcagaagaa gaccatgggc  5880
tgggaggcct cctccgagcg gatgtacccc gaggacggtg ccctgaaggg caagatcaag  5940
atgaggctga agctgaagga cggcggccac tacacctccg aggtcaagac cacctacaag  6000
gccaagaagc ccgtgcagct gcccggcgcc tacatcgtcg acatcaagtt ggacatcacc  6060
tcccacaacg aggactacac catcgtggaa cagtacgaac gcgccgaggg ccgccactcc  6120
accggcggca tggacgagct gtacaaggga tctaagaagc gtaggatcaa gcaagattag  6180
aacccagcgg tactcgctga ggaattcgcg atcgttcaaa catttggcaa taaagtttct  6240
taagattgaa tcctgttgcc ggtcttgcga tgattatcat ataatttctg ttgaattacg  6300
ttaagcatgt aataattaac atgtaatgca tgacgttatt tatgagatgg gtttttatga  6360
ttagagtccc gcaattatac atttaatacg cgatagaaaa caaaatatag cgcgcaaact  6420
aggataaatt atcgcgcgcg gtgtcatcta tgttactaga tc                    6462
```

```
SEQ ID NO: 63           moltype = DNA  length = 3960
FEATURE                 Location/Qualifiers
misc_feature            1..3960
                        note = Synthetic polynucleotide.NLS-FnCpf1-CO3-NLS
source                  1..3960
                        mol_type = other DNA
                        organism = synthetic construct
SEQUENCE: 63
ggtagcaaaa agaggcgtat caagcaggac atgagcatct accaggagtt cgtgaacaag  60
tacagcctgt cgaagaccct ccggttcgag ctgatccctc aggggaagac gctggagaac  120
atcaaggcgc gcggcctcat cctcgacgac gagaagcggg cgaaggacta caaaaaggca  180
aagcagatca tcgacaagta ccaccaattc tttattgagg agatcctcag ctccgtctgc  240
atcagcgagg acttgctcca gaactactcc gacgtctatt tcaagctcaa gaagtcagac  300
gacgacaacc tccagaagga cttcaagtcc gcgaaggaca cgatcaaaaa gcagatcagc  360
gagtacatca aggactccga gaagttcaag aacctcttca accagaacct gatcgacgcc  420
aagaagggcc gggaatcgga cctcatcctg tggctcaagc agtcgaagga caacggcatc  480
gagctgttca aggccaactc cgacatcacc gacatcgacg aggcgctgga gatcatcaag  540
tcgttcaagg ggtggaccac ctacttcaag ggcttccacg agaaccgcaa gaacgtttac  600
tccagcaacg acatccccac ctcgatcatc taccggatcg tggacgacaa cctgcccaag  660
ttcctggaga acaaggccaa gtacgagtcc ctcaaggaca aggccccgga ggcgatcaac  720
tacgagcaga ttaaaaagga ccttgctgag gagctgacct tcgacatcga ctacaagacc  780
tccgaggtga accagcgggt gttcagcctc gacgaggtgt tcgagatcgc caacttcaac  840
aactacctga accagtccgg gatcaccaag ttcaacacga tcatcggcgg gaagttcgtc  900
aacggcgaga acacgaagcg gaagggcatc aacgagtaca tcaacctcta cagccagcag  960
atcaacgaca agaccctcaa aaaatacaaa atgtcggtcc tgttcaagca gatcctgtcc  1020
gacaccgagt ccaagagctt cgtcatcgac aagctggagg acgactccga cgtcgtgacc  1080
accatgcagt ccttctacga gcagatcgcc gccttcaaga ccgtggagga gaagtccatc  1140
aaggagaccc tcagcctcct cttcgacgac ctcaaggcgc agaagctgga cctctccaag  1200
atatacttca agaacgacaa gagcctcacc gacctgtccc agcaagtatt cgacgactac  1260
agcgtgatcg ggacggcggt gctggagtac atcacccagc agatagcgcc caagaacctg  1320
gacaacccct ccaagaaaga acaggagctg attgctaaaa agaccgaaaa ggctaagtac  1380
ctgtccctgg agaccatcaa gctcgcgctg gaggagttca acaagcaccg ggacatcgac  1440
aagcagtgcc ggttcgagga gatcctagca aacttcgccg cgatccccat gatcttcgac  1500
```

```
gagatcgccc agaacaagga caacctggcc cagatcagca tcaagtacca gaaccagggc  1560
aagaaggacc ttcttcaagc tagtgccgag gacgacgtga aggcgattaa ggatctgctc  1620
gaccagacca acaacctgct ccacaagctc aagatattcc acatctccca gtccgaggac  1680
aaggccaaca tcctggacaa ggacgagcac ttctacctgg tgttcgagga gtgctacttc  1740
gagctggcca acatcgtgcc gctgtacaac aagatccgga actacatcac ccagaagccc  1800
tactccgacg agaagttcaa gctgaacttc gagaactcca ccctggcgaa cgggtgggac  1860
aagaacaagg agcccgacaa cacggccatc ctcttcatca aggacgacaa atattatctg  1920
ggcgtcatga acaaaaagaa caacaagata ttcgatgaca aggcgatcaa ggagaacaag  1980
ggcgagggct acaagaaaat agtatataaa ctactgcccg gcgcgaacaa gatgctcccg  2040
aaggtgtttt ttagtgcaaa gtctattaag ttctacaacc ccagcgagga catcctccgc  2100
atccggaacc acagcacgca caccaagaac ggcagcccac agaagggcta cgagaagttc  2160
gagttcaaca tcgaggactg ccgcaagttc atcgacttct acaagcagtc catctccaag  2220
caccccgagt ggaaggactt cgggttccgg ttcagcgaca cccagcgcta caacagcatc  2280
gacgagttct accgggaggt cgagaaccag gggtacaagc tgacgttcga gaacatctcc  2340
gagagctaca tcgacagcgt ggtgaaccag gggaagctgt acctgtttca gatatacaac  2400
aaggacttct cagcctacag caaggggcgg ccgaacctgc acaccctgta ctggaaggcc  2460
ctgttcgacg agcggaacct ccaggacgtc gtgtacaagc tcaacggcga ggcggagctg  2520
ttctaccgga agcagtccat ccccaaaaag attactcacc ccgcgaagga ggccatcgcc  2580
aacaagaaca aggacaaccc caaaaaggaa tcagtgttcg agtacgacct catcaaggac  2640
aagcgcttca ccgaggacaa attcttcttt cactgcccga tcacgatcaa cttcaagtcc  2700
tccggggcga acaagttcaa cgacgagatc aacctgctgc tcaaggagaa ggccaacgac  2760
gtgcacatcc tcagcatcga ccggggcgag cgccacctgg cctactacac cctggtggac  2820
gggaagggca acatcataaa gcaagatacc ttcaacatca tcgggaacga ccggatgaag  2880
acgaactacc acgacaagct ggcggccatc gagaaggacc gggacagcgc ccgcaaggac  2940
tggaaaaaga taaacaacat taaggagatg aaggagggct acctgtccca ggtggtccac  3000
gagatcgcca agctcgtcat cgagtacaac gccatcgtcg tgttcgagga cttgaacttc  3060
gggttcaagc ggggccggtt caaggtggag aaacaagtct atcaaaagct ggagaagatg  3120
ctcatcgaga agctcaacta cctcgtgttc aaggacaacg agttcgacaa gaccggcggc  3180
gtcctgcggg cctaccagct caccgcgccg ttcgagacgt tcaagaagat ggggaagcag  3240
acggggatca tctactacgt ccccgccggg ttcaccagca agatatgccc ggtcacgggg  3300
ttcgtcaacc agctctaccc caagtacgag tcggtgagca agagccagga gttcttcagc  3360
aagttcgaca agatctgcta caacctggac aagggctact tcgagttctc gttcgactac  3420
aagaacttcg ggacaaggcg ggcgaagggc aagtggacca tcgccagctt cggctcccgc  3480
ctcatcaact tccggaactc ggacaagaac cacaactggg acacccgcga ggtgtacccc  3540
acgaaggagc tggagaagct gctcaaggac tacagcatcg agtacgggca cggcgagtgc  3600
atcaaggccg ccatctgcgg ggagtccgac aagaaattct ttgccaagct gacctccgtg  3660
ctgaacacca tcctccagat gcggaacagc aagaccggga ccgagctgga ctacctgatc  3720
tccccggtcg ccgacgtcaa cggcaacttc ttcgattctc gccaggctcc caagaacatg  3780
ccccaggacg ccgacgccaa cggggcctac cacatcgggc tcaagggcct catgctgctc  3840
gggcggatca agaacaacca ggagggcaag aaactcaacc tggtcatcaa gaacgaggag  3900
tactttgagt tcgtccagaa ccggaacaac ggatctaaga agcgtaggat caagcaagat  3960
```

```
SEQ ID NO: 64           moltype = DNA  length = 530
FEATURE                 Location/Qualifiers
source                  1..530
                        mol_type = unassigned DNA
                        organism = Oryza sativa
SEQUENCE: 64
atccaagtaa attaagttgg atcagtagag atgcatggtt ggtgttctca tgtggtctga  60
atctgtgttc tgtttcatct tttgtgtaag tgtgcaactt cgattctgta aaacttggca  120
agtagatgaa cgatgtcatt tatatgcgtg tagcttgtca aaatacaaag tagaaacctg  180
tatctgaata agatggcatt catgaaataa tattatcgat tgaacgaacg aagcaacaga  240
atgatcttcc aaattgaagc aaaggaattg atggacaacg agttgctgta ctttggagct  300
gtaaatctgt agtacttctc aacgatgcta tggaccgtgg gccgtccata atcgctgggt  360
ggaatgagcc cactgtccat gtgcttctgc atttggcccg tgtacagccc atataatgtc  420
gaaaaaccta atacgcgcgc gccgccggcg cgcgtttcgg acccagaacg cctagcgccg  480
ctgcgccgac gtgcgcgcgt ctccactttt tttttcgttt tctttccatt            530
```

```
SEQ ID NO: 65           moltype = DNA  length = 6530
FEATURE                 Location/Qualifiers
misc_feature            1..6530
                        note = Synthetic polynucleotide.Expression cassette
                         comprising Zea maysUbiquitin promoter cassette,
                         NLS-FnCpf1-CO3-NLS and an Oryzasativa transcription
                         termination sequence
source                  1..6530
                        mol_type = other DNA
                        organism = synthetic construct
SEQUENCE: 65
gtcgtgcccc tctctagaga taaagagcat tgcatgtcta aagtataaaa aattaccaca  60
tatttttttg tcacacttat ttgaagtgta gtttatctat ctctatacat atatttaaac  120
ttcactctac aaataatata gtctataata ctaaaataat attagtgttt tagaggatca  180
tataaataaa ctgctagaca tggtctaaag gataattgaa tattttgaca atctacagtt  240
ttatcttttt agtgtgcatg tgatctctct gttttttttg caaatagctt gacctatata  300
atacttcatc cattttatta gtacatccat ttaggattta gggttgatgg tttctataga  360
ctaattttta gtacatccat tttattcttt ttagtctcta aatttttttaa aactaaaact  420
ctattttagt tttttattta ataatttaga tataaaatga aataaaataa attgactaca  480
aataaaaacaa atacccttta agaaataaaa aaactaagca aacatttttc ttgtttcgag  540
tagataatga caggctgttc aacgccgtcg acgagtctaa cggacaccaa ccagcgaacc  600
```

-continued

```
agcagcgtcg cgtcgggcca agcgaagcag acggcacggc atctctgtag ctgcctctgg  660
acccctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acgggggatt cctttcccac cgctccttcg ctttcccttc ctcgcccgcc  840
gtaataaata gacacccct ccacaccctc tttccccaac ctcgtgttcg ttcggagcgc  900
acacacacgc aaccagatct cccccaaatc cagccgtcgg cacctccgct tcaaggtacg  960
ccgctcatcc tcccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc ttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgttgg gtgatacttc tgcagcggac cgacggtacc atgggtagca aaaagaggcg  2040
tatcaagcag gacatgagca tctaccagga gttcgtgaac aagtacagcc tgtcgaagac  2100
cctccggttc gagctgatcc ctcaggggaa gacgctggag aacatcaagg cgcgcggcct  2160
catcctcgac gacgagaagc gggcgaagga ctacaaaaag gcaaagcaga tcatcgacaa  2220
gtaccaccaa ttctttattg aggagatcct cagctccgtc tgcatcagcg aggacttgct  2280
ccagaactac tccgacgtct atttcaagct caagaagtca gacgacgaca acctccagaa  2340
ggacttcaag tccgcgaagg acacgatcaa aaagcagatc agcgagtaca tcaaggactc  2400
cgagaagttc aagaacctct tcaaccagaa cctgatcgac gccaagaagg gccgggaatc  2460
ggacctcatc ctgtggctca agcagtcgaa ggacaacggc atcgagctgt tcaaggccaa  2520
ctccgacatc accgacatcg acgaggcgct ggagatcatc aagtcgttca aggggtggac  2580
cacctacttc aagggcttcc acgagaaccg caagaacgtt tactccagca acgacatccc  2640
cacctcgatc atctaccgga tcgtggacga caacctgccc aagttcctgg agaacaaggc  2700
caagtacgag tccctcaagg acaaggcccc ggaggcgatc aactacgagc agattaaaaa  2760
ggaccttgct gaggagctga ccttcgacat cgactacaag acctccgagg tgaaccagcg  2820
ggtgttcagc ctcgacgagg tgttcgagat cgccaacttc aacaactacc tgaaccagtc  2880
cgggatcacc aagttcaaca cgatcatcgg cgggaagttc gtcaacggcg agaacacgaa  2940
gcggaagggc atcaacgagt acatcaacct ctacagccag cagatcaacg acaagaccct  3000
caaaaaatac aaaatgtcgg tcctgttcaa gcagatcctg tccgacaccg agtccaagag  3060
cttcgtcatc gacaagctgg aggacgactc cgacgtcgtg accaccatgc agtccttcta  3120
cgagcagatc gccgccttca agaccgtgga ggagaagtcc atcaaggaga ccctcagcct  3180
cctcttcgac gacctcaagg cgcagaagct ggacctctcc aagatatact tcaagaacga  3240
caagagcctc accgacctgt cccagcaagt attcgacgac tacagcgtga tcgggacggc  3300
ggtgctggag tacatcaccc agcagatagc gcccaagaac ctggacaacc cctccaagaa  3360
agaacaggag ctgattgcta aaaagaccga aaaggctaag tacctgtccc tggagaccat  3420
caagctcgcg ctggaggagt tcaacaagca ccgggacatc gacaagcagt gccggttcga  3480
ggagatccta gcaaacttcg ccgcgatccc catgatcttc gacgagatcg cccagaacaa  3540
ggacaacctg gcccagatca gcatcaagta ccagaaccag ggcaagaagg accttcttca  3600
agctagtgcc gaggacgacg tgaaggcgat taaggatctg ctcgaccaga ccaacaacct  3660
gctccacaag ctcaagatat tccacatctc ccagtccgag gacaaggcca acatcctgga  3720
caaggacgag cacttctacc tggtgttcga ggagtgctac ttcgagctgg ccaacatcgt  3780
gccgctgtac aacaagatcc ggaactacat cacccagaag ccctactccg acgagaagtt  3840
caagctgaac ttcgagaact ccaccctggc gaacgggtgg gacaagaaca aggagcccga  3900
caacacggcc atcctcttca tcaaggacga caaatattat ctgggcgtca tgaacaaaaa  3960
gaacaacaag atattcgatg acaaggcgat caaggagaac aagggcgagg gctacaagaa  4020
aatagtatat aaactactgc ccggcgcgaa caagatgctc ccgaaggtgt tttttagtgc  4080
aaagtctatt aagttctaca accccagcga ggacatcctc cgcatccgga accacagcac  4140
gcacaccaag aacggcagcc cacagaaggg ctacgagaag ttcgagttca acatcgagga  4200
ctgccgcaag ttcatcgact tctacaagca gtccatctcc aagcaccccg agtggaagga  4260
cttcgggttc cggttcagcg acacccagcg ctacaacagc atcgacgagt tctaccggga  4320
ggtcgagaac caggggtaca agctgacgtt cgagaacatc tccgagagct acatcgacag  4380
cgtggtgaac caggggaagc tgtacctgtt tcagatatac aacaaggact tctcagccta  4440
cagcaagggg cggccgaacc tgcacaccct gtactggaag gccctgttcg acgagcggaa  4500
cctccaggac gtcgtgtaca agctcaacgg cgaggcggag ctgttctacc ggaagcagtc  4560
catccccaaa aagattactc accccgcgaa ggaggccatc gccaacaaga acaaggacaa  4620
ccccaaaaag gaatcagtgt tcgagtacga cctcatcaag gacaagcgct tcaccgagga  4680
caaattcttc tttcactgcc cgatcacgat caacttcaag tcctccgggg cgaacaagtt  4740
caacgacgag atcaacctgc tgctcaagga gaaggccaac gacgtgcaca tcctcagcat  4800
cgaccggggc gagcgccacc tggcctacta caccctggtg gacgggaagg gcaacatcat  4860
aaagcaagat accttcaaca tcatcgggaa cgaccggatg aagacgaact accacgacaa  4920
gctggcggcc atcgagaagg accgggacag cgcccgcaag gactggaaaa agataaacaa  4980
cattaaggag atgaaggagg gctacctgtc ccaggtggtc cacgagatcg ccaagctcgt  5040
catcgagtac aacgccatcg tcgtgttcga ggacttgaac ttcgggttca agcggggccg  5100
gttcaaggtg gagaaacaag tctatcaaaa gctggagaag atgctcatcg agaagctcaa  5160
ctacctcgtg ttcaaggaca acgagttcga caagaccggc ggcgtcctgc gggcctacca  5220
gctcaccgcg ccgttcgaga cgttcaagaa gatggggaag cagacgggga tcatctacta  5280
cgtccccgcc gggttcacca gcaagatatg cccggtcacg ggttcgtca accagctcta  5340
```

-continued

```
ccccaagtac gagtcggtga gcaagagcca ggagttcttc agcaagttcg acaagatctg  5400
ctacaacctg gacaagggct acttcgagtt ctcgttcgac tacaagaact tcggggacaa  5460
ggcggcgaag ggcaagtgga ccatcgccag cttcggctcc cgcctcatca acttccggaa  5520
ctcggacaag aaccacaact gggacacccg cgaggtgtac cccacgaagg agctggagaa  5580
gctgctcaag gactacagca tcgagtacgg gcacggcgag tgcatcaagg ccgccatctg  5640
cggggagtcc gacaagaaat tctttgccaa gctgacctcc gtgctgaaca ccatcctcca  5700
gatgcggaac agcaagaccg ggaccgagct ggactacctg atctccccgg tcgccgacgt  5760
caacggcaac ttcttcgatt ctcgccaggc tcccaagaac atgccccagg acgccgacgc  5820
caacggggcc taccacatcg ggctcaaggg cctcatgctg ctcgggcgga tcaagaacaa  5880
ccaggagggc aagaaactca acctggtcat caagaacgag gagtactttg agttcgtcca  5940
gaaccggaac aacggatcta agaagcgtag gatcaagcaa gattgattaa ttaagggccc  6000
atccaagtaa attaagttgg atcagtagag atgcatggtt ggtgttctca tgtggtctga  6060
atctgtgttc tgtttcatct tttgtgtaag tgtgcaactt cgattctgta aaacttggca  6120
agtagatgaa cgatgtcatt tatatgcgtg tagcttgtca aaatacaaag tagaaacctg  6180
tatctgaata agatggcatt catgaaataa tattatcgat tgaacgaacg aagcaacaga  6240
atgatcttcc aaattgaagc aaaggaattg atggacaacg agttgctgta ctttggagct  6300
gtaaatctgt agtacttctc aacgatgcta tggaccgtgg gccgtccata atcgctgggt  6360
ggaatgagcc cactgtccat gtgcttctgc atttggcccg tgtacagccc atataatgtc  6420
gaaaaaccta atacgcgcgc gccgccggcg cgcgtttcgg acccagaacg cctagcgccg  6480
ctgcgccgac gtgcgcgcgt ctccactttt tttttcgttt tctttccatt             6530

SEQ ID NO: 66           moltype = DNA  length = 3960
FEATURE                 Location/Qualifiers
misc_feature            1..3960
                        note = Synthetic polynucleotide.NLS-FnCpf1-CO4-NLS
source                  1..3960
                        mol_type = other DNA
                        organism = synthetic construct
SEQUENCE: 66
ggtagcaaaa agaggcgtat caagcaggac atgagcatct accaggagtt cgtgaacaag  60
tacagcctga gcaagaccct gcgcttcgag ctgattcctc aggggaagac cctggagaac  120
atcaaggcgc gcggcctgat cctggacgac gagaagcggg cgaaggacta caaaaaggcg  180
aagcagatca tcgacaagta ccatcagttt ttcatcgagg agattctcag ctccgtgtgc  240
atcagcgaag acctgctcca gaactacagc gacgtttact tcaagctcaa gaaatcggac  300
gacgacaacc tccagaagga cttcaagagc gcgaaggaca cgattaagaa acagatcagc  360
gagtacatca aggactccga gaagttcaag aacctgttca accagaacct catcgacgcc  420
aagaaaggcc aagagtcgga cctcatcctc tggctcaagc agagcaagga caacggcatc  480
gagctgttca aggcgaacag cgacatcacc gacatcgacg aggcgctgga gatcatcaag  540
tcgttcaagg gctggacgac ctacttcaag ggcttccacg agaaccgcaa gaatgtctac  600
tcgagcaacg acatccccac gtcgatcatc taccgcatcg tggacgacaa cctcccgaag  660
ttcctggaga acaaggcgaa gtacgagagc ctcaaggaca aggccccgga ggccatcaac  720
tacgagcaga tcaaaaagga tttggctgag gagctgacgt tcgacatcga ctacaagacc  780
tccgaggtga accagcgcgt cttcagcctc gacgaggtgt tcgagatcgc caacttcaac  840
aactacctca accagtcggg catcaccaag ttcaacacca tcatcggcgg gaagttcgtc  900
aacggcgaga acacgaagcg caaggggatc aacgagtaca tcaacctgta cagccagcag  960
atcaacgaca agaccctcaa gaagtataaa atgtcggtgc tgttcaagca gatcctctcg  1020
gacaccgaga gcaagtcgtt cgtcatcgac aagctggagg acgacagcga cgtggtgacc  1080
accatgcaga gcttctacga gcagatcgcg gccttcaaga ccgtcgagga gaagtcgatc  1140
aaggagacgc tcagcctgct gttcgacgac ctcaaggccc agaagctcga cctgtccaag  1200
atatacttta agaacgacaa gagcctcacg gacctgtccc agcaggtatt cgacgactac  1260
agcgtgatcg ggacggccgt gctggagtac atcacccaac agatcgcgcc caagaacctg  1320
gacaacccgt ccaagaagga acaagagcta atcgccaaaa agactgagaa ggcgaagtac  1380
ctgtcgctgg agacgatcaa gctcgcgctt gaggagttta acaagcaccg cgacatcgac  1440
aagcagtgcc ggttcgagga gatcctggcc aacttcgcgg cgatcccgat gatcttcgac  1500
gagatcgccc agaacaagga caacctggcg cagatcagca tcaagtacca gaaccagggc  1560
aaaaaagact tgctccaagc tagtgcggag gacgacgtga aggcgattaa ggatctgctg  1620
gaccagacta acaatctgct gcacaagctc aagatctttc acatctctca gtcggaggac  1680
aaggcgaaca tcctggacaa ggacgagcac ttctacctag tgttcgagga gtgctacttc  1740
gagctggcga acatcgtgcc cctgtacaac aagatccgga actacatcac ccagaagccc  1800
tacagcgacg agaagttcaa gctgaacttc gagaacagca cgctggcgaa cgggtgggac  1860
aagaacaagg agcccgacaa caccgccatc ctgttcatca aggacgacaa atattacctc  1920
ggcgtcatga acaaaaagaa taacaagata ttcgatgaca aggcgatcaa ggagaacaag  1980
ggcgagggct acaagaagat cgtatataaa ctcctgccgg gagcgaacaa gatgctcccg  2040
aaggtttttct ttagtgccaa gtccatcaag ttctacaacc ccagcgagga catcctccgc  2100
atccggaacc actccaccca caccaagaac ggctcgccgc agaagggcta cgagaagttc  2160
gagttcaaca tcgaggactg ccgcaagttc atcgacttct acaagcagtc catctccaag  2220
cacccggagt ggaaggactt cgggttccgg ttctccgaca cgcagcgcta caactccatc  2280
gacgagttct accgggaggt ggagaaccag ggctacaagc tgacgttcga gaacatctcg  2340
gagtcctaca tcgactccgt ggtcaaccag ggcaagctgt acctcttcca gatatacaat  2400
aaggacttct ccgcctacag caaggggcgg cccaacctcc acaccctgta ctggaaggcg  2460
ctcttcgacg agcggaacct ccaggacgtc gtgtacaagc tgaacggcga ggcggagctg  2520
ttctaccgca agcagagcat ccccaagaag atcacgcacc ccgcgaagga ggccatcgcc  2580
aacaagaaca aggacaaccc caagaaggaa tcggtcttcg agtacgacct catcaaggac  2640
aagcggttca cggaggacaa attcttttttc cactgcccga tcactattaa cttcaagtcc  2700
agcggcgcga acaagttcaa cgacgagatc aacctgctcc tcaaggagaa ggcgaacgac  2760
gtgcacatcc tcagcatcga ccggggcgag cgccacctcg cctactacac gctggtggac  2820
gggaagggca acatcatcaa gcaagacacc ttcaacatca tcggcaacga ccggatgaag  2880
accaactacc acgacaagct ggccgccatc gagaaggacc gcgactcggc ccgcaaggac  2940
tggaaaaaga tcaacaatat caaggagatg aaggagggct acctgagcca agttgtccac  3000
```

```
gagatcgcca agctggtgat cgagtacaac gccatcgtcg tgttcgaaga cctgaacttc  3060
ggcttcaagc gcggccggtt caaggtcgag aaacaagtct atcagaaact tgagaagatg  3120
ctgatcgaga agctgaacta cctcgtcttc aaggacaacg agttcgacaa gaccggcggc  3180
gtcctccgcg cgtaccagct caccgcgccg ttcgagacgt tcaagaaaat gggcaagcag  3240
accggcatca tctactacgt gcccgccggg ttcacgagca aaatatgtcc cgtgaccggc  3300
ttcgtcaacc agctctaccc caagtacgag tccgtgtcga agtcccagga attcttcagc  3360
aagttcgaca agatatgcta caacctggac aagggctact tcgagttctc cttcgactac  3420
aagaacttcg gggacaaggc ggcgaagggg aagtggacca tcgcctcgtt cgggtcgcgc  3480
ctcatcaact tccggaacag cgacaagaac cacaactggg acacccgcga ggtgtacccg  3540
acgaaggagc tggagaagct cctcaaggac tacagcatcg agtacggcca cggggagtgc  3600
atcaaggcgg ccatctgcgg cgagtcggac aaaaagttct ttgccaaact cacctcggtc  3660
ctcaacacca tcctccagat gcggaacagc aagacgggca cggagctgga ctacctcatc  3720
agcccggtgg ccgacgtgaa cggcaatttc tttgactcac gccaggcccc taagaacatg  3780
ccccaggacg ccgacgccaa cggcgcgtac cacatcggcc tcaagggcct gatgctgctc  3840
ggccggatca agaacaacca ggagggcaag aagctcaacc tggtcatcaa gaacgaggag  3900
tatttcgagt tcgtccagaa ccgcaacaac ggatctaaga agcgtaggat caagcaagat  3960
```

```
SEQ ID NO: 67          moltype = DNA  length = 6530
FEATURE                Location/Qualifiers
misc_feature           1..6530
                       note = Synthetic polynucleotide.Expression cassette
                        comprising Zea maysUbiquitin promoter cassette,
                        NLS-FnCpf1-CO4-NLS and an Oryzasativa transcription
                        termination sequence
source                 1..6530
                       mol_type = other DNA
                       organism = synthetic construct
SEQUENCE: 67
gtcgtgcccc tctctagaga taaagagcat tgcatgtcta aagtataaaa aattaccaca  60
tattttttttg tcacacttat ttgaagtgta gtttatctat ctctatacat atatttaaac  120
ttcactctac aaataatata gtctataata ctaaaataat attagtgttt tagaggatca  180
tataaataaa ctgctagaca tggtctaaag gataattgaa tattttgaca atctacagtt  240
ttatcttttt agtgtgcatg tgatctctct gtttttttttg caaatagctt gacctatata  300
atacttcatc cattttatta gtacatccat ttaggattta gggttgatgg tttctataga  360
ctaattttta gtacatccat tttattcttt ttagtctcta aatttttttaa aactaaaact  420
ctattttagt tttttattta ataatttaga tataaaatga aataaaataa attgactaca  480
aataaaaacaa atacccttta agaaataaaa aaactaagca aacatttttc ttgtttcgag  540
tagataatga caggctgttc aacgccgtcg acgagtctaa cggacaccaa ccagcgaacc  600
agcagcgtcg cgtcgggcca agcgaagcag acggcacggc atctctgtag ctgcctctgg  660
acccctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acgggggatt cctttcccac cgctccttcg ctttcccttc ctcgcccgcc  840
gtaataaata gacacccccct ccacaccctc tttccccaac ctcgtgttcg ttcggagcgc  900
acacacacgc aaccagatct cccccaaatc cagccgtcgg cacctccgct tcaaggtacg  960
ccgctcatcc tccccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc ttttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgttgg gtgatacttc tgcagcggac cgacggtacc atgggtagca aaaagaggcg  2040
tatcaagcag gacatgagca tctaccagga gttcgtgaac aagtacagcc tgagcaagac  2100
cctgcgcttc gagctgattc ctcaggggaa gaccctggag aacatcaagg cgcgcggcct  2160
gatcctggac gacgagaagc gggcgaagga ctacaaaaag gcgaagcaga tcatcgacaa  2220
gtaccatcag tttttcatcg aggagattct cagctccgtg tgcatcagcg aagacctgct  2280
ccagaactac agcgacgttt acttcaagct caagaaatcg gacgacgaca acctccagaa  2340
ggacttcaag agcgcgaagg acacgattaa gaaacagatc agcgagtaca tcaaggactc  2400
cgagaagttc aagaacctgt tcaaccagaa cctcatcgac gccaagaaag gccaagagtc  2460
ggacctcatc ctctggctca agcagagcaa ggacaacggc atcgagctgt tcaaggcgaa  2520
cagcgacatc accgacatcg acgaggcgct ggagatcatc aagtcgttca agggctggac  2580
gacctacttc aagggcttcc acgagaaccg caagaatgtc tactcgagca acgacatccc  2640
cacgtcgatc atctaccgca tcgtggacga caacctcccg aagttcctgg agaacaaggc  2700
gaagtacgag agcctcaagg acaaggcccc ggaggccatc aactacgagc agatcaaaaa  2760
ggatttggct gaggagctga cgttcgacat cgactacaag acctccgagg tgaaccagcg  2820
cgtcttcagc ctcgacgagg tgttcgagat cgccaacttc aacaactacc tcaaccagtc  2880
gggcatcacc aagttcaaca ccatcatcgg cgggaagttc gtcaacggcg agaacacgaa  2940
gcgcaagggg atcaacgagt acatcaacct gtacagccag cagatcaacg acaagaccct  3000
caagaagtat aaaatgtcgg tgctgttcaa gcagatcctc tcggacaccg agagcaagtc  3060
```

```
gttcgtcatc gacaagctgg aggacgacag cgacgtggtg accaccatgc agagcttcta  3120
cgagcagatc gcggccttca agaccgtcga ggagaagtcg atcaaggaga cgctcagcct  3180
gctgttcgac gacctcaagg cccagaagct cgacctgtcc aagatatact ttaagaacga  3240
caagagcctc acggacctgt cccagcaggt attcgacgac tacagcgtga tcgggacggc  3300
cgtgctggag tacatcaccc aacagatcgc gcccaagaac ctggacaacc cgtccaagaa  3360
ggaacaagag ctaatcgcca aaaagactga gaaggcgaag tacctgtcgc tggagacgat  3420
caagctcgcg cttgaggagt ttaacaagca ccgcgacatc gacaagcagt gccggttcga  3480
ggagatcctg gccaacttcg cggcgatccc gatgatcttc gacgagatcg cccagaacaa  3540
ggacaacctg gcgcagatca gcatcaagta ccagaaccag ggcaaaaaag acttgctcca  3600
agctagtgcg gaggacgacg tgaaggcgat taaggatctg ctggaccaga ctaacaatct  3660
gctgcacaag ctcaagatct ttcacatctc tcagtcggag gacaaggcga acatcctgga  3720
caaggacgag cacttctacc tagtgttcga ggagtgctac ttcgagctgg cgaacatcgt  3780
gcccctgtac aacaagatcc ggaactacat cacccagaag ccctacagcg acgagaagtt  3840
caagctgaac ttcgagaaca gcacgctggc gaacgggtgg gacaagaaca aggagcccga  3900
caacaccgcc atcctgttca tcaaggacga caaatattac ctcggcgtca tgaacaaaaa  3960
gaataacaag atattcgatg acaaggcgat caaggagaac aagggcgagg gctacaagaa  4020
gatcgtatat aaactcctgc cgggagcgaa caagatgctc ccgaaggttt tctttagtgc  4080
caagtccatc aagttctaca accccagcga ggacatcctc cgcatccgga accactccac  4140
ccacaccaag aacggctcgc cgcagaaggg ctacgagaag ttcgagttca acatcgagga  4200
ctgccgcaag ttcatcgact tctacaagca gtccatctcc aagcacccgg agtggaagga  4260
cttcgggttc cggttctccg acacgcagcg ctacaactcc atcgacgagt tctaccggga  4320
ggtggagaac cagggctaca agctgacgtt cgagaacatc tcggagtcct acatcgactc  4380
cgtggtcaac cagggcaagc tgtacctctt ccagatatac aataaggact tctccgccta  4440
cagcaagggg cggcccaacc tccacaccct gtactggaag gcgctcttcg acgagcggaa  4500
cctccaggac gtcgtgtaca agctgaacgg cgaggcggag ctgttctacc gcaagcagag  4560
catccccaag aagatcacgc accccgcgaa ggaggccatc gccaacaaga acaaggacaa  4620
ccccaagaag gaatcggtct tcgagtacga cctcatcaag gacaagcggt tcacggagga  4680
caaattcttt ttccactgcc cgatcactat taacttcaag tccagcggcg cgaacaagtt  4740
caacgacgag atcaacctgc tcctcaagga gaaggcgaac gacgtgcaca tcctcagcat  4800
cgaccggggc gagcgccacc tcgcctacta cacgctggtg gacgggaagg gcaacatcat  4860
caagcaagac accttcaaca tcatcggcaa cgaccggatg aagaccaact accacgacaa  4920
gctggccgcc atcgagaagg accgcgactc ggcccgcaag gactggaaaa agatcaacaa  4980
tatcaaggag atgaaggagg gctacctgag ccaagttgtc cacgagatcg ccaagctggt  5040
gatcgagtac aacgccatcg tcgtgttcga agacctgaac ttcggcttca agcgcggccg  5100
gttcaaggtc gagaaacaag tctatcagaa acttgagaag atgctgatcg agaagctgaa  5160
ctacctcgtc ttcaaggaca acgagttcga caagaccggc ggcgtcctcc gcgcgtacca  5220
gctcaccgcg ccgttcgaga cgttcaagaa aatgggcaag cagaccggca tcatctacta  5280
cgtgcccgcc gggttcacga gcaaaatatg tcccgtgacc ggcttcgtca accagctcta  5340
ccccaagtac gagtccgtgt cgaagtccca ggaattcttc agcaagttcg acaagatatg  5400
ctacaacctg gacaagggct acttcgagtt ctccttcgac tacaagaact tcggggacaa  5460
ggcggcgaag gggaagtgga ccatcgcctc gttcgggtcg cgcctcatca acttccggaa  5520
cagcgacaag aaccacaact gggacacccg cgaggtgtac ccgacgaagg agctggagaa  5580
gctcctcaag gactacagca tcgagtacgg ccacggggag tgcatcaagg cggccatctg  5640
cggcgagtcg gacaaaaagt tctttgccaa actcacctcg gtcctcaaca ccatcctcca  5700
gatgcggaac agcaagacgg gcacggagct ggactacctc atcagcccgg tggccgacgt  5760
gaacggcaat ttctttgact cacgccaggc ccctaagaac atgccccagg acgccgacgc  5820
caacggcgcg taccacatcg gcctcaaggg cctgatgctg ctcggccgga tcaagaacaa  5880
ccaggagggc aagaagctca acctggtcat caagaacgag gagtatttcg agttcgtcca  5940
gaaccgcaac aacggatcta agaagcgtag gatcaagcaa gattagttaa ttaagggccc  6000
atccaagtaa attaagttgg atcagtagag atgcatggtt ggtgttctca tgtggtctga  6060
atctgtgttc tgtttcatct tttgtgtaag tgtgcaactt cgattctgta aaacttggca  6120
agtagatgaa cgatgtcatt tatatgcgtg tagcttgtca aaatacaaag tagaaacctg  6180
tatctgaata agatggcatt catgaaataa tattatcgat tgaacgaacg aagcaacaga  6240
atgatcttcc aaattgaagc aaaggaattg atggacaacg agttgctgta ctttggagct  6300
gtaaatctgt agtacttctc aacgatgcta tggaccgtgg gccgtccata atcgctgggt  6360
ggaatgagcc cactgtccat gtgcttctgc atttggcccg tgtacagccc atataatgtc  6420
gaaaaaccta atacgcgcgc gccgccggcg cgcgtttcgg acccagaacg cctagcgccg  6480
ctgcgccgac gtgcgcgcgt ctccactttt tttttcgttt tctttccatt             6530
```

```
SEQ ID NO: 68           moltype = DNA  length = 3960
FEATURE                 Location/Qualifiers
misc_feature            1..3960
                        note = Synthetic polynucleotide.NLS-FnCpf1-CO5-NLS
source                  1..3960
                        mol_type = other DNA
                        organism = synthetic construct
SEQUENCE: 68
ggtagcaaaa agaggcgtat caagcaggac atgtccatat accaggagtt tgttaataaa  60
tatagcttgt ccaaaaccct gcggtttgaa ctcatacctc aggggaagac tttggagaat  120
atcaaagcgc ggggactgat actggacgac gaaaagcgcg caaaagatta caagaaagcg  180
aaacagatca tcgataaata ccatcaattt ttcatagagg agattctcag ttctgtctgt  240
atcagtgagg acctcctcca aaattattca gacgtctatt ttaaactcaa gaagtcggac  300
gacgacaacc ttcagaaaga ttttaagtca gcaaaagaca caatcaaaaa acaaatatcg  360
gaatacataa aggactcaga aaagttcaag aatcttttta accaaaatct gatagacgcg  420
aagaaaggcc aggaatctga tcttatactc tggcttaagc agtctaaaga caacggcata  480
gaactcttta aggcaaacag cgatataacc gacatagatg aagccctcga gataattaag  540
tccttcaaag gctggactac atattttaaa gggttccatg agaataggaa gaacgtgtat  600
tcctcgaatg atattcccac ctcgataatc taccggattg tggatgataa tctgcctaaa  660
tttttggaaa ataaagcgaa gtacgaaagt ttgaaagata aagcaccaga agcaattaat  720
```

-continued

```
tatgaacaaa ttaagaaaga tctggctgag gaacttacgt tcgatatcga ttataaaaca  780
tcagaagtta atcagcgggt ttttagcctg gatgaagttt ttgagatcgc caacttcaac  840
aattatctta atcagagcgg gattaccaaa ttcaacacta ttatcggtgg taaattcgtt  900
aatggtgaga acacaaagag aaaaggtata aacgaataca taaatttgta cagtcaacag  960
attaacgata aaactttgaa aaagtacaag atgtcagtgc ttttcaaaca aatcctttcc  1020
gacacagaat ccaaaagttt tgtgatagac aaattggaag atgatagcga cgtcgtcacg  1080
accatgcaat cattttatga gcaaattgca gccttcaaga cggttgagga aaaaagtata  1140
aaagaaacgt tgtcgctctt gttcgacgac ctgaaagcac agaaattgga tttgtctaag  1200
atatacttta aaaacgacaa atccctcacg gacttgtcgc agcaagtctt tgatgattat  1260
tcggtgattg ggacagccgt gctcgaatac atcacccagc aaatcgctcc gaaaaatctg  1320
gacaatccgt ctaaaaaaga gcaagagctg atcgcaaaga aaaccgaaaa agcgaaatac  1380
ctgtctctgg agacaatcaa attggccttg gaagagttca ataagcacag agacattgat  1440
aaacaatgtc ggtttgagga aattcttgct aactttgccg ctatcccgat gatcttcgat  1500
gagattgcgc aaaataagga taatctggcc caaatctcga tcaagtatca aaatcagggt  1560
aagaaggacc tgcttcaagc atcggcggag gatgatgtga aagcgattaa ggacttgttg  1620
gatcagacca acaatttgtt gcacaagctg aagatattcc acatctccca gagtgaggat  1680
aaggccaaca tcctggacaa ggatgaacat ttctatttgg tcttcgaaga gtgttatttt  1740
gaattggcca acatagttcc tctttataac aagatccgca attatattac acaaaagcct  1800
tattccgatg aaaaatttaa acttaacttc gaaaatagca cattggcgaa tggttgggat  1860
aaaaataagg agcctgacaa tactgctata cttttcatta aggacgataa gtactacctc  1920
ggcgttatga acaagaagaa taataagatc tttgacgaca aagcaatcaa agagaacaaa  1980
ggcgaaggtt acaaaaaaat cgtgtacaaa ctcctgcctg gcgcgaataa aatgcttccg  2040
aaggtttttt tcagtgcgaa gtccattaag ttttataacc cttccgagga tatttgaga  2100
attagaaatc actccaccca taccaagaat ggcagccccc agaaggggta tgaaaagttc  2160
gaatttaata tcgaagactg ccgcaagttt atagactttt ataaacagtc catatctaaa  2220
catcccgaat ggaaagattt tggtttccgg ttttctgaca ctcagaggta caacagcata  2280
gatgagttct accgcgaagt tgaaaaccaa ggctacaagc ttacatttga gaacatcagc  2340
gagtcatata ttgactcagt cgttaatcag ggcaaacttt atttgttcca aatttacaac  2400
aaagactttt cagcgtacag caagggaagg ccaaatctcc atacactgta ttggaaggcg  2460
ctgtttgacg agcggaatct tcaagatgtt gtgtataaac tcaacgggga ggccgaattg  2520
ttctacagga agcaaagcat tcctaagaaa attacccacc ccgctaagga agcgatagca  2580
aataaaaata aagacaatcc gaaaaaagag agcgtttttg agtacgacct tataaaggat  2640
aagagattca ccgaggataa gtttttcttc cactgtccaa taactattaa ctttaaatcc  2700
tccggagcca acaagtttaa cgacgaaatt aatttgctgc tgaaagagaa ggcgaacgac  2760
gttcacattc tgtcaataga cagaggggag agacacttgg catactacac gctcgttgat  2820
ggaaaaggta acattattaa gcaagatact ttcaacatca ttgggaatga cagaatgaaa  2880
acaaactatc acgataaact cgcggcaatt gagaaggacc gggattcggc gaggaaagac  2940
tggaagaaaa tcaacaatat aaaggagatg aaggaaggat acctgtctca agtcgtccac  3000
gaaatagcca agcttgttat agagtataat gcgattgtgg tctttgaaga ccttaacttt  3060
ggatttaaac gcggccggtt taaagtcgag aaacaagtgt atcaaaaact ggaaaaaatg  3120
ttgatcgaga aactgaatta tctcgtcttc aaggacaacg agttcgataa aaccgggggc  3180
gtcttgcgcg cttatcaact gacggcaccg tttgaaactt tcaagaagat gggcaaacag  3240
actgggatta tctactacgt tcctgccgga ttcacctcca aaatatgccc agttactgga  3300
tttgttaacc agttgtaccc taagtacgaa tcagtcagca agtcccaaga gtttttctca  3360
aaatttgata agatctgcta taacctggac aaggggtact tcgagttttc cttcgactat  3420
aaaaatttcg gcgacaaggc agctaaaggt aaatggacga ttgcaagttt cggctccagg  3480
cttattaatt tcagaaacag cgacaaaaac cataactggg acacgcgcga ggtctaccct  3540
acgaaggaac tggaaaaact tctcaaggat tacagtatag aatacggaca cggggagtgt  3600
atcaaagctg cgatatgcgg agagtcggat aaaaagtttt tcgcaaagtt gacatcagtt  3660
ttgaacacta tcttgcagat gagaaattcc aagactggca cggagttgga ctaccttatt  3720
agcccagtgg cggatgtcaa cgggaacttt tttgattcga ggcaagcccc taagaatatg  3780
cctcaagacg ctgatgcaaa cggggcatat cacataggac tcaaagggtt gatgctgctg  3840
ggcagaatta agaacaacca ggaaggaaag aagctcaatc ttgttatcaa aaatgaagag  3900
tactttgaat tcgttcaaaa ccggaataac ggatctaaga agcgtaggat caagcaagat  3960

SEQ ID NO: 69          moltype = DNA  length = 6530
FEATURE                Location/Qualifiers
misc_feature           1..6530
                       note = Synthetic polynucleotide.Expression cassette
                        comprising Zea maysUbiquitin promoter cassette,
                        NLS-FnCpf1-CO5-NLS and an Oryzasativa transcription
                        termination sequence
source                 1..6530
                       mol_type = other DNA
                       organism = synthetic construct
SEQUENCE: 69
gtcgtgcccc tctctagaga taaagagcat tgcatgtcta aagtataaaa aattaccaca  60
tattttttttg tcacacttat ttgaagtgta gtttatctat ctctatacat atatttaaac  120
ttcactctac aaataatata gtctataata ctaaaataat attagtgttt tagaggatca  180
tataaataaa ctgctagaca tggtctaaag gataattgaa tattttgaca atctacagtt  240
ttatcttttt agtgtgcatg tgatctctct gttttttttg caaatagctt gacctatata  300
atacttcatc cattttatta gtacatccat ttaggattta gggttgatgg tttctataga  360
ctaattttta gtacatccat tttattcttt ttagtctcta aatttttttaa aactaaaact  420
ctattttagt tttttattta ataatttaga tataaaatga aataaaataa attgactaca  480
aataaaacaa ataccctta agaaataaaa aaactaagca aacatttttc ttgtttcgag  540
tagataatga caggctgttc aacgccgtcg acgagtctaa cggacaccaa ccagcgaacc  600
agcagcgtcg cgtcgggcca agcgaagcag acggcacggc atctctgtag ctgcctctgg  660
acccctctcg agagttccgc tccaccgttg gacttgctcc gctgtcggca tccagaaatt  720
gcgtggcgga gcggcagacg tgaggcggca cggcaggcgg cctcttcctc ctctcacggc  780
```

-continued

```
accggcagct acgggggatt cctttcccac cgctccttcg ctttcccttc ctcgcccgcc  840
gtaataaata gacacccccct ccacaccctc tttccccaac ctcgtgttcg ttcggagcgc  900
acacacacgc aaccagatct cccccaaatc cagccgtcgg cacctccgct tcaaggtacg  960
ccgctcatcc tccccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc ttttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgttgg gtgatacttc tgcagcggac cgacggtacc atgggtagca aaaagaggcg  2040
tatcaagcag gacatgtcca tataccagga gtttgttaat aaatatagct tgtccaaaac  2100
cctgcggttt gaactcatac ctcaggggaa gactttggag aatatcaaag cgcggggact  2160
gatactggac gacgaaaagc gcgcaaaaga ttacaagaaa gcgaaacaga tcatcgataa  2220
ataccatcaa tttttcatag aggagattct cagttctgtc tgtatcagtg aggacctcct  2280
ccaaaattat tcagacgtct attttaaact caagaagtcg gacgacgaca accttcagaa  2340
agattttaag tcagcaaaag acacaatcaa aaaacaaata tcggaataca taaaggactc  2400
agaaaagttc aagaatcttt ttaaccaaaa tctgatagac gcgaagaaag ggcaggaatc  2460
tgatcttata ctctggctta agcagtctaa agacaacggc atagaactct ttaaggcaaa  2520
cagcgatata accgacatag atgaagccct cgagataatt aagtccttca aaggctggac  2580
tacatatttt aaagggttcc atgagaatag gaagaacgtg tattcctcga atgatattcc  2640
cacctcgata atctaccgga ttgtggatga taatctgcct aaatttttgg aaaataaagc  2700
gaagtacgaa agtttgaaag ataaagcacc agaagcaatt aattatgaac aaattaagaa  2760
agatctggct gaggaactta cgttcgatat cgattataaa acatcagaag ttaatcagcg  2820
ggtttttagc ctggatgaag tttttgagat cgccaacttc aacaattatc ttaatcagag  2880
cgggattacc aaattcaaca ctattatcgg tggtaaattc gttaatggtg agaacacaaa  2940
gagaaaaggt ataaacgaat acataaattt gtacagtcaa cagattaacg ataaaacttt  3000
gaaaaagtac aagatgtcag tgcttttcaa acaaatcctt tccgacacag aatccaaaag  3060
ttttgtgata gacaaattgg aagatgatag cgacgtcgtc acgaccatgc aatcatttta  3120
tgagcaaatt gcagccttca agacggttga ggaaaaaagt ataaaagaaa cgttgtcgct  3180
cttgttcgac gacctgaaag cacagaaatt ggatttgtct aagatatact ttaaaaacga  3240
caaatccctc acggacttgt cgcagcaagt ctttgatgat tattcggtga ttgggacagc  3300
cgtgctcgaa tacatcaccc agcaaatcgc tccgaaaaat ctggacaatc cgtctaaaaa  3360
agagcaagag ctgatcgcaa agaaaaccga aaaagcgaaa tacctgtctc tggagacaat  3420
caaattggcc ttggaagagt tcaataagca cagagacatt gataaacaat gtcggtttga  3480
ggaaattctt gctaactttg ccgctatccc gatgatcttc gatgagattg cgcaaaataa  3540
ggataatctg gcccaaatct cgatcaagta tcaaaatcag ggtaagaagg acctgcttca  3600
agcatcggcg gaggatgatg tgaaagcgat taaggacttg ttggatcaga ccaacaattt  3660
gttgcacaag ctgaagatat tccacatctc ccagagtgag gataaggcca acatcctgga  3720
caaggatgaa catttctatt tggtcttcga agagtgttat tttgaattgg ccaacatagt  3780
tcctctttat aacaagatcc gcaattatat tacacaaaag ccttattccg atgaaaaatt  3840
taaacttaac ttcgaaaata gcacattggc gaatggttgg gataaaaata aggagcctga  3900
caatactgct atacttttca ttaaggacga taagtactac ctcggcgtta tgaacaagaa  3960
gaataataag atctttgacg acaaagcaat caaagagaac aaaggcgaag gttacaaaaa  4020
aatcgtgtac aaactcctgc ctggcgcgaa taaaatgctt ccgaaggttt ttttcagtgc  4080
gaagtccatt aagttttata acccttccga ggatattttg agaattagaa atcactccac  4140
ccataccaag aatggcagcc cccagaaggg gtatgaaaag ttcgaattta atatcgaaga  4200
ctgccgcaag tttatagact tttataaaca gtccatatct aaacatcccg aatggaaaga  4260
ttttggtttc cggttttctg acactcagag gtacaacagc atagatgagt tctaccgcga  4320
agttgaaaac caaggctaca agcttacatt tgagaacatc agcgagtcat atattgactc  4380
agtcgttaat cagggcaaac tttatttgtt ccaaatttac aacaaagact tttcagcgta  4440
cagcaaggga aggccaaatc tccatacact gtattggaag gcgctgtttg acgagcggaa  4500
tcttcaagat gttgtgtata aactcaacgg ggaggccgaa ttgttctaca ggaagcaaag  4560
cattcctaag aaaattaccc accccgctaa ggaagcgata gcaaataaaa ataaagacaa  4620
tccgaaaaaa gagagcgttt ttgagtacga ccttataaag gataagagat tcaccgagga  4680
taagtttttc ttccactgtc caataactat taactttaaa tcctccggag ccaacaagtt  4740
taacgacgaa attaatttgc tgctgaaaga gaaggcgaac gacgttcaca ttctgtcaat  4800
agacagaggg gagagacact tggcatacta cacgctcgtt gatggaaaag gtaacattat  4860
taagcaagat actttcaaca tcattgggaa tgacagaatg aaaacaaact atcacgataa  4920
actcgcggca attgagaagg accgggattc ggcgaggaaa gactggaaga aaatcaacaa  4980
tataaaggag atgaaggaag gatacctgtc tcaagtcgtc cacgaaatag ccaagcttgt  5040
tatagagtat aatgcgattg tggtctttga agaccttaac tttggattta aacgcggccg  5100
gtttaaagtc gagaaacaag tgtatcaaaa actggaaaaa atgttgatcg agaaactgaa  5160
ttatctcgtc ttcaaggaca acgagttcga taaaaccggg ggcgtcttgc gcgcttatca  5220
actgacggca ccgtttgaaa ctttcaagaa gatgggcaaa cagactggga ttatctacta  5280
cgttcctgcc ggattcacct ccaaaatatg cccagttact ggatttgtta accagttgta  5340
ccctaagtac gaatcagtca gcaagtccca agagtttttc tcaaaatttg ataagatctg  5400
ctataacctg gacaaggggt acttcgagtt ttccttcgac tataaaaatt tcggcgacaa  5460
ggcagctaaa ggtaaatgga cgattgcaag tttcggctcc aggcttatta atttcagaaa  5520
```

```
cagcgacaaa aaccataact gggacacgcg cgaggtctac cctacgaagg aactggaaaa  5580
acttctcaag gattacagta tagaatacgg acacggggag tgtatcaaag ctgcgatatg  5640
cggagagtcg gataaaaagt ttttcgcaaa gttgacatca gttttgaaca ctatcttgca  5700
gatgagaaat tccaagactg gcacggagtt ggactacctt attagcccag tggcggatgt  5760
caacgggaac ttttttgatt cgaggcaagc ccctaagaat atgcctcaag acgctgatgc  5820
aaacggggca tatcacatag gactcaaagg gttgatgctg ctgggcagaa ttaagaacaa  5880
ccaggaagga aagaagctca atcttgttat caaaaatgaa gagtactttg aattcgttca  5940
aaaccggaat aacggatcta agaagcgtag gatcaagcaa gattgattaa ttaagggccc  6000
atccaagtaa attaagttgg atcagtagag atgcatggtt ggtgttctca tgtggtctga  6060
atctgtgttc tgtttcatct tttgtgtaag tgtgcaactt cgattctgta aaacttggca  6120
agtagatgaa cgatgtcatt tatatgcgtg tagcttgtca aaatacaaag tagaaacctg  6180
tatctgaata agatggcatt catgaaataa tattatcgat tgaacgaacg aagcaacaga  6240
atgatcttcc aaattgaagc aaaggaattg atggacaacg agttgctgta ctttggagct  6300
gtaaatctgt agtacttctc aacgatgcta tggaccgtgg gccgtccata atcgctgggt  6360
ggaatgagcc cactgtccat gtgcttctgc atttggcccg tgtacagccc atataatgtc  6420
gaaaaaccta atacgcgcgc gccgccggcg cgcgtttcgg acccagaacg cctagcgccg  6480
ctgcgccgac gtgcgcgcgt ctccactttt tttttcgttt tctttccatt             6530

SEQ ID NO: 70            moltype = DNA  length = 3960
FEATURE                  Location/Qualifiers
misc_feature             1..3960
                         note = Synthetic polynucleotide.NLS-FnCpf1-CO6-NLS
source                   1..3960
                         mol_type = other DNA
                         organism = synthetic construct
SEQUENCE: 70
ggtagcaaaa agaggcgtat caagcaggac atgagtattt atcaagagtt cgttaataag  60
tacagtcttt ctaagacgct caggtttgag ctcattccac aaggtaagac ccttgagaat  120
attaaagccc gcggactgat cctggacgac gagaagcgcg ccaaagacta taagaaggcg  180
aaacagatca tagataagta tcaccaattc ttcatagaag agatacttag ctctgtttgt  240
atctcagagg atctgctcca gaactactcg gatgtgtact ttaaactcaa gaagtctgac  300
gatgacaatc tccagaagga ctttaagtcc gccaaagaca caatcaagaa gcagatttcg  360
gaatacataa aggacagtga gaagttcaag aacttgttca accagaatct catagacgcc  420
aagaagggtc aggagagcga tcttattctg tggttgaaac aatcaaagga caacggtatt  480
gagttgttta aagcaaactc tgacatcacc gacattgacg aggctctgga gatcattaag  540
agttttaaag ggtggacaac ctactttaag ggatttcatg agaatcgcaa gaacgtgtac  600
tcgagcaatg acatacctac aagcataatc tatcggatag tcgacgataa cctcccgaag  660
ttcctcgaga ataaagcgaa gtacgaatcg cttaaggata aggcgccgga ggcgataaac  720
tatgaacaga ttaagaagga tctggctgaa gaattgacct ttgatattga ctataagacc  780
agcgaagtca accaacgcgt tttcagcctg gatgaagtgt ttgagatcgc caacttcaat  840
aattacttga atcaatcggg gataacaaag tttaatacga ttatcggcgg gaagtttgtc  900
aacggggaga acacaaagag gaagggcata aatgagtaca ttaatctcta tagtcaacag  960
ataaatgaca agacgttgaa gaaatacaag atgtcagtcc ttttcaagca gatcctgtct  1020
gacacagaat cgaagagctt cgtgatagat aagctggaag atgattccga cgttgtcaca  1080
accatgcaat cgttttacga gcagatcgcg gccttcaaga ccgttgagga gaagtctatt  1140
aaagagactc tttctcttct gtttgatgac ttgaaggccc agaagcttga cttgtccaag  1200
atctacttca agaacgataa atctctgaca gatctcagcc agcaagtgtt tgacgactat  1260
tctgttatcg gaacggccgt gctggagtac atcacacagc agatcgcgcc taagaacctt  1320
gataatccga gcaagaaaga acaggagttg attgcaaaga agacagagaa ggccaaatac  1380
ctttctctgg agacaattaa acttgcactg gaagaattca ataagcacag agatatcgac  1440
aagcagtgtc gctttgagga gatcctggca aattttgctg ccatcccaat gatttttgat  1500
gagattgccc agaacaagga caatctcgcg cagatatcaa tcaagtatca gaaccaaggc  1560
aagaaggacc tcctgcaagc ctcagccgaa gatgacgtta aggccataaa ggatctcctt  1620
gatcagacca ataacttgct gcacaagctg aagatctttc atatcagcca gtcggaagac  1680
aaagcaaata tccttgacaa ggacgagcat ttctatctgg tgttcgaaga atgctatttc  1740
gagctggcca atatcgtgcc tctgtacaat aagatccgca attatatcac gcagaagccg  1800
tatagcgacg agaagttcaa gctgaatttc gagaactcca ccttggccaa tggttgggat  1860
aagaacaaag aaccggacaa tacggccatc ttgtttatca aagatgacaa gtactatctg  1920
ggagtgatga ataagaagaa caataagatc ttcgatgaca aagccattaa ggagaataaa  1980
ggggaaggtt acaagaagat tgtctataaa ctgctccccg gggccaacaa gatgctgccc  2040
aaagtttttt tcagtgccaa gagcatcaag ttttataatc cctcagaaga catactgaga  2100
atcagaaacc actcgaccca taccaagaac ggctctccgc agaaggggta cgagaaattc  2160
gaattcaaca tcgaagactg tagaaagttc atcgattttt acaagcaatc gatatcaaag  2220
caccctgaat ggaaggattt tggttttcgc tttagtgaca ctcagcggta taatagcatt  2280
gatgagttct accgcgaagt tgagaatcag ggatacaaat tgacattcga gaatatcagc  2340
gaatcgtaca ttgatagcgt cgtcaaccag gggaaacttt acctcttcca gatttataat  2400
aaagacttct cggcgtactc caagggaaga ccaaatcttc atactctgta ttggaaggca  2460
ctcttcgatg agagaaatct tcaggatgtc gtttataaac ttaatgggga agcggagctg  2520
ttctaccgca agcagagcat ccctaagaag atcacgcacc ccgcgaagga ggcgatagcc  2580
aataagaaca aggataaccc gaagaaggag tccgtcttcg aatatgacct gatcaaggat  2640
aagagattca ctgaggacaa attcttcttc cattgcccta ttacgattaa ttttaaatcg  2700
agcggcgcga ataaattcaa cgacgagatc aacctgctcc tcaaagagaa ggccaatgat  2760
gtccacattc tctcaatcga cagaggggag aggcaccttg cctactatac gctcgttgat  2820
ggtaaaggta acatcattaa gcaggacacg ttcaacatca tcgggaacga ccgcatgaag  2880
acaaactatc acgataaatt ggcggcaatc gagaaggatc gggatagtgc caggaaggac  2940
tggaagaaga ttaataacat caaggagatg aaggagggat atctttctca agtcgtccac  3000
gagatcgcga agctggttat cgagtacaac gccatagtgg tcttcgaaga tctgaacttc  3060
ggattcaaga gagggagatt taaggtggag aagcaagttt atcagaaact ggagaagatg  3120
ctgatagaga agctcaacta cctcgtgttt aaagacaacg agtttgacaa gacaggtggg  3180
```

```
gtgttgaggg cctatcagct cacggccccc ttcgagacct tcaagaagat gggaaagcag  3240
acggggataa tctactacgt ccctgctggc ttcacttcga agatctgccc agttacagga  3300
ttcgttaacc agttgtatcc caaatacgag tccgtctcaa agtcacaaga attcttttct  3360
aaattcgata agatctgcta caacctggat aagggctact tcgagtttag ctttgactat  3420
aagaatttcg ggacaaagc ggcaaagggg aagtggacaa tcgcaagttt tggctcccgg  3480
ctgattaact ttcggaattc tgacaagaat cacaactggg atactagaga ggtctatcca  3540
actaaagagt tggagaagtt gctcaaggac tactccattg aatatggtca cggggaatgc  3600
attaaagcgg ccatctgcgg agagtccgat aagaagttct ttgccaaact tacatcggtc  3660
ttgaacacca tactgcagat gcggaacagc aagacgggaa cggaactcga ctaccttatc  3720
tcacctgtgg cggatgttaa tggaaacttt ttcgattcga ggcaggcgcc caagaacatg  3780
ccgcaagatg cagatgccaa tggagcatat cacatcggtc ttaaagggct catgctgctt  3840
ggccgcatca agaacaacca agaggggaag aagttgaacc tggttattaa gaacgaagaa  3900
tacttcgaat ttgtccagaa ccgcaacaac ggatctaaga agcgtaggat caagcaagat  3960

SEQ ID NO: 71           moltype = DNA  length = 6530
FEATURE                 Location/Qualifiers
misc_feature            1..6530
                        note = Synthetic polynucleotide.Expression cassette
                         comprising Zea maysUbiquitin promoter cassette,
                         NLS-FnCpf1-CO6-NLS and an Oryzasativa transcription
                         termination sequence
source                  1..6530
                        mol_type = other DNA
                        organism = synthetic construct
SEQUENCE: 71
gtcgtgcccc tctctagaga taaagagcat tgcatgtcta aagtataaaa aattaccaca  60
tatttttttg tcacacttat ttgaagtgta gtttatctat ctctatacat atatttaaac  120
ttcactctac aaataatata gtctataata ctaaaataat attagtgttt tagaggatca  180
tataaataaa ctgctagaca tggtctaaag gataattgaa tattttgaca atctacagtt  240
ttatctttttt agtgtgcatg tgatctctct gtttttttg caaatagctt gacctatata  300
atacttcatc cattttatta gtacatccat ttaggattta gggttgatgg tttctataga  360
ctaattttta gtacatccat tttattcttt ttagtctcta aatttttttaa aactaaaact  420
ctattttagt tttttattta ataatttaga tataaaatga aataaaataa attgactaca  480
aataaaacaa ataccctttta agaaataaaa aaactaagca aacatttttc ttgtttcgag  540
tagataatga caggctgttc aacgccgtcg acgagtctaa cggacaccaa ccagcgaacc  600
agcagcgtcg cgtcgggcca agcgaagcag acggcacggc atctctgtag ctgcctctgg  660
acccctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acgggggatt cctttcccac cgctccttcg ctttcccttc ctcgcccgcc  840
gtaataaata gacaccccct ccacaccctc tttccccaac ctcgtgttcg ttcggagcgc  900
acacacacgc aaccagatct cccccaaatc cagccgtcgg cacctccgct tcaaggtacg  960
ccgctcatcc tcccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc tttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgttgg gtgatacttc tgcagcggac cgacggtacc atgggtagca aaaagaggcg  2040
tatcaagcag gacatgagta tttatcaaga gttcgttaat aagtacagtc tttctaagac  2100
gctcaggttt gagctcattc cacaaggtaa gacccttgag aatattaaag cccgcggact  2160
gatcctggac gacgagaagc gcgccaaaga ctataagaag gcgaaacaga tcatagataa  2220
gtatcaccaa ttcttcatag aagagatact tagctctgtt tgtatctcag aggatctgct  2280
ccagaactac tcggatgtgt actttaaact caagaagtct gacgatgaca atctccagaa  2340
ggactttaag tccgccaaag acacaatcaa gaagcagatt tcggaataca taaaggacag  2400
tgagaagttc aagaacttgt tcaaccagaa tctcatagac gccaagaagg gtcaggagag  2460
cgatcttatt ctgtggttga aacaatcaaa ggacaacggt attgagttgt ttaaagcaaa  2520
ctctgacatc accgacattg acgaggctct ggagatcatt aagagtttta aagggtggac  2580
aacctacttt aagggatttc atgagaatcg caagaacgtg tactcgagca atgacatacc  2640
tacaagcata atctatcgga tagtcgacga taacctcccg aagttcctcg agaataaagc  2700
gaagtacgaa tcgcttaagg ataaggcgcc ggaggcgata aactatgaac agattaagaa  2760
ggatctggct gaagaattga cctttgatat tgactataag accagcgaag tcaaccaacg  2820
cgttttcagc ctggatgaag tgtttgagat cgccaacttc aataattact tgaatcaatc  2880
ggggataaca aagtttaata cgattatcgg cgggaagttt gtcaacgggg agaacacaaa  2940
gaggaagggc ataaatgagt acattaatct ctatagtcaa cagataaatg acaagacgtt  3000
gaagaaatac aagatgtcag tcctttttcaa gcagatcctg tctgacacag aatcgaagag  3060
cttcgtgata gataagctgg aagatgattc cgacgttgtc acaaccatgc aatcgtttta  3120
cgagcagatc gcggccttca agaccgttga ggagaagtct attaaagaga ctctttctct  3180
tctgtttgat gacttgaagg cccagaagct tgacttgtcc aagatctact tcaagaacga  3240
```

```
taaatctctg acagatctca gccagcaagt gtttgacgac tattctgtta tcggaacggc  3300
cgtgctggag tacatcacac agcagatcgc gcctaagaac cttgataatc cgagcaagaa  3360
agaacaggag ttgattgcaa agaagacaga gaaggccaaa tacctttctc tggagacaat  3420
taaacttgca ctggaagaat tcaataagca cagagatatc gacaagcagt gtcgctttga  3480
ggagatcctg gcaaattttg ctgccatccc aatgattttt gatgagattg cccagaacaa  3540
ggacaatctc gcgcagatat caatcaagta tcagaaccaa ggcaagaagg acctcctgca  3600
agcctcagcc gaagatgacg ttaaggccat aaaggatctc cttgatcaga ccaataactt  3660
gctgcacaag ctgaagatct ttcatatcag ccagtcggaa gacaaagcaa atatccttga  3720
caaggacgag catttctatc tggtgttcga agaatgctat ttcgagctgg ccaatatcgt  3780
gcctctgtac aataagatcc gcaattatat cacgcagaag ccgtatagcg acgagaagtt  3840
caagctgaat ttcgagaact ccaccttggc caatggttgg gataagaaca aagaaccgga  3900
caatacggcc atcttgttta tcaaagatga caagtactat ctgggagtga tgaataagaa  3960
gaacaataag atcttcgatg acaaagccat taaggagaat aaaggggaag gttacaagaa  4020
gattgtctat aaactgctcc ccggggccaa caagatgctg cccaaagttt ttttcagtgc  4080
caagagcatc aagttttata atccctcaga agacatactg agaatcagaa accactcgac  4140
ccataccaag aacggctctc cgcagaaggg gtacgagaaa ttcgaattca acatcgaaga  4200
ctgtagaaag ttcatcgatt tttacaagca atcgatatca aagcaccctg aatggaagga  4260
ttttggtttt cgctttagtg acactcagcg gtataatagc attgatgagt tctaccgcga  4320
agttgagaat cagggataca aattgacatt cgagaatatc agcgaatcgt acattgatag  4380
cgtcgtcaac caggggaaac tttacctctt ccagatttat aataaagact tctcggcgta  4440
ctccaaggga agaccaaatc ttcatactct gtattggaag gcactcttcg atgagagaaa  4500
tcttcaggat gtcgtttata aacttaatgg ggaagcggag ctgttctacc gcaagcagag  4560
catccctaag aagatcacgc accccgcgaa ggaggcgata gccaataaga acaaggataa  4620
cccgaagaag gagtccgtct tcgaatatga cctgatcaag gataagagat tcactgagga  4680
caaattcttc ttccattgcc ctattacgat taattttaaa tcgagcggcg cgaataaatt  4740
caacgacgag atcaacctgc tcctcaaaga gaaggccaat gatgtccaca ttctctcaat  4800
cgacagaggg gagaggcacc ttgcctacta tacgctcgtt gatggtaaag gtaacatcat  4860
taagcaggac acgttcaaca tcatcgggaa cgaccgcatg aagacaaact atcacgataa  4920
attggcggca atcgagaagg atcgggatag tgccaggaag gactggaaga agattaataa  4980
catcaaggag atgaaggagg gatatctttc tcaagtcgtc cacgagatcg cgaagctggt  5040
tatcgagtac aacgccatag tggtcttcga agatctgaac ttcggattca agagagggag  5100
atttaaggtg gagaagcaag tttatcagaa actggagaag atgctgatag agaagctcaa  5160
ctacctcgtg tttaaagaca acgagtttga caagacaggt ggggtgttga gggcctatca  5220
gctcacggcc ccttcgaga ccttcaagaa gatgggaaag cagacgggga taatctacta  5280
cgtccctgct ggcttcactt cgaagatctg cccagttaca ggattcgtta accagttgta  5340
tcccaaatac gagtccgtct caaagtcaca agaattcttt tctaaattcg ataagatctg  5400
ctacaacctg gataagggct acttcgagtt tagctttgac tataagaatt tcggggacaa  5460
agcggcaaag gggaagtgga caatcgcaag ttttggctcc cggctgatta actttcggaa  5520
ttctgacaag aatcacaact gggatactag agaggtctat ccaactaaag agttggagaa  5580
gttgctcaag gactactcca ttgaatatgg tcacggggaa tgcattaaag cggccatctg  5640
cggagagtcc gataagaagt tctttgccaa acttacatcg gtcttgaaca ccatactgca  5700
gatgcggaac agcaagacgg gaacggaact cgactacctt atctcacctg tggcggatgt  5760
taatggaaac tttttcgatt cgaggcaggc gcccaagaac atgccgcaag atgcagatgc  5820
caatggagca tatcacatcg gtcttaaagg gctcatgctg cttggccgca tcaagaacaa  5880
ccaagagggg aagaagttga acctggttat taagaacgaa gaatacttcg aatttgtcca  5940
gaaccgcaac aacggatcta agaagcgtag gatcaagcaa gattgattaa ttaagggccc  6000
atccaagtaa attaagttgg atcagtagag atgcatggtt ggtgttctca tgtggtctga  6060
atctgtgttc tgtttcatct tttgtgtaag tgtgcaactt cgattctgta aaacttggca  6120
agtagatgaa cgatgtcatt tatatgcgtg tagcttgtca aaatacaaag tagaaacctg  6180
tatctgaata agatggcatt catgaaataa tattatcgat tgaacgaacg aagcaacaga  6240
atgatcttcc aaattgaagc aaaggaattg atggacaacg agttgctgta ctttggagct  6300
gtaaatctgt agtacttctc aacgatgcta tggaccgtgg gccgtccata atcgctgggt  6360
ggaatgagcc cactgtccat gtgcttctgc atttggcccg tgtacagccc atataatgtc  6420
gaaaaaccta atacgcgcgc gccgccggcg cgcgtttcgg acccagaacg cctagcgccg  6480
ctgcgccgac gtgcgcgcgt ctccactttt tttttcgttt tctttccatt              6530
```

```
SEQ ID NO: 72          moltype = DNA  length = 3960
FEATURE                Location/Qualifiers
misc_feature           1..3960
                       note = Synthetic polynucleotide.NLS-FnCpf1-CO7-NLS
source                 1..3960
                       mol_type = other DNA
                       organism = synthetic construct
SEQUENCE: 72
ggtagcaaaa agaggcgtat caagcaggac atgtccatct atcaggaatt tgttaacaag  60
tactctctta gcaaaactct taggttcgaa ttgatacctc agggaaagac acttgagaat  120
attaaggcgc gcgggctgat acttgatgat gaaaagcggg caaaggacta taagaaagct  180
aagcaaataa ttgataagta ccaccagttt tttattgaag agatcctgtc ctccgtttgt  240
atatccgaag acttgcttca gaattactca gatgtttatt ttaaattgaa gaaatctgac  300
gatgataatc ttcaaaagga tttcaaatcg gcaaaagaca caatcaaaaa acagattagc  360
gagtacatca aggactccga aaagtttaag aatctcttta atcagaatct tatagacgca  420
aagaaaggac aggaatcgga cttgattttg tggttgaagc agtccaagga taacgggata  480
gaactcttta aagccaactc cgatataacg gacatcgacg aagccctcga aatcattaag  540
tcgtttaaag gttggaccac gtacttcaaa ggattccacg agaacagaaa gaacgtttac  600
tcgagcaacg acattcctac tagcatcata tatagaatag tggatgataa tttgcccaaa  660
ttccttgaga acaaggcaaa atatgaatcc ctgaaagaca aggcgcccga agctatcaac  720
tacgagcaga taaagaaaga tctggctgag gagctgacgt ttgacattga ttacaaaaca  780
agcgaggtca accagagggt tttttcgctg gacgaggttt ttgaaatagc gaattttaat  840
aactacctga accaatccgg catcactaaa tttaacacaa tcatagggggg gaagttcgtg  900
```

-continued

```
aacggagaga acacaaagcg caaagggatt aatgagtaca tcaatttgta cagccagcag  960
atcaatgaca aaacgttgaa gaaatataag atgagcgtct tgtttaagca gattctctcg  1020
gatacggaat ccaaatcatt cgtcattgac aagctggagg atgacagcga tgtggtgaca  1080
actatgcagt ccttctatga acaaattgca gcttttaaaa cggtcgaaga gaagtcgatt  1140
aaagaaacgc tttcgctcct gttcgatgac ctgaaagcgc agaagctgga cctttcgaag  1200
atatatttca aaaacgataa gtcactcacg gaccttagcc aacaggtttt cgatgactat  1260
tctgtcatag ggactgctgt gcttgagtat attactcagc aaatagcccc caaaaacctg  1320
gacaacccgt ctaagaagga acaagagctg atagcgaaga aaacagagaa agctaaatat  1380
ctttcacttg aaactataaa gcttgcactg gaggaattca acaaacatcg cgacatcgac  1440
aagcagtgca gatttgagga gatcttggcc aacttcgcag ctattccaat gatttttgac  1500
gagatagcac agaataagga caacctggca cagattagca taaaatacca gaatcagggg  1560
aagaaggatc ttcttcaggc ttcggctgag gacgatgtca aagccatcaa agatctgctc  1620
gaccagacca acaatttgtt gcataaactc aagatcttcc acatatcgca gtccgaagat  1680
aaagcgaaca tacttgacaa agacgaacat ttttatcttg ttttcgagga gtgttatttt  1740
gagttggcaa acatcgttcc cctctacaac aaaattcgca actatataac tcagaagccc  1800
tattctgacg agaaattcaa acttaatttc gaaaacagca ctctcgcaaa cggctgggat  1860
aaaaacaagg aacccgacaa caccgccata ctttttatta aggatgataa atattatttg  1920
ggcgtgatga ataaaaagaa caataaaata ttcgatgata aagcaattaa ggaaaataaa  1980
ggggaagggt ataaaaaaat cgtgtataag ctgcttccag gagctaataa aatgctgcca  2040
aaagtcttct tctctgccaa gtcgatcaag ttttacaatc cttctgaaga tattttgcgg  2100
atcagaaatc actctactca cactaaaaac ggttcacccc agaaaggata cgagaagttt  2160
gagttcaaca tcgaagactg tcggaagttt atcgactttt acaagcagtc tatatcaaaa  2220
caccccgaat ggaaagattt tggttttcgg ttcagcgaca cgcagagata taattcaatt  2280
gatgagttct acagggaggt ggagaaccaa gggtataaac ttacttttga gaacatttcc  2340
gaatcctata ttgattcggt ggtcaatcag gggaaactgt acctgtttca gatatataac  2400
aaagacttct ccgcgtattc taaaggacgg cccaatctcc atactcttta ttggaaggcg  2460
ctgtttgacg agcggaacct tcaggatgtt gtctataagt tgaacgggga agctgagctg  2520
ttctatcgga agcagtctat tccaaaaaag ataacgcacc ccgcgaagga ggcaattgca  2580
aacaagaaca aagacaatcc aaagaaggag tcggtgtttg agtacgatct gataaaagac  2640
aaaaggttta ccgaggacaa gttttttttc cactgtccga tcaccatcaa ttttaagtct  2700
tccggcgcca acaaattcaa tgacgaaata aatctgctgc tcaaggaaaa ggcaaatgat  2760
gttcatattc tgtcgataga ccgcggggaa agacacctcg cgtattatac attggtcgat  2820
gggaaaggca atattatcaa acaagacacc ttcaatatca ttggtaacga taggatgaaa  2880
acgaactatc atgataaact tgcagctatt gaaaaggaca gagactcggc tcggaaagat  2940
tggaaaaaga tcaataacat caaggaaatg aaggaagggt atctctccca ggtcgttcat  3000
gaaatcgcca aactggttat tgagtacaat gctatagtgg tttttgaaga tcttaatttt  3060
gggtttaaga gagggagatt taaagtcgag aaacaggttt atcaaaaact tgaaaaaatg  3120
ttgatagaaa aattgaacta tcttgtgttt aaggacaatg agttcgataa aaccgggggg  3180
gttttgagag cttatcaact gacggctccc ttcgagacat tcaaaaaaat ggggaagcag  3240
accggcatca tttattatgt gcccgcgggc ttcacttcta aaatttgtcc tgtgacaggg  3300
ttcgtgaacc aattgtaccc caagtacgaa agcgtctcca agtcccaaga attctttagc  3360
aagtttgaca aaatttgcta taacctggac aaagggtact ttgagttttc ctttgattat  3420
aagaatttcg gggataaagc tgcgaaaggt aagtggacga tagcctcttt cgggtcgcgc  3480
cttattaact tcaggaattc cgacaaaaac cataattggg acacccgcga ggtctaccct  3540
acaaaggaac tcgaaaagtt gcttaaggat tattcaatag agtatggtca tggcgagtgt  3600
attaaggctg ctatctgtgg tgagtcagat aagaaattct tcgcgaaatt gacatctgtt  3660
ttgaacacca tcctccaaat gaggaactct aaaacgggga cggagcttga ttatctcatc  3720
tcacccgttg ctgatgtgaa cggtaatttc tttgattcac gccaagcccc gaagaacatg  3780
ccccaagacg ccgatgctaa cggcgcttat catatagggc tgaaggggct catgcttctg  3840
gggcgcatca aaaataacca agaagggaag aaactcaatc tggttatcaa aaatgaggaa  3900
tatttcgaat tcgtgcaaaa ccgcaacaat ggatctaaga agcgtaggat caagcaagat  3960
```

```
SEQ ID NO: 73          moltype = DNA  length = 6530
FEATURE                Location/Qualifiers
misc_feature           1..6530
                       note = Synthetic polynucleotide.Expression cassette
                        comprising Zea maysUbiquitin promoter cassette,
                        NLS-FnCpf1-CO7-NLS and an Oryzasativa transcription
                        termination sequence
source                 1..6530
                       mol_type = other DNA
                       organism = synthetic construct
SEQUENCE: 73
gtcgtgcccc tctctagaga taaagagcat tgcatgtcta aagtataaaa aattaccaca  60
tatttttttg tcacacttat ttgaagtgta gtttatctat ctctatacat atatttaaac  120
ttcactctac aaataatata gtctataata ctaaaataat attagtgttt tagaggatca  180
tataaataaa ctgctagaca tggtctaaag gataattgaa tattttgaca atctacagtt  240
ttatcttttt agtgtgcatg tgatctctct gttttttttg caaatagctt gacctatata  300
atacttcatc cattttatta gtacatccat ttaggattta gggttgatgg tttctataga  360
ctaattttta gtacatccat tttattcttt ttagtctcta aatttttttaa aactaaaact  420
ctattttagt tttttattta ataatttaga tataaaatga aataaaataa attgactaca  480
aataaaacaa ataccctttta agaaataaaa aaactaagca aacatttttc ttgtttcgag  540
tagataatga caggctgttc aacgccgtcg acgagtctaa cggacaccaa ccagcgaacc  600
agcagcgtcg cgtcgggcca agcgaagcag acggcacggc atctctgtag ctgcctctgg  660
acccctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acgggggatt cctttcccac cgctccttcg ctttcccttc ctcgcccgcc  840
gtaataaata gacacccccct ccacaccctc tttccccaac ctcgtgttcg ttcggagcgc  900
acacacacgc aaccagatct cccccaaatc cagccgtcgg cacctccgct tcaaggtacg  960
```

-continued

```
ccgctcatcc tcccccccc cctctctcta ccttctctag atcggcgatc cggtccatgg 1020
ttagggcccg gtagttctac ttctgttcat gtttgtgtta gagcaaacat gttcatgttc 1080
atgtttgtga tgatgtggtc tggttgggcg gtcgttctag atcggagtag gatactgttt 1140
caagctacct ggtggattta ttaattttgt atctgtatgt gtgtgccata catcttcata 1200
gttacgagtt taagatgatg gatggaaata tcgatctagg ataggtatac atgttgatgc 1260
gggttttact gatgcatata cagagatgct ttttttctcg cttggttgtg atgatatggt 1320
ctggttgggc ggtcgttcta gatcggagta gaatactgtt tcaaactacc tggtggattt 1380
attaaaggat aaagggtcgt tctagatcgg agtagaatac tgtttcaaac tacctggtgg 1440
atttattaaa ggatctgtat gtatgtgcct acatcttcat agttacgagt ttaagatgat 1500
ggatggaaat atcgatctag gataggtata catgttgatg cgggttttac tgatgcatat 1560
acagagatgc ttttttttcgc ttggttgtga tgatgtggtc tggttgggcg gtcgttctag 1620
atcggagtag aatactgttt caaactacct ggtggattta ttaattttgt atctttatgt 1680
gtgtgccata catcttcata gttacgagtt taagatgatg gatggaaata ttgatctagg 1740
ataggtatac atgttgatgt gggttttact gatgcatata catgatggca tatgcggcat 1800
ctattcatat gctctaacct tgagtaccta tctattataa taaacaagta tgttttataa 1860
ttattttgat cttgatatac ttggatgatg gcatatgcag cagctatatg tggatttttt 1920
agccctgcct tcatacgcta tttatttgct tggtactgtt tcttttgtcc gatgctcacc 1980
ctgttgttgg gtgatacttc tgcagcggac cgacggtacc atgggtagca aaaagaggcg 2040
tatcaagcag gacatgtcca tctatcagga atttgttaac aagtactctc ttagcaaaac 2100
tcttaggttc gaattgatac ctcagggaaa gacacttgag aatattaagg cgcgcgggct 2160
gatacttgat gatgaaaagc gggcaaagga ctataagaaa gctaagcaaa taattgataa 2220
gtaccaccag tttttttattg aagagatcct gtcctccgtt tgtatatccg aagacttgct 2280
tcagaattac tcagatgttt attttaaatt gaagaaatct gacgatgata atcttcaaaa 2340
ggatttcaaa tcggcaaaag acacaatcaa aaaacagatt agcgagtaca tcaaggactc 2400
cgaaaagttt aagaatctct ttaatcagaa tcttatagac gcaaagaaag gacaggaatc 2460
ggacttgatt ttgtggttga agcagtccaa ggataacggg atagaactct ttaaagccaa 2520
ctccgatata acggacatcg acgaagccct cgaaatcatt aagtcgttta aaggttggac 2580
cacgtacttc aaaggattcc acgagaacag aaagaacgtt tactcgagca acgacattcc 2640
tactagcatc atatatagaa tagtggatga taatttgccc aaattccttg agaacaaggc 2700
aaaatatgaa tccctgaaag acaaggcgcc cgaagctatc aactacgagc agataaagaa 2760
agatctggct gaggagctga cgtttgacat tgattacaaa acaagcgagg tcaaccagag 2820
ggttttttcg ctggacgagg tttttgaaat agcgaatttt aataactacc tgaaccaatc 2880
cggcatcact aaatttaaca caatcatagg ggggaagttc gtgaacggag agaacacaaa 2940
gcgcaaaggg attaatgagt acatcaattt gtacagccag cagatcaatg acaaaacgtt 3000
gaagaaatat aagatgagcg tcttgtttaa gcagattctc tcggatacgg aatccaaatc 3060
attcgtcatt gacaagctgg aggatgacag cgatgtggtg acaactatgc agtccttcta 3120
tgaacaaatt gcagctttta aaacggtcga agagaagtcg attaaagaaa cgctttcgct 3180
cctgttcgat gacctgaaag cgcagaagct ggacctttcg aagatatatt tcaaaaacga 3240
taagtcactc acggacctta gccaacaggt tttcgatgac tattctgtca tagggactgc 3300
tgtgcttgag tatattactc agcaaatagc cccaaaaaac ctggacaacc cgtctaagaa 3360
ggaacaagag ctgatagcga agaaaacaga gaaagctaaa tatctttcac ttgaaactat 3420
aaagcttgca ctggaggaat tcaacaaaca tcgcgacatc gacaagcagt gcagatttga 3480
ggagatcttg gccaacttcg cagctattcc aatgattttt gacgagatag cacagaataa 3540
ggacaacctg gcacagatta gcataaaata ccagaatcag gggaagaagg atcttcttca 3600
ggcttcggct gaggacgatg tcaaagccat caaagatctg ctcgaccaga ccaacaattt 3660
gttgcataaa ctcaagatct tccacatatc gcagtccgaa gataaagcga acatacttga 3720
caaagacgaa catttttatc ttgttttcga ggagtgttat tttgagttgg caaacatcgt 3780
tcccctctac aacaaaattc gcaactatat aactcagaag ccctattctg acgagaaatt 3840
caaacttaat ttcgaaaaca gcactctcgc aaacggctgg gataaaaaca aggaacccga 3900
caacaccgcc atacttttta ttaaggatga taaatattat ttgggcgtga tgaataaaaa 3960
gaacaataaa atattcgatg ataaagcaat taaggaaaat aaaggggaag ggtataaaaa 4020
aatcgtgtat aagctgcttc caggagctaa taaaatgctg ccaaaagtct tcttctctgc 4080
caagtcgatc aagttttaca atccttctga agatatttttg cggatcagaa atcactctac 4140
tcacactaaa aacggttcac cccagaaagg atacgagaag tttgagttca acatcgaaga 4200
ctgtcggaag tttatcgact tttacaagca gtctatatca aaacaccccg aatggaaaga 4260
ttttggtttt cggttcagcg acacgcagag atataattca attgatgagt tctacaggga 4320
ggtggagaac caagggtata aacttacttt tgagaacatt tccgaatcct atattgattc 4380
ggtggtcaat caggggaaac tgtacctgtt tcagatatat aacaaagact tctccgcgta 4440
ttctaaagga cggcccaatc tccatactct ttattggaag gcgctgtttg acgagcggaa 4500
ccttcaggat gttgtctata agttgaacgg ggaagctgag ctgttctatc ggaagcagtc 4560
tattccaaaa aagataacgc accccgcgaa ggaggcaatt gcaaacaaga acaaagacaa 4620
tccaaagaag gagtcggtgt ttgagtacga tctgataaaa gacaaaaggt ttaccgagga 4680
caagtttttt ttccactgtc cgatcaccat caattttaag tcttccggcg ccaacaaatt 4740
caatgacgaa ataaatctgc tgctcaagga aaaggcaaat gatgttcata ttctgtcgat 4800
agaccgcggg gaaagacacc tcgcgtatta tacattggtc gatgggaaag gcaatattat 4860
caaacaagac accttcaata tcattggtaa cgataggatg aaaacgaact atcatgataa 4920
acttgcagct attgaaaagg acagagactc ggctcggaaa gattggaaaa agatcaataa 4980
catcaaggaa atgaaggaag ggtatctctc ccaggtcgtt catgaaatcg ccaaactggt 5040
tattgagtac aatgctatag tggtttttga agatcttaat tttgggttta agagagggag 5100
atttaaagtc gagaaacagg tttatcaaaa acttgaaaaa atgttgatag aaaaattgaa 5160
ctatcttgtg tttaaggaca atgagttcga taaaaccggg ggggttttga gagcttatca 5220
actgacggct cccttcgaga cattcaaaaa aatggggaag cagaccggca tcatttatta 5280
tgtgcccgcg ggcttcactt ctaaaatttg tcctgtgaca gggttcgtga accaattgta 5340
ccccaagtac gaaagcgtct ccaagtccca agaattcttt agcaagtttg acaaaatttg 5400
ctataacctg gacaaagggt actttgagtt ttcctttgat tataagaatt tcggggataa 5460
agctgcgaaa ggtaagtgga cgatagcctc tttcgggtcg cgccttatta acttcaggaa 5520
ttccgacaaa aaccataatt gggacacccg cgaggtctac cctacaaagg aactcgaaaa 5580
gttgcttaag gattattcaa tagagtatgg tcatggcgag tgtattaagg ctgctatctg 5640
tggtgagtca gataagaaat tcttcgcgaa attgacatct gttttgaaca ccatcctcca 5700
```

```
aatgaggaac tctaaaacgg ggacggagct tgattatctc atctcacccg ttgctgatgt  5760
gaacggtaat ttctttgatt cacgccaagc cccgaagaac atgccccaag acgccgatgc  5820
taacggcgct tatcatatag ggctgaaggg gctcatgctt ctggggcgca tcaaaaataa  5880
ccaagaaggg aagaaactca atctggttat caaaaatgag gaatatttcg aattcgtgca  5940
aaaccgcaac aatggatcta agaagcgtag gatcaagcaa gattgattaa ttaagggccc  6000
atccaagtaa attaagttgg atcagtagag atgcatggtt ggtgttctca tgtggtctga  6060
atctgtgttc tgtttcatct tttgtgtaag tgtgcaactt cgattctgta aaacttggca  6120
agtagatgaa cgatgtcatt tatatgcgtg tagcttgtca aaatacaaag tagaaacctg  6180
tatctgaata agatggcatt catgaaataa tattatcgat tgaacgaacg aagcaacaga  6240
atgatcttcc aaattgaagc aaaggaattg atggacaacg agttgctgta ctttggagct  6300
gtaaatctgt agtacttctc aacgatgcta tggaccgtgg gccgtccata atcgctgggt  6360
ggaatgagcc cactgtccat gtgcttctgc atttggcccg tgtacagccc atataatgtc  6420
gaaaaaccta atacgcgcgc gccgccggcg cgcgtttcgg acccagaacg cctagcgccg  6480
ctgcgccgac gtgcgcgcgt ctccactttt tttttcgttt tctttccatt             6530

SEQ ID NO: 74           moltype = DNA  length = 6062
FEATURE                 Location/Qualifiers
misc_feature            1..6062
                        note = Synthetic polynucleotide.Expression cassette
                         comprising Zea maysUbiquitin promoter cassette,
                         NLS-LbCpf1-CO2-NLS and an Oryzasativa transcription
                         termination sequence
source                  1..6062
                        mol_type = other DNA
                        organism = synthetic construct
SEQUENCE: 74
gtcgtgcccc tctctagaga taaagagcat tgcatgtcta aagtataaaa aattaccaca  60
tattttttttg tcacacttat ttgaagtgta gtttatctat ctctatacat atatttaaac  120
ttcactctac aaataatata gtctataata ctaaaataat attagtgttt tagaggatca  180
tataaataaa ctgctagaca tggtctaaag gataattgaa tattttgaca atctacagtt  240
ttatcttttt agtgtgcatg tgatctctct gtttttttttg caaatagctt gacctatata  300
atacttcatc cattttatta gtacatccat ttaggattta gggttgatgg tttctataga  360
ctaattttta gtacatccat tttattcttt ttagtctcta aatttttttaa aactaaaact  420
ctattttagt tttttattta ataatttaga tataaaatga aataaaataa attgactaca  480
aataaaacaa ataccctttta agaaataaaa aaactaagca aacatttttc ttgtttcgag  540
tagataatga caggctgttc aacgccgtcg acgagtctaa cggacaccaa ccagcgaacc  600
agcagcgtcg cgtcgggcca agcgaagcag acggcacggc atctctgtag ctgcctctgg  660
acccctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acggggggatt cctttcccac cgctccttcg ctttcccttc ctcgcccgcc  840
gtaataaata gacacccccct ccacaccctc tttccccaac ctcgtgttcg ttcggagcgc  900
acacacacgc aaccagatct cccccaaatc cagccgtcgg cacctccgct tcaaggtacg  960
ccgctcatcc tcccccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatggaaata tcgatctagg ataggtatac atgttgatgc  1260
gggttttact gatgcatata cagagatgct tttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc ttttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgtttg gtgatacttc tgcaggtcgc cgccatggcg ggatctaaga agagaagaat  2040
taaacaagat tcgaagctcg agaagttcac caactgctac tcgctgagca agacgctgcg  2100
gttcaaggcg atccccgtcg ggaagaccca ggagaacatc gacaacaagc ggctcctggt  2160
cgaggacgag aagcgcgccg aggactacaa gggcgtcaag aagctgctgg accggtacta  2220
cctctccttc atcaacgacg tcctgcactc gatcaagctc aagaacctga acaactacat  2280
ctcgctgttc cgcaagaaga cacggaccga gaaggagaac aaggagctcg agaacctcga  2340
gatcaacctg cgcaaggaga tcgcgaaggc gttcaagggc aacgaggggt acaagagcct  2400
gttcaagaaa gacatcatcg agaccatcct gccggagttc ctggacgaca aggacgagat  2460
cgcgctggtg aactcgttca acgggttcac cacggccttc accgggtttt tcgacaaccg  2520
ggagaacatg ttcagcgagg aggccaagtc gaccagcatc gccttccggt gcatcaacga  2580
gaacctcacc cgctacatca gcaacatgga catcttcgag aaggtggacg ccatcttcga  2640
caagcacgag gtccaggaga tcaaggaaaa gatcctgaac tcggactacg acgtggaaga  2700
cttctttgag ggcgagttct tcaacttcgt cctcacccag gagggcatcg acgtctacaa  2760
cgccatcatc ggcggcttcg tgacggagag cggcgagaag atcaagggcc tcaacgagta  2820
catcaacctc tacaaccaga agactaagca gaagctcccg aagttcaagc cgctgtacaa  2880
gcaagtcctg agcgaccggg agtccctctc gttctacggc gagggctaca cgagcgacga  2940
ggaggtgctg gaggtgttcc gcaacacgct gaacaagaac agcgagatct tcagctcgat  3000
caagaaactc gagaagctgt tcaagaactt cgacgagtac agcagcgccg gcatcttcgt  3060
caagaacggg cccgcgatca gcaccatcag caaggacatc ttcggggagt ggaacgtgat  3120
ccgcgacaag tggaacgccg agtacgacga catccacctc aagaaaaagg cggtggtcac  3180
```

```
ggagaagtac gaggacgacc gccggaagtc cttcaagaaa atcgggagct tcagcctcga  3240
gcagctccag gagtacgcgg acgccgacct gagcgtggtg gagaagctca aggagatcat  3300
catccagaag gtcgacgaga tctacaaggt ctacggctcg agcgagaagc tgttcgacgc  3360
ggacttcgtg ctggagaagt ccctcaagaa gaacgacgcc gtggtggcca tcatgaagga  3420
tctgctcgac agcgtgaagt cgttcgagaa ctacatcaag gcattctttg ggagggcaa  3480
ggagacgaac cgggacgagt ccttctacgg ggacttcgtg ctcgcgtacg acatcctcct  3540
gaaggtcgac cacatctacg acgcgatccg gaactacgtc acgcagaagc cctacagcaa  3600
ggacaagttc aagctctact tccagaaccc gcagttcatg ggcgggtggg acaaggacaa  3660
ggagaccgac taccgggcca cgatcctgcg gtacgggtcc aagtactacc tcgccatcat  3720
ggacaagaag tacgccaagt gcctccagaa gattgacaag gacgacgtga acgggaacta  3780
cgagaagatc aactacaagc tcctcccggg gcccaacaag atgctgccga aggtgttctt  3840
cagcaagaag tggatggcct actacaaccc ctcggaggac atccagaaga tatacaagaa  3900
cggcacgttc aaaaaggggg acatgttcaa cctgaacgac tgccacaagc tgatcgactt  3960
tttcaaggac agcatcagcc gctacccgaa gtggtcgaac gcctacgact tcaacttctc  4020
ggagacggag aagtacaagg acattgcggg cttctaccgg gaggtggagg agcagggcta  4080
caaggtctcc ttcgagagcg cctccaagaa agaggtggac aagctcgtgg aggagggcaa  4140
gctgtacatg ttccagatct acaacaagga cttctcggac aagtcgcacg gcaccccgaa  4200
cctccacacg atgtacttca agctgctgtt cgacgagaac aaccacgggc agatccgcct  4260
cagcggcggg gcggagctgt tcatgcgccg cgcgtccctc aagaaggagg agctggtcgt  4320
gcaccccgcc aactccccga tcgcgaacaa gaaccccgac aaccccaaga agacaaccac  4380
cctctcgtac gacgtctaca aggacaagcg gttctcggag gaccagtacg agctgcacat  4440
cccgatcgcc atcaacaagt gccccaagaa catcttcaag atcaacaccg aggtgcgggt  4500
gctgctcaag cacgacgaca acccctacgt catcgggatc gaccgcggcg agcggaacct  4560
gctctacatc gtggtcgtgg acgggaaggg gaacatcgtg gagcagtaca gcctgaacga  4620
gatcatcaac aacttcaacg gcatccgcat caagacggac taccacagcc tcctggacaa  4680
gaaggagaag gagcggttcg aggcgcggca gaactggacc tccatcgaga acatcaagga  4740
gctgaaggcc ggctacatca gccaggtcgt gcacaagatc tgcgagctcg tggagaagta  4800
cgacgcggtg atcgcgctgg aggacttgaa cagcgggttc aagaactccc gggtcaaggt  4860
cgagaagcag gtctaccaga agttcgagaa gatgctgatc gacaagctca actacatggt  4920
ggacaagaag tccaacccct gcgccaccgg cggcgccctc aagggctacc agatcaccaa  4980
caagttcgag tccttcaagt cgatgtctac gcagaacggg ttcatttttct acatcccggc  5040
gtggctcacc agcaagatcg acccgagcac gggcttcgtc aacctcctga agaccaagta  5100
caccagcatc gcggacagca agaagttcat ctcctcgttc gaccgcatca tgtacgtccc  5160
cgaggaagac ctgttcgagt tcgccctcga ctacaagaac ttctcccgga cggacgccga  5220
ctacatcaaa aagtggaagc tctacagcta cggcaaccgg atccgcatct tccgcaaccc  5280
caagaagaac aatgtgttcg actgggagga ggtgtgcctg acgagcgcct acaaggagct  5340
cttcaacaag tacggcatca actaccagca aggggacatc cgcgcgctgc tctgcgagca  5400
gtccgacaag gcgttctact cgtcgttcat ggccctgatg agcctcatgc tccagatgcg  5460
caacagcatc accggccgga cggacgtgga cttcctgatc agcccggtca agaacagcga  5520
cggcattttc tacgacagcc ggaactacga ggcccaggag aacgccatcc tccccaagaa  5580
cgccgacgcg aacggcgcct acaacatcgc gcggaaggtg ctgtgggcca tcggccagtt  5640
taaaaaggcg gaggacgaga agctggacaa ggtcaagatc gccatcagca acaaggagtg  5700
gctcgagtac gcgcagacga gcgtgaagca cggatctaag aagagaagaa ttaaacaaga  5760
ttgataatcg atcctccgat cccttaatta ccataccatt acaccatgca tcaatatcca  5820
tatatatata aaccctttcg cacgtactta tactatgttt tgtcatacat atatatgtgt  5880
cgaacgatcg atctatcact gatatgatat gattgatcca tcagcctgat ctctgtatct  5940
tgttatttgt ataccgtcaa ataaaagttt cttccacttg tgttaataat tagctactct  6000
catctcatga accctatata taactagttt aatttgctgt caattgaaca tgatgatcga  6060
tg                                                                 6062

SEQ ID NO: 75          moltype = DNA  length = 3684
FEATURE                Location/Qualifiers
misc_feature           1..3684
                       note = Synthetic polynucleotide.Codon optimized
                        LbCpf1(TAT)- CO2
source                 1..3684
                       mol_type = other DNA
                       organism = synthetic construct
SEQUENCE: 75
atgtcgaagc tcgagaagtt caccaactgc tactcgctga gcaagacgct gcggttcaag  60
gcgatccccg tcgggaagac ccaggagaac atcgacaaca agcggctcct ggtcgaggac  120
gagaagcgcg ccgaggacta caagggcgtc aagaagctgc tggaccggta ctacctctcc  180
ttcatcaacg acgtcctgca ctcgatcaag ctcaagaacc tgaacaacta catctcgctg  240
ttccgcaaga agacacggac cgagaaggag aacaaggagc tcgagaacct cgagatcaac  300
ctgcgcaagg agatcgcgaa ggcgttcaag ggcaacgagg ggtacaagag cctgttcaag  360
aaagacatca tcgagaccat cctgccggag ttcctggacg acaaggacga gatcgcgctg  420
gtgaactcgt tcaacgggtt caccacggcc ttcaccgggt ttttcgacaa ccgggagaac  480
atgttcagcg aggaggccaa gtcgaccagc atcgccttcc ggtgcatcaa cgagaacctc  540
acccgctaca tcagcaacat ggacatcttc gagaaggtgg acgccatctt cgacaagcac  600
gaggtccagg agatcaagga aaagatcctg aactcggact acgacgtgga agacttcttt  660
gagggcgagt tcttcaactt cgtcctcacc caggagggca tcgacgtcta caacgccatc  720
atcggcggct tcgtgacgga gagcggcgag aagatcaagg gcctcaacga gtacatcaac  780
ctctacaacc agaagactaa gcagaagctc ccgaagttca agccgctgta caagcaagtc  840
ctgagcgacc gggagtccct ctcgttctac ggcgagggct acacgagcga cgaggaggtg  900
ctggaggtgt tccgcaacac gctgaacaag aacagcgaga tcttcagctc gatcaagaaa  960
ctcgagaagc tgttcaagaa cttcgacgag tacagcagcg ccggcatctt cgtcaagaac  1020
gggcccgcga tcagcaccat cagcaaggac atcttcgggg agtggaacgt gatccgcgac  1080
aagtggaacg ccgagtacga cgacatccac ctcaagaaaa aggcggtggt cacggagaag  1140
tacgaggacg accgccggaa gtccttcaag aaaatcggga gcttcagcct cgagcagctc  1200
```

-continued

```
caggagtacg cggacgccga cctgagcgtg gtggagaagc tcaaggagat catcatccag  1260
aaggtcgacg agatctacaa ggtctacggc tcgagcgaga agctgttcga cgcggacttc  1320
gtgctggaga agtccctcaa gaagaacgac gccgtggtgg ccatcatgaa ggatctgctc  1380
gacagcgtga agtcgttcga gaactacatc aaggcattct ttggggaggg caaggagacg  1440
aaccgggacg agtccttcta cggggacttc gtgctcgcgt acgacatcct cctgaaggtc  1500
gaccacatct acgacgcgat ccggaactac gtcacgcaga agccctacag caaggacaag  1560
ttcaagctct acttccagaa cccgcagttc atgcgcgggt gggacaagga cgtggagacc  1620
gaccgccggg ccacgatcct gcggtacggg tccaagtact acctcgccat catggacaag  1680
aagtacgcca agtgcctcca gaagattgac aaggacgacg tgaacgggaa ctacgagaag  1740
atcaactaca agctcctccc ggggcccaac aagatgctgc cgaaggtgtt cttcagcaag  1800
aagtggatgg cctactacaa cccctcggag gacatccaga agatatacaa gaacggcacg  1860
ttcaaaaagg gggacatgtt caacctgaac gactgccaca agctgatcga ctttttcaag  1920
gacagcatca gccgctaccc gaagtggtcg aacgcctacg acttcaactt ctcggagacg  1980
gagaagtaca aggacattgc gggcttctac cgggaggtgg aggagcaggg ctacaaggtc  2040
tccttcgaga gcgcctccaa gaaagaggtg gacaagctcg tggaggaggg caagctgtac  2100
atgttccaga tctacaacaa ggacttctcg gacaagtcgc acggcacccc gaacctccac  2160
acgatgtact tcaagctgct gttcgacgag aacaaccacg ggcagatccg cctcagcggc  2220
ggggcggagc tgttcatgcg ccgcgcgtcc ctcaagaagg aggagctggt cgtgcacccc  2280
gccaactccc cgatcgcgaa caagaacccc gacaacccca agaagacaac caccctctcg  2340
tacgacgtct acaaggacaa gcggttctcg gaggaccagt acgagctgca catcccgatc  2400
gccatcaaca agtgccccaa gaacatcttc aagatcaaca ccgaggtgcg ggtgctgctc  2460
aagcacgacg acaaccccta cgtcatcggg atcgaccgcg gcgagcggaa cctgctctac  2520
atcgtggtcg tggacgggaa ggggaacatc gtggagcagt acagcctgaa cgagatcatc  2580
aacaacttca acggcatccg catcaagacg gactaccaca gcctcctgga caagaaggag  2640
aaggagcggt tcgaggcgcg gcagaactgg acctccatcg agaacatcaa ggagctgaag  2700
gccggctaca tcagccaggt cgtgcacaag atctgcgagc tcgtggagaa gtacgacgcg  2760
gtgatcgcgc tggaggactt gaacagcggg ttcaagaact cccgggtcaa ggtcgagaag  2820
caggtctacc agaagttcga gaagatgctg atcgacaagc tcaactacat ggtggacaag  2880
aagtccaacc cctgcgccac cggcggcgcc ctcaagggct accagatcac caacaagttc  2940
gagtccttca agtcgatgtc tacgcagaac gggttcattt tctacatccc ggcgtggctc  3000
accagcaaga tcgacccgag cacgggcttc gtcaacctcc tgaagaccaa gtacaccagc  3060
atcgcggaca gcaagaagtt catctcctcg ttcgaccgca tcatgtacgt ccccgaggaa  3120
gacctgttcg agttcgccct cgactacaag aacttctccc ggacggacgc cgactacatc  3180
aaaaagtgga agctctacag ctacggcaac cggatccgca tcttccgcaa ccccaagaag  3240
aacaatgtgt tcgactggga ggaggtgtgc ctgacgagcg cctacaagga gctcttcaac  3300
aagtacggca tcaactacca gcaaggggac atccgcgcgc tgctctgcga gcagtccgac  3360
aaggcgttct actcgtcgtt catggccctg atgagcctca tgctccagat gcgcaacagc  3420
atcaccggcc ggacggacgt ggacttcctg atcagcccgg tcaagaacag cgacggcatt  3480
ttctacgaca gccggaacta cgaggcccag gagaacgcca tcctccccaa gaacgccgac  3540
gcgaacggcg cctacaacat cgcgcggaag gtgctgtggg ccatcggcca gtttaaaaag  3600
gcggaggacg agaagctgga caaggtcaag atcgccatca gcaacaagga gtggctcgag  3660
tacgcgcaga cgagcgtgaa gcac                                        3684
```

```
SEQ ID NO: 76          moltype = AA  length = 1228
FEATURE                Location/Qualifiers
REGION                 1..1228
                       note = Synthetic polypeptide.LbCpf1(TAT)-CO2
                        comprisingG532R/K538V/Y542R substitutions
source                 1..1228
                       mol_type = protein
                       organism = synthetic construct
SEQUENCE: 76
MSKLEKFTNC YSLSKTLRFK AIPVGKTQEN IDNKRLLVED EKRAEDYKGV KKLLDRYYLS  60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNPQF MRGWDKDVET  540
DRRATILRYG SKYYLAIMDK KYAKCLQKID KDDVNGNYEK INYKLLPGPN KMLPKVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI AINKCPKNIF KINTEVRVLL KHDDNPYVIG IDRGERNLLY  840
IVVVDGKGNI VEQYSLNEII NNFNGIRIKT DYHSLLDKKE KERFEARQNW TSIENIKELK  900
AGYISQVVHK ICELVEKYDA VIALEDLNSG FKNSRVKVEK QVYQKFEKML IDKLNYMVDK  960
KSNPCATGGA LKGYQITNKF ESFKSMSTQN GFIFYIPAWL TSKIDPSTGF VNLLKTKYTS  1020
IADSKKFISS FDRIMYVPEE DLFEFALDYK NFSRTDADYI KKWKLYSYGN RIRIFRNPKK  1080
NNVFDWEEVC LTSAYKELFN KYGINYQQGD IRALLCEQSD KAFYSSFMAL MSLMLQMRNS  1140
ITGRTDVDFL ISPVKNSDGI FYDSRNYEAQ ENAILPKNAD ANGAYNIARK VLWAIGQFKK  1200
AEDEKLDKVK IAISNKEWLE YAQTSVKH                                    1228
```

COMPOSITIONS AND METHODS FOR GENOME EDITING IN PLANTA

CROSS-REFERENCE TO RELATED APPLICATIONS

This application is a continuation of U.S. patent application Ser. No. 17/817,196, filed Aug. 3, 2022, which is a continuation of U.S. patent application Ser. No. 16/563,581, filed Sep. 6, 2019 (now U.S. Pat. No. 11,414,669), which claims the benefit of U.S. Provisional Application No. 62/727,784, filed Sep. 6, 2018, which is are thereby incorporated by reference in its their entirety herein.

INCORPORATION OF SEQUENCE LISTING

A sequence listing contained in the file named 777052058702SEQLIST.xml, which is 339,621 bytes (measured in MS-Windows®) and created on Nov. 2, 2023, and comprises 76 sequences, is filed electronically herewith and incorporated by reference in its entirety.

FIELD

This disclosure relates to plant-optimized recombinant nucleic acids encoding Cpf1 and their use in planta.

BACKGROUND

Clustered Regularly Interspaced Short Palindromic Repeats from Prevotella and Francisella 1 or CRISPR/Cpf1 (also known as Cas12a) was first demonstrated for genome editing in mammalian cells in 2015 (Zetsche et al., 2015, Cell 163, 759-771). Cpf1 (CRISPR from Prevotella and Francisella 1) is a large, 1,300 amino acid protein, belonging to class 2 CRISPR system. Different from Cas9 nuclease, the PAM motif of Cpf1 is located at 5' of the target site and the mature gRNA is a single strand of approximately 44 bp.

Cpf1 genome editing in plants was first observed in rice (Xu et al., 2017, Plant Biotechnology Journal 15, 713-717), where up to 41% mutation rate was achieved at OsBel locus using pre-crRNA gRNA structure and LbCpf1. Subsequently, Cpf1 genome editing of rice and tobacco were observed in different laboratories using both LbCpf1 and FnCpf1 (Endo et al., Scientific Reports volume 6, Article number: 38169 (2016); Hu et al., 2017, Journal of Genetics and Genomics 44, 71-73; Tang et al., Nature Plants volume 3, Article number: 17018 (2017); Begemann et al., 2017, Sci Rep. 7, 11606). However, there remains a need for more effective Cpf1-based genome editing technologies in plants.

SUMMARY

Several embodiments relate to a recombinant nucleic acid comprising a sequence selected from the group consisting of: SEQ ID NOs 1, 10, 38, 45-51 and 75. In some embodiments, the recombinant nucleic acid further comprises a nucleic acid sequence encoding one or more nuclear localization signals operably linked to the recombinant nucleic acid comprising a sequence selected from the group consisting of: SEQ ID NOs 1, 10, 38, 45-51 and 75. In some embodiments, the nuclear localization signal is provided on the 5' end of Cpf1. In some embodiments, the nuclear localization signal is provided on the 3' end of Cpf1. In some embodiments, the nuclear localization signal is provided on the 5' and 3' end of Cpf1. In some embodiments, the recombinant nucleic acid further comprises a promoter operably linked to the recombinant nucleic acid comprising a sequence selected from the group consisting of: SEQ ID NOs 1, 10, 38, 45-51 and 75. In some embodiments, the promoter comprises a sequence selected from the group consisting of SEQ ID NOs 7, 22, 27, and 32. In some embodiments, the recombinant nucleic acid further comprising one or more of an intron, a kozak sequence, a leader sequence and a terminator sequence. Several embodiments relate to a recombinant nucleic acid comprising a sequence selected from the group consisting of SEQ ID NOs 4, 6, 12, 14, 41, 63, 66, 68, 70, and 72.

Several embodiments relate to a plant cell comprising a recombinant nucleic acid comprising a sequence selected from the group consisting of: SEQ ID NOs 1, 10, 38, 45-51 and 75. Several embodiments relate to a plant cell comprising a recombinant nucleic acid comprising a nucleic acid sequence encoding one or more nuclear localization signals operably linked to the recombinant nucleic acid comprising a sequence selected from the group consisting of: SEQ ID NOs 1, 10, 38, 45-51 and 75. In some embodiments, the nuclear localization signal is provided on the 5' end of Cpf1. In some embodiments, the nuclear localization signal is provided on the 3' end of Cpf1. In some embodiments, the nuclear localization signal is provided on the 5' and 3' end of Cpf1. Several embodiments relate to a plant cell comprising a promoter operably linked to a recombinant nucleic acid comprising a sequence selected from the group consisting of: SEQ ID NOs 1, 10, 38, 45-51 and 75, and optionally one or more nuclear localization signals, an intron, a kozak sequence, a leader sequence and a terminator sequence. In some embodiments, the promoter comprises a sequence selected from the group consisting of SEQ ID NOs 7, 22, 27, and 32. Several embodiments relate to a plant cell comprising recombinant nucleic acid comprising a sequence selected from the group consisting of SEQ ID NOs 4, 6, 12, 14, 41, 63, 66, 68, 70, and 72. In some embodiments, the plant cell is a monocot or a dicot. In some embodiments, the plant cell is a maize, cotton, soybean, canola, wheat, tomato, rice, brassica, melon, cucurbit, or lettuce cell.

Several embodiments relate to an expression cassette comprising a recombinant nucleic acid sequence selected from the group consisting of SEQ ID NOs 15, 20, 26, 31, 36, 40, 56, 59, 65, 67, 69, 71, and 73. Several embodiments relate to a plant cell comprising an expression cassette comprising a recombinant nucleic acid sequence selected from the group consisting of SEQ ID NOs 15, 20, 26, 31, 36, 40, 56, 59, 65, 67, 69, 71, and 73. Several embodiments relate to an agrobacterium T-DNA vector comprising an expression SEQ ID NOs 15, 20, 26, 31, 36, 40, 56, 59, 65, 67, 69, 71, and 73. Several embodiments relate to an Agrobacterium cell comprising an agrobacterium T-DNA vector comprising an expression SEQ ID NOs 15, 20, 26, 31, 36, 40, 56, 59, 65, 67, 69, 71, and 73. In some embodiments, the agrobacterium T-DNA vector further comprises an expression cassette for a selectable marker gene. In some embodiments, the agrobacterium T-DNA vector further comprising a promoter operably linked to a one or more crRNA sequences and one or more spacer sequences, where in the spacer sequence is complementary to at least 23 base pairs of a target site. In some embodiments, the crRNA sequence is a pre-crRNA or a mature crRNA.

Several embodiments relate to a composition comprising: (a) recombinant nucleic acid comprising a sequence selected from the group consisting of: SEQ ID NOs 1, 10, 38, 45-51 and 75, and (b) a recombinant nucleic acid encoding a guide RNA comprised of at least one crRNA and at least one spacer RNA sequence. Several embodiments relate to a composition comprising: (a) recombinant nucleic acid comprising a sequence selected from the group consisting of: SEQ ID NOs 6, 12, 14, 41, 63, 66, 68, 70, and 72, and (b) a recombinant nucleic acid encoding a guide RNA comprised of at least one crRNA and at least one spacer RNA sequence. In some embodiments, the composition is provided on a particle suitable for biolistic delivery to a plant cell.

Several embodiments relate to a method for modifying a target sequence in the genome of a plant cell, comprising: introducing into the plant cell a recombinant nucleic acid comprising a sequence selected from the group consisting of: SEQ ID NOs 1, 10, 38, 45-51 and 75 operably linked to a promoter, and introducing into the plant cell a guide polynucleotide comprising a nucleic acid sequence that is complementary to a target sequence or a recombinant nucleic acid encoding the guide polynucleotide, wherein the guide polynucleotide and a Cpf1 nuclease expressed from the recombinant nucleic acid comprising a sequence selected from the group consisting of: SEQ ID NOs 1, 10, 38, 45-51 and 75 form a complex that can bind to and modify the target sequence. Several embodiments relate to a method for modifying a target sequence in the genome of a plant cell, comprising: introducing into the plant cell a recombinant nucleic acid comprising a sequence selected from the group consisting of: SEQ ID NOs 1, 10, 38, 45-51 and 75 operably linked to a promoter, and introducing into the plant cell a guide polynucleotide comprising a nucleic acid sequence that is complementary to a target sequence or a recombinant nucleic acid encoding the guide polynucleotide, wherein the guide polynucleotide and a Cpf1 nuclease expressed from the recombinant nucleic acid comprising a sequence selected from the group consisting of: SEQ ID NOs 1, 10, 38, 45-51 and 75 form a complex that can bind to and modify the target sequence, wherein the recombinant nucleic acid comprising a sequence selected from the group consisting of: SEQ ID NOs 1, 10, 38, 45-51 and 75 is operably linked to a promoter comprising a sequence selected from the group consisting of SEQ ID NOs 7, 22, 27, and 32. In some embodiments, the method further comprises incubating the plant cell at temperatures between 24° C. and 35° C. for a period of at least about 1-8 hours. In some embodiments, the method further comprises incubating the plant cell at temperatures between 28° C. and 35° C. for a period of at least about 4 hours. In some embodiments, the plant cell is a monocot or a dicot. In some embodiments, the plant cell is a maize, cotton, soybean, canola, wheat, tomato, rice, brassica, melon, cucurbit, or lettuce cell. In some embodiments, the method further comprises introducing a donor DNA to the plant cell. In some embodiments, the method further comprises identifying at least one plant cell comprising in its genome the donor DNA, or a portion thereof, integrated into or near said target sequence.

Several embodiments relate to a method for modifying a target sequence in the genome of a plant cell, the method comprising: introducing a guide polynucleotide comprising a nucleic acid sequence that is substantially complementary to the target sequence, or a recombinant nucleic acid encoding the guide polynucleotide, into a plant cell comprising in its genome a recombinant nucleic acid comprising a sequence selected from the group consisting of: SEQ ID NOs 1, 10, 38, 45-51 and 75 operably linked to a promoter, wherein the guide polynucleotide and a Cpf1 nuclease expressed from the recombinant nucleic acid comprising a sequence selected from the group consisting of: SEQ ID NOs 1, 10, 38, 45-51 and 75 form a complex that can bind to and modify the target sequence. Several embodiments relate to a method for modifying a target sequence in the genome of a plant cell, the method comprising: introducing a guide polynucleotide comprising a nucleic acid sequence that is substantially complementary to the target sequence, or a recombinant nucleic acid encoding the guide polynucleotide, into a plant cell comprising in its genome a recombinant nucleic acid comprising a sequence selected from the group consisting of: SEQ ID NOs 1, 10, 38, 45-51 and 75 operably linked to a promoter comprising a sequence selected from the group consisting of SEQ ID NOs 7, 22, 27, and 32, wherein the guide polynucleotide and a Cpf1 nuclease expressed from the recombinant nucleic acid comprising a sequence selected from the group consisting of: SEQ ID NOs 1, 10, 38, 45-51 and 75 form a complex that can bind to and modify the target sequence. In some embodiments, the method further comprises incubating the plant cell at temperatures between 24° C. and 35° C. for a period of at least about 1-8 hours. In some embodiments, the method further comprises incubating the plant cell at temperatures between 28° C. and 35° C. for a period of at least about 4 hours. In some embodiments, the plant cell is a monocot or a dicot. In some embodiments, the plant cell is a maize, cotton, soybean, canola, wheat, tomato, rice, brassica, melon, cucurbit, or lettuce cell. In some embodiments, the method further comprises introducing a donor DNA to the plant cell. In some embodiments, the method further comprises identifying at least one plant cell comprising in its genome the donor DNA, or a portion thereof, integrated into or near said target sequence.

Several embodiments relate to a kit for modifying a target sequence in the genome of a plant cell, the kit comprising a guide polynucleotide comprising a nucleic acid sequence that is complementary to a target sequence or a recombinant nucleic acid encoding the guide polynucleotide, and recombinant nucleic acid comprising a sequence selected from the group consisting of: SEQ ID NOs 1, 10, 38, 45-51 and 75. Several embodiments relate to a kit for modifying a target sequence in the genome of a plant cell, the kit comprising a guide polynucleotide comprising a nucleic acid sequence that is complementary to a target sequence or a recombinant nucleic acid encoding the guide polynucleotide, and recombinant nucleic acid comprising a sequence selected from the group consisting of: SEQ ID NOs 4, 6, 7, 12, 14, 15, 20, 22, 26, 27, 31, 32, 36, 40, 41, 56, 59, 63, 65, 66, 67, 68, 69, 70, 71, 72 and 73. Several embodiments relate to a kit for modifying a target sequence in the genome of a plant cell, the kit comprising a guide polynucleotide comprising a nucleic acid sequence that is complementary to a target sequence or a recombinant nucleic acid encoding the guide polynucleotide, a recombinant nucleic acid comprising a sequence selected from the group consisting of: SEQ ID NOs 1, 4, 6, 7, 10, 12, 14, 15, 20, 22, 26, 27, 31, 32, 36, 40, 41, 56, 59, 63, 65, 66, 67. 68, 69, 70, 71, 72, 73 and 75, and a recombinant nucleic acid encoding a selectable marker.

BRIEF DESCRIPTION OF THE DRAWINGS

The accompanying drawings, which are incorporated in and form a part of the specification, illustrate the aspects of this disclosure and together with the description, serve to explain the principles of the disclosure. In the drawings.

DETAILED DESCRIPTION

Figure 1:
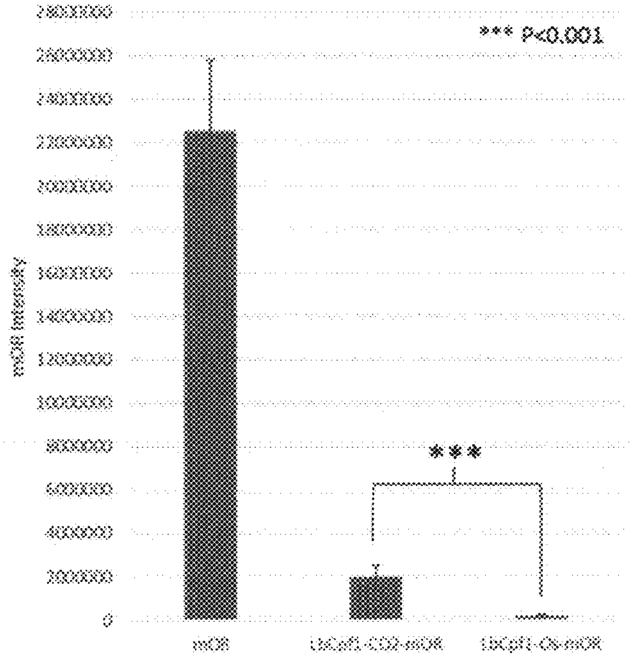
FIG. 1 illustrates the expression of LbCpf1-mOrange fluorescent proteins in corn protoplasts denoted by average mOrange intensities.

Unless defined otherwise, all technical and scientific terms used herein have the same meaning as commonly understood by one of ordinary skill in the art to which this disclosure belongs. Where a term is provided in the singular, the inventors also contemplate aspects of the disclosure described by the plural of that term. Where there are discrepancies in terms and definitions used in references that are incorporated by reference, the terms used in this application shall have the definitions given herein. Other technical terms used have their ordinary meaning in the art in which they are used.

The practice of the present disclosure employs, unless otherwise indicated, conventional techniques of biochemistry, chemistry, molecular biology, microbiology, cell biology, genomics, plant breeding, and biotechnology, which are within the skill of the art. See, e.g., Green and Sambrook, MOLECULAR CLONING: A LABORATORY MANUAL, 4th edition (2012); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)); Harlow and Lane, eds. (1988) ANTIBODIES, A LABORATORY MANUAL; ANIMAL CELL CULTURE (R. I. Freshney, ed. (1987)); RECOMBINANT PROTEIN PURIFICATION: PRINCIPLES AND METHODS, 18-1142-75, GE Healthcare Life Sciences; C. N. Stewart, A. Touracv, V. Citovsky, T. Tzfira eds. (2011) PLANT TRANSFORMATION TECHNOLOGIES (Wiley-Blackwell); and R. H. Smith (2013) PLANT TISSUE CULTURE. TECHNIQUES AND EXPERIMENTS (Academic Press, Inc.). The inventors do not intend to be limited to a mechanism or mode of action. Reference thereto is provided for illustrative purposes only.

Any references cited herein are incorporated by reference in their entireties.

As used herein, the singular form “a,” “an,” and “the” include plural references unless the context clearly dictates otherwise. For example, the term “a compound” or “at least one compound” may include a plurality of compounds, including mixtures thereof. Thus, for example, reference to “plant,” “the plant,” or “a plant” also includes a plurality of plants; also, depending on the context, use of the term “plant” can also include genetically similar or identical progeny of that plant; use of the term “a nucleic acid” optionally includes, as a practical matter, many copies of that nucleic acid molecule.

As used herein, the term “about” indicates that a value includes the inherent variation of error for the method being employed to determine a value, or the variation that exists among experiments.

As used herein, “encoding” refers either to a polynucleotide (DNA or RNA) encoding for the amino acids of a polypeptide or a DNA encoding for the nucleotides of an RNA. As used herein, “coding sequence” and “coding region” are used interchangeably and refer to a polynucleotide that encodes a polypeptide. The boundaries of a coding region are generally determined by a translation start codon at its 5' end and a translation stop codon at its 3' end.

As used herein, the term “identity” when used in relation to nucleic acids, describes the degree of similarity between two or more nucleotide sequences. The percentage of “sequence identity” between two sequences can be determined by comparing two optimally aligned sequences over a comparison window, such that the portion of the sequence in the comparison window may comprise additions or deletions (gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. An alignment of two or more sequences may be performed using any suitable computer program. For example, a widely used and accepted computer program for performing sequence alignments is CLUSTALW v1.6 (Thompson, et al. (1994) Nucl. Acids Res., 22: 4673-4680).

As used herein, the terms “nucleic acid,” “polynucleotide,” and “oligonucleotide are used interchangeably and refer to deoxyribonuclotides (DNA), ribonucleotides (RNA), and functional analogues thereof, such as complementary DNA (cDNA) in linear or circular conformation. Nucleic acid molecules provided herein can be single stranded or double stranded. Nucleic acid molecules comprise the nucleotide bases adenine (A), guanine (G), thymine (T), cytosine (C). Uracil (U) replaces thymine in RNA molecules. Analogues of the natural nucleotide bases, as well as nucleotide bases that are modified in the base, sugar, and/or phosphate moieties are also provided herein. The symbol “N” can be used to represent any nucleotide base (e.g., A, G, C, T, or U). The symbol “Y” can be used to represent thymine or cytosine bases. The symbol “V” can be used to represent the nucleotide bases A, C or G. As used herein, “complementary” in reference to a nucleic acid molecule or nucleotide bases refers to A being complementary to T (or U), and G being complementary to C. Two complementary nucleic acid molecules are capable of hybridizing with each other under appropriate conditions. In an aspect of the present disclosure, two nucleic acid sequences are homologous if they have at least 70%, at least 75%, at least 80%, at least 85%, at least 90%, at least 95%, at least 96%, at least 97%, at least 98%, at least 99% or 100% sequence identity with each other.

As used herein, the term “plant” refers to any photosynthetic, cukaryotic, unicellular or multicellular organism of the kingdom Plantae and includes a whole plant or a cell or tissue culture derived from a plant, comprising any of: whole plants, plant components or organs (e.g., leaves, stems, roots, etc.), plant tissues, seeds, plant cells, protoplasts and/or progeny of the same. A progeny plant can be from any filial generation, e.g., F1, F2, F3, F4, F5, F6, F7, etc. A “plant cell” is a biological cell of a plant, taken from a plant or derived through culture from a cell taken from a plant. The term plant encompasses monocotyledonous and dicotyledonous plants. The methods, systems, and compositions described herein are useful across a broad range of plants. Suitable plants in which the methods, systems, and compositions disclosed herein can be used include, but are not limited to, cereals and forage grasses (e.g., alfalfa, rice, maize, wheat, barley, oat, sorghum, pearl millet, finger millet, cool-season forage grasses, and bahiagrass), oilseed crops (e.g., soybean, oilseed brassicas including canola and oilseed rape, sunflower, peanut, flax, sesame, and safflower), legume grains and forages (e.g., common bean, cowpea, pea, faba bean, lentil, tepary bean, Asiatic beans, pigeonpea, vetch, chickpea, lupine, alfalfa, and clovers), temperate fruits and nuts (e.g., apple, pear, peach, plums, berry crops, cherries, grapes, olive, almond, and Persian walnut), tropical and subtropical fruits and nuts (e.g., citrus including limes, oranges, and grapefruit; banana and plantain, pineapple, papaya, mango, avocado, kiwifruit, passionfruit, and persimmon), vegetable crops (e.g., solanaceous plants including tomato, eggplant, and peppers; vegetable brassicas; radish, carrot, cucurbits, alliums, asparagus, and leafy vegetables), sugar cane, tubers (e.g., beets, parsnips, potatoes, turnips, sweet potatoes), and fiber crops (sugarcane, sugar beet, stevia, potato, sweet potato, cassava, and cotton), plantation crops, ornamentals, and turf grasses (tobacco, coffee, cocoa, tea, rubber tree, medicinal plants, ornamentals, and turf grasses), and forest tree species.

As used herein, "plant genome" refers to a nuclear genome, a mitochondrial genome, or a plastid (e.g., chloroplast) genome of a plant cell. In some embodiments, a plant genome may comprise a parental genome contributed by the male and a parental genome contributed by the female. In some embodiments, a plant genome may comprise only one parental genome.

As used herein, "polynucleotide" refers to a nucleic acid molecule containing multiple nucleotides and generally refers both to "oligonucleotides" (a polynucleotide molecule of 18-25 nucleotides in length) and polynucleotides of 26 or more nucleotides. Aspects of this disclosure include compositions including oligonucleotides having a length of 18-25 nucleotides (e. g., 18-mers, 19-mers, 20-mers, 21-mers, 22-mers, 23-mers, 24-mers, or 25-mers), or medium-length polynucleotides having a length of 26 or more nucleotides (e. g., polynucleotides of 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides), or long polynucleotides having a length greater than about 300 nucleotides (e. g., polynucleotides of between about 300 to about 400 nucleotides, between about 400 to about 500 nucleotides, between about 500 to about 600 nucleotides, between about 600 to about 700 nucleotides, between about 700 to about 800 nucleotides, between about 800 to about 900 nucleotides, between about 900 to about 1000 nucleotides, between about 300 to about 500 nucleotides, between about 300 to about 600 nucleotides, between about 300 to about 700 nucleotides, between about 300 to about 800 nucleotides, between about 300 to about 900 nucleotides, or about 1000 nucleotides in length, or even greater than about 1000 nucleotides in length, for example up to the entire length of a target gene including coding or non-coding or both coding and non-coding portions of the target gene). Where a polynucleotide is double-stranded, its length can be similarly described in terms of base pairs.

As used herein, terms "polypeptide", "peptide" and "protein" are used interchangeably to refer to a polymer of amino acid residues. The term also applies to amino acid polymers in which one or more amino acids are chemical analogues or modified derivatives of a corresponding naturally-occurring amino acids.

As used herein, "protoplast" refers to a plant cell that has had its protective cell wall completely or partially removed using, for example, mechanical or enzymatic means resulting in an intact biochemical competent unit of living plant that can reform their cell wall, proliferate and regenerate grow into a whole plant under proper growing conditions.

As used herein, a "recombinant nucleic acid" refers to a nucleic acid molecule (DNA or RNA) having a coding and/or non-coding sequence distinguishable from endogenous nucleic acids found in natural systems. In some aspects, a recombinant nucleic acid provided herein is used in any composition, system or method provided herein. In some aspects, a recombinant nucleic acid may encode any CRISPR enzyme provided herein can be used in any composition, system or method provided herein. In some aspects, a recombinant nucleic acid may comprise or encode any guide RNA provided herein can be used in any composition, system or method provided herein. In an aspect, a vector provided herein comprises any recombinant nucleic acid provided herein. In another aspect, a cell provided herein comprises a recombinant nucleic acid provided herein. In another aspect, a cell provided herein comprises a vector provided herein.

As used herein, the term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as meristem, or particular cell types (e.g., pollen). Regulatory elements may also direct expression in a temporal-dependent manner, such as in a cell-cycle dependent or developmental stage-dependent manner, which may or may not also be tissue or cell-type specific. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); and SV40 enhancer.

As used herein, the terms "target sequence" or "target site" refer to a nucleotide sequence against which a guide RNA is capable of hybridizing. A target sequence may be genic or non-genic. In some aspects, a target sequence provided herein comprises a genic region. In other aspects, a target sequence provided herein comprises an intergenic region. In yet another aspect, a target sequence provided herein comprises both a genic region and an intergenic region. In an aspect, a target sequence provided herein comprises a coding nucleic acid sequence. In another aspect, a target sequence provided herein comprises a non-coding nucleic acid sequence. In an aspect, a target sequence provided herein is located in a promoter. In another aspect, a target sequence provided herein comprises an enhancer sequence. In yet another aspect, a target sequence provided herein comprises both a coding nucleic acid sequence and a non-coding nucleic acid sequence. In one aspect, a target sequence provided herein is recognized and cleaved by a double-strand break inducing agent, such as a system comprising a Cpf1 enzyme and a guide RNA.

As used herein, the term "donor" or "donor DNA" means a single stranded or double stranded DNA that comprises a polynucleotide sequence to be inserted at or near the target site of a Cpf1 enzyme and guide system. In some embodiments, the donor DNA comprises a transgene for insertion into the plant cell genome. In some embodiments, the donor DNA comprises a first and a second region of homology that flank the transgene, where the first and second regions of homology share homology to a first and a second genomic region present in or flanking the target site. A region of homology can be of any length that is sufficient to promote homologous recombination at the target site. For example, a region of homology can comprise at least 5-10, 10-15, 15-20, 20-25, 25-30, 30-35, 35-40, 40-45, 45- 50, 50-55, 55-60, 60-65, 65-70, 70-75, 75-80, 80-85, 85-90, 90-95, 95-100, 100-150, 150-200, 200-250, 250-300, 300-350, 350-400, 400-450, 450-500, 500-550, 550-600, 600-650, 650-700, 700-750, 750-800, 800-850, 850-900, 900-950, 950-1,000, 1,000-1,150, 1,150-1,200, 1,200-1,250, 1,250-1,300, 1,300-1,350, 1,350-1,400, 1,400-1,450, 1,450-1,500, 1,500-1,550,1,550 -1,600, 1,600-1,650, 1,650-1,700, 1,700-1,750, 1,750-1,800, 1,800-1,850, 1,850-1,900, 1,900-1,950, 1,950-2,000, or more bases in length. In some embodiments, the donor DNA comprises a polynucleotide sequence that comprises at least 1, 2, 3, 4, 5, 6, 7, 8, 9, 10 or more nucleotide modifications compared to the target site. In some embodiments, the donor DNA comprises a polynucleotide sequence that is at least 80%, 81%, 82%, 83%, 84%, 85%, 86%, 87%, 88%, 89%, 90%, 91%, 92%, 93%, 94%, 95%, 96%, 97%, 98%, 99% identical to a polynucleotide sequence at or adjacent to the target site. In some embodiments, the donor DNA is 20, 25, 26, 27, 28, 29, 30, 31, 30-35, 35-40, 40-45, 45- 50, 50-55, 55-60, 60-65, 65-70, 70-75, 75-80, 80-85, 85-90, 90-95, 95-100, 100-150, 150-200, 200-250, 250-300, 300-350, 350-400, 400-450, 450-500, 500-550, 550-600, 600-650, 650-700, 700-750, 750-800, 800-850, 850-900, 900-950, 950-1,000, 1,000-1,150, 1,150-1,200, 1,200-1,250, 1,250-1,300, 1,300-1,350, 1,350-1,400, 1,400-1,450, 1,450-1,500, 1,500-1,550, 1,550-1,600, 1,600-1,650, 1,650-1,700, 1,700-1,750, 1,750-1,800, 1,800-1,850, 1,850-1,900, 1,900-1,950, 1,950-2,000, 2,000-2,100, 2,000-2,200, 2,000-2,300, 2,000-2,400, 2,000-2,500, 2,000-2,600, 2,000-2,700, 2,000-2,800, 2,000-2,900, 2,000-3,000, 3,000-3,100, 3,000-3,200, 3,000-3,300, 3,000-3,400, 3,000-3,500, 3,000-3,600, 3,000-3,700, 3,000-3,800, 3,000-3,900, 3,000-4,000, 4,000-4,100, 4,000-4,200, 4,000-4,300, 4,000-4,400, 4,000-4,500, 4,000-4,600, 4,000-4,700, 4,000-4,800, 4,000-4,900, 4,000-5,000, or more nucleotides in length.

In an aspect, a Cpf1 nuclease provided herein is a *Lachnospiraceae bacterium* Cpf1 (LbCpf1) nuclease. In another aspect, a Cpf1 nuclease provided herein is a *Francisella novicida* Cpf1 (FnCpf1) nuclease.

A prerequisite for cleavage of the target site by a CRISPR ribonucleoprotein is the presence of a conserved Protospacer Adjacent Motif (PAM) near the target site. Depending on the CRISPR nuclease, cleavage can occur within a certain number of nucleotides (e.g., between 18-23 nucleotides for Cpf1) from the PAM site. PAM sites are only required for type I and type II CRISPR associated proteins, and different CRISPR endonucleases recognize different PAM sites. Without being limiting, the Cpf1 from *Lachnospiraceae bacterium* can recognize at least the following PAM sites: TTTN, and YTN; (where T is thymine; Y is thymine or cytosine; and N is thymine, cytosine, guanine, or adenine). Without being limiting, the Cpf1 from *Francisella novicida* can recognize at least the following PAM sites: TTN (where T is thymine; and N is thymine, cytosine, guanine, or adenine). In certain embodiments, the LbCpf1 protein disclosed here has been modified to recognize a non-natural PAM. LbCpf1 variants comprising one or more amino acid substitutions resulting in altered PAM sequence specificities have been disclosed in the art (for example see Gao et. al., Nature Biotech., 2017 August; 35(8):789-792). Gao et. al. have disclosed two LbCpf1 variants: SEQ ID NO: 39 comprising the amino acid substitutions G532R/K595R that can recognize TYCV PAM (where T is thymine; Y is thymine or cytosine; C is cytosine and V is cytosine, guanine, or adenine) and SEQ ID NO: 76 comprising the amino acid substitutions G532R/K538V/Y542R that can recognize the TATV PAM (where T is thymine; A is adenine; and V is cytosine, guanine, or adenine). As used herein, LbCpf1(TYC) variant refers to an LbCpf1 nuclease comprising the amino acid substitutions G532R/K595R. As used herein, LbCpf1(TAT) variant (SEQ ID NO: 76) refers to an LbCpf1 nuclease comprising the mutations G532R/K538V/Y542R.

The instant disclosure provides a recombinant nucleic acid encoding the Cpf1 nuclease of SEQ ID NO 2, 39, 43, 76 or a fragment thereof, wherein the recombinant nucleic acid is optimized for expression in a plant cell. A sequence can be optimized for expression in a plant cell by modifying a nucleotide sequence encoding a protein such as, for example, the nucleic acid sequence encoding the Cpf1 nuclease of SEQ ID NO 2, 39, 43 or a fragment thereof, using one or more plant-preferred codons for improved expression. In some embodiments, the plant-optimized recombinant nucleic acid encoding the Cpf1 nuclease of SEQ ID NO 2, or a fragment thereof, comprises a sequence having at least 80% identity, at least 81% identity, at least 82% identity, at least 83% identity, at least 84% identity, at least 85% identity, at least 90% identity, at least 91% identity, at least 92% identity, at least 93% identity, at least 94% identity, at least 95% identity, at least 96% identity, at least 97% identity, at least 98% identity, at least 99%, or 100% identity to a sequence selected from SEQ ID NOs: 1 and 10, or a fragment thereof. In some embodiments, the plant-optimized recombinant nucleic acid encoding the LbCpf1(TYC) nuclease (SEQ ID NO: 39), or a fragment thereof, comprises a sequence having at least 80% identity, at least 81% identity, at least 82% identity, at least 83% identity, at least 84% identity, at least 85% identity, at least 90% identity, at least 91% identity, at least 92% identity, at least 93% identity, at least 94% identity, at least 95% identity, at least 96% identity, at least 97% identity, at least 98% identity, at least 99%, or 100% identity to a sequence selected from SEQ ID NOs: 38, or a fragment thereof. In some embodiments, the plant-optimized recombinant nucleic acid encoding the LbCpf1(TAT) nuclease (SEQ ID NO: 76) or a fragment thereof, comprises a sequence having at least 80% identity, at least 81% identity, at least 82% identity, at least 83% identity, at least 84% identity, at least 85% identity, at least 90% identity, at least 91% identity, at least 92% identity, at least 93% identity, at least 94% identity, at least 95% identity, at least 96% identity, at least 97% identity, at least 98% identity, at least 99%, or 100% identity to a sequence selected from SEQ ID NOs: 75, or a fragment thereof.

In some embodiments, the plant-optimized recombinant nucleic acid encoding the FnCpf1 nuclease (SEQ ID NO 43), or a fragment thereof, comprises a sequence having at least 80% identity, at least 81% identity, at least 82% identity, at least 83% identity, at least 84% identity, at least 85% identity, at least 90% identity, at least 91% identity, at least 92% identity, at least 93% identity, at least 94% identity, at least 95% identity, at least 96% identity, at least 97% identity, at least 98% identity, at least 99%, or 100% identity to a sequence selected from SEQ ID NOs: 45-48,50, 51 or a fragment thereof.

In some embodiments, the plant-optimized recombinant nucleic acid is operably linked to a heterologous promoter. In one aspect, a recombinant nucleic acid provided herein comprises one or more, two or more, three or more, four or more, five or more, six or more, seven or more, eight or more, nine or more, or ten or more heterologous promoters operably linked to one or more, two or more, three or more, four or more, five or more, six or more, seven or more, eight or more, nine or more, or ten or more plant-optimized recombinant nucleic acids encoding a Cpf1 nuclease. In some embodiments, a plant-optimized recombinant nucleic acids encoding a Cpf1 nuclease provided herein is provided to a plant cell in combination with one or more, two or more, three or more, four or more, five or more, six or more, seven or more, eight or more, nine or more, or ten or more guide polynucleotides. As used herein, the term "guide polynucleotide" refers to a polynucleotide sequence that can form a complex with a Cpf1 endonuclease and enables the Cpf1 endonuclease to bind to, and optionally cleave, a target site. The guide polynucleotide sequence can be a RNA sequence, a DNA sequence, or any combination thereof (e.g., a RNA-DNA hybrid sequence). In one aspect, a guide polynucleotide provided herein comprises a CRISPR repeat sequence and a spacer sequence that is complementary to a target site. In one aspect, a guide polynucleotide provided herein comprises one or more repeats of a CRISPR repeat sequence, a spacer sequence, and a CRISPR repeat sequence. In some embodiments, the guide polynucleotide comprises two or more spacer sequences that are complementary to different target sites. In some embodiments, the guide polynucleotide comprises one or more CRISPR repeat sequences selected from a pre-crRNA and a mature cr-RNA. In some embodiments, the guide polynucleotide is operably linked to a promoter. In certain embodiments, recombinant nucleic acids encoding guide polynucleotides may be designed in an array format such that multiple guide polynucleotides can be simultaneously released. In some embodiments, expression of one or more guide polynucleotides is U6-driven. In some embodiments, Cpf1 enzymes complex with multiple guide polynucleotides to mediate genome editing and at multiple target sequences. Some embodiments relate to expression of singly or in tandem array format from 1 up to 4 or more different guide sequences; e.g. up to about 20 or about 30 guides sequences. Each individual guide sequence may target a different target sequence. Such may be processed from, e.g. one chimeric pol3 transcript. Pol3 promoters such as U6 or H1 promoters may be used.

In some embodiments, a plant-optimized recombinant nucleic acid as disclosed herein is expressed or delivered in a vector. As used herein, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is an Agrobacterium T-DNA. Another type of vector is a viral vector, wherein virally-derived DNA or RNA sequences are present in the vector for packaging into a virus (e.g., retroviruses, replication defective retroviruses, Tobacco mosaic virus (TMV), Potato virus X (PVX) and Cowpea mosaic virus (CPMV), tobamovirus, Gemini viruses, adenoviruses, replication defective adeno-viruses, and adeno-associated viruses). Viral vectors also include polynucleotides carried by a virus for transfection into a host cell. In some embodiments, a viral vector may be delivered to a plant using Agrobacterium. Certain vectors are capable of autonomous replication in a host cell into which they are introduced. Other vectors are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). In some embodiments, an expression vector can comprise a plant-optimized recombinant nucleic acid in a form suitable for expression of the plant-optimized recombinant nucleic acid in a plant cell, which means that the expression vector comprises one or more regulatory elements that are operatively-linked to the plant-optimized recombinant nucleic acid to be expressed. Regulatory elements may include enhancers, termination sequences, introns, etc.

In certain embodiments, the plant-optimized recombinant nucleic acid may be operably linked to a nucleic acid sequence encoding one or more nuclear localization signal (NLS), nuclear export signal (NES), functional domains, and flexible linkers. The one or more of the NLS, the NES or the functional domain may be conditionally activated or inactivated. In particular embodiments it can be of interest to target the Cpf1 encoded by the plant-optimized recombinant nucleic acid to the chloroplast. In many cases, this targeting may be achieved by the operably linking the plant-optimized recombinant nucleic acid encoding Cpf1 to a nucleic acid encoding a chloroplast transit peptide (CTP) or plastid transit peptide. Other options for targeting to the chloroplast which have been described are the maize cab-m7 signal sequence (U.S. Pat. No. 7,022,896, WO 97/41228, incorporated by reference herein) a pea glutathione reductase signal sequence (WO 97/41228, incorporated by reference herein) and the CTP described in US2009029861, incorporated by reference herein.

Several embodiments relate to a method for modifying a target sequence in the genome of a plant cell, the method comprising: introducing a recombinant nucleic acid optimized for expression in a plant cell comprising one or more of SEQ ID NOs: 1, 4, 6, 10, 12, 14, 15, 26, 31, 36, 38, 40, 41, 45, 46, 47, 48, 49, 50, 51, 63 ,65, 66, 67, 68, 68, 70, 71, 72, 73, and 75 and a guide polynucleotide comprising a targeting domain that is complementary to a target sequence into the plant cell, where the recombinant nucleic acid expresses Cpf1 endonuclease in the plant cell and the Cpf1 endonuclease and the guide polynucleotide are capable of forming a complex that can recognize, bind to, and optionally nick or cleave the target sequence. In some embodiments, the guide polynucleotide and/or the recombinant nucleic acid are introduced into the plant cell by biolistic delivery. Several embodiments relate to a method for modifying a target sequence in the genome of a plant cell, the method comprising: introducing a guide polynucleotide comprising a targeting domain that is complementary to a target sequence in the plant genome into a plant cell comprising a recombinant nucleic acid optimized for expression in a plant cell, wherein the recombinant nucleic acid comprises one or more of SEQ ID NOs: 11, 4, 6, 10, 12, 14, 15, 26, 31, 36, 38, 40, 41, 45, 46, 47, 48, 49, 50, 51, 63 ,65, 66, 67, 68, 68, 70, 71, 72, 73, and 75 where the recombinant nucleic acid expresses Cpf1 endonuclease in the plant cell and the Cpf1 endonuclease and the guide polynucleotide are capable of forming a complex that can recognize, bind to, and optionally nick or cleave the target sequence. In some embodiments, the guide polynucleotide is introduced into the plant cell by biolistic delivery. In some embodiments, the method further comprises incubating the plant cell at temperatures between 24° C. and 25° C., 25° C. and 26° C., 26° C. and 27° C., 27° C. and 28° C., 28° C. and 29° C., 29° C. and 30° C., 30° C. and 31° C., 31° C. and 32° C., 32° C. and 33° C., 33° C. and 34° C., 34° C. and 35° C., 35° C. and 36° C., 36° C. and 37° C., 37° C. and 38° C., 38° C. and 39° C., 39° C. and 40° C., for a period of at least about 10 min., 15 min., 20 min., 25 min., 30 min., 35 min., 40 min., 45 min., 50 min., 55 min., 1 hr., 2 hrs., 3 hr., 4 hrs., 5 hrs., 6 hrs., 7 hrs., 8 hrs., 9 hrs., 10 hrs., 11 hrs., 12 hrs., 13 hrs., 14 hrs., 15 hrs., 16 hrs., 17 hrs., 18 hrs, 19 hrs., 20 hrs. 21 hrs., 22 hrs., 23 hrs., 24 hrs., 25 hrs., 26 hrs., 27 hrs., 28 hrs., 29 hrs., 30 hrs., 31 hrs., 32 hrs., 33 hrs., 34 hrs., 35 hrs., 36 hrs., 37 hrs., 38 hrs., 39 hrs., 40 hrs., 41 hrs., 42 hrs., 43 hrs. 44 hrs., 45 hrs., 46 hrs., 47 hrs., 48 hrs., 3 days, 4 days, 5 days, 6 days, or 7 days. In some embodiments, the methods described herein can further comprise identifying at least one plant cell, plant or progeny plant that has a modification at the target sequence, where the modification at the target sequence is selected from the group consisting of (i) a replacement of at least one nucleotide, (ii) a deletion of at least one nucleotide, (iii) an insertion of at least one nucleotide, and (iv) any combination of (i)-(iii). The method can further provide a donor DNA to the plant cell, where the donor DNA comprises a polynucleotide sequence of interest. This can produce a plant cell or plant having a detectable targeted genome modification.

Several embodiments relate to a method for modifying a target sequence in the genome of a plant cell, method comprising: obtaining a plant cell comprising in its genome a recombinant nucleic acid comprising a sequence selected from the group consisting of: SEQ ID NOs 1, 4, 6, 10, 12, 14, 15, 26, 31, 36, 38, 40, 41, 45, 46, 47, 48, 49, 50, 51, 63 ,65, 66, 67, 68, 68, 70, 71, 72, 73, and 75 and introducing into the plant cell a guide polynucleotide comprising a targeting domain that is complementary to a target sequence in the plant genome or a recombinant nucleic acid encoding the guide polynucleotide, where the guide polynucleotide and Cpf1 endonuclease encoded by the recombinant nucleic acid are capable of forming a complex that can bind to, and modify the target sequence. In some embodiments, the guide polynucleotide is introduced into the plant cell by biolistic delivery. In some embodiments, the method further comprises incubating the plant cell at temperatures between 24° C. and 25° C. 25° C. and 26° C., 26° C. and 27° C., 27° C. and 28° C., 28° C. and 29° C., 29° C. and 30° C., 30° C. and 31° C., 31° C. and 32° C., 32° C. and 33° C., 33° C. and 34° C., 34° C. and 35° C., 35° C. and 36° C., 36° C. and 37° C., 37° C. and 38° C., 38° C. and 39° C., 39° C. and 40° C., for a period of at least about 10 min., 15 min., 20 min., 25 min., 30 min., 35 min., 40 min., 45 min., 50 min., 55 min., 1 hr., 2 hrs., 3 hr., 4 hrs., 5 hrs., 6 hrs., 7 hrs., 8 hrs., 9 hrs., 10 hrs., 11 hrs., 12 hrs., 13 hrs., 14 hrs., 15 hrs., 16 hrs., 17 hrs., 18 hrs, 19 hrs., 20 hrs. 21 hrs., 22 hrs., 23 hrs., 24 hrs., 25 hrs., 26 hrs., 27 hrs., 28 hrs., 29 hrs., 30 hrs., 31 hrs., 32 hrs., 33 hrs., 34 hrs., 35 hrs., 36 hrs., 37 hrs., 38 hrs., 39 hrs., 40 hrs., 41 hrs., 42 hrs., 43 hrs. 44 hrs., 45 hrs., 46 hrs., 47 hrs., 48 hrs., 3 days, 4 days, 5 days, 6 days, or 7 days. In some embodiments, the methods described herein can further comprise identifying at least one plant cell, plant or progeny plant that has a modification at the target sequence, where the modification at the target sequence is selected from the group consisting of (i) a replacement of at least one nucleotide, (ii) a deletion of at least one nucleotide, (iii) an insertion of at least one nucleotide, and (iv) any combination of (i)-(iii). The method can further provide a donor DNA to the plant cell, where the donor DNA comprises a polynucleotide sequence of interest. This can produce a plant cell or plant having a detectable targeted genome modification.

The plant cell may be of a monocot or dicot. In some embodiments, the plant cell may be from or of a crop or grain plant such as cassava, corn, sorghum, alfalfa, cotton, soybean, canola, wheat, oat or rice. The plant cell may also be of an algae, tree or production plant, fruit or vegetable (e.g., trees such as citrus trees, e.g., orange, grapefruit or lemon trees; peach or nectarine trees; apple or pear trees; nut trees such as almond or walnut or pistachio trees; nightshade plants; plants of the genus *Brassica*; plants of the genus *Lactuca*; plants of the genus *Spinacia*; plants of the genus *Capsicum*; cotton, tobacco, asparagus, avocado, papaya, cassava, carrot, cabbage, broccoli, cauliflower, tomato, eggplant, pepper, lettuce, spinach, strawberry, potato, squash, melon, blueberry, raspberry, blackberry, grape, coffee, cocoa, etc).

The methods for genome editing using the recombinant nucleic acid molecules as described herein can be used to confer desired traits on essentially any plant. A wide variety of plants and plant cell systems may be engineered for the desired physiological and agronomic characteristics described herein using the nucleic acid constructs of the present disclosure and the various transformation methods mentioned above.

EXAMPLES

The following examples are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); ss, single stranded; ds, double stranded and the like.

Example 1

Design and Analysis of LbCpf1-CO1, an Engineered Polynucleotide Optimized for Expression in Plant Cells.

This example describes the creation and testing of a synthetic polynucleotide encoding *Lachnospiraceae bacterium* ND2006 (LbCpf1) nuclease that is optimized for expression in plant cells.

A nucleotide sequence of Cpf1 from *Lachnospiraceae bacterium* ND2006 (LbCpf1) that was codon optimized for expression in human cells has been described by Zetsche et.

al, (Cell 2015, 163, 759-771). The human codon optimized sequence disclosed by Zetsche et. al., was modified through algorithmic methods, partly based on corn codon preference, to design LbCpf1-CO1(Coding sequence Optimized version 1) (SEQ ID NO: 1) to optimize the sequence for expression of the LbCpf1 protein (SEQ ID NO: 2) in plant cells.

The plant-optimized LbCpf1-CO1 sequence was then incorporated into six different expression vectors to test its activity in corn cells. Three of the expression vectors were designed with an expression cassette (SEQ ID NO: 3) comprising the LbCpf1-CO1 nuclease and a nucleotide sequence encoding the Nuclear Localization Sequence (NLS) from the heat stress transcription factor 1 (HSFA1) gene from *Solanum lycopersicum* (SEQ ID NO:4) on the 5' and 3' ends. Three of the expression vectors were designed with an expression cassette (SEQ ID NO:5) comprising a processable potato LS1 intron sequence (SEQ ID NO: 6) introduced into the NLS-LbCpf1-CO1-NLS sequence to eliminate expression of the LbCpf1protein in Agrobacterium. The NLS-LbCpf1-CO1-NLS expression cassettes also comprised a *Zea mays* Ubiquitin M1 promoter leader and intron sequence (SEQ ID NOs:7) operably linked to the NLS-LbCpf1-CO1-NLS nuclease and a transcription terminator sequence from a rice Lipid transfer protein (LTP) gene (SEQ ID NO:8). Each plant vector also comprised a gRNA expression array comprising either 2 or 4 guide RNA sequences (mature crRNA+spacer) positioned in tandem and targeting 2 or 4 sites in a corn chromosome. The first crRNA sequence was 35 nt while the remaining ones were 20 nt and the spacer sequence was 30 nt. The gRNA arrays were operably linked to the maize U6 Pol III promoter (SEQ ID NO:9) and a poly T terminator sequence. All the expression vectors also included a third expression cassette containing the selectable marker gene CP4 that provides resistance to the herbicide glyphosate. See Table 1.

Corn 01DKD2 cultivar embryos were transformed with agrobacterium containing the plant expression vectors described in Table 1. Transformed plants were selected on glyphosate, leaf samples from regenerated plantlets were harvested after 2 weeks and genomic DNA was extracted for Fragment Length Analysis (FLA). FLA is a PCR-based molecular assay that can be used to identify indel (insertion or deletion) mutations introduced at the target site by NHEJ-mediated (Non Homologous End Joining) DNA repair following dsDNA cleavage by the Cpf1-guide complex. Genomic DNA was subjected to a PCR reaction with primers flanking the target site to generate amplicons. The amplicons fragment length was then compared to a wild type amplicon to identify mutants. PCR reactions were carried out using 5' FAM-labeled primer, a standard primer and Phusion™ polymerase (New England Biolabs, MA) according to manufactures instructions to generate 200 to 500 bp PCR fragments. 1 ul PCR product was combined with 0.5 ul GeneScan 1200 LIZ Size Standard (Thermo Fisher, MA), 8.5 ul formamide and run on ABI sequencer (Thermo Fisher, MA). Two FLA reactions were multiplexed and subsequently analyzed for fragment length variation to identify plants with mutations at the target sites. As shown in Table 1, 258 plants returned high quality FLA data, out of which only 1 plant was identified as having mutations at one of the target sites.

Example 2

Design and Analysis of LbCpf1-CO2, an Engineered Polynucleotide Optimized for Expression in Plant Cells.

This example describes the design and expression analysis of *Lachnospiraceae bacterium* ND2006 (LbCpf1) nuclease that is optimized for expression in plant cells.

The LbCpf1-CO1 nucleotide sequence described in Example 1 was manually analyzed for the presence of deleterious motifs that could potentially reduce gene expression. These deleterious motifs were given a higher priority for removal/replacement by nucleotide sequences coding for synonymous codons. Additionally, a monocot-specific codon frequency table was used for optimization of the nucleotide sequence for expression in monocots. Based on these criteria, a second optimized LbCpf1 (referred to as LbCpf1-CO2) nucleotide sequence was generated (SEQ ID NO: 10) for expression of the LbCpf1 protein (SEQ ID NO: 2) in planta. When compared to LbCpf1-CO1, the LbCpf1-CO2 sequence was determined to have a threefold reduction in the presence of deleterious motifs within its coding sequence. The full length LbCpf1-CO2 nucleotide sequence shows only 85.6% sequence identity with the human codon optimized LbCpf1 nucleotide sequence disclosed by Zetsche et. al., (Cell 2015, 163, 759-771), only 77.5% sequence identity with LbCpf1-CO1 and only 69.4% sequence identity with the native bacterial LbCpf1 sequence.

Three expression cassettes (Prom35S::HIStag:NLS:LbCpf1-CO2:mOrange:NLS::TermNOS; Prom35S::HIStag:NLS:LbCpf1-Os:mOrange:NLS::TermNOS; and

TABLE 1

SUMMARY OF RESULTS OF FRAGMENT LENGTH ANALYSIS (FLA) GENERATED FROM CORN PLANTS STABLY TRANSFORMED WITH LBCPF1-CO1 AND GRNAS TARGETING 8 UNIQUE GENOMIC TARGET SITES.

| Vector | Intron in Cpf1-CO1 cassette | Genomic sites targeted (TS) | Plants tested | Plants returning data | # Edited samples by FLA | Mutation efficiency (%) |
|---|---|---|---|---|---|---|
| 1 | No | ZmTS1, ZmTS2 | 47 | 34 | 0 | 0 |
| 2 | No | ZmTS3, ZmTS4, ZmTS5, ZmTS6 | 55 | 50 | 0 | 0 |
| 3 | No | ZmTS7, ZmTS8 | 45 | 44 | 0 | 0 |
| 4 | Yes | ZmTS7, ZmTS8 | 38 | 37 | 1 | 2.63 |
| 5 | Yes | ZmTS1, Zm TS2 | 65 | 64 | 0 | 0 |
| 6 | Yes | ZmTS3, ZmTS4, ZmTS5, ZmTS6 | 35 | 29 | 0 | 0 |
| Total | | | 285 | 258 | 1 | |

$Prom_{35S}$::HIStag:NLS:mOrange:NLS::$Term_{NOS}$) were generated by standard cloning techniques and as described below:

(1) Prom35S::HIS tag:NLS:LbCpf1-CO2:mOrange: NLS::TermNOS

The LbCpf1-CO2 coding sequence was fused 5' to the coding sequence of mOrange (mOr) from *Entacmaea quadricolor* (SEQ ID NO: 52). The LbCpf1-CO2:mOrange fusion gene was then flanked at the 5' and 3' ends with the NLS sequence from tomato HSFA1 gene (SEQ ID NO:3) and a nucleotide sequence encoding a HIS tag (MGSS7H) (SEQ ID NO: 54) was introduced to the 5' end. The nucleotide sequence was operably linked to the Cauliflower mosaic virus 35S promoter and an Agrobacterium NOS terminator.

(2) $Prom_{35S}$::HIS tag:NLS:LbCpf1-Os:mOrange:NLS:: $Term_{NOS}$

The rice codon-optimized Cpf1 (LbCpf1-Os) nucleotide sequence described by Xu et. al. (Plant Biotechnology Journal, 2017, 15, 713-717) (SEQ ID NO: 11) was used as a control to compare in planta expression. The LbCpf1-Os coding sequence was fused 5' to the coding sequence of mOrange (mOr) from *Entacmaea quadricolor* (SEQ ID NO: 52). The LbCpf1-Os:mOrange fusion gene was then flanked at the 5' and 3' ends with the NLS sequence from tomato HSFA1 gene (SEQ ID NO:3) and a nucleotide sequence encoding a HIS tag (MGSS7H) (SEQ ID NO:54) was introduced to the 5' end. The nucleotide sequence was operably linked to the Cauliflower mosaic virus 35S promoter and an Agrobacterium NOS terminator.

(3) $Prom_{35S}$::HIS tag:NLS:mOrange:NLS::$Term_{NOS}$

The coding sequence of mOrange (mOr) gene (SEQ ID NO:52) from *Entacmaea quadricolor* was flanked at the 5' and 3' ends with the NLS sequence from tomato HSFA1 gene (SEQ ID NO:3) and a nucleotide sequence encoding a HIS tag (MGSS7H) (SEQ ID NO:54) was introduced to the 5' end. The nucleotide sequence was operably linked to the Cauliflower mosaic virus 35S promoter and an Agrobacterium NOS terminator.

The expression cassettes described above were cloned into plant expression constructs. Corn leaf protoplasts were transfected with either the LbCpf1-CO2-mOr construct, the LbCpf1-Os-mOr construct, or the control mOr construct to evaluate expression levels (Table 2). Since mOrange was fused to LbCpf1-CO2 and LbCpf1-Os, the relative mOrange fluorescence levels reflects LbCpf-CO2 and LbCpf1-Os expression levels. Transformations were carried out using standard polyethylene glycol (PEG) based transfection methods. To quantify transformation frequency, an expression vector comprising the luciferase gene was co-transfected. Following transformation, the protoplasts were incubated in the dark in incubation buffer and harvested after 48 hours. Transformation efficiency was calculated by quantifying luciferase expression. The average mOrange expression from 3 technical replicates was determined using Operetta™ (Perkin Elmer) analysis software. As shown in FIG. 1 and Table 2, mOrange intensity was significantly higher in protoplasts expressing LbCpf1-CO2-mOrange than in cells expressing LbCpf1-Os-mOrange.

TABLE 2

EXPRESSION ANALYSIS OF LBCPF1-CO2-MOR AND LBCPF1-OS-MOR FLUORESCENT PROTEINS IN CORN PROTOPLASTS

| Expression Construct | Fluorescence detected | Fold increase in expression compared to Cpf1-Os-mOr |
|---|---|---|
| Prom35S::HIStag:NLS:LbCpf1-CO2:mOrange:NLS::TermNOS | Yes | 14 |
| Prom35S::HIStag:NLS:LbCpf1-Os:mOrange:NLS::TermNOS | Yes | 1 |
| $Prom_{35S}$:: HIS tag:NLS:mOrange:NLS::$Term_{NOS}$ | Yes | 135 |

Example 3

Analysis of LbCpf1-CO2 Activity in Corn Plants.

This example describes testing the LbCpf1-CO2 nucleotide sequence for activity at multiple genomic sites in corn plants using multiplexed guide RNAs.

An agrobacterium LbCpf1-CO2 T-DNA vector comprising: an expression cassette for a selectable marker conferring resistance to the herbicide glyphosate; an expression cassette (SEQ ID NO:15) comprising NLS-LbCpf1-CO2-NLS (SEQ ID NO: 12) linked to a 5' Kozak sequence (SEQ ID NO:13) resulting in Koz-NLS-LbCpf1-CO2-NLS (SEQ ID NO: 14), which was operably linked to a *Zea mays* Ubiquitin M1 promoter cassette (SEQ ID NOs:7) and the transcription terminator sequence from rice LTP (SEQ ID NO:8); and an expression cassette comprising the *Zea mays* U6 promoter (SEQ ID NO:9) and a polyT terminator operably linked to gRNA expression array comprising three gRNAs positioned in tandem and targeting the three genomic sites, was created. Each gRNA comprised a 21 bp crRNA sequence linked to a 23 bp spacer sequence that was complementary to target site ZmTS9, ZmTS10 or ZmTS11 in the corn genome.

As a control, an agrobacterium LbCpf1-Os T-DNA vector comprising: an expression cassette for a selectable marker conferring resistance to the herbicide glyphosate; an expression cassette (SEQ ID NO: 18) comprising a Kozak sequence immediately upstream of the coding sequence of LbCpf1-Os (SEQ ID NO: 11) fused to the tomato HSFA NLS (SEQ ID NO:3) at the 5' end and the 3' end which was operably linked to the *Zea mays* Ubiquitin M1 promoter cassette (SEQ ID NO: 7) and to the rice LTP terminator (SEQ ID NO: 8); and an expression cassette comprising the *Zea mays* U6 promoter (SEQ ID NO:9) operably linked to gRNA expression array comprising three gRNAs positioned in tandem and targeting the three genomic sites, was created. Each gRNA comprised a 21 bp crRNA sequence linked to a 23bp spacer sequence that was complementary to target site ZmTS9, ZmTS10 or ZmTS11 in the corn genome.

Corn 01DKD2 cultivar embryos were transformed with either the LbCpf1-CO2 or LbCpf1-Os T-DNA vectors described above by agrobacterium-mediated transformation. Transformed plants were selected on glyphosate, leaf samples from regenerated plantlets were harvested after 2 weeks and genomic DNA was extracted for Fragment Length Analysis (FLA) to determine genome mutation rates, as described in Example 1. Table 3 summarizes the results and shows the mutation rate detected at each site in stably transformed corn plants.

TABLE 3

SUMMARY OF RESULTS OF FLA GENERATED FROM CORN PLANTS STABLY TRANSFORMED WITH EITHER LBCPF1-CO2 OR LBCPF1-OS AND GRNA ARRAY TARGETING 3 UNIQUE GENOMIC TARGET SITES

| T-DNA Vector | Target site | Plants assayed | # Edited plants by FLA analysis | Mutation frequency |
|---|---|---|---|---|
| LbCpf1-CO2 | ZmTS9 | 48 | 20 | 41.6% |
| | ZmTS10 | 47 | 6 | 12.7% |
| | ZmTS11 | 46 | 2 | 4.3% |
| LbCpf1-Os | ZmTS9 | 49 | 4 | 8% |
| | ZmTS10 | 49 | 1 | 2% |
| | ZmTS11 | 47 | 2 | 4.3% |

As shown in Table 3, all three sites targeted for cleavage with the guide/LbCpf1-CO2 system described above exhibited the presence of mutations which is indicative of DNA cleavage and repair. The frequency of mutations at the three sites ranged from 4.3% at ZmTS11, 12.7% for ZmTS10 to almost 42% at ZmTS9. 20 plants identified as having mutations in ZmTS9 were further analyzed to confirm the presence of mutations at the target site. PCR primers flanking the target site were used to generate amplicons which were cloned via Zero blunt-end Topo™M cloning (LifeTechnologies), sequenced and compared to the reference sequence. The presence of mutations was confirmed in all 20 events. For the guide/LbCpf1-Os system, mutations were identified at all three sites and the frequency of mutations at the three sites ranged from 2% at TS10, 4.3% for TS11 to almost 9% at TS1. Taken together, the data shows that the plant coding sequence optimized LbCpf1-CO2 is properly transcribed and translated in the corn host cell, is functional and can successfully promote gRNA directed chromosomal cleavage at target sites.

Example 4

Analysis of LbCpf1-CO2 Activity in Combination with a Single gRNA Expression System in Corn Plants.

This example describes the testing the LbCpf1-CO2 nucleotide sequence for the ability to induce cleavage and subsequent edits at a genomic target site in corn plants utilizing a single gRNA expression cassette.

An agrobacterium T-DNA vector comprising: an expression cassette for a selectable marker gene that conferred resistance to the herbicide glyphosate; an expression cassette (SEQ ID NO:15) comprising a Kozak sequence introduced 5' to the NLS-LbCpf1-CO2-NLS nucleotide sequence and operably linked to a *Zea mays* Ubiquitin M1 promoter cassette and the transcription terminator sequence from rice LTP; and an expression cassette comprising the *Zea mays* U6 Pol III promoter (SEQ ID NO: 9) and a poly T terminator operably linked to a single guide RNA (gRNA) comprising a crRNA sequence linked to a 23 bp spacer sequence complementary to a unique target site (ZmTS12) in the corn chromosome.

Corn 01DKD2 cultivar embryos were transformed with agrobacterium containing the T-DNA vector and stably transformed plants were selected on glyphosate. Leaf samples from regenerated plantlets were harvested after 2 weeks and genomic DNA was extracted for Fragment Length Analysis (FLA) to determine genome mutation rates, as described in Example 1.

TABLE 4

FLA RESULTS GENERATED FROM CORN PLANTS STABLY TRANSFORMED WITH LBCPF1-CO2 AND GRNA TARGETING ZMTS12 GENOMIC TARGET SITE.

| Nuclease sequence | Target site | Plants assayed | # Edited plants by FLA analysis | Mutation frequency |
|---|---|---|---|---|
| LbCpf1-CO2 | ZmTS12 | 247 | 158 | 64% |

As shown in Table 4, mutations were identified at the target site in 64% of corn plants stably transformed with a vector comprising the LbCp1-CO2 nucleotide sequence and a single guide RNA.

Example 5

Analysis of the Effect of the Addition of a Kozak Fragment Upstream of the LbCpf1-Os Nucleotide Sequence on Nuclease Activity in Plant Cells.

This example describes testing the addition of the Kozak sequence (SEQ ID NO:15) upstream of the LbCpf1-Os nucleotide sequence for the ability to enhance nuclease activity in corn plants.

An agrobacterium LbCpf1-Os (Kozak minus) T-DNA vector comprising: an expression cassette for a selectable marker conferring resistance to the herbicide glyphosate; an expression cassette (SEQ ID NO:19) comprising NLS-LbCpf1-Os-NLS (SEQ ID NO:16), with an ATG sequence incorporated immediately 5' to SEQ ID NO: 16 and operably linked to a *Zea mays* Ubiquitin M1 promoter cassette (SEQ ID NOs:7) and the transcription terminator sequence from rice LTP (SEQ ID NO:8); and an expression cassette comprising the *Zea mays* U6 promoter (SEQ ID NO:9) operably linked to gRNA expression array comprising three gRNAs positioned in tandem and targeting the three genomic sites, was created. Each gRNA comprised a 21 bp crRNA sequence linked to a 23 bp spacer sequence that was complementary to target site ZmTS9, ZmTS10 or ZmTS11 in the corn genome.

Corn plants were transformed with agrobacterium containing either the T-DNA vector described above comprising the LbCpf1-Os (Kozak minus) expression cassette (SEQ ID NO:19) or the T-DNA vector described in Example 3 comprising a Kozak sequence immediately upstream of the coding sequence of LbCpf1-Os (SEQ ID NO:18). Transformed plants were selected on glyphosate, leaf samples from regenerated plantlets were harvested after 2 weeks and genomic DNA was extracted for Fragment Length Analysis (FLA) to determine genome mutation rates, as described in Example 1. Table 5 summarizes the results and shows the mutation rate for each site in stably transformed corn plants.

TABLE 5

SUMMARY OF FLA RESULTS GENERATED FROM CORN PLANTS STABLY TRANSFORMED WITH LBCPF1-OS AND GRNA ARRAY TARGETING 3 UNIQUE GENOMIC TARGET SITES

| Kozak sequence | Nuclease sequence | Target site | Plants assayed | # Edited plants by FLA analysis | Mutation frequency |
|---|---|---|---|---|---|
| + | LbCpf1-Os | ZmTS9 | 49 | 4 | 8% |
| | | ZmTS10 | 49 | 1 | 2% |
| | | ZmTS11 | 47 | 2 | 4.3% |

TABLE 5-continued

SUMMARY OF FLA RESULTS GENERATED FROM CORN PLANTS STABLY TRANSFORMED WITH LBCPF1-OS AND GRNA ARRAY TARGETING 3 UNIQUE GENOMIC TARGET SITES

| Kozak sequence | Nuclease sequence | Target site | Plants assayed | # Edited plants by FLA analysis | Mutation frequency |
|---|---|---|---|---|---|
| – | LbCpf1-Os | ZmTS9 | 33 | 0 | 0% |
| | | ZmTS10 | 35 | 0 | 0% |
| | | ZmTS11 | 35 | 0 | 0% |

Plants transformed with the LbCpf1-Os comprising a Kozak sequence upstream of the nuclease coding sequence exhibited mutations at all three target sites at frequency ranging from 2% at ZmTS10, 4.3% for ZmTS11 to almost 8% at ZmTS9. No mutants were identified at any of the three target sites in plants transformed with the LbCpf1-Os expression cassette lacking the Kozak sequence.

Example 6

Analysis of LbCpf1-CO2 Activity in Soybean Plants.

This example describes testing the LbCpf1-CO2 nucleotide sequence for activity in soybean plants by assaying the ability of the nuclease to target cleavage at multiple unique genomic sites using multiplexed guides.

An agrobacterium LbCpf1-CO2 T-DNA vector was created comprising: an expression cassette for a selectable marker conferring resistance to the antibiotic spectinomycin; an expression cassette (SEQ ID NO: 20) comprising NLS-LbCpf1-CO2-NLS (SEQ ID NO:12) with ATGGCG fused in frame 5' to SEQ ID NO 12 as the translational start site, which was operably linked to a promoter sequence (SEQ ID NO:37) and a transcriptional terminator sequence from *Medicago truncatula* (disclosed in US20140283200); and an expression cassette comprising the Glycine max U6 Pol III promoter (disclosed in US20170166912) and a polyT terminator operably linked to a gRNA array comprising three gRNAs arranged in tandem and a transcriptional terminator sequence. Each gRNA comprised a 21 bp mature crRNA sequence linked to a 23 bp spacer sequence that was complementary to either the GmFAD2-1A-TS, GmPDS-TS1 or GmPDS-TS2 target site.

An agrobacterium LbCpf1-Os T-DNA control vector was created comprising: an expression cassette for a selectable marker conferring resistance to the antibiotic spectinomycin; an expression cassette (SEQ ID NO: 21) comprising NLS-LbCpf1-Os-NLS with ATGGCG fused in frame 5' as the translational start site, which was operably linked to a promoter sequence (SEQ ID NO:37) and a transcriptional terminator sequence from *Medicago truncatula* (disclosed in US20140283200); and an expression cassette comprising the Glycine max U6 Pol III promoter (disclosed in US20170166912) and polyT terminator operably linked to a gRNA array comprising three gRNAs arranged in tandem and a transcriptional terminator sequence. Each gRNA comprised a 21bp mature crRNA sequence linked to a 23 bp spacer sequence that was complementary to either the GmFAD2-1A-TS, GmPDS-TS1 or GmPDS-TS2 target site.

Excised embryos from A3555 soybean plants were co-cultured with the Agrobacterium containing either the LbCpf1-CO2 T-DNA vector or the LbCpf1-Os T-DNA control vector described above. Transformed plants were selected on spectinomycin, leaf samples from regenerated plantlets were harvested after 4 weeks, and genomic DNA was extracted for Fragment Length Analysis (FLA) to determine genome mutation rates, as described in Example 1. A summary of FLA results generated from soy plants stably transformed with either LbCpf1-CO2 or LbCpf1-Os and gRNA array targeting 3 unique genomic target sites is provided in Table 6.

The plants were also scored for the albino phenotype typically associated with reduction/loss of PDS gene function (Table 7). PDS catalyzes a rate-limiting step in the biosynthesis of carotenoids in plants (Misawa, et. al., *The Plant Journal,* 1993, 4; 833-840). Reducing the endogenous PDS gene expression will therefore result in plants with a bleached phenotype and lowered chlorophyll content. Presence of an albino phenotype is therefore indicative of mutations at the PDS locus.

TABLE 6

SUMMARY OF FLA RESULTS GENERATED FROM SOY PLANTS STABLY TRANSFORMED WITH EITHER LBCPF1-CO2 OR LBCPF1-OS AND GRNA ARRAY TARGETING 3 UNIQUE GENOMIC TARGET SITES

| Nuclease seq variant | Target sites | Plants assayed | # Edited plants by FLA | Mutation rate |
|---|---|---|---|---|
| LbCpf1-CO2 | GmFAD2-1A | 62 | 22 | 36% |
| | GmPDS-TS1 | 62 | 0 | 0% |
| | GmPDS-TS2 | 62 | 28 | 45% |
| LbCpf1-Os | GmFAD2-1A | 88 | 20 | 22% |
| | GmPDS-TS1 | 88 | 0 | 0% |
| | GmPDS-TS2 | 88 | 37 | 42% |

TABLE 7

SUMMARY OF PLANTS SCORED FOR PDS GENE MUTATIONS INDICATED BY AN ALBINO PHENOTYPE.

| Nuclease | Plants assayed | Albino plants | Albino frequency rate |
|---|---|---|---|
| LbCpf1-CO2 | 62 | 52 | 84% |
| LbCpf1-Os | 88 | 60 | 68% |

As summarized in Table 6, of the 3 sites targeted by LbCpf1-Os and LbCpf1-CO2, soybean plants were recovered where mutations were identified at FAD2 and PDS1-TS2 sites. The mutations at the PDS locus was further confirmed by scoring for the albino phenotype (see Table 7).

Example 7

Plant Expression Vectors with Unique Cpf1-CO2 Expression Cassettes $Prom_{Mt.Ubiq}$::NLS:LbCpf1-CO2:NLS::$Term_{Mt}$: An expression cassette (SEQ ID NO: 26) for the expression of a Cpf1-CO2 endonuclease was created comprising: a promoter (SEQ ID NO:22), leader (SEQ ID NO:23) and intron (SEQ ID NO:24) derived from *Medicago truncatula* Ubiquitin operably linked 5' to the NLS- LbCpf1-CO2-NLS coding sequence (SEQ ID NO: 12) wherein ATGGCG sequence was fused in frame 5' to SEQ ID NO 12 and served as the translational start site. The resulting sequence was in turn operably linked 5' to a UTR sequence from a gene from *Medicago truncatula* (SEQ ID NO:25).

The expression cassette was introduced into an agrobacterium vector that also comprised a gRNA cassette designed to guide LbCpf1 to a unique GmTS1 target site on the soy chromosome. The gRNA comprised a 21 bp crRNA sequence linked to a 23 bp spacer sequence that was complementary to GmTS1 within the soy genome. The gRNA was operably linked to Glycine max U6 Pol III promoter (disclosed in US20170166912, incorporated by reference herein) and a poly T terminator. The vector also comprised an expression cassette for a selectable marker conferring resistance to the antibiotic spectinomycin.

$Prom_{EF1a}$::NLS:LbCpf1-CO2:NLS::$Term_{Mt}$: An expression cassette (SEQ ID NO: 31) for the expression of a Cpf1-CO2 endonuclease was created comprising: a promoter (SEQ ID NO:27), leader 5' (SEQ ID NO:28), intron (SEQ ID NO:29), leader 3' (SEQ ID NO:30) derived from *Cucumis melo* EIF1alpha gene operably linked 5' to the NLS-LbCpf1-CO2-NLS coding sequence (SEQ ID NO: 12) wherein ATGGCG sequence was fused in frame 5' to SEQ ID NO 12 and served as the translational start site. The resulting sequence was operably linked to a UTR sequence from a gene from *Medicago truncatula* (SEQ ID NO:25). The expression cassette was introduced into an agrobacterium vector that also comprised a gRNA cassette designed to guide LbCpf1 to a unique GmTS2 target site on the soy chromosome. The gRNA comprised a 21 bp crRNA sequence linked to a 23 bp spacer sequence that was complementary to GmTS2 within the soy genome. The gRNA was operably linked to Glycine max U6 Pol III promoter (disclosed in US20170166912) and a poly T terminator. The vector also comprised an expression cassette for a selectable marker conferring resistance to the antibiotic spectinomycin.

$Prom_{At.Ubiq}$::NLS:LbCpf1-CO2:NLS::$Term_{Gh}$: An expression cassette (SEQ ID NO: 36) for the expression of a Cpf1-CO2 endonuclease was created comprising a promoter (SEQ ID NO:32), leader (SEQ ID NO:33) and intron (SEQ ID NO:34) derived from Arabidopsis Ubiquitin 10 gene operably linked 5' to the NLS-LbCpf1-CO2-NLS coding sequence (SEQ ID NO: 12) where ATGGCG sequence was fused in frame 5' to SEQ ID NO 12 and served as the translational start site. The resulting sequence was operably linked to a UTR sequence from a gene from *Gossypium barbadense* (SEQ ID NO: 35).

The expression cassette was introduced into an agrobacterium vector that also comprised a gRNA cassette designed to guide LbCpf1 to a unique GmTS3 target site on the soy chromosome. The gRNA comprised a 21 bp crRNA sequence linked to a 23 bp spacer sequence that was complementary to GmTS3 within the soy genome. The gRNA was operably linked to Glycine max U6 Pol III promoter (disclosed in US20170166912) and a poly T terminator. The vector also comprised an expression cassette for a selectable marker conferring resistance to the antibiotic spectinomycin.

Example 8

Testing the Activity of LbCpf1-CO2 Expression Cassettes

The Agrobacterium T-DNA vectors described in Example 7, were introduced into *A. tumefaciens*. Excised embryos from A3555 Soybean plants were co-cultured with the Agrobacterium containing the vectors by standard methods known in the art and grown on spectinomycin to select for transformed plants. Leaf samples from regenerated plantlets were harvested after 2 weeks and genomic DNA was extracted for Fragment Length Analysis (FLA) to determine genome mutation rates at the target sites GmTS1, GmTS2 and GmTS3 as described in Example 1. A summary of FLA results generated from soy plants stably transformed with the three LbCpf1-CO2 expression cassettes and gRNAs targeting the unique soy genomic target sites is provided in Table 8.

TABLE 8

SUMMARY OF FLA RESULTS GENERATED FROM SOY PLANTS STABLY TRANSFORMED WITH LBCPF1-CO2 EXPRESSION CASSETTES AND GRNA TARGETING 3 UNIQUE GENOMIC TARGET SITES

| Expression vector with LbCpf1 cassette | Genomic target site | Plants assayed | # of edited plants by FLA | Target site mutation |
|---|---|---|---|---|
| $Prom_{Mt.Ubiq}$::NLS:LbCpf1-CO2:NLS::$Term_{Mt}$ | GmTS1 | 84 | 68 | 81% |
| $Prom_{EF1a}$::NLS:LbCpf1-CO2:NLS::$Term_{Mt}$ | GmTS2 | 84 | 58 | 69% |
| $Prom_{At.Ubiq}$::NLS:LbCpf1-CO2:NLS::$Term_{Gb}$ | GmTS3 | 84 | 72 | 86% |

As shown in Table 8, all three sites targeted for cleavage with the guide/LbCpf1 -CO2 expression systems described above exhibited the presence of mutations which is indicative of DNA cleavage and repair.

Example 9

Analysis of LbCpf1(TYC)-CO2 Variant Activity in Corn Plants.

This example describes the testing of a recombinant polynucleotide encoding Lachnospiraceae LbCpf1(TYC) PAM variant nuclease that is optimized for expression in plant cells.

LbCpf1 variants comprising amino acid mutations resulting in altered PAM sequence specificities have been described by Gao et. al. (see Nature Biotech., 2017 August; 35(8):789-792). For example, Gao et. al. have described an LbCpf1(TYC) variant comprising the mutations G532R/K595R that can be engineered to recognize TYCV PAM. Two nucleotide substitutions were introduced into the LbCpf1-CO2 sequence (SEQ ID NO: 10) resulting in LbCpf1(TYC)-CO2 (SEQ ID NO:38) encoding the LbCpf1 (TYC) protein (SEQ ID NO:39) comprising the mutations G532R/K595R.

To test the activity of LbCpf1(TYC), an agrobacterium T-DNA vector was generated. The vector comprised a Cpf1 expression cassette (SEQ ID NO:40) comprising the maize ubiquitin promoter (SEQ ID NO: 7) operably linked to a sequence (SEQ ID NO: 41) encoding LbCpf1(TYC)-CO2 comprising two nuclear localization signals (SEQ ID NOs: 42 and 3). The NLS-LbCpf1(TYC)-CO2-NLS was operably linked to a transcription terminator sequence from a rice Lipid transfer protein (LTP) gene (disclosed in US201801058230-0175, incorporated herein by reference). The vector also comprised a gRNA expression cassette encoding gRNAs designed to target two unique target sites in the corn genome, ZmTS13 and ZMTS14. The ZmTS13 and ZMTS14 sites were chosen since the TYCV PAM was present immediately upstream to each site. The 5'PAM for ZmTS13 was the sequence TTCA. The 5'PAM for ZmTS14 was the sequence TCCA. The gRNA expression cassette comprised the *Zea mays* U6 Pol III promoter (SEQ ID NO: 9) operably linked to two guide RNAs positioned in tandem and targeting the ZmTS13 and ZmTS14 sites. The expression vector also included a third expression cassette containing the selectable marker gene that provides resistance to the herbicide glyphosate.

Corn 01DKD2 cultivar embryos were transformed with the LbCpf1(TYC)-CO2 vector described above by agrobacterium-mediated transformation. Transformed plants were selected on glyphosate, leaf samples from regenerated plantlets were harvested and genomic DNA was extracted for Fragment Length Analysis (FLA) to determine genome mutation rates specifically at ZmTS13 and ZmTS14 sites, as described in Example 1. ZmTS13 and ZmTS14 are arrayed in antisense orientation relative to each other in the genome and overlap by 8 nts, thus individual editing rates at each gRNA target site were not able to be ascertained. Table 9 summarizes the results and shows the cumulative mutation rate detected at or near the two sites in stably transformed corn plants. As shown in Table 9, 48% (40 of the 83) plants tested exhibited the presence of mutations at the expected region which is indicative of DNA cleavage by LbCpf1 (TYC) and subsequent repair.

TABLE 9

FLA RESULTS GENERATED FROM CORN PLANTS STABLY TRANSFORMED WITH LBCPF1(TYC)-CO2 EXPRESSION CASSETTE AND GRNA TARGETING 2 UNIQUE GENOMIC TARGET SITES.

| T-DNA Vector | Target sites tested | Plants assayed | # Edited plants by FLA analysis | Cumulative Mutation frequency |
|---|---|---|---|---|
| LbCpf1(TYC)-CO2 | ZmTS13 ZmTS14 | 83 | 40 | 48% |

Example 10

Analysis of FnCpf1 Engineered Polynucleotides Optimized for Expression in Plant Cells.

This example describes the design and expression analysis of polynucleotide sequences encoding *Francisella novicida* (FnCpf1) nuclease that are optimized for expression in plant cells.

A nucleotide sequence of Cpf1 from *Francisella novicida* (FnCpf1) that was codon optimized for expression in human cells has been described by Zetsche et. al, (Cell 2015, 163, 759-771). To optimize the expression of the FnCpf1 protein (SEQ ID NO:43) in plant cells, the human codon optimized sequence disclosed by Zetsche et. al., (SEQ ID NO:44), described here as FnCpf1-Hs was modified through algorithmic methods, partly based on plant codon frequency tables, to design seven FnCpf1 CO (Codon optimized) sequences (see Table 10).

TABLE 10

CODON OPTIMIZED FNCPF1 AND THE CODON FREQUENCY TABLES USED TO DESIGN EACH SEQUENCE.

| Codon optimized FnCpf1 | Codon frequency table | SEQ ID NO: |
|---|---|---|
| FnCpf1-CO1 | Glycine max | 45 |
| FnCpf1-CO2 | Monocot | 46 |
| FnCpf1-CO3 | Glycine max | 47 |
| FnCpf1-CO4 | Monocot | 48 |
| FnCpf1-CO5 | Oryza sativa | 49 |
| FnCpf1-CO6 | Oryza sativa | 50 |
| FnCpf1-CO7 | Zea mays | 51 |

Expression Analysis of FnCpf1-CO Variants Via Quantification of FnCpf1-mOr Intensity:

Three expression cassettes (Prom35S::HIStag:NLS:FnCpf1-CO1:mOrange:NLS::TermNOS; Prom35S::HIStag:NLS:FnCpf1-CO2:mOrange:NLS::TermNOS; and $Prom_{35S}$::HIStag:NLS:FnCpf1-Hs:mOrange:NLS::$Term_{NOS}$) were generated by standard cloning techniques and are described below:

(1) $Prom_{35S}$::HIS tag:NLS:FnCpf1-CO1:mOrange:NLS::$Term_{NOS}$

The FnCpf1-CO1 coding sequence (SEQ ID NO: 45) was fused 5' to the coding sequence of mOrange (mOr) from *Entacmaea quadricolor*. (SEQ ID NO:52) The FnCpf1-CO1:mOrange fusion gene was flanked at the 5' end with an NLS sequence from potato (SEQ ID NO: 42) and at the 3' end with an NLS sequence from tomato HSFA1 gene (SEQ ID NO:3) resulting in NLS:FnCpf1-CO1:mOrange:NLS (SEQ ID NO: 53). A nucleotide sequence encoding a HIS tag (MGSS7H) (SEQ ID NO: 54) was introduced at the 5' end of SEQ ID NO:53. A ‘TAG’ termination codon was introduced to the 3' end of the resulting nucleotide sequence (SEQ ID NO: 55) which was then operably linked to the Cauliflower mosaic virus 35S promoter (disclosed in US9938535-0047, incorporated herein by reference) and an Agrobacterium NOS terminator (MK078637). The expression cassette (SEQ ID NO: 56) was cloned into a plant expression vector.

(2) $Prom_{35S}$::HIS tag:NLS:FnCpf1-CO2:mOrange:NLS::$Term_{NOS}$

The FnCpf1-CO2 coding sequence (SEQ ID NO: 46) was fused 5' to the coding sequence of mOrange (mOr) from *Entacmaea quadricolor*. (SEQ ID NO:52). The FnCpf1-CO2:mOrange fusion gene was flanked at the 5' end with an NLS sequence from potato (SEQ ID NO: 42) and at the 3' end with an NLS sequence from tomato HSFA1 gene (SEQ ID NO:3) resulting in NLS-FnCpf1-CO2-NLS(SEQ ID NO:57). A nucleotide sequence encoding a HIS tag (MGSS7H) (SEQ ID NO: 54) was introduced at the 5' end of SEQ ID NO:57. A ‘TAG’ termination codon was introduced to the 3' end of the resulting nucleotide sequence(SEQ ID NO:58) which was then operably linked to the Cauliflower mosaic virus 35S promoter and an Agrobacterium NOS terminator (MK078637). The expression cassette (SEQ ID NO:59) was cloned into a plant expression vector.

(3) $Prom_{35S}$::HIS tag:NLS:FnCpf1-Hs:mOrange:NLS::$Term_{NOS}$

The human codon-optimized Cpf1 (FnCpf1-Hs) nucleotide sequence described by Zetsche et. al. (Cell 2015, 163, 759-771) (SEQ ID NO:44) was fused 5' to the coding sequence of mOrange (mOr) from *Entacmaea quadricolor*. (SEQ ID NO:52). The FnCpf1-Hs:mOrange fusion gene was then flanked at the 5' end with an NLS sequence from potato (SEQ ID NO: 42) and at the 3' end with an NLS sequence from tomato HSFA1 gene (SEQ ID NO:3) resulting in NLS-FnCpf1-Hs:mOrange-NLS(SEQ ID NO: 60). A nucleotide sequence encoding a HIS tag (MGSS7H) (SEQ ID NO: 54) was introduced at the 5' end of SEQ ID NO:60. A ‘TAG’ termination codon was introduced to the 3' end of the resulting nucleotide sequence (SEQ ID NO:61) which was then operably linked to the Cauliflower mosaic virus 35S promoter and an Agrobacterium NOS terminator (MK078637). The expression cassette (SEQ ID NO:62) was cloned into a plant expression vector.

Figure 2:
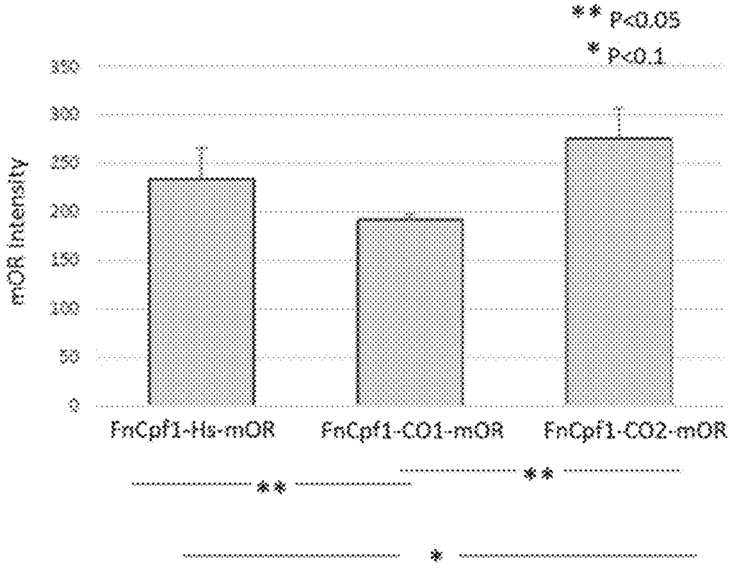
FIG. 2 illustrates the expression of FnCpf1-mOrange fluorescent proteins in corn protoplasts denoted by average mOrange intensities.

To evaluate and quantify the expression of the fusion proteins, corn leaf protoplasts were transfected with expression vectors comprising either of the three expression cassettes described above. Since mOrange was fused to FnCpf1-CO1, FnCpf1-CO2 and FnCpf1-Hs, the relative mOrange fluorescence levels reflects FnCpf1 expression levels. Transformations were carried out using standard polyethylene glycol (PEG) based transfection methods. To quantify transformation frequency, an expression vector comprising the luciferase gene was co-transfected. Following transformation, the protoplasts were incubated in the dark in incubation buffer and harvested after 48 hours. Transformation efficiency was calculated by quantifying luciferase expression. The average mOrange expression from 5 technical replicates was determined using Operetta™ (Perkin Elmer) analysis software. As shown in FIG. 2, mOrange fluorescence was detected from all three samples. The observed intensity was the highest in protoplasts expressing the FnCpf1-CO2-mOrange expression construct.

Expression Analysis FnCpf1-CO Variants Via Qualitative Western Blots:

In addition to the three expression constructs described above, five expression constructs were generated and are described below:

(4) $Prom_{Ubiq}$::NLS:FnCpf1-CO3:NLS::$Term_{Os}$:

The FnCpf1-CO3 sequence (SEQ ID NO:47) was flanked at the 5' end with an NLS sequence from potato (SEQ ID NO: 42) and at the 3' end with an NLS sequence from tomato HSFA1 gene (SEQ ID NO:3) resulting in NLS-FnCpf1-CO3-NLS (SEQ ID NO:63). An ATG sequence encoding the translation initiation codon was added 5' to the potato NLS sequence and a TGA termination codon sequence was introduced 3' to the tomato NLS sequence. The resulting sequence was operably linked to the maize ubiquitin promoter (SEQ ID NO: 7) and a transcription terminator sequence from a rice (SEQ ID NO:64). The FnCpf1-CO3 expression cassette sequence is set forth as SEQ ID NO:65. The expression cassette was cloned into a plant expression vector.

(5) $Prom_{Ubiq}$::NLS:FnCpf1-CO4:NLS::$Term_{Os}$:

The FnCpf1-CO4 sequence (SEQ ID NO:48) was flanked at the 5' end with an NLS sequence from potato (SEQ ID NO: 42) and at the 3' end with an NLS sequence from tomato HSFA1 gene (SEQ ID NO:3) resulting in NLS-FnCpf1-CO4-NLS(SEQ ID NO:66). An ATG sequence encoding the translation initiation codon was added 5' to the potato NLS sequence and a TAG termination codon sequence was introduced 3' to the tomato NLS sequence. The resulting sequence was operably linked to the maize ubiquitin promoter (SEQ ID NO: 7) and a transcription terminator sequence from a rice (SEQ ID NO: 64). The FnCpf1-CO4 expression cassette sequence is set forth as SEQ ID NO:67. The expression cassette was cloned into a plant expression vector.

(6) $Prom_{Ubiq}$::NLS:FnCpf1-CO5:NLS::$Term_{Os:}$

The FnCpf1-CO5 sequence (SEQ ID NO:49) was flanked at the 5' end with an NLS sequence from potato (SEQ ID NO: 42) and at the 3' end with an NLS sequence from tomato HSFA1 gene (SEQ ID NO:3) resulting in NLS-FnCpf1-CO5-NLS (SEQ ID NO:68). An ATG sequence encoding the translation initiation codon was added 5' to the potato NLS sequence and a TGA termination codon sequence was introduced 3' to the tomato NLS sequence. The resulting sequence was operably linked to the maize ubiquitin promoter (SEQ ID NO: 7) and a transcription terminator sequence from a rice (SEQ ID NO: 64). The FnCpf1-CO5 expression cassette sequence is set forth as SEQ ID NO:69. The expression cassette was cloned into a plant expression vector.

(7) $Prom_{Ubiq}$::NLS:FnCpf1-CO6:NLS::$Term_{Os}$:

The FnCpf1-CO6 sequence (SEQ ID NO:50) was flanked at the 5' end with an NLS sequence from potato (SEQ ID NO: 42) and at the 3' end with an NLS sequence from tomato HSFA1 gene (SEQ ID NO:3) resulting in NLS-FnCpf1-CO6-NLS (SEQ ID NO:70). An ATG sequence encoding the translation initiation codon was added 5' to the potato NLS sequence and a TGA termination codon sequence was introduced 3' to the tomato NLS sequence. The resulting sequence was operably linked to the maize ubiquitin promoter (SEQ ID NO: 7) and a transcription terminator sequence from a rice (SEQ ID NO: 64). The FnCpf1-CO6 expression cassette sequence is set forth as SEQ ID NO:71. The expression cassette was cloned into a plant expression vector.

(8) $Prom_{Ubiq}$::NLS:FnCpf1-CO7:NLS::$Term_{Os}$:

The FnCpf1-CO7 sequence (SEQ ID NO:51) was flanked at the 5' end with an NLS sequence from potato (SEQ ID NO: 42) and at the 3' end with an NLS sequence from tomato HSFA1 gene (SEQ ID NO:3) resulting in NLS-FnCpf1-CO7-NLS (SEQ ID NO:72). An ATG sequence encoding the translation initiation codon was added 5' to the potato NLS sequence and a TGA termination codon sequence was introduced 3' to the tomato NLS sequence. The resulting sequence was operably linked to the maize ubiquitin promoter (SEQ ID NO: 7) and a transcription terminator sequence from a rice (SEQ ID NO: 64). The FnCpf1-CO7 expression cassette sequence is set forth as SEQ ID NO:73. The expression cassette was cloned into a plant expression vector.

Corn protoplast cells were transformed with the eight plant expression vectors described above and in Table 11. As a negative control, cells were transformed with an expression vector for GFP. Transformations were carried out using standard polyethylene glycol (PEG) based transfection methods. Following transformation, the protoplasts were incubated in the dark in incubation buffer and harvested after 48 hours. $32*10^4$ cells from each transformation were lysed using 50 uL of lysis buffer. Total protein was extracted from each of the lysed samples and 30 ug protein per sample was resolved on an SDS-PAGE gel and electro-blotted onto nitrocellulose membranes by standard methods. 5 ng, 1 ng and 500 pg of purified FnCpf1 protein were loaded as positive controls. Western blots using anti-FnCpf1 antibody (Cell Signaling Technology, Danvers, MA) were performed to detect the presence of FnCpf1 proteins using standard methods. As noted in Table 11, a band corresponding to the FnCpf1-mOr was visually observed in the lanes containing protein extract from protoplasts expressing FnCpf1-CO2-mOr (Sample 3). Similarly, bands corresponding to FnCpf1 were visually observed in the lanes containing protein extract from protoplasts expressing FnCpf1 -CO3 and FnCpf1-CO4 (Samples 4 and 5).

TABLE 11

EXPRESSION ANALYSIS FNCPF1-CODON OPTIMIZED VARIANTS VIA QUALITATIVE WESTERN BLOTS

| Sample | Expression cassette | Protein band observed |
|---|---|---|
| 1 | $Prom_{35S}$::HIStag:NLS:FnCpf1Hs:mOrange:NLS::$Term_{NOS}$ | No |
| 2 | $Prom_{35S}$:: HIS tag:NLS:FnCpf1-CO1:mOrange:NLS::$Term_{NOS}$ | No |

TABLE 11-continued

EXPRESSION ANALYSIS FNCPF1-CODON OPTIMIZED VARIANTS VIA QUALITATIVE WESTERN BLOTS

| Sample | Expression cassette | Protein band observed |
|---|---|---|
| 3 | $Prom_{35S}$:: HIS tag:NLS:FnCpf1-CO2:mOrange:NLS::$Term_{NOS}$ | Yes |
| 4 | $Prom_{Ubiq}$::NLS:FnCpf1-CO3:NLS::$Term_{Os}$ | Yes |
| 5 | $Prom_{Ubiq}$::NLS:FnCpf1-CO4:NLS::$Term_{Os}$ | Yes |
| 6 | $Prom_{Ubiq}$::NLS:FnCpf1-CO5:NLS::$Term_{Os}$ | No |
| 7 | $Prom_{Ubiq}$::NLS:FnCpf1-CO6:NLS::$Term_{Os}$ | No |
| 8 | $Prom_{Ubiq}$::NLS:FnCpf1-CO7:NLS::$Term_{Os}$ | No |
| 9 | 5 ng purified FnCpf1 protein (Positive control) | Yes |
| 10 | 1 ng purified FnCpf1 protein (Positive control) | Yes |
| 11 | 500 pg purified FnCpf1 protein (Positive control) | Yes |
| 12 | $Prom_{35S}$::GFP::$Term_{NOS}$ (Negative control) | No |

Example 11

Analysis of FnCpf1 Activity in Corn Protoplasts.

The assay used to evaluate FnCpf1 activity in corn protoplasts was integration of a blunt-end, double-stranded DNA (dsDNA) fragment into the DSB (Double stranded break) created by FnCpf1 protein at a specific target site.

The blunt-end dsDNA fragment (disclosed in WO2019084148-021, incorporated herein by reference) was prepared by pre-annealing complementary ssDNA oligonucleotides. The ZmTS9 target site was chosen as the insertion site and a gRNA expression cassette targeting TS9 was designed. The expression cassette comprised a synthetic U6 promoter operably linked to a 21 bp crRNA sequence linked to a 23 bp spacer sequence that was complementary to ZmTS9 in the corn genome. The gRNA expression cassette was introduced into a plant expression vector. The gRNA vector and the eight plant vectors described in Example 11, each containing an expression cassette for a codon optimized FnCpf1 variant were co-transformed into isolated corn leaf protoplasts along with the double-stranded DNA (dsDNA) fragment essentially as described in patent application publication WO2015131101 (incorporated herein by reference), with minor modifications. Approximately $3.2\times10^5$ protoplasts were transformed using PEG with a total of 12 μg of plasmid DNA and 50 pmoles of the dsDNA fragment (assays 2-9 in Table 12). Protoplast samples lacking the nuclease expressing plasmids served as a negative control (see assay 10 in Table 12). Additionally, protoplast samples transformed with nuclease vectors and gRNA cassettes lacking the spacer sequence were used as negative controls (see assays 11-19 in Table 12). As a positive control (assay 1 in Table 12), protoplasts were transformed with the gRNA cassette and a vector comprising an expression cassette (SEQ ID NO:74) for LbCpf1-CO2 that has been shown to be active in corn (see Examples 3-4). The expression cassette (SEQ ID NO: 20) comprised NLS-LbCpf1-CO2-NLS (SEQ ID NO:12) with ATGGCG fused in frame 5' to SEQ ID NO 12 as the translational start site, and TGA termination codon fused 3' to SEQ ID NO:12. The resulting sequence was operably linked to the maize ubiquitin promoter (SEQ ID NO: 7) and a transcription terminator sequence from a rice (SEQ ID NO:64). To determine transformation efficiency, 3 ug of GFP internal control plasmid was transformed along with test constructs. Following transformation, the corn protoplasts were incubated in the dark and harvested after 48 hours. Genomic DNA was extracted and assayed for integration of the dsDNA fragment. Integration of the dsDNA fragment into the genomic DNA was detected by standard PCR and agarose gel electrophoresis to assess PCR amplicons. The dsDNA fragment may have integrated in either a 5' or 3' orientation with respect to the 5'- and 3'-ends of the DSB. Therefore, two PCR primer sets were run for the target site where the primer sets contained a primer specific to the dsDNA fragment and a primer specific to either the 5' side or the 3' side of the DSB at TS11. The PCR amplicons were separated using standard agarose gel electrophoresis and the size of the amplicon was confirmed by comparison to a molecular weight marker. The presence of a band of expected size was indicative of site-directed integration of the donor oligo at the ZmTS9 site following FnCpf1 mediated dsDNA cleavage. As shown in Table 12, expected bands were amplified from protoplasts expressing LbCpf1-CO2, FnCpf1-CO1, FnCpf1-CO2, FnCpf1-CO3, FnCpf1-CO4, FnCpf1-CO6, FnCpf1-CO7 along with the cognate gRNA cassette and ds DNA. Expected bands were not amplified from protoplasts expressing FnCpf1-CO5 or any of the negative controls.

TABLE 12

FNCPF1 MEDIATED SITE DIRECTED INTEGRATION OF DSDNA OLIGO AT ZMTS9 TARGET SITE.

| Assay | Nuclease Expression cassette | gRNA targeting ZmTS9 | Expected band amplified |
|---|---|---|---|
| 1 | $Prom_{Ubiq}$::NLS:LbCpf1-CO2:NLS::$Term_{Os}$ (Positive control) | + | Yes |
| 2 | $Prom_{35S}$::HIStag:NLS:FnCpf1Hs:mOrange:NLS::$Term_{NOS}$ | + | No |
| 3 | $Prom_{35S}$:: HIS tag:NLS:FnCpf1-CO1:mOrange:NLS::$Term_{NOS}$ | + | Yes |
| 4 | $Prom_{35S}$:: HIS tag:NLS:FnCpf1-CO2:mOrange:NLS::$Term_{NOS}$ | + | Yes |
| 5 | $Prom_{Ubiq}$::NLS:FnCpf1-CO3:NLS::$Term_{Os}$ | + | Yes |
| 6 | $Prom_{Ubiq}$::NLS:FnCpf1-CO4:NLS::$Term_{Os}$ | + | Yes |
| 7 | $Prom_{Ubiq}$::NLS:FnCpf1-CO5:NLS::$Term_{Os}$ | + | No |
| 8 | $Prom_{Ubiq}$::NLS:FnCpf1-CO6:NLS::$Term_{Os}$ | + | Yes |

TABLE 12-continued

| FNCPF1 MEDIATED SITE DIRECTED INTEGRATION OF DSDNA OLIGO AT ZMTS9 TARGET SITE. | | | |
|---|---|---|---|
| Assay | Nuclease Expression cassette | gRNA targeting ZmTS9 | Expected band amplified |
| 9 | $Prom_{Ubiq}$::NLS:FnCpf1-CO7:NLS::$Term_{Os}$ | + | Yes |
| 10 | None | + | No |
| 11 | $Prom_{Ubiq}$::NLS:LbCpf1-CO2:NLS::$Term_{Os}$ | − | No |
| 12 | $Prom_{35S}$::HIStag:NLS:FnCpf1Hs:mOrange:NLS::$Term_{NOS}$ | − | No |
| 13 | $Prom_{35S}$:: HIS tag:NLS:FnCpf1-CO1:mOrange:NLS::$Term_{NOS}$ | − | No |
| 14 | $Prom_{35S}$:: HIS tag:NLS:FnCpf1-CO2:mOrange:NLS::$Term_{NOS}$ | − | No |
| 15 | $Prom_{Ubiq}$::NLS:FnCpf1-CO3:NLS::$Term_{Os}$ | − | No |
| 16 | $Prom_{Ubiq}$::NLS:FnCpf1-CO4:NLS::$Term_{Os}$ | − | No |
| 17 | $Prom_{Ubiq}$::NLS:FnCpf1-CO5:NLS::$Term_{Os}$ | − | No |
| 18 | $Prom_{Ubiq}$::NLS:FnCpf1-CO6:NLS::$Term_{Os}$ | − | No |
| 19 | $Prom_{Ubiq}$::NLS:FnCpf1-CO7:NLS::$Term_{Os}$ | − | No |

The invention claimed is:

1. A recombinant nucleic acid comprising the sequence of SEQ ID No: 75.

2. The recombinant nucleic acid of claim 1, further comprising one or more components selected from the group consisting of: a nucleic acid sequence encoding one or more nuclear localization signals, an operably linked promoter, one or more introns, one or more Kozak sequences, one or more leader sequences, and one or more terminator sequences.

3. The recombinant nucleic acid of claim 2, wherein the promoter comprises a sequence selected from the group consisting of SEQ ID Nos: 7, 22, 27, and 32.

4. A plant cell comprising the recombinant nucleic acid of claim 1.

5. A composition comprising: (a) the recombinant nucleic acid of claim 1, and (b) a recombinant nucleic acid encoding a guide RNA comprising at least one crRNA and at least one spacer RNA sequence.

6. The composition of claim 5, wherein the composition is provided on a particle suitable for biolistic delivery to a plant cell.

7. A method for modifying a target sequence in the genome of a plant cell, comprising:

a) introducing into the plant cell the recombinant nucleic acid of claim 1 operably linked to a promoter, and b) introducing into the plant cell a guide polynucleotide comprising a nucleic acid sequence that is complementary to a target sequence or a recombinant nucleic acid encoding the guide polynucleotide, wherein the guide polynucleotide and a Cpf1 nuclease expressed from the recombinant nucleic acid form a complex that can bind to and modify the target sequence.

8. The method of claim 7, wherein the promoter comprises a sequence selected from the group consisting of SEQ ID Nos: 7, 22, 27, and 32.

9. The method of claim 7, wherein the plant cell is a maize, cotton, soybean, canola, wheat, tomato, rice, Brassica, melon, cucurbit, or lettuce cell.

10. The method of claim 7, further comprising introducing a donor DNA to the plant cell.

11. The method of claim 10, further comprising identifying at least one plant cell comprising in its genome the donor DNA, or a portion thereof, integrated into or near said target sequence.

12. A method for modifying a target sequence in the genome of a plant cell, the method comprising: introducing a guide polynucleotide comprising a nucleic acid sequence that is substantially complementary to the target sequence, or a recombinant nucleic acid encoding the guide polynucleotide, into a plant cell comprising in its genome the recombinant nucleic acid of claim 1 operably linked to a promoter, wherein the guide polynucleotide and a Cpf1 nuclease expressed from the recombinant nucleic acid form a complex that can bind to and modify the target sequence.

13. The method of claim 12, wherein the promoter comprises a sequence selected from the group consisting of SEQ ID Nos: 7, 22, 27, and 32.

14. The method of claim 12, wherein the plant cell is a maize, cotton, soybean, canola, wheat, tomato, rice, Brassica, melon, cucurbit, or lettuce cell.

15. The method of claim 12, further comprising introducing a donor DNA to the plant cell.

16. The method of claim 15, further comprising identifying at least one plant cell comprising in its genome the donor DNA, or a portion thereof, integrated into or near said target sequence.

17. A kit for modifying a target sequence in the genome of a plant cell, the kit comprising a guide polynucleotide comprising a nucleic acid sequence that is complementary to a target sequence or a recombinant nucleic acid encoding the guide polynucleotide, and the recombinant nucleic acid of claim 1.

18. The kit of claim 17, further comprising a recombinant nucleic acid encoding a selectable marker.

* * * * *